(12) United States Patent
Katakura et al.

(10) Patent No.: US 8,367,224 B2
(45) Date of Patent: *Feb. 5, 2013

(54) ORGANIC ELECTROLUMINESCENCE ELEMENT, NEW COMPOUND FOR THE SAME, DISPLAY DEVICE AND LIGHTING DEVICE USING THE SAME

(75) Inventors: Rie Katakura, Hino (JP); Shuichi Sugita, Akishima (JP); Eisaku Katoh, Hachioji (JP); Motoaki Sugino, Akishima (JP); Rie Fujisawa, Ebina (JP)

(73) Assignee: Konica Minolta Holdings, Inc. (JP)

( * ) Notice: Subject to any disclaimer, the term of this patent is extended or adjusted under 35 U.S.C. 154(b) by 407 days.

This patent is subject to a terminal disclaimer.

(21) Appl. No.: 12/752,252

(22) Filed: Apr. 1, 2010

(65) Prior Publication Data
US 2011/0006670 A1 Jan. 13, 2011

(30) Foreign Application Priority Data

Jul. 7, 2009 (JP) ................................ 2009-160591
Oct. 26, 2009 (JP) ................................ 2009-245225

(51) Int. Cl.
*H01L 51/54* (2006.01)
*C07D 407/10* (2006.01)
*C07D 409/10* (2006.01)
*C07D 471/04* (2006.01)
*C07F 15/00* (2006.01)

(52) U.S. Cl. ........ 428/690; 313/504; 313/506; 548/444; 548/402; 546/87

(58) Field of Classification Search .................... None
See application file for complete search history.

(56) References Cited

U.S. PATENT DOCUMENTS 6,097,147 A 8/2000 Baldo et al.
2005/0093422 A1* 5/2005 Wang et al. .................. 313/487

FOREIGN PATENT DOCUMENTS

JP 2005-112765 A 4/2005
JP 2007-126403 A 5/2007
JP 2009-267255 A * 11/2009

OTHER PUBLICATIONS

Machine translation for JP 2009-267255 A which was published Nov. 2009 (printed in two sections, Part 1 and Part 2).*

* cited by examiner

*Primary Examiner* — Dawn L. Garrett
(74) *Attorney, Agent, or Firm* — Cantor Colburn LLP

(57) ABSTRACT

Disclosed is an organic electroluminescence element comprising an anode, a cathode and a plurality of organic compound layers between the anode and the cathode, provided that one of the organic compound layers is a light emitting layer containing a phosphorescence emitting compound, wherein at least one of the organic compound layers contains a compound represented by Formula (1),

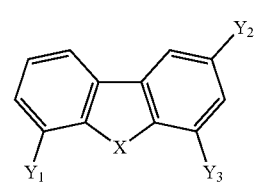

Formula (1)

wherein, X represents O or S; $Y_1$ to $Y_3$ each represents a hydrogen atom, a substituent or a group represented by Formula (A) disclosed in the specification, provided that at least two of $Y_1$ to $Y_3$ are groups represented by Formula (A), not all of $Y_1$ to $Y_3$ are the same group, and at least one of the groups represented by Formula (A) has Ar of a carbazolyl group, or an azacarbazolyl group containing 2 to 5 nitrogen atoms.

12 Claims, 5 Drawing Sheets

LIGHT

LIGHT

ORGANIC ELECTROLUMINESCENCE ELEMENT, NEW COMPOUND FOR THE SAME, DISPLAY DEVICE AND LIGHTING DEVICE USING THE SAME

CROSS REFERENCE TO RELATED APPLICATIONS

This application is based on Japanese Patent Application Nos. 2009-160591 and 2009-245225 each respectively filed on Jul. 7, 2009 and Oct. 26, 2009 with Japan Patent Office, the entire contents of which are hereby incorporated by reference.

TECHNICAL FIELD

The present invention relates to an organic electroluminescence element, a new compound used for the same, and a display device and a lighting device using the same. More specifically, the present invention relates to a new compound preferably used for an organic electroluminescence element, a display device and a lighting device.

BACKGROUND

Conventionally, an emission type electronic display device includes an electroluminescence display (hereinafter, referred to as an ELD). A constituent element of an ELD includes such as an inorganic electroluminescence element and an organic electroluminescence element (hereinafter, referred to as an organic EL element). An inorganic electroluminescence element has been utilized as a flat light source, however, it requires a high voltage of alternating current to operate an emission element.

On the other hand, an organic electroluminescence element is an element provided with a constitution comprising an emitting layer containing a emitting substance being sandwiched with a cathode and an anode, and an exciton is generated by an electron and a positive hole being injected into the emitting layer to be recombined, resulting emission utilizing light release (fluorescence phosphorescence) at the time of deactivation of said exciton; the emission is possible at a voltage of approximately a few to a few tens volts, and an organic electroluminescence element is attracting attention with respect to such as superior viewing angle and high visual recognition due to a self-emission type as well as space saving and portability due to a completely solid element of a thin layer type.

As a development of an organic EL element toward a practical application, there was a disclosure by a research group of Princeton University concerning an organic EL device using phosphorescence luminescence from an excited triplet (for example, refer to Non-patent document 1). Since the, investigations of materials which exhibit phosphorescence at room temperature have been actively done (for example, refer to Patent document 2 and Non-patent document 2).

Furthermore, in the organic EL element using phosphorescence luminescence recently discovered, since theoretically about 4 times of the luminescence efficiency can be realized compared with the formerly known EL element using fluorescence luminescence, the development of the materials, the layer structures and electrodes for it has been made all over the world.

For example, many compounds mainly belonging to heavy metal complexes such as iridium complexes have been synthesized and studied (for example, refer to Non-patent document 3).

Thus, although the organic EL element using phosphorescence luminescence has a very high potential, this element largely differs from the organic EL element using fluorescence luminescence. It has been important technical investigational work in order to improve power efficiency and lifetime of the element such as: the way of controlling the location of a luminescence center, in particular, the way how to carry out light emitting stably by performing recombination inside the light emitting layer.

In recent years, there have been well known the multilayer lamination type element which is provided with a positive hole transport layer (located in an anode side of a light emission layer) and an electron transport layer (located in a cathode side of a light emission layer), both of which are adjacent to the light emitting layer (for example, refer to patent documents 2).

Especially, when blue phosphorescence luminescence is utilized, since the blue phosphorescence luminescent material itself has a high T1 (exited triple), development of surrounding materials and control of the precise luminescence center are strongly requested.

In recent years, in the light emitting layer of the organic EL element using a phosphorescence luminescent material, there were disclosed a technology of using a dibenzothiophene derivative as a host material (for example, refer to Patent document 3) and a technology using a dibenzothiophene derivative and a dibenzofuran derivative as a hole injection material and/or a light emitting material (for example, refer to Patent document 2).

However, from the viewpoint of providing an organic EL element exhibiting high luminous efficiency and low driving voltage, and excellent in thermal stability and raw stock stability, and moreover having a long lifetime, it is still insufficient and it is required further solutions.

On the other hand, the expectation for the wet method (it is also called a wet process or a wet coating process) is large from the request to a large size production, a low-cost production, and high productivity. As compared with film forming in a vacuum process, since a film can be formed at low temperature, the wet process can reduce the damage of an under-laying organic layer, and this technology is largely expected to achieve improvement of light emitting efficiency and an element lifetime.

However, in the organic EL element using blue phosphorescence luminescence, in order to realize wet film forming, especially the host compound contained in the light emitting layer and the electron transport material laminated on the light emitting layer will give investigational work.

From the practical viewpoint, it was revealed that that it is still insufficient and the further improvement technique is indispensable in respect of the solubility in a solvent, solution stability, driving voltage with the host material and electron transport material which have been disclosed until now.

Patent document 1: U.S. Pat. No. 6,097,147
Patent document 2: Japanese Patent Application Publication (JP-A) No. 2005-112765
Patent document 3: JP-A No. 2007-126403
Non-patent document 1: A. Baldo et al., Nature, vol. 395, pp. 151-154 (1998)
Non-patent document 2: A. Baldo et al., Nature, vol. 403, No. 17, pp. 750-753 (2000)
Non-patent document 3: S. Lamansky et al., J. Am. Chem. Soc., vol. 123, p. 4304 (2001)

SUMMARY

An object of the present invention is to provide an organic EL element which has high emission efficiency with low driving voltage and has a long emission lifetime, and to provide a material used for the organic EL element having the above-describe features.

An object of the present invention described above has been achieved by the following constitutions.

1. An organic electroluminescence element comprising an anode, a cathode and a plurality of organic compound layers between the anode and the cathode, provided that one of the organic compound layers is a light emitting layer containing a phosphorescence emitting compound, wherein at least one of the organic compound layers contains a compound represented by Formula (1),

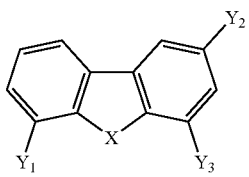

Formula (1)

wherein, X represents O or S; $Y_1$ to $Y_3$ each represents a hydrogen atom, a substituent or a group represented by Formula (A), provided that at least two of $Y_1$ to $Y_3$ are groups represented by Formula (A), not all of $Y_1$ to $Y_3$ are the same group, and at least one of the groups represented by Formula (A) has Ar of a carbazolyl group, or an azacarbazolyl group containing 2 to 5 nitrogen atoms,

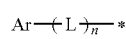

Formula (A)

wherein, L represents a divalent linking group derived from an aromatic hydrocarbon ring or an aromatic heterocycle; n represents an integer of 0 to 3, provided that when n is 2 or 3, a plurality of ns may be the same or different; "*" indicates a linking position with Formula (1); and Ar represents a group represented by Formula (A'),

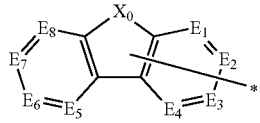

Formula (A')

wherein, $X_0$ represents N(R), O or S; $E_1$ to $E_8$ each represents $C(R_1)$, or N, provided that R and $R_1$ each represents a hydrogen atom, a substituent or a linking position with L; and "*" indicates a linking position with L.

2. The organic electroluminescence element of the above-described item 1,
wherein at least one of the groups represented by Formula (A) has Ar of a carbazolyl group.

3. The organic electroluminescence element of the above-described item 1,
wherein $Y_1$ in Formula (1) is represented by Formula (A); one of $Y_2$ and $Y_3$ is represented by Formula (A), and the other one of $Y_2$ and $Y_3$ is a hydrogen atom; and Ar in Formula (A) is a carbazolyl group which is bonded to L though a nitrogen position, provided that the carbazolyl group may have a substituent.

4. The organic electroluminescence element of the above-described item 1,
wherein $Y_1$ in Formula (1) is represented by Formula (A), and Ar in Formula (A) is an azacarbazolyl group containing 2 to 5 nitrogen atoms, provided that the azacarbazolyl group may have a substituent; and at least one of $Y_2$ and $Y_3$ is represented by Formula (A).

5. The organic electroluminescence element of the above-described item 1,
wherein Formula (1) is further represented by Formula (2),

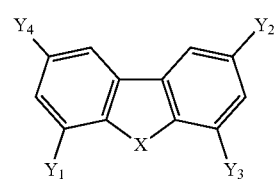

Formula (2)

wherein, X represents O or S; three of $Y_1$ and $Y_4$ each are a group represented by Formula (2A), and one of $Y_1$ and $Y_4$ is a hydrogen atom; and at least one of the groups represented by Formula (2A) has $Ar_1$ of a carbazolyl group which may have a substituent,

Formula (2A)

wherein, $L_1$ represents a divalent linking group derived from an aromatic hydrocarbon ring or an aromatic heterocycle; $n_1$ represents an integer of 0 to 3, provided that when $n_1$ is 2 or 3, a plurality of $L_1$s may be the same or different; "*" indicates a linking position with Formula (2); and $Ar_1$ represents a carbazolyl group which may have a substituent, or a group represented by Formula (2A'),

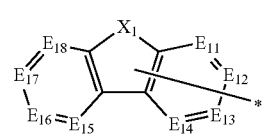

Formula (2A')

wherein, $X_1$ represents O or S; $E_{11}$ to $E_{18}$ each represents $C(R_{11})$, or N, provided that $R_{11}$ represents a hydrogen atom, a substituent or a linking position with $L_1$; and "*" indicates a linking position with $L_1$.

6. The organic electroluminescence element of any one of the above-described items 1 to 3,
wherein n in Formula (A) represents an integer of 0 or 1.

7. The organic electroluminescence element of above-described item 5,
wherein $n_1$ in Formula (2A) represents an integer of 0 or 1.

8. The organic electroluminescence element of any one of the above-described items 1 to 5,
wherein the compound represented by Formula (1) is contained in the light emitting layer.

9. The organic electroluminescence element of any one of the above-described items 1 to 6,
wherein at least one of the organic compound layers is an electron transport layer and the compound represented by Formula (1) is contained in the electron transport layer.

10. The organic electroluminescence element of any one of the above-described items 1 to 7,
wherein the organic compound layer containing the compound represented by Formula (1) is prepared with a wet coating process.
11. The organic electroluminescence element of any one of the above-described items 1 to 8,
wherein the organic electroluminescence element emits a white light.
12. A lighting device comprising the organic electroluminescence element of any one of the above-described items 1 to 9.
13. A display device comprising the organic electroluminescence element of any one of the above-described items 1 to 9.
14. A compound represented by Formula (1),

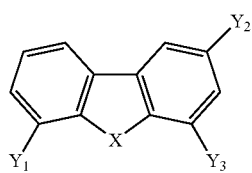

Formula (1)

wherein, X represents O or S; $Y_1$ to $Y_3$ each represents a hydrogen atom, a substituent or a group represented by Formula (A), provided that at least two of $Y_1$ to $Y_3$ are groups represented by Formula (A), not all of $Y_1$ to $Y_3$ are the same group, and at least one of the groups represented by Formula (A) has Ar of a carbazolyl group, or an azacarbazolyl group containing 2 to 5 nitrogen atoms,

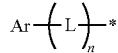

Formula (A)

wherein, L represents a divalent linking group derived from an aromatic hydrocarbon ring or an aromatic heterocycle; n represents an integer of 0 to 3, provided that when n is 2 or 3, a plurality of ns may be the same or different; "*" indicates a linking position with Formula (1); and Ar represents a group represented by Formula (A'),

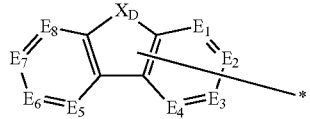

Formula (A')

wherein, $X_0$ represents N(R), O or S; $E_1$ to $E_3$ each represents $C(R_1)$, or N, provided that R and $R_1$ each represents a hydrogen atom, a substituent or a linking position with L; and "*" indicates a linking position with L.

By the present invention, it has been achieved to provide an organic EL element which has high emission efficiency with low driving voltage and has a long emission lifetime.

It has been achieved to provide a display device and a lighting device provided with the aforesaid organic EL element.

DESCRIPTION OF ALPHANUMERICAL SYMBOLS IN FIGURES

Figure 1:
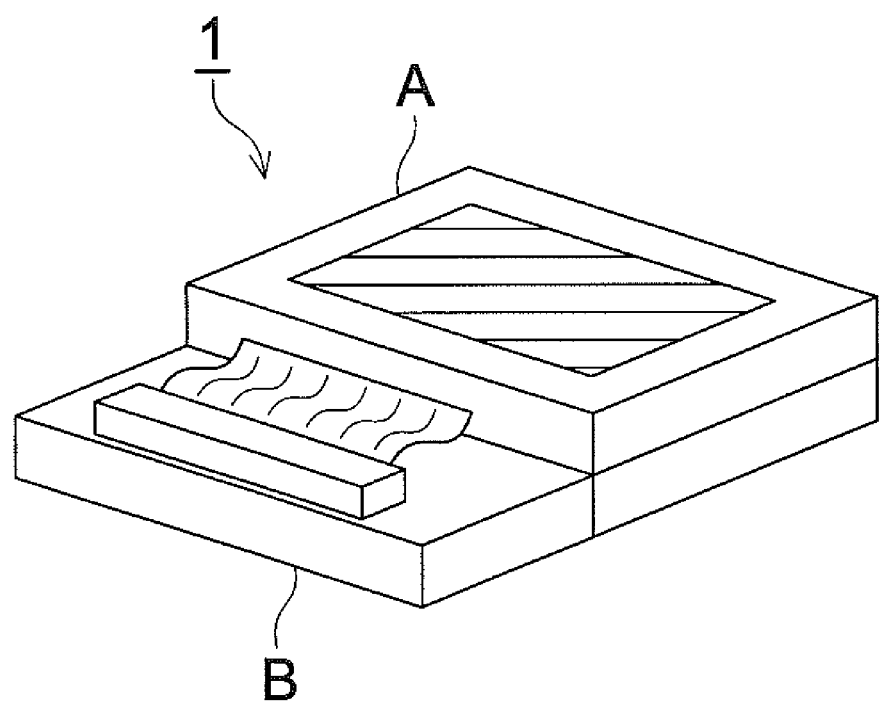
FIG. 1 is a schematic drawing to show an example of a display device constituted of an organic EL element.

1: display
3: pixel
5: scanning line
6: data line
7: electric source line
10: organic EL element
11: switching transistor
12: operating transistor
13: capacitor
A: display section
B: control diction
101: organic EL element
102: glass cover
105: cathode
106: organic EL layer
107: glass substrate having a transparent electrode
108: nitrogen gas
109: water catching agent
201: glass substrate
202: ITO transparent electrode
203: dividing wall
204: positive hole injection layer
205B, 205G and 205R: light emitting layer

DESCRIPTION OF THE PREFERRED EMBODIMENTS

The inventors of the present invention acquired the following knowledge, as a result of intensive investigation in order to attain the above-mentioned object. The molecular design was performed based on this knowledge, and the compound represented by the above-mentioned Formula (1) was found out. By using the compound represented by the above-mentioned Formula (1) of the present invention in at least one layer of the organic compound layers in an organic electroluminescence element (organic EL element), it was found out that the organic EL element with low driving voltage and exhibiting high luminous efficiency and a long lifetime was obtained.

Since the derivative of carbazole or azacarbazole has a high carrier transporting property, it has been conventionally used for the host material or the electron transport material. However, when the present inventors examined it was revealed the followings. When the compound composed of only a carbazole ring or an azacarbazole ring with an aromatic hydrocarbon ring was used, the driving voltage of an organic EL device tended to become high. Furthermore, when an aromatic hydrocarbon ring except benzene ring was included in the molecule, the triplet energy (T1) of a compound will become small. Therefore, this compound cannot be used together with a blue phosphorescence dopant having a short emission wavelength.

On the other hand, it became clear that the derivative which is composed of a carbazole ring or an azacarbazole ring, with other aromatic heterocycle (for example, a compound made of a combination of a carbazole ring or an azacarbazole ring with a single ring such as a pyridine ring or an imidazole ring) had the tendency of showing a lower Tg and also a higher driving voltage of the organic EL element incorporated the compound. However, the derivatives bonded at the $2^{nd}$ or the $4^{th}$ position of a dibenzofuran ring or a dibenzothiophene ring have no conjugation with the rings, it was found out that the derivatives maintained a high T1 while having a high Tg. Further, it was revealed that the driving voltage of the organic EL element using these compounds tended to be low.

Furthermore, when study was continued about the bonding position with a dibenzofuran ring or a dibenzothiophene ring, it was revealed the following facts. In the case of the derivative having a substituent introduced only at the 2nd position or the $8^{th}$ position of a dibenzofuran ring or a dibenzothiophene ring, the derivative tented to have a lower solubility to a solvent, while the derivative which was introduced a group represented by Formula (A) at the $4^{th}$ position as indicated in the present invention greatly improved the solubility. Moreover, although it is desirable in organic EL element that membrane is an amorphous-state from a view point of carrier transport, the compound which has bilaterally symmetrical structure has a high tendency to form a thin film of high crystallization. On the other hand, in the compound of the present invention, not all of $Y_1$-$Y_3$ are the same group, and since the compound of the present invention has the unsymmetrical molecule, it can control crystallization of membrane as mentioned above. Moreover, the molecule which has unsymmetrical structure is advantageous of solubility to a solvent. By these findings, it became possible to provide a material suitable for a wet process (a wet coating process).

Moreover, in an organic EL element, the shift of a luminous region can be considered to be one of the causes of life degradation. That is, when the balance of carrier migration changes while driving the EL element with a constant voltage, and the luminous region inside a light emitting layer moves, it may be possible that that luminescence is quenched by the adjacent layer if the light emitting layer coating thickness is thin. One of the ways to resolve this problem is to thicken the light emitting layer, however, if coating thickness is made large, there will occur a problem that the driving voltage will increase. On the other hand, in the thin film using the compound of the present invention, it became clear that the driving voltage was low, and the increase of the driving voltage was not large even if coating thickness was made large. It can be considered that a high density and a uniform thin film are formed, and since carrier mobility in this film is highly improved. Especially the characteristics in which the above-mentioned constant voltage drive is possible are useful when this compound is used in a light emitting layer having a thickness is required. By the above effects, it became possible to resolve the above-mentioned problems and to provide an organic EL element having high efficiency, low driving voltage, and a long lifetime element by the present invention.

There will be detailed later the elements composing the organic EL element such as: an anode, a cathode and the composition layers (organic layers, such as a positive hole injection layer, a positive hole transport layer, a light emitting layer, an electron transport layer, and an electron injection layer etc.) which are sandwiched between the anode and the cathode.

Hereafter, the compound represented by Formula (1) is described.

<Compound Represented by Formula (1)>

In Formula (1), as a group represented by $Y_1$ to $Y_3$, at least two of $Y_1$ to $Y_3$ are represented by Formula (A) and at least one of Formula (A) has Ar of a carbazolyl group, or an azacarbazolyl group containing 2 to 5 nitrogen atoms, and the other group represented by Formula (A) has Ar represented by Formula (A'); and X represents O or S.

In Formula (A), L represents a divalent linking group derived from an aromatic hydrocarbon ring or an aromatic heterocycle.

Examples of a divalent linking group derived from an aromatic hydrocarbon ring are: an o-phenylene group, m-phenylene group, a p-phenylene group, a naphthalenediyl group, an anthracenediyl group, a naphthacenediyl group, a pyrenediyl group, a naphthylnaphthalenediyl group, a biphenyldiyldiyl group (for example, [1,1'-biphenyl]-4,4'-diyl group, a 3,3'-biphenyldiyl group, and 3,6-biphenyldiyl group), a terphenyldiyl groups, a quaterphenyldiyl group, a quinqphenyldiyl group, a sexiphenyldiyl group, a septiphenyldiyl group, an octiphenyldiyl group, a noviphenyldiyl group and a deciphenyldiyl group.

Examples of an aromatic heterocycle from which a divalent linking group is derived are: a triazole ring, an imidazole ring, a pyrazole ring, a pyrrole ring, a pyridine ring, a pyrazine ring, a pyrimidine ring, a triazine ring, a quinoxaline ring, a thiophene ring, a triazole ring, a silol ring, an oxadiazole ring, a dibenzofuran ring, a dibenzothiophene ring, an indole ring, a thienothiophene ring, a dibenzocarbazole ring, a benzodithiophene ring and a phenanthroline ring. A divalent linking group may be derived from a condensed aromatic heterocycle which composed of three or more condensed rings. Preferred condensed aromatic heterocycles composed of three or more condensed rings incorporate a heteroatom of N, O or S as a constituting atom of the condensed ring. Examples of a condensed aromatic heterocycle include: an acridine ring, a benzoquinoline ring, a carbazole ring, a phenazine ring, a phenanthridine ring, a phenanthroline ring, a cycladine ring, a quindoline ring, a thebenidine ring, a quinindoline ring, a triphenodithiazine ring, a triphenodioxazine ring, a phenanthrazine ring, an anthrazine ring, a perimizine ring, an azacarbazole ring (indicating a ring structure in which one or more of the carbon atoms constituting the carbazole ring are replaced with nitrogen atoms), a phenanthroline ring, a dibenzofuran ring, a dibenzothiophene ring, a ring structure in which one or more of the carbon atoms constituting the benzothiophene ring or the dibenzofuran ring are replaced with nitrogen atoms), a naphthofuran ring, a naphthothiophene ring, a benzodifuran ring, a benzodithiophene ring, a naphthodifuran ring, a naphthodithiophene ring, an anthrafuran ring, an anthradifuran ring, an anthrathiophene ring, an anthradithiophene ring, a thianthrene ring, a phenoxathiine ring, and a thiophanthrene ring (naphthothiophene ring).

The above-described divalent linking groups may further have a substituent which will be described later.

The linking group represented by L is preferably to be a linking group of non conjugated system in order to keep high the triplet excitation energy (T1) of the compound represented by Formula (1). And further, the linking group represented by L is preferably composed of an aromatic ring (an aromatic hydrocarbon ring and an aromatic heterocycle) in order to raise Tg (it also being called a glass transition point and glass transition temperature).

Here, "non-conjugation" indicates the case where a connecting group cannot be drawn by repetition of a single bond and a double bond, or the conjugation of the aromatic rings which constitute a connecting group is cut in three dimensions.

In Formula (A), n represents an integer of 0 to 3, provided that when n is 2 or 3, a plurality of ns may be the same or different. Preferably, n is an integer of 0 or 1, and more preferably, n is an integer of 0.

In Formula (A), "*" indicates a linking position with Formula (1).

In Formula (A'), $X_0$ represents N(R), O or S; $E_1$ to $E_8$ each represents $C(R_1)$, or N, provided that R and $R_1$ each represents a hydrogen atom, a substituent or a linking position with L. As a group represented by R and $R_1$, there can be cited the same groups for the remaining group represented by one of $Y_1$ to $Y_3$ in Formula (1). "*" indicates a linking position with L.

Examples of the remaining group represented by one of $Y_1$ to $Y_3$ in Formula (1) include: an alkyl group (for example, a methyl group, an ethyl group, a propyl group, an isopropyl group, a tert-butyl group, a pentyl group, a hexyl group, an octyl group, a dodecyl group, a tridecyl group, a tetradecyl group, and a pentadecyl group); a cycloalkyl group (for example, a cyclopentyl group, and a cyclohexyl group); an alkenyl group (for example, a vinyl group and an allyl group); an alkynyl group (for example, an ethynyl group and a propargyl group); an aromatic hydrocarbon ring group (also called an aromatic carbon ring or an aryl group, for example, a phenyl group, a p-chlorophenyl group, a mesityl group, a tolyl group, a xylyl group, a naphthyl group, an anthryl group, an azulenyl group, an acenaphthenyl group, a fluorenyl group, a phenantolyl group, an indenyl group, a pyrenyl group, and a biphenyryl group); an aromatic heterocyclic group (for example, a pyridyl group, a pyrazyl group, a pyrimidinyl group, a triazyl group, a furyl group, a pyrrolyl group, an imidazolyl group, a benzoimidazolyl group, a pyrazolyl group, a pyradinyl group, a triazolyl group (for example, 1,2,4-triazole-1-yl group and 1,2,3-triazole-1-yl group), an oxazolyl group, a benzoxazolyl group, a thiazolyl group, an isooxazolyl group, an isothiazolyl group, a furazanyl group, a thienyl group, a quinolyl group, a benzofuryl group, a dibenzofuryl group, a benzothienyl group, a dibenzothenyl group, an indolyl group, a carbazolyl group, an azacarbazolyl group (indicating a ring structure in which one or more of the carbon atoms constituting the carbazolyl group are replaced with nitrogen atoms), a quinoxalinyl group, a pyridazinyl group, a triazinyl group, a quinazolinyl group, a phthalazinyl group); a heterocyclic group (for example, a pyrrolidyl group, an imidazolidyl group, a morpholyl group, and an oxazolidyl group); an alkoxyl group (for example, a methoxy group, an ethoxy group, a propyloxy group, a pentyloxy group, an hexyloxy group, an octyloxy group, and a dodecyloxy group); a cycloalkoxy group (for example, a cyclopentyloxy group and a cyclohexyloxy group); an aryloxy group (for example, a phenoxy group and a naphthyloxy group); an alkylthio group (for example, a methylthio group, an ethylthio group, a propylthio group, a pentylthio group, a hexylthio group, an octylthio group, and a dodecylthio group); a cycloalkylthio group (for example, a cyclopentylthio group and a cyclohexylthio group); an arylthio group (for example, a phenylthio group and a naphthylthio group); an alkoxycarbonyl group (for example, a methyloxycarbonyl group, an ethyloxycarbonyl group, a butyloxycarbonyl group, an octyloxycarbonyl group, and a dodecyloxycarbonyl group); an aryloxycarbonyl group (for example, a phenyloxycarbonyl group and a naphthyloxycarbonyl group); a sulfamoyl group (for example, an aminosulfonyl group, a methylaminosulfonyl group, a dimethylaminosulfonyl group, a butylaminosulfonyl group, a hexylaminosulfonyl group, a cyclohexylaminosulfonyl group, an octylaminosulfonyl group, a dodecylaminosulfonyl group, a phenylaminosulfonyl group, a naphthylaminosulfonyl group, and a 2-pyridylaminosulfonyl group); an acyl group (for example, an acetyl group, an ethylcarbonyl group, a propylcarbonyl group, a pentylcarbonyl group, a cyclohexylcarbonyl group, an octylcarbonyl group, a 2-ethylhexylcarbonyl group, a dodecylcarbonyl group, a phenylcarbonyl group, a naphthylcarbonyl group, and a pyridylcarbonyl group); an acyloxy group (for example, an acetyloxy group, an ethylcarbonyloxy group, a butylcarbonyloxy group, an octylcarbonyloxy group, a dodecylcarbonyloxy group, and a phenylcarbonyloxy group); an amido group (for example, a methylcarbonylamino group, an ethylcarbonylamino group, a dimethylcarbonylamino group, a propylcarbonylamino group, a pentylcarbonylamino group, a cyclohexylcarbonylamino group, a 2-ethylhexylcarbonylamino group, an octylcarbonylamino group, a dodecylcarbonylamino group, a phenylcarbonylamino group, and a naphthylcarbonylamino group); a carbamoyl group (for example, an aminocarbonyl group, a methylaminocarbonyl group, a dimethylaminocarbonyl group, a propylaminocarbonyl group, a pentylaminocarbonyl group, a cyclohexylaminocarbonyl group, an octylaminocarbonyl group, a 2-ethylhexylaminocarbonyl group, a dodecylaminocarbonyl group, a phenylaminocarbonyl group, a naphthylaminocarbonyl group, and a 2-pyridylaminocarbonyl group); a ureido group (for example, a methylureido group, an ethylureido group, a pentylureido group, a cyclohexylureido group, an octylureido group, a dodecylureido group, a phenylureido group, a naphthylureido group, and a 2-oyridylaminoureido group); a sulfinyl group (for example, a methylsulfinyl group, an ethylsulfinyl group, a butylsulfinyl group, a cyclohexylsulfinyl group, a 2-ethylhexylsulfinyl group, a dodecylsulfinyl group, a phenylsulfinyl group, a naphthylsulfinyl group, and a 2-pyridylsulfinyl group); an alkylsulfonyl group (for example, a methylsulfonyl group, an ethylsulfonyl group, a butylsulfinyl group, a cyclohexylsulfonyl group, a 2-ethylhexylsulfonyl group, and a dodecylsulfonyl group, an arylsulfonyl group or a heteroarylsulfonyl group (for example, a phenylsulfonyl group, a naphthylsulfonyl group, and a 2-pyridylsulfonyl group); an amino group (for example, an amino group, an ethylamino group, a dimethylamino group, a butylamino group, a cyclopentylamino group, a dodecylamino group, an anilino group, a naphthylamino group, and a 2-pyridylamino group); a cyano group; a nitro group; a hydroxyl group; a mercapto group; a silyl group (for example, a trimethylsilyl group, a triisopropylsilyl group, a triphenylsilyl group, and a phenyldiethylsilyl group) and a phosphono group.

Moreover, these substituents may be further substituted by the above-mentioned substituent. Further, a plurality of these substituents may combine with each other to form a ring.

Furthermore, the compound represented by Formula (1) may have a substituent in addition to $Y_1$ to $Y_3$.

In Formula (1), it is preferable that $Y_1$ is represented by Formula (A), one of $Y_2$ and $Y_3$ is represented by Formula (A), and the other one of $Y_2$ and $Y_3$ is a hydrogen atom. In addition, Ar in Formula (A) is preferably a carbazolyl group which is bonded to L though a nitrogen position, provided that the carbazolyl group may have a substituent.

In Formula (1), it is preferable that each ring position not bonded with $Y_1$ to $Y_3$ have a hydrogen atom. More preferably, $Y_2$ is represented by Formula (A) and $Y_3$ is a hydrogen atom.

In Formula (A), n in Formula (A) is preferably an integer of 0 or 1, and more preferably, n in Formula (A) which represents $Y_1$ is O, Still more preferably, n in Formula (A) which represents $Y_2$ or $Y_3$ is 0.

The above-described compounds are preferably contained in a light emitting layer or an electron transport layer.

In Formula (1), it is preferable that $Y_1$ is represented by Formula (A) and Ar in Formula (A) is an azacarbazolyl group containing 2 to 5 nitrogen atoms, provided that the azacarbazolyl group may have a substituent, and at least one of $Y_2$ and $Y_3$ is represented by Formula (A).

More preferably, Ar in Formula (A) for $Y_2$ or $Y_3$ is an azacarbazolyl group containing 2 to 5 nitrogen atoms, provided that the azacarbazolyl group may have a substituent.

Still more preferably, $Y_2$ is represented by Formula (A). The azacarbazolyl group containing 2 to 5 nitrogen atoms which may have a substituent is preferably an azacarbazolyl group containing 2 to 3 nitrogen atoms.

n in Formula (A) is preferably an integer of 0 or 1, and more preferably n in Formula (A) which represents $Y_1$ is 0, Still more preferably, n in Formula (A) which represents $Y_2$ or $Y_3$ is 0.

Furthermore, the compound represented by Formula (1) may have a substituent in addition to $Y_1$ to $Y_3$.

The above-described compounds are preferably contained in an electron transport layer.

The compound represented by Formula (1) is preferably further represented by Formula (2).

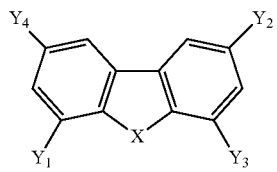

Formula (2)

In Formula (2), three of $Y_1$ and $Y_4$ each are a group represented by Formula (2A), and one of $Y_1$ and $Y_4$ is a hydrogen atom. At least one of the groups represented by Formula (2A) has $Ar_1$ of a carbazolyl group which may have a substituent. $Ar_1$ in Formula (2A) for the other group represented by Formula (2A) is a carbazolyl group which may have a substituent or a group represented by Formula (2A'). X represents O or S.

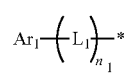

Formula (2A)

In Formula (2A), $L_1$ represents a divalent linking group derived from an aromatic hydrocarbon ring or an aromatic heterocycle. As a divalent linking group derived from an aromatic hydrocarbon ring or an aromatic heterocycle represented by $L_1$, the same divalent linking groups for L in Formula (A) are cited. $n_1$ represents an integer of 0 to 3, provided that when $n_1$ is 2 or 3, a plurality of $L_1$s may be the same or different. "*" indicates a linking position with Formula (2), and $Ar_1$ represents a carbazolyl group which may have a substituent, or a group represented by Formula (2A'),

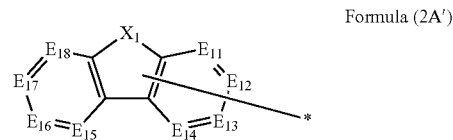

Formula (2A')

In Formula (2A'), $X_1$ represents O or S; $E_{11}$ to $E_{18}$ each represents $C(R_{11})$, or N, provided that $R_{11}$ represents a hydrogen atom, a substituent or a linking position with $L_1$. As a group represented by $R_{11}$, the same groups cited for the remaining one group of $Y_1$ to $Y_3$ in Formula (1) are cited. "*" indicates a linking position with $L_1$.

In Formula (2), it is preferable that $Y_1$ is represented by Formula (2A), and Ar in Formula (2A) is a carbazolyl group which may have a substituent. It is more preferable that $Y_2$ is represented by Formula (2A), and Ar in Formula (2A) for $Y_2$ is a carbazolyl group which may have a substituent. It is still more preferable that $Y_4$ is represented by Formula (2A).

In Formula (2A'), it is preferable that $E_1$ to $E_8$ each respectively represents $C(R_1)$.

In Formula (2A), preferably $n_1$ represents 0 or 1, and it is more preferable that $n_1$ in Formula (2A) for $Y_1$ is 0 and it is still more preferable that at least one of $n_1$ in Formula (2A) for $Y_2$ to $Y_4$ is 0.

In Formula (1), it is preferable that each ring position not bonded with $Y_1$ to $Y_4$ have a hydrogen atom.

The above-described compounds are preferably contained in a light emitting layer or an electron transport layer.

Specific examples of a compound represented by Formula (A) or Formula (A') are shown below, however, the present invention is not limited to these.

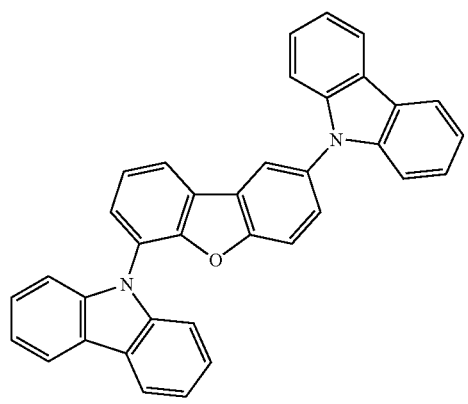

I-1

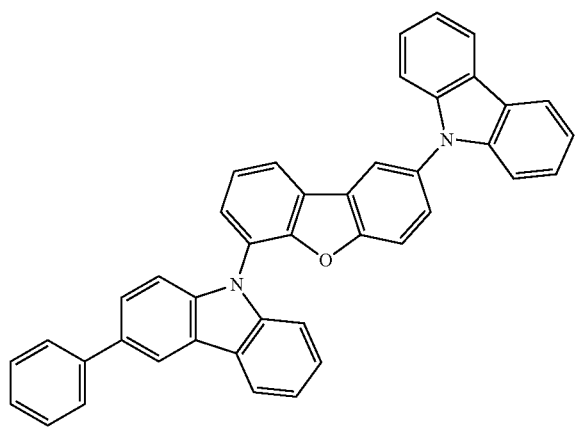

I-2

-continued
I-3
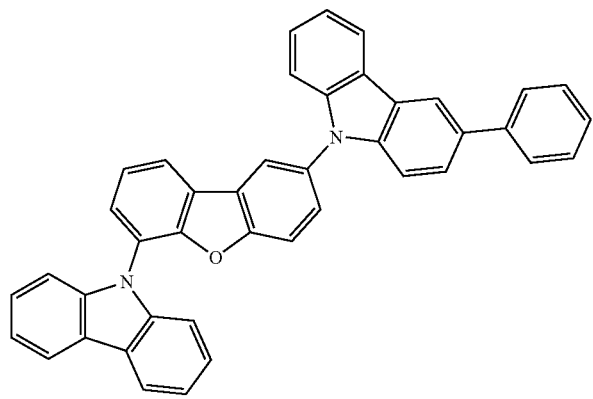
I-4
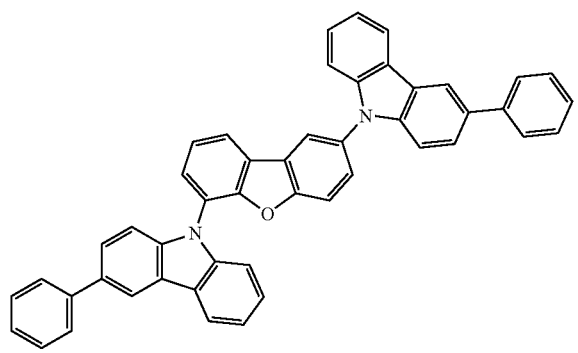
I-5
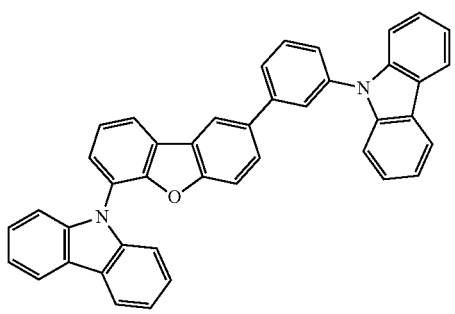
I-6
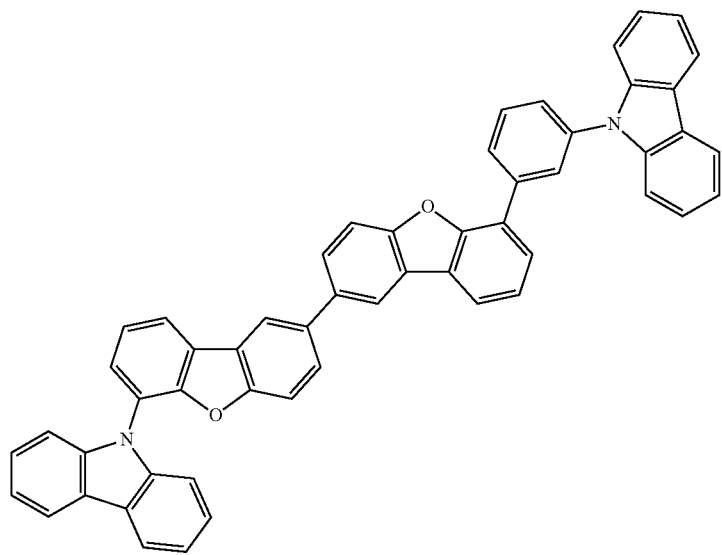

-continued
I-7
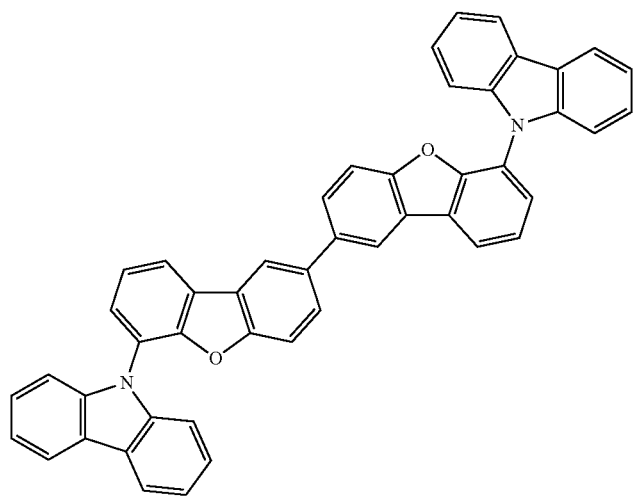
I-8
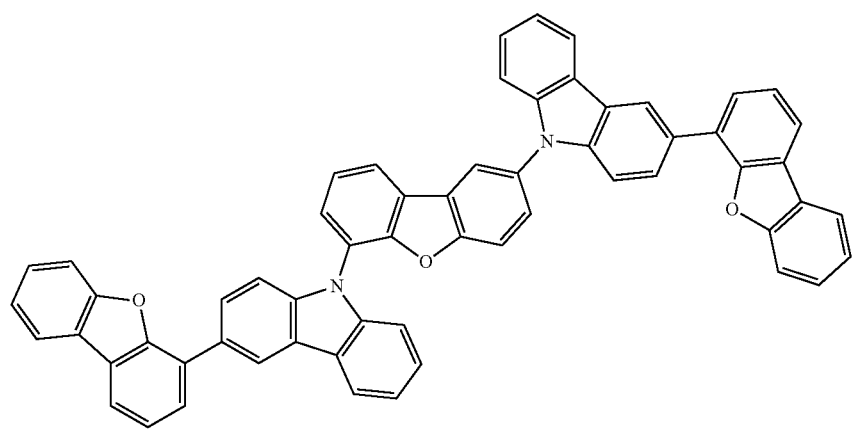
I-9
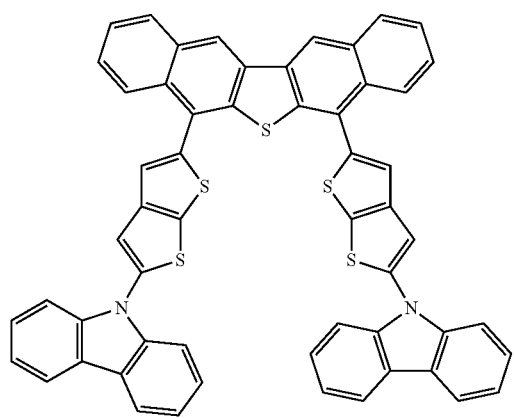
I-10
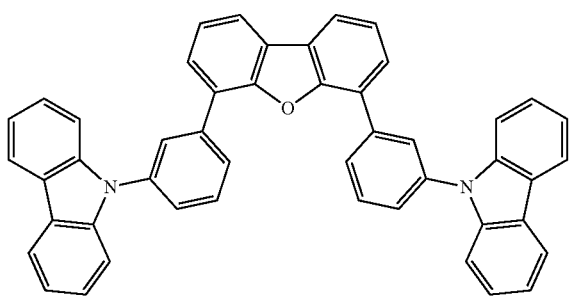

I-11
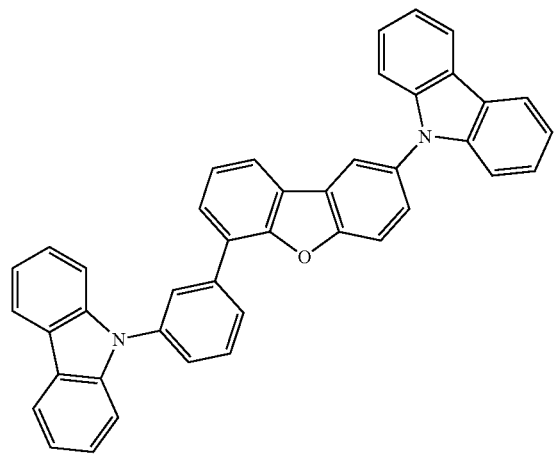
I-12
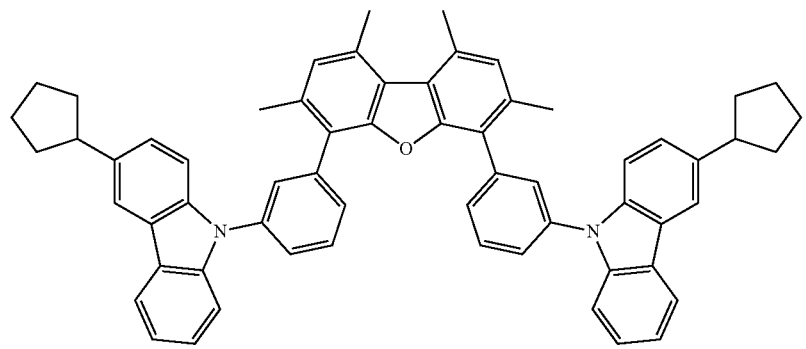
I-13
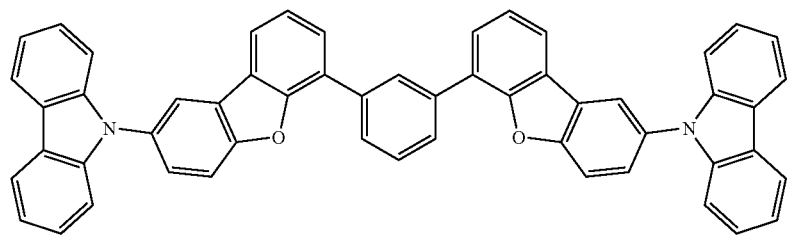
I-14
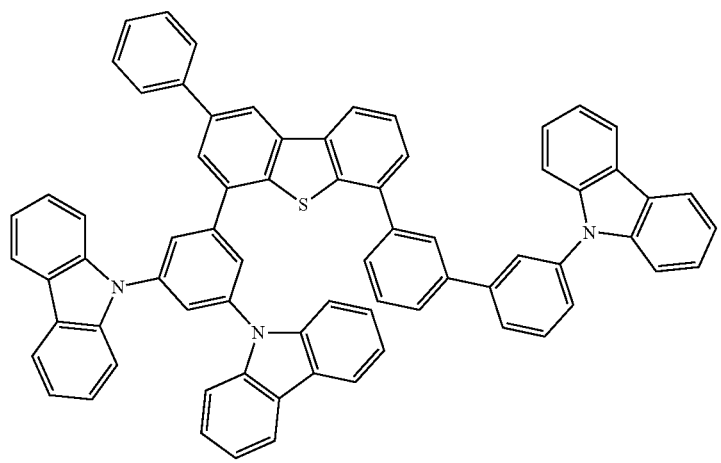

-continued
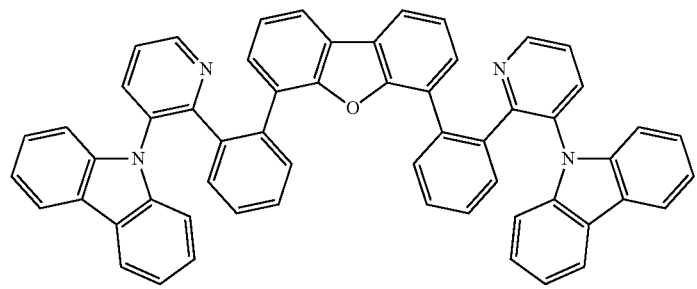
I-15
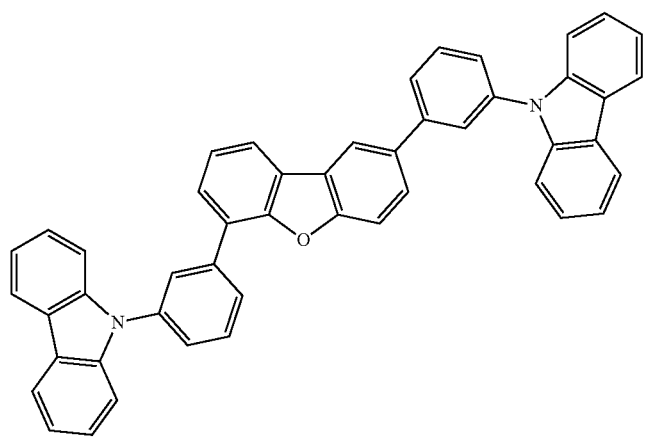
I-16
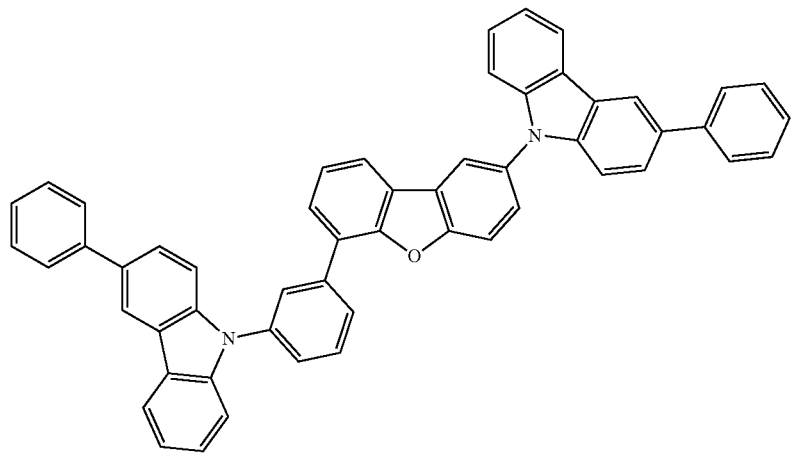
I-17

I-18
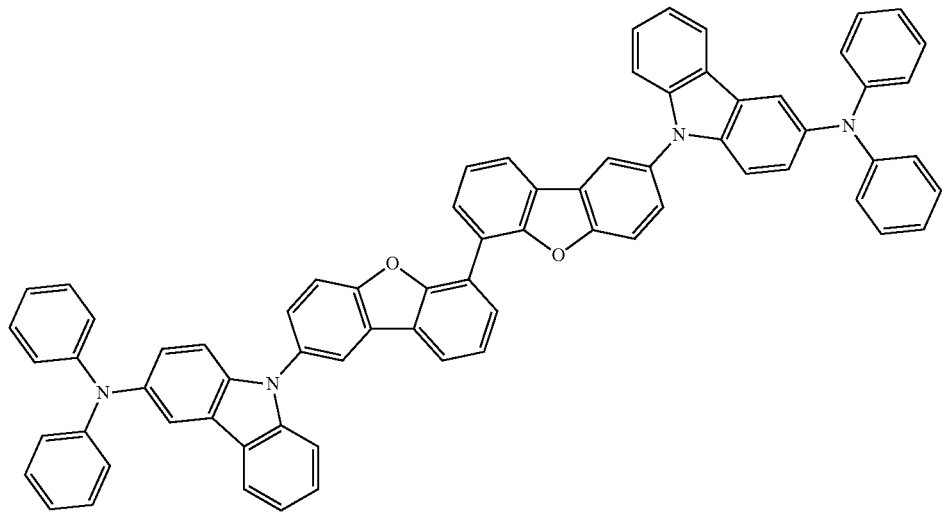
I-19
I-20
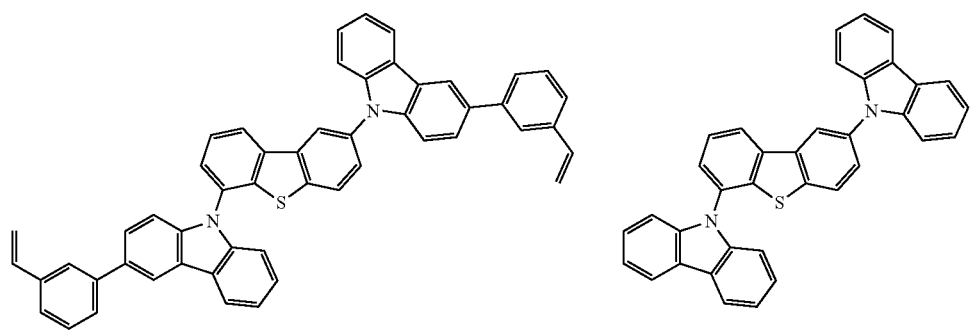
I-21
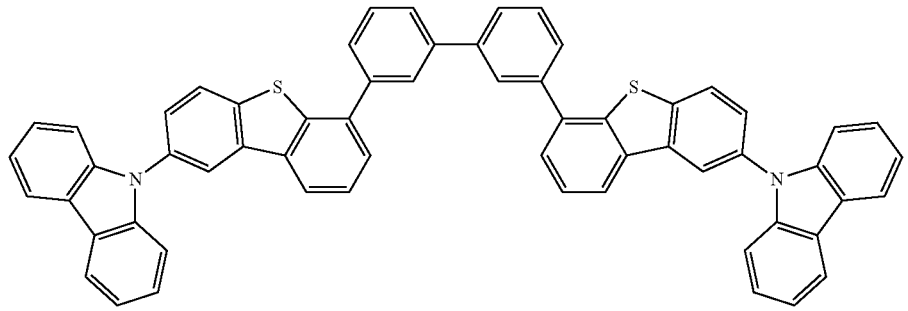

-continued
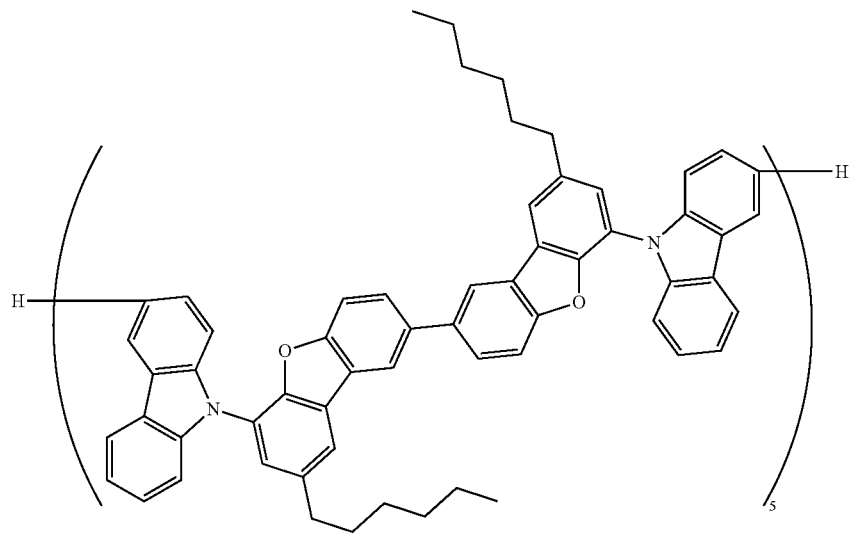
I-22
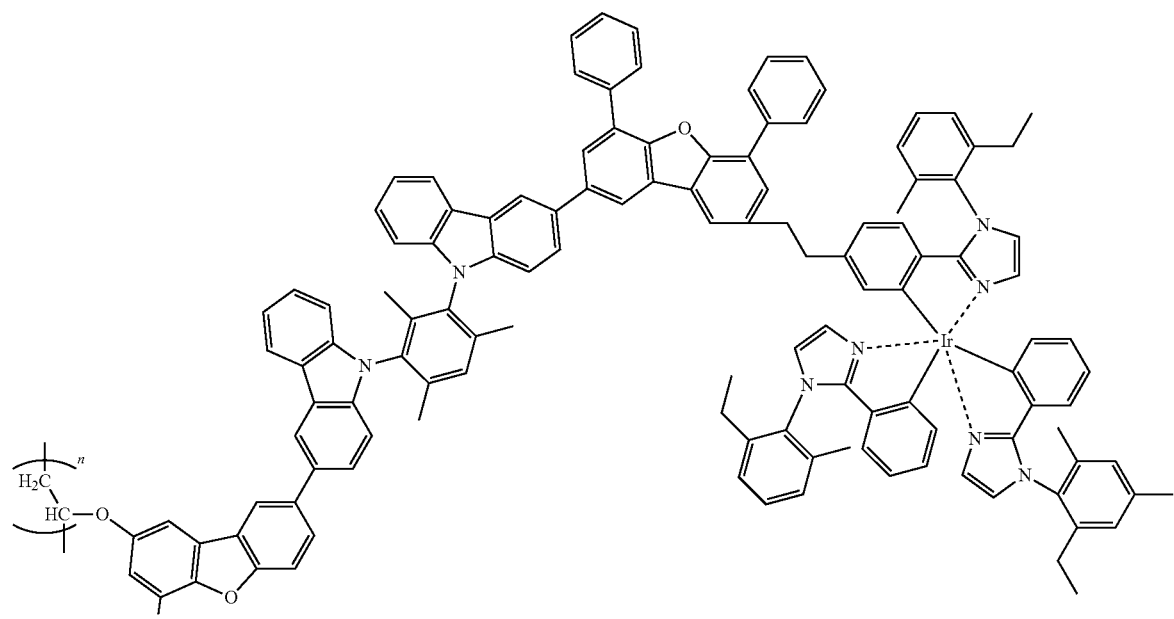
I-23
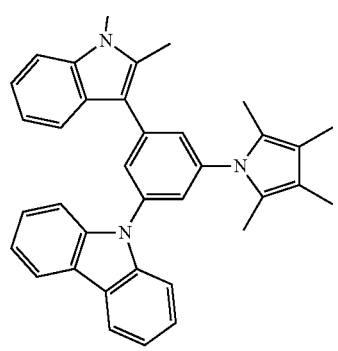

I-24
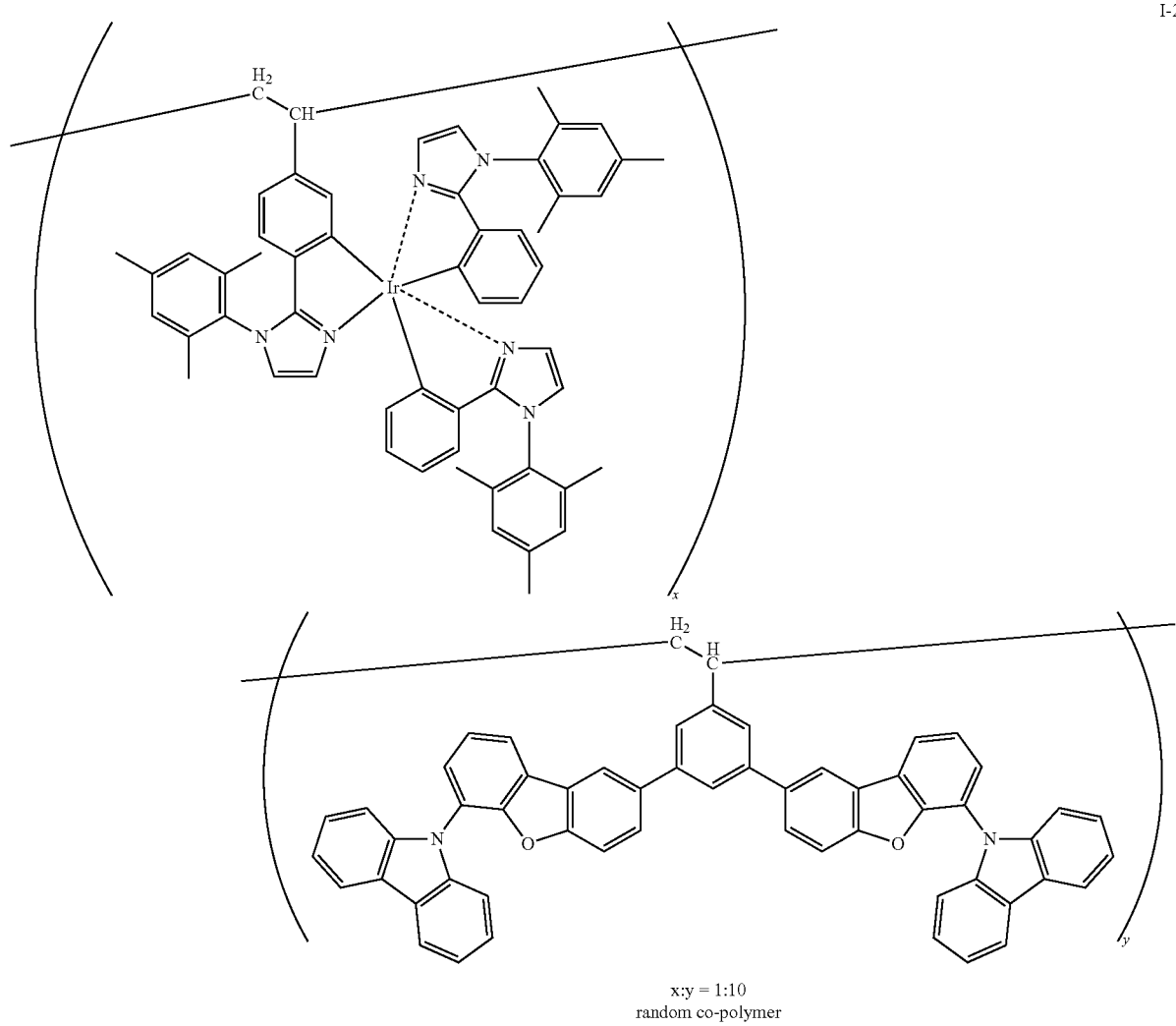
x:y = 1:10
random co-polymer
I-25
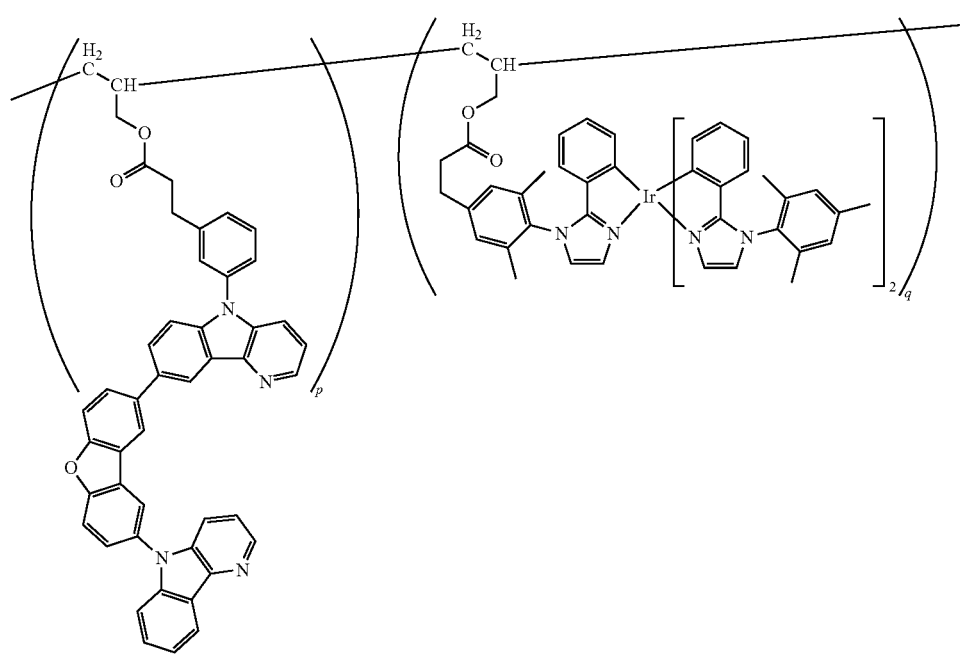

-continued
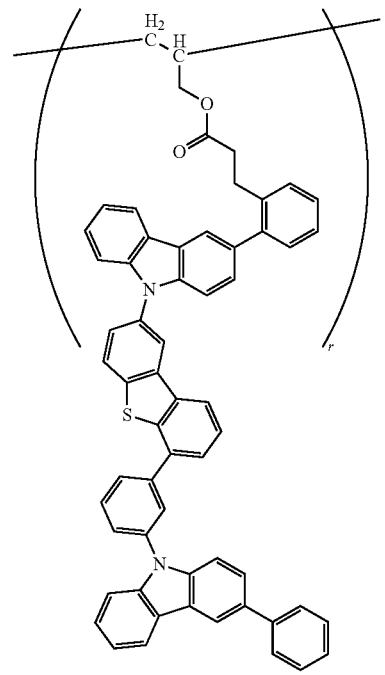
I-26
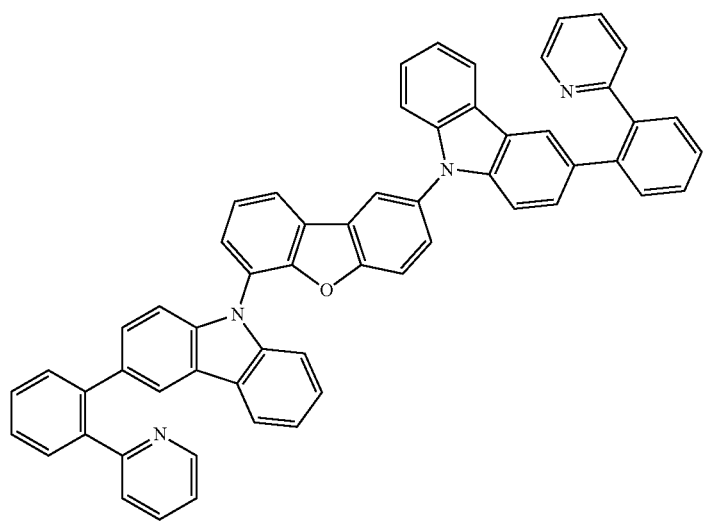
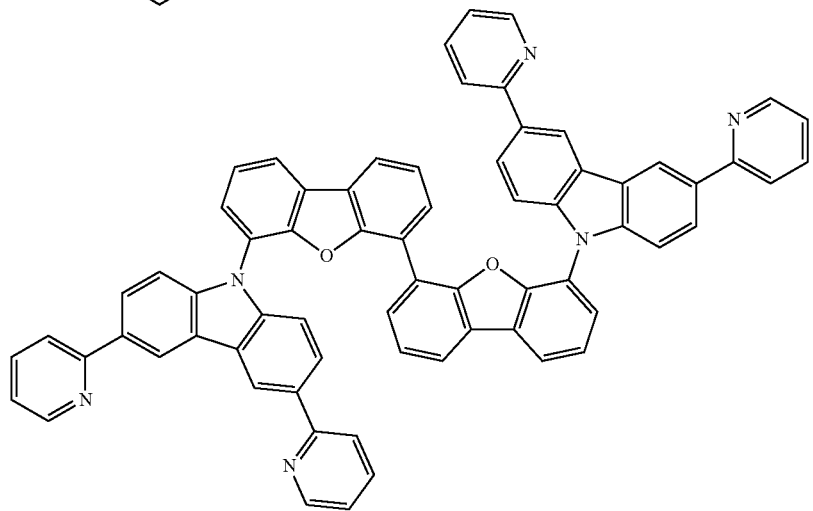
I-27

I-28
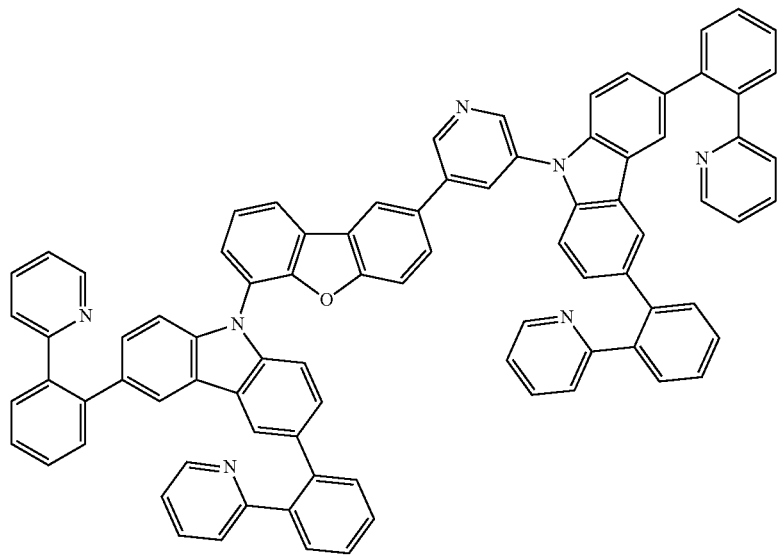
I-29
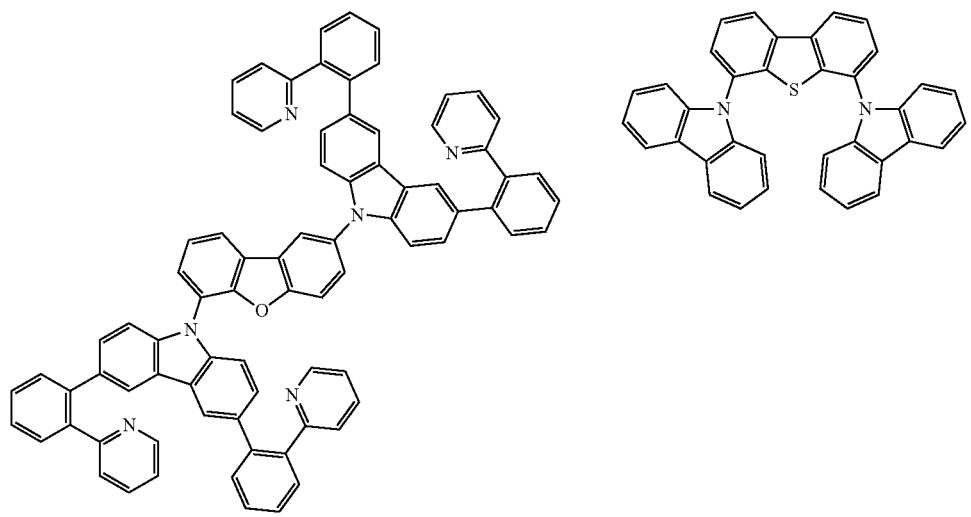
I-30
I-31
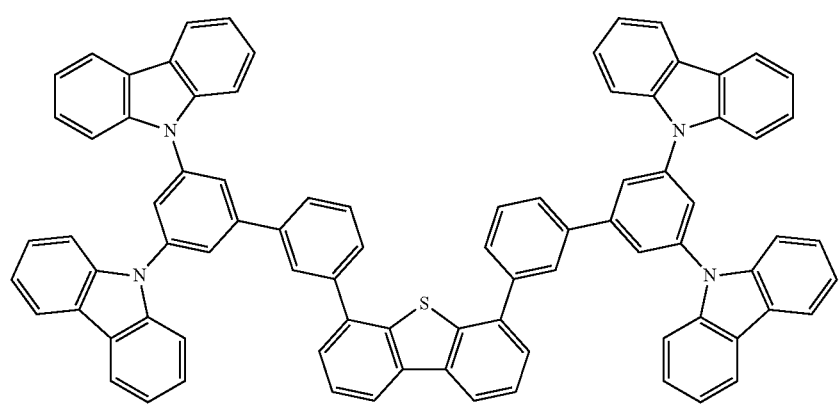

-continued
I-32
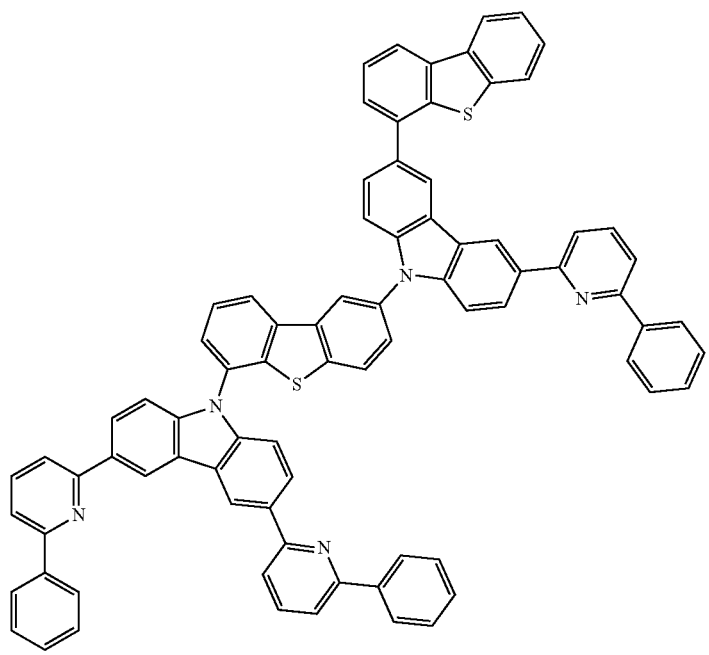
I-33
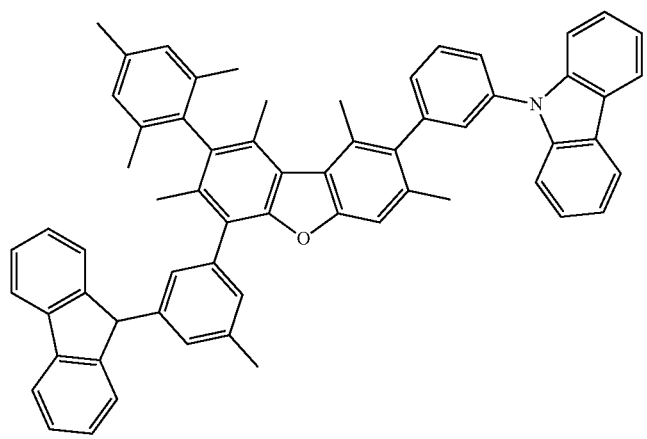
I-34
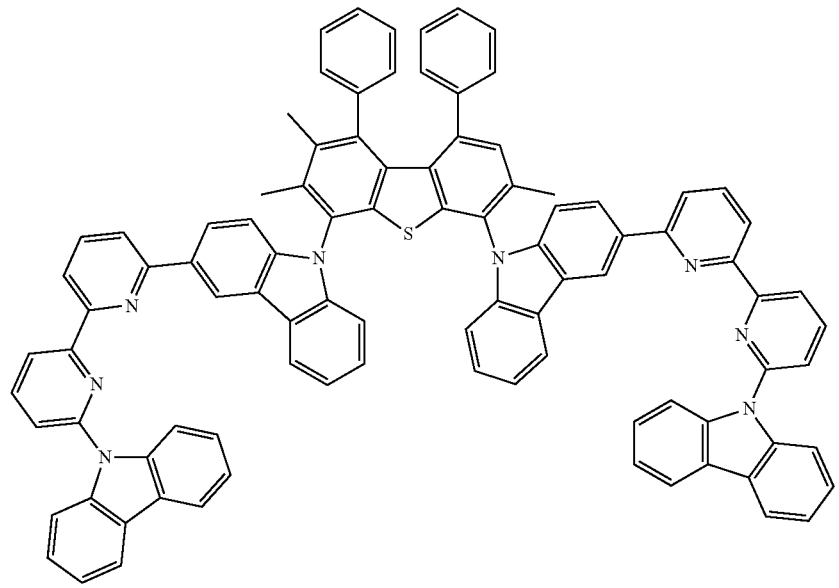

-continued
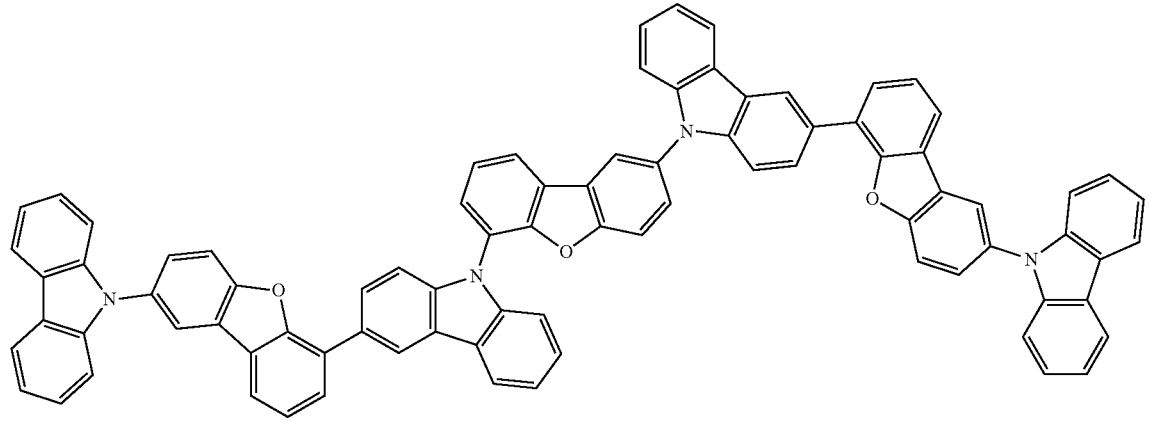
I-35
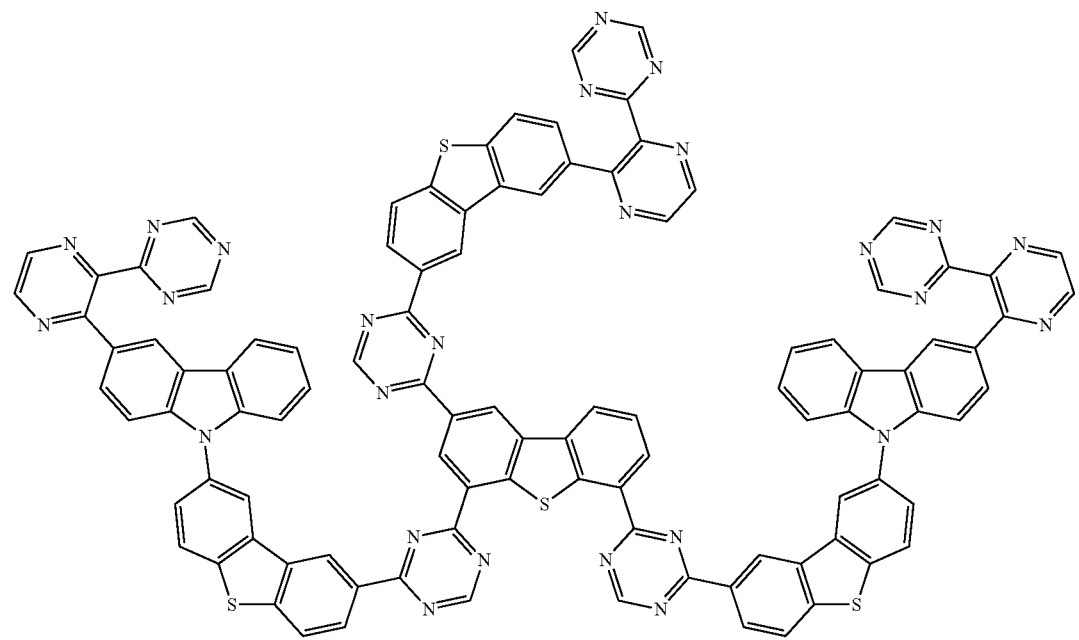
I-36

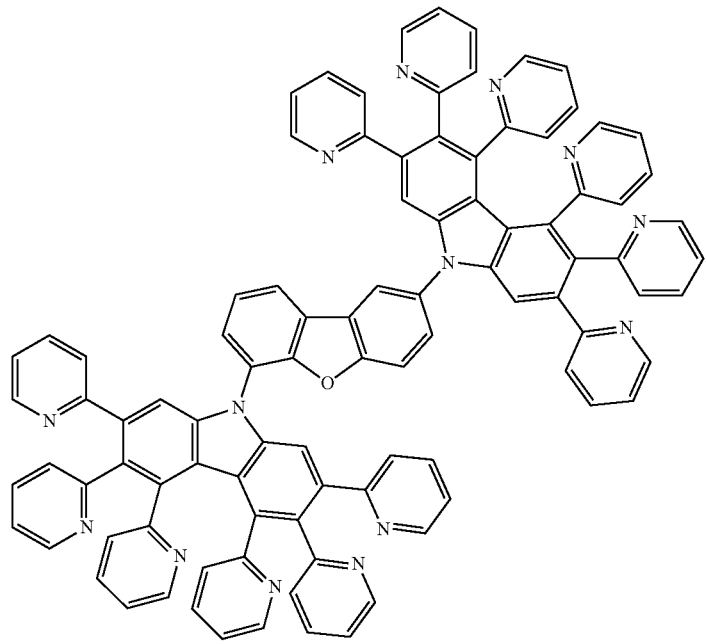
I-37
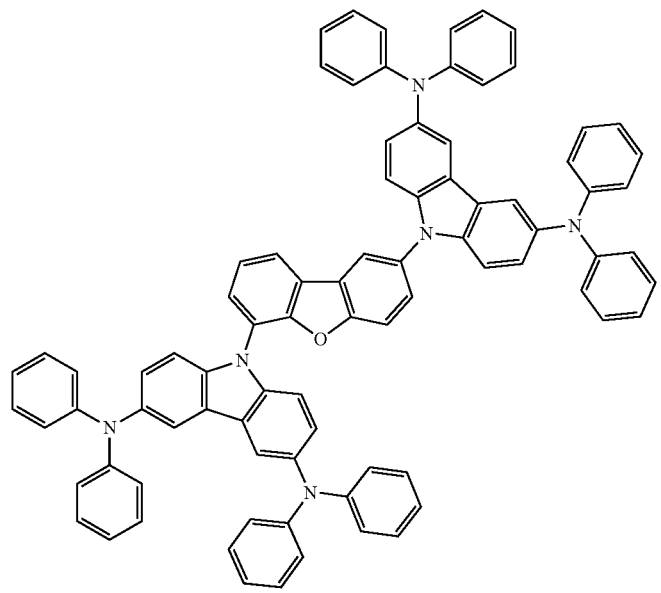
I-38

-continued
I-39
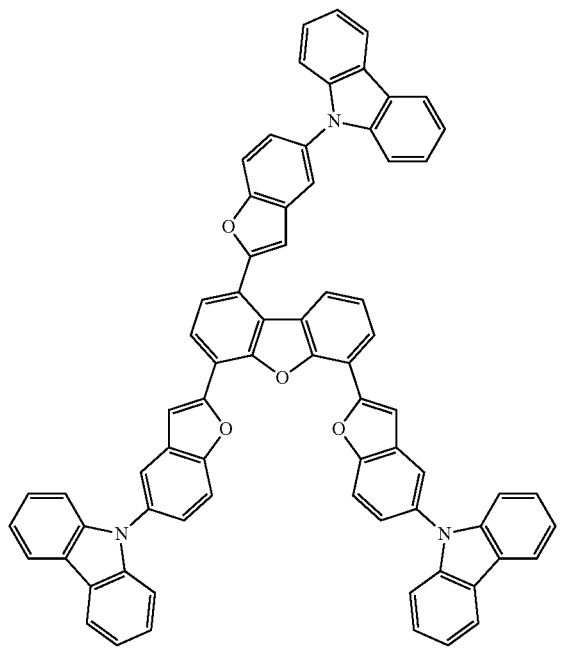
I-40
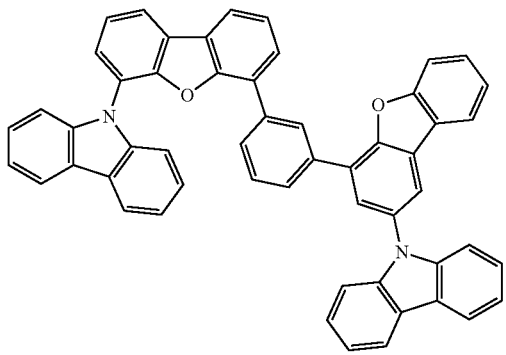
I-41
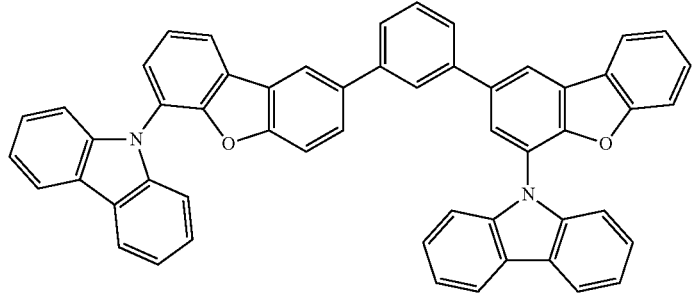
I-42
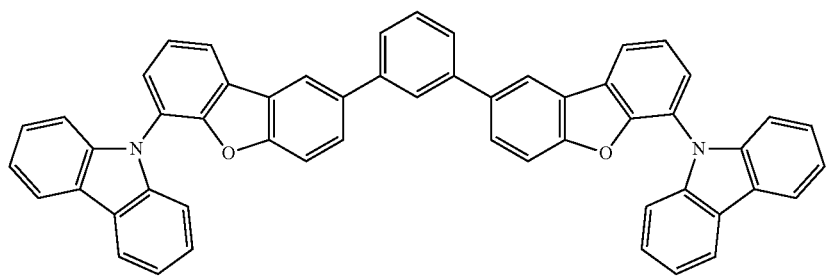
I-43
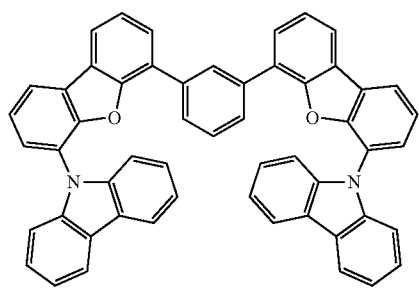
I-44
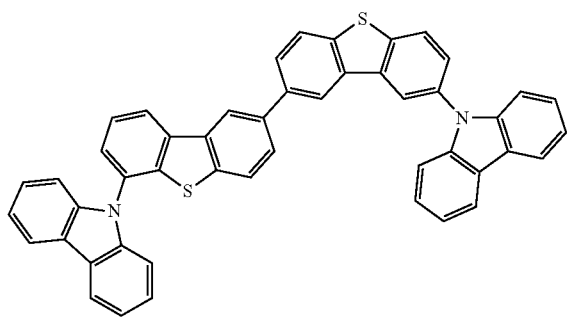

-continued
I-45
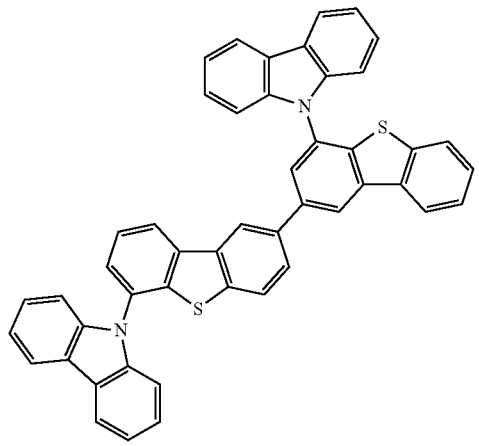
I-46
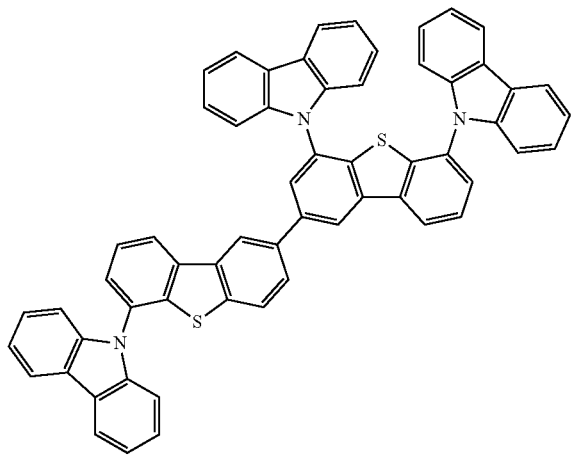
I-47
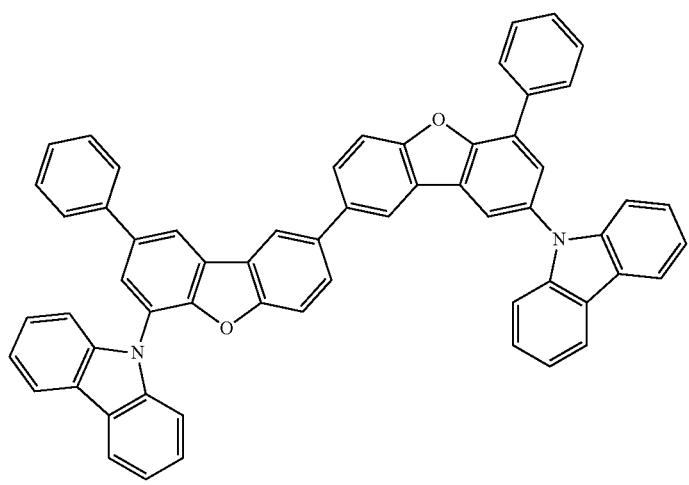
I-48
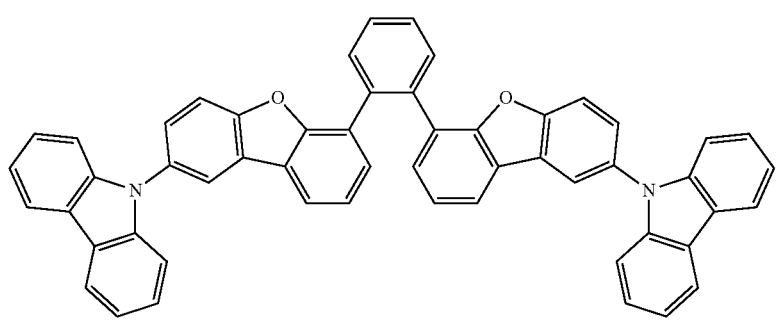
I-49
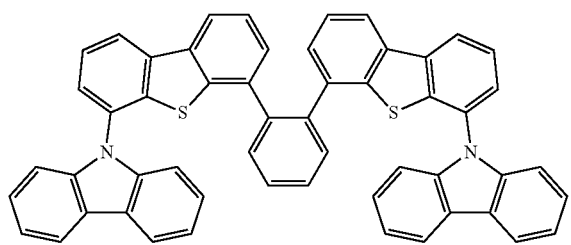
I-50
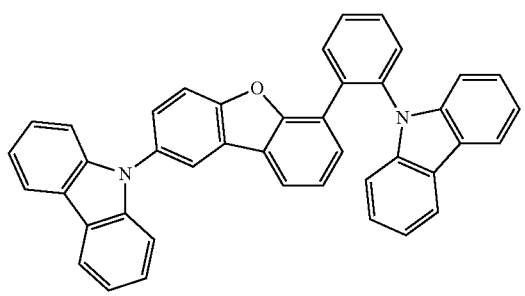

-continued
I-51
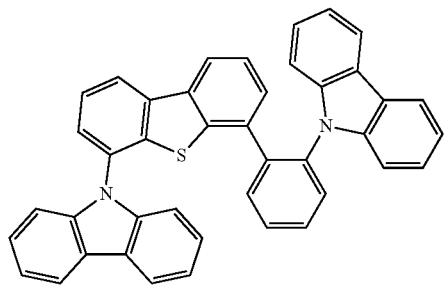
I-52
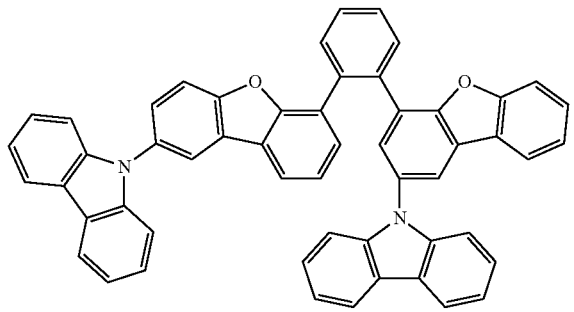
I-53
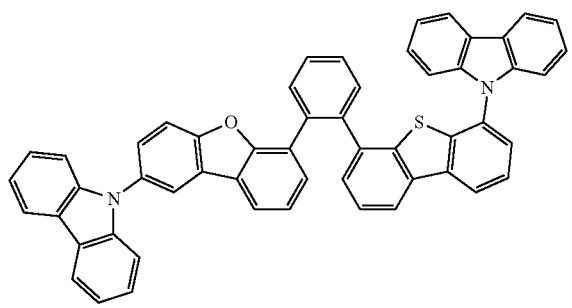
I-54
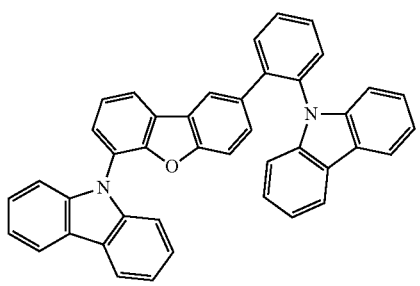
I-55
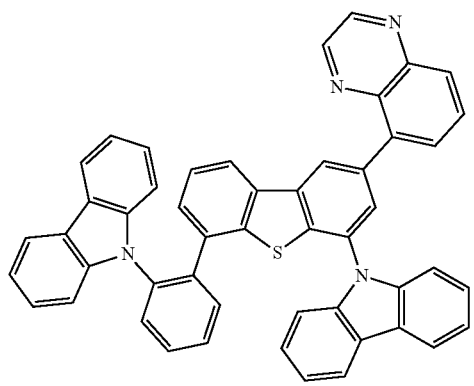
I-56
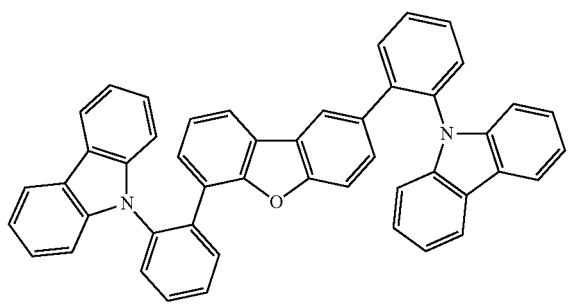
I-57
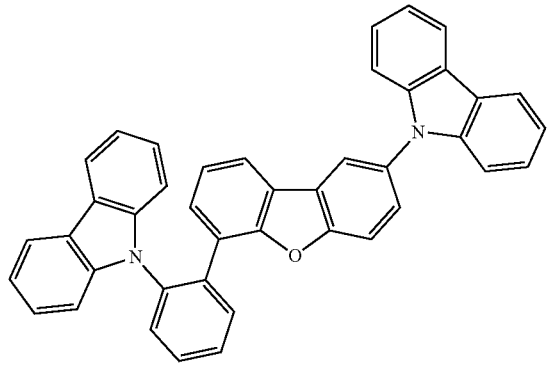
I-58
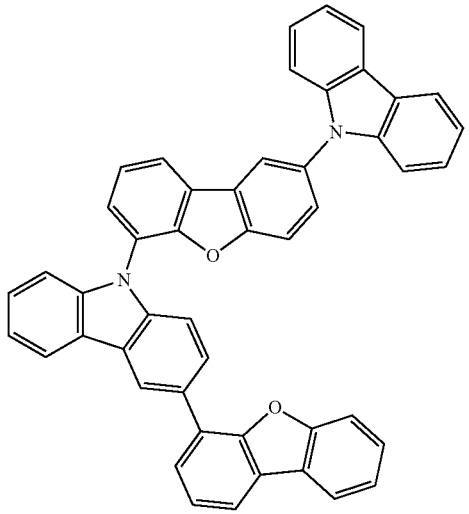

-continued
I-59
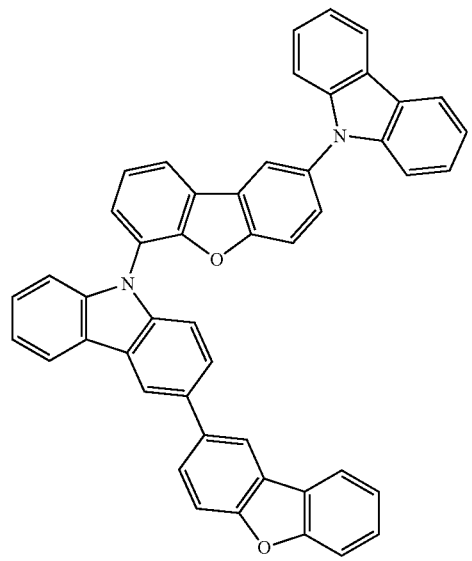
I-60
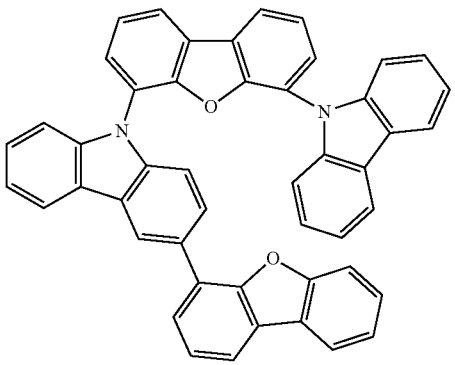
I-61
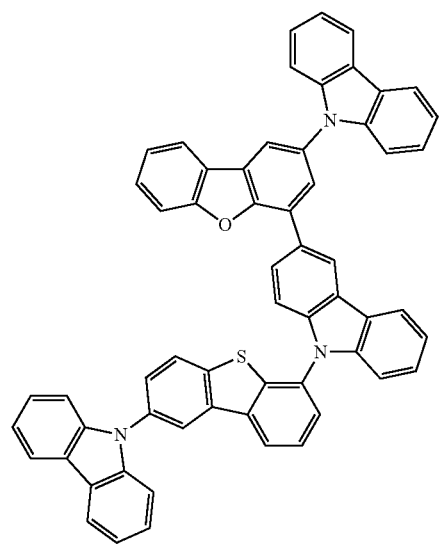
I-62
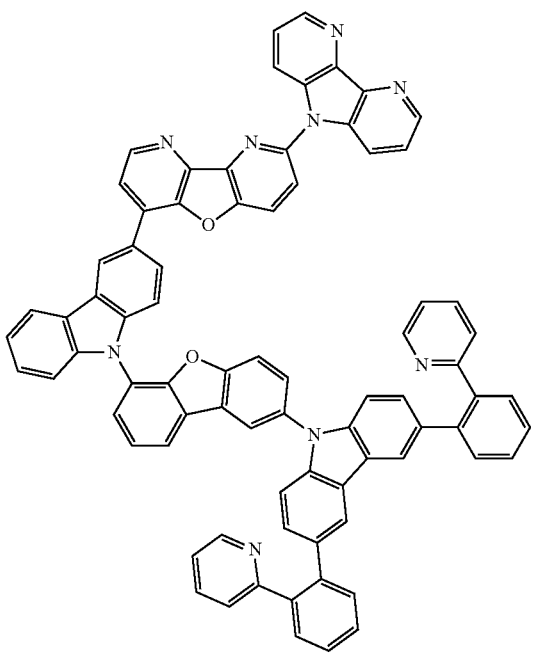

-continued
I-63
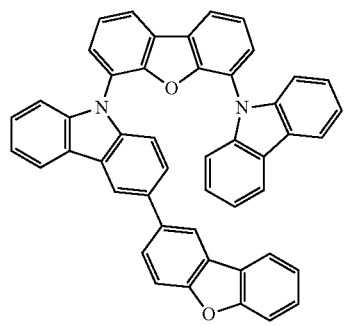
I-64
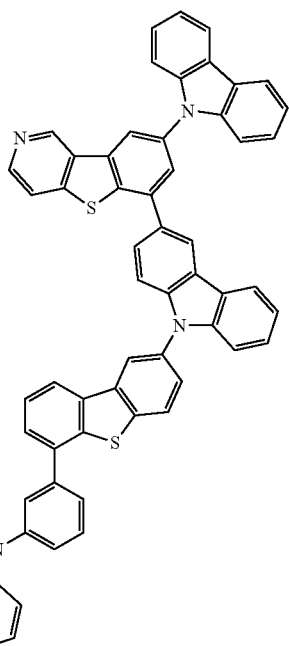
I-65
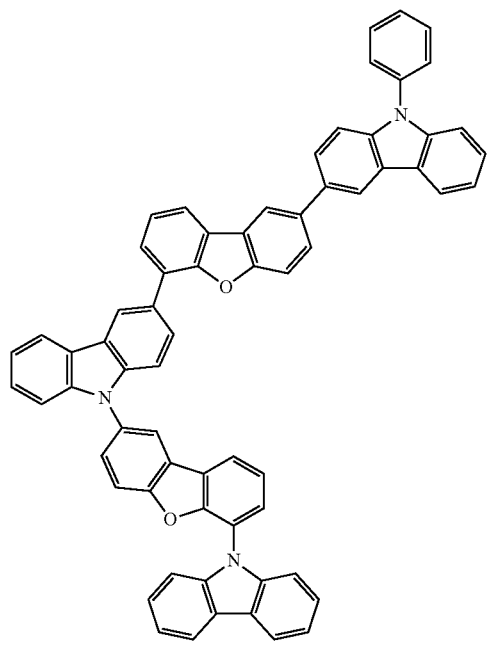
I-66
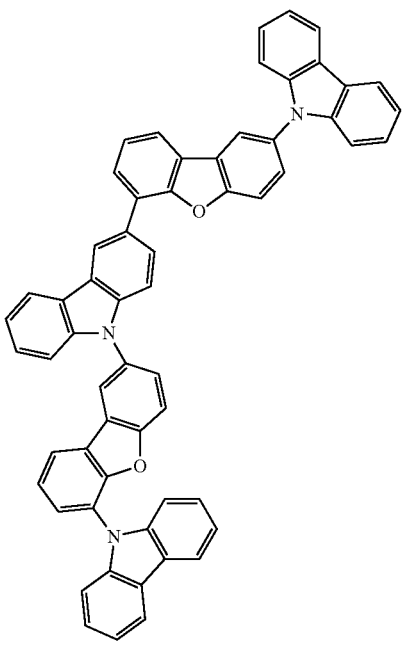
I-67
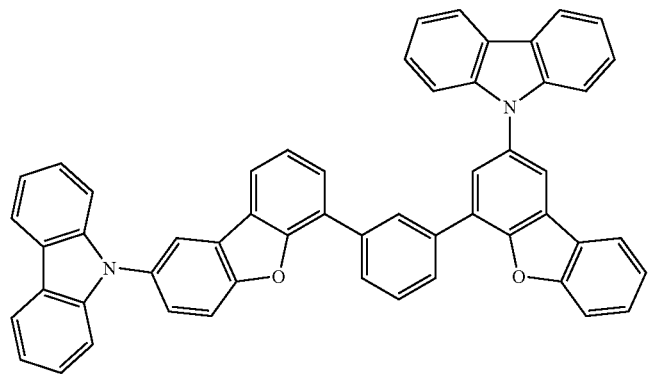

-continued
I-68
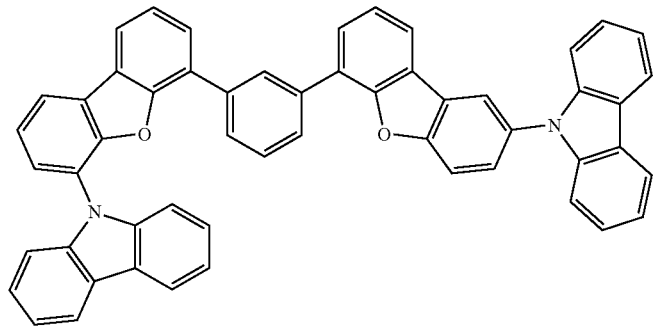
I-69
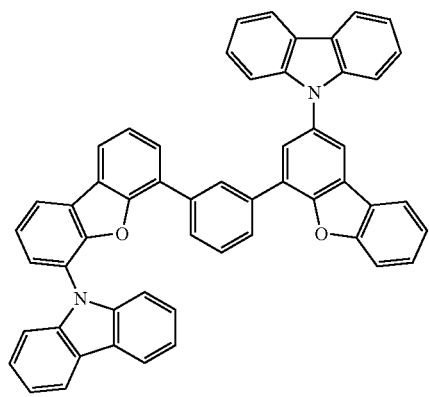
I-70
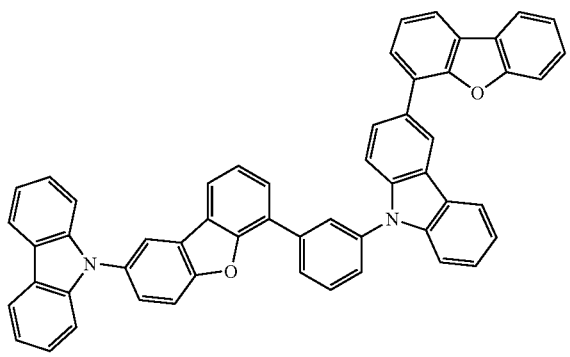
I-71
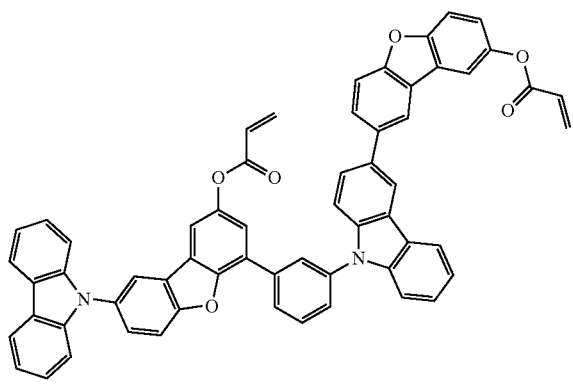
II-1
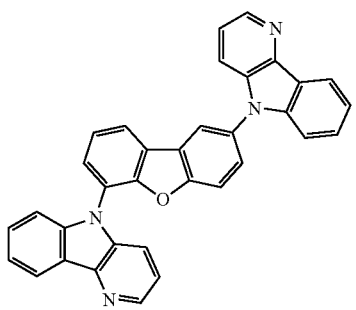
II-2
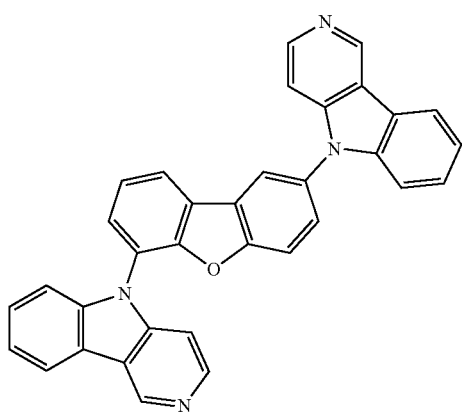
II-3
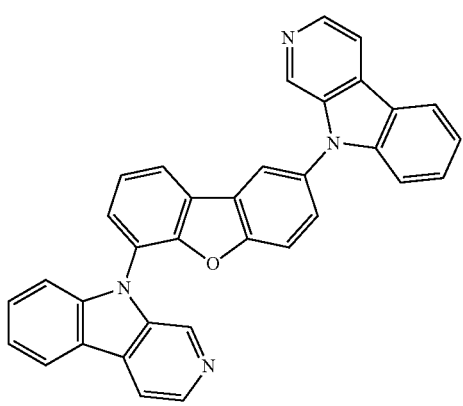

-continued
II-4
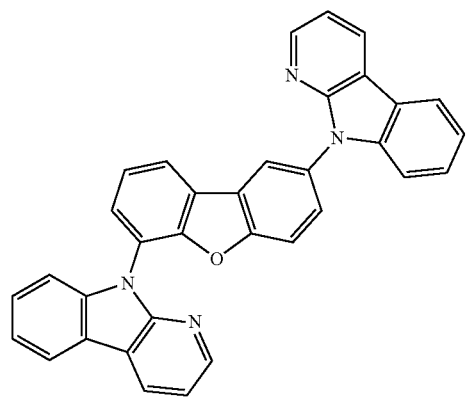
II-5
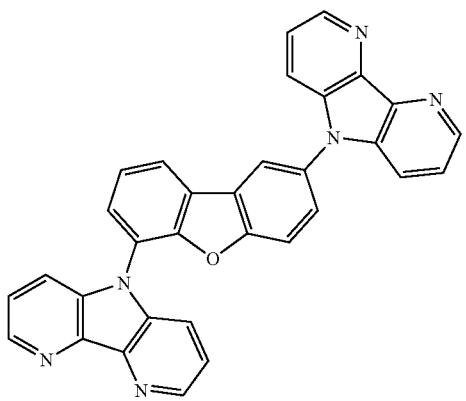
II-6
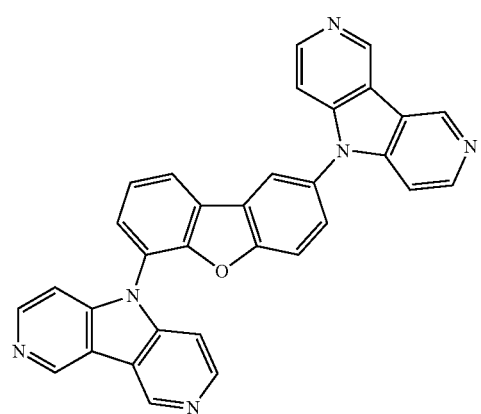
II-7
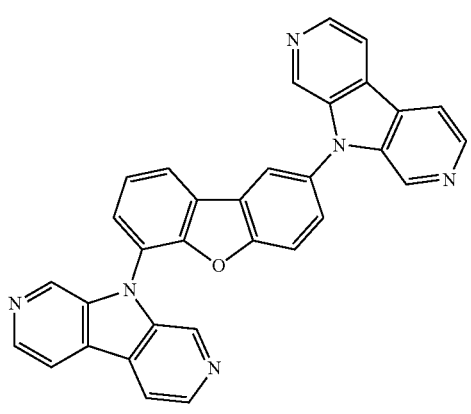
II-8
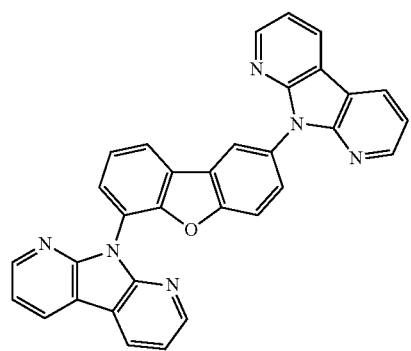
II-9
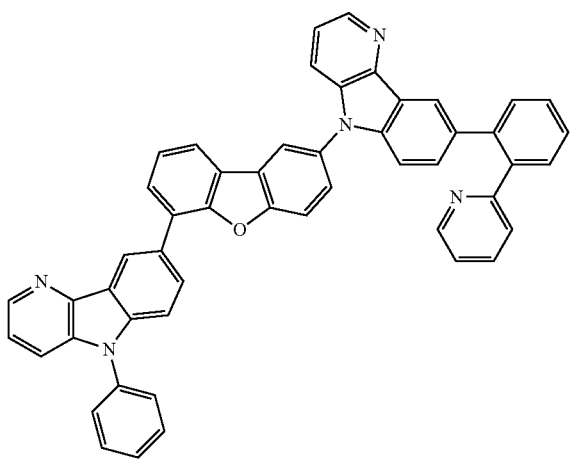

-continued
II-10
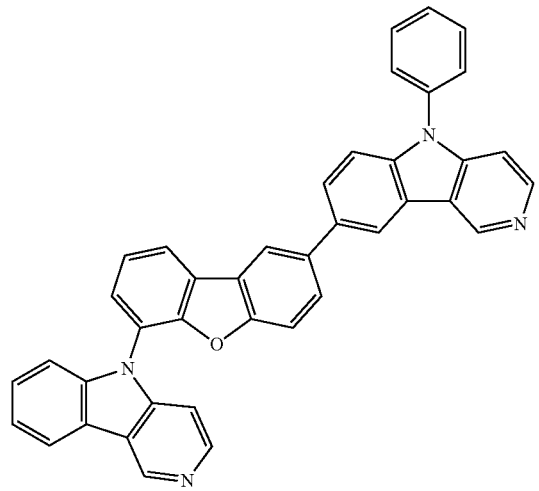
II-11
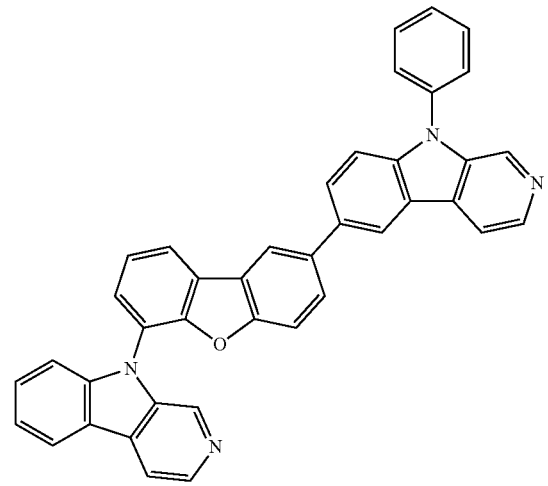
II-12
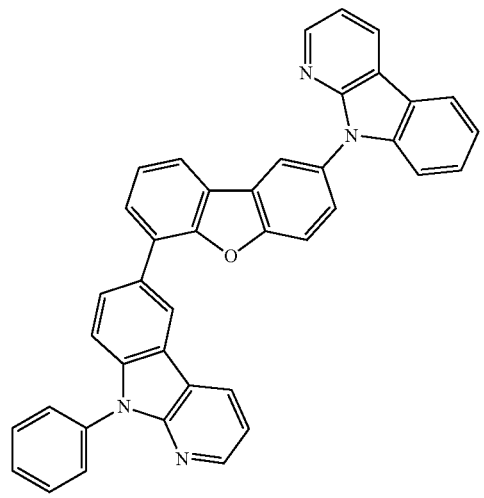
II-13
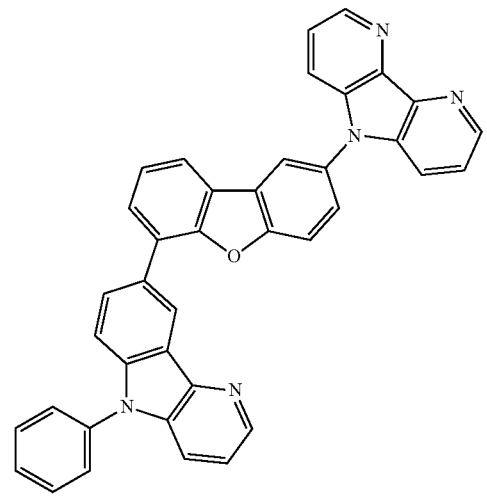
II-14
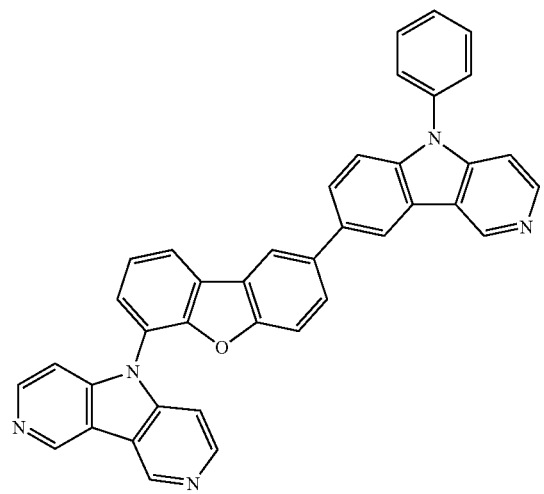
II-15
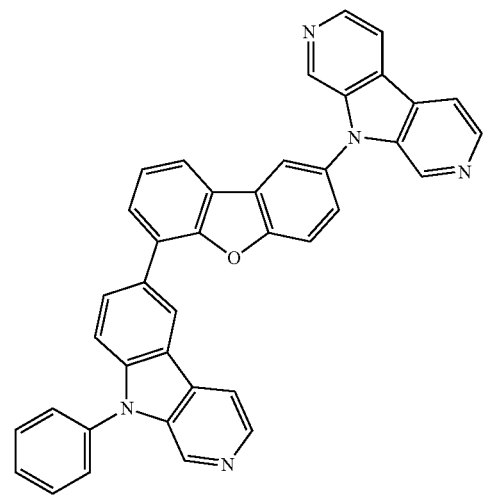

-continued
II-16
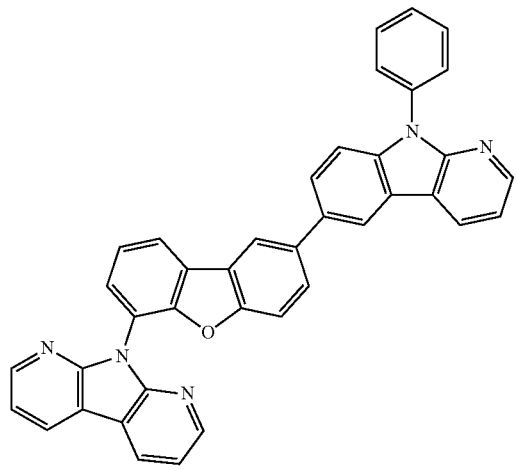
II-17
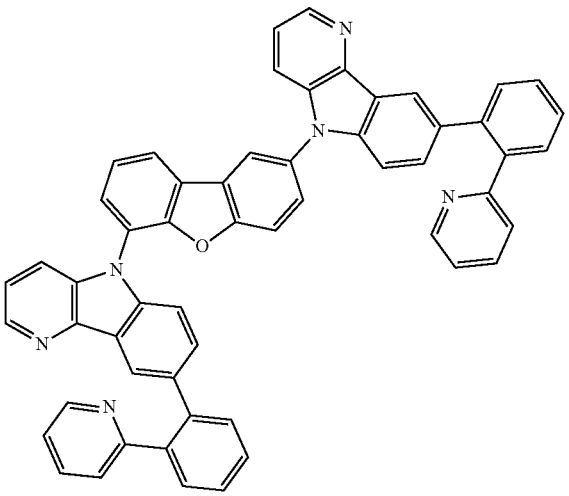
II-18
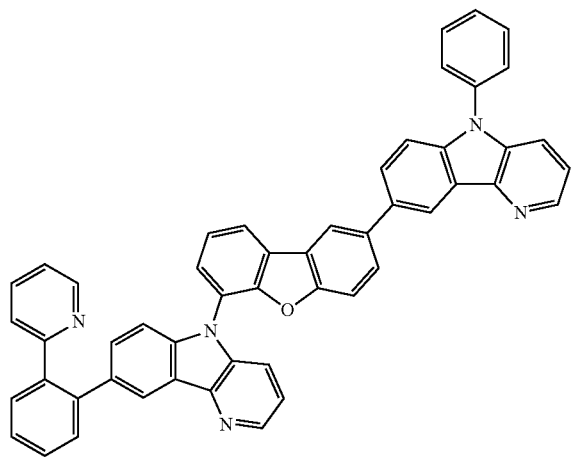
II-19
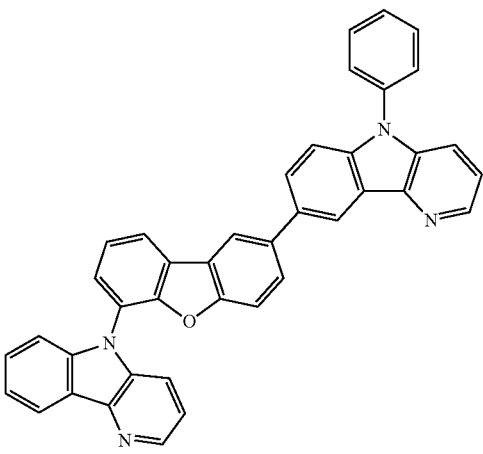
II-20
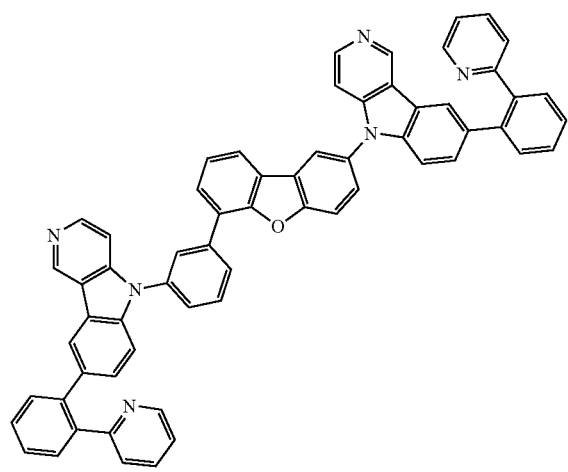
II-21
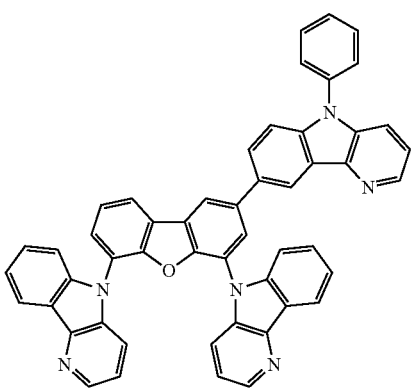

-continued
II-22
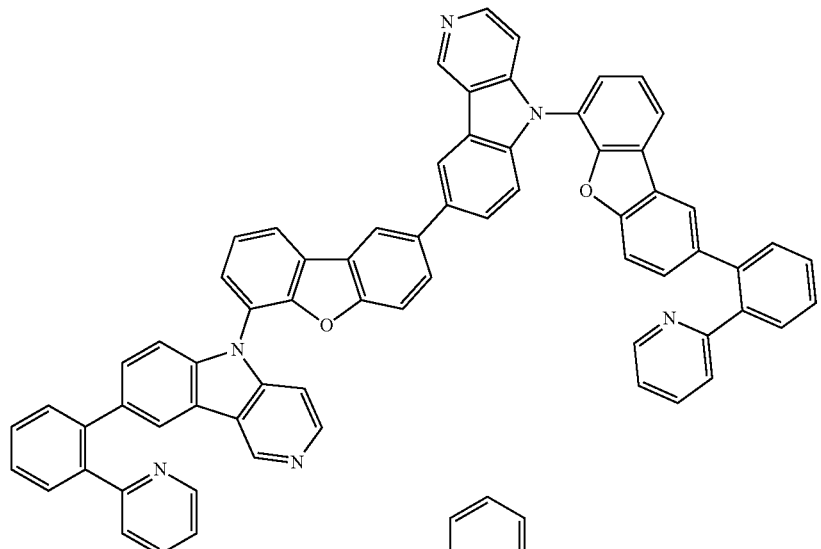
II-23
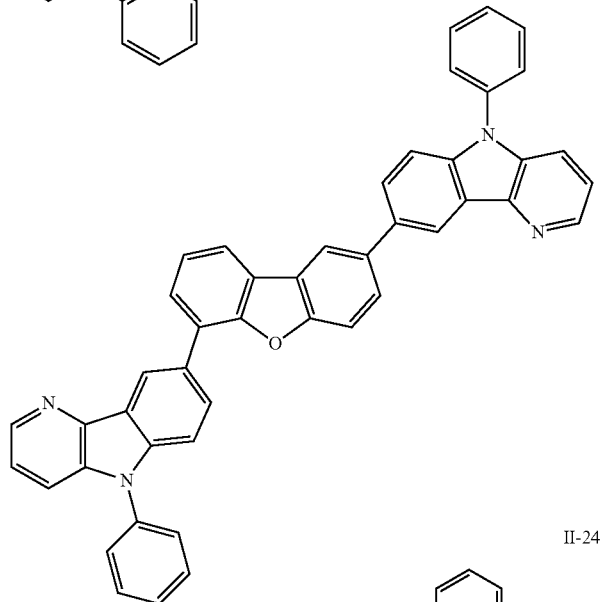
II-24
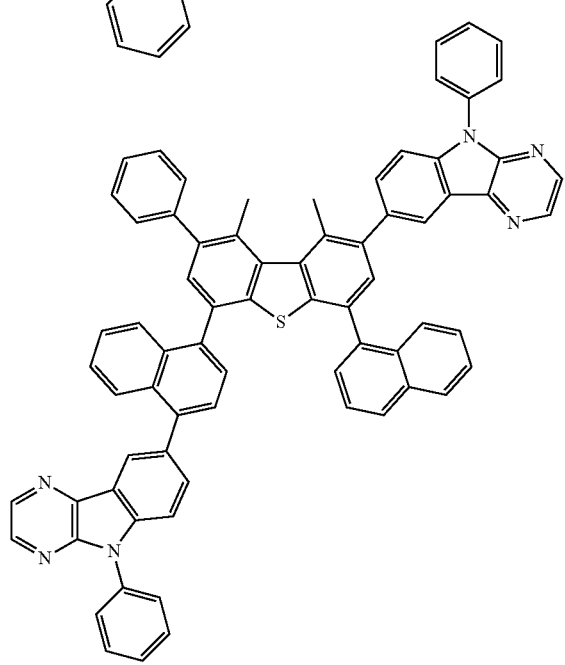
II-25
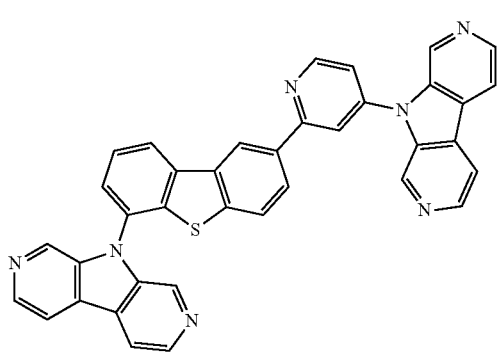

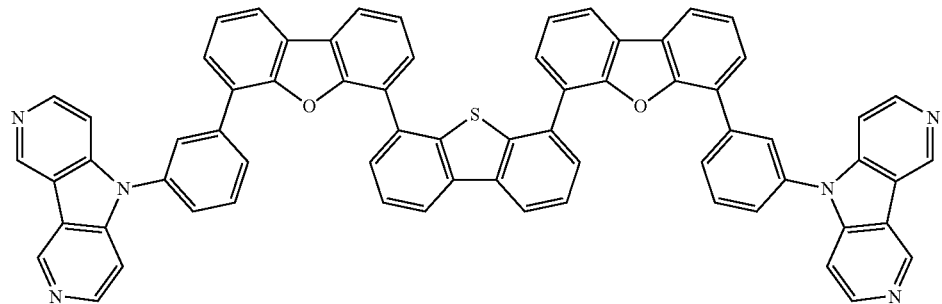
II-26
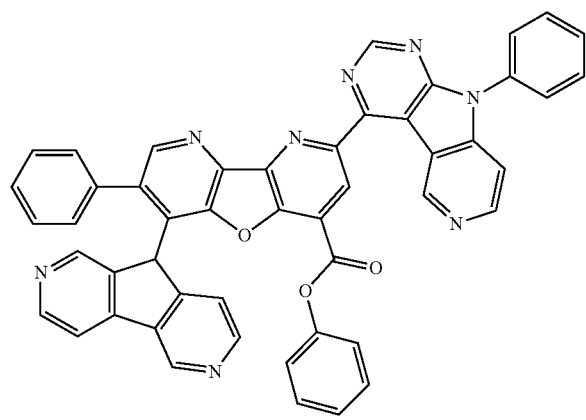
II-27
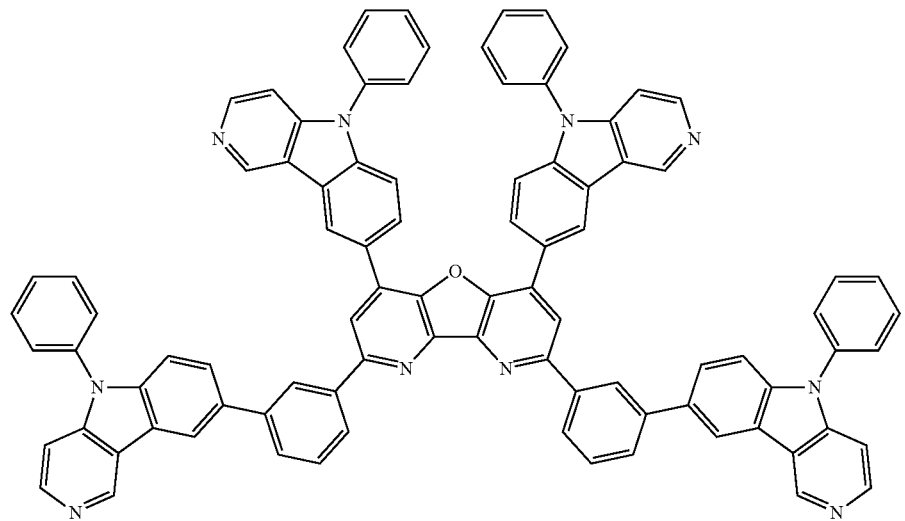
II-28

-continued
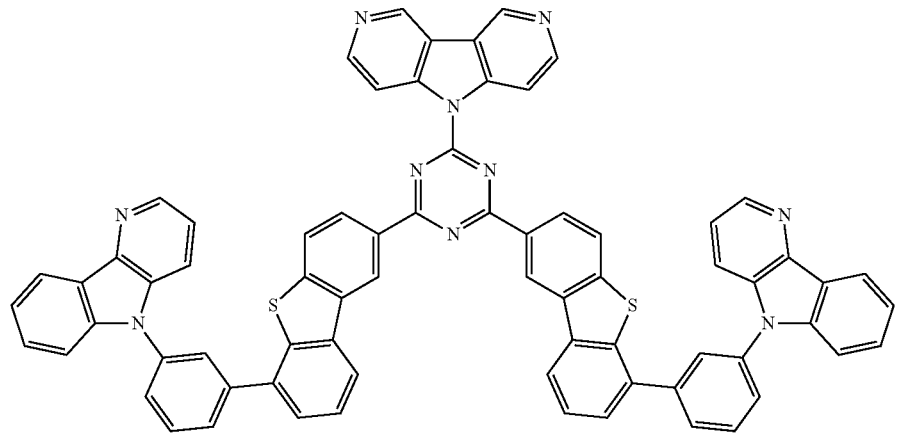
II-29
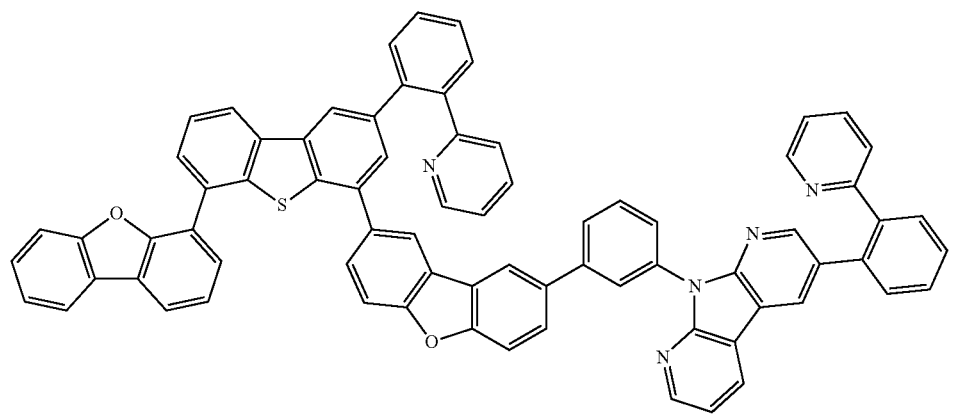
II-30
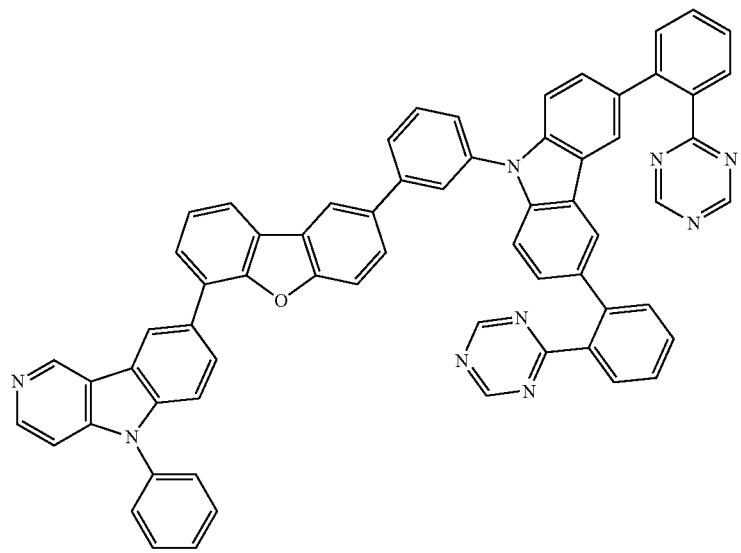
II-31

-continued
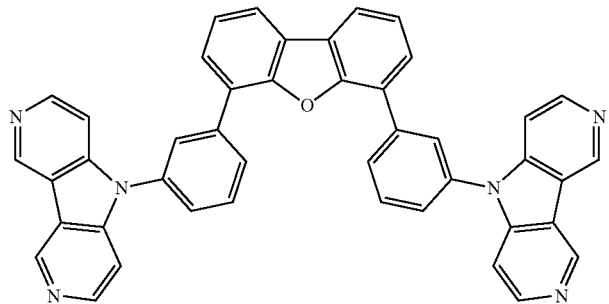
II-32
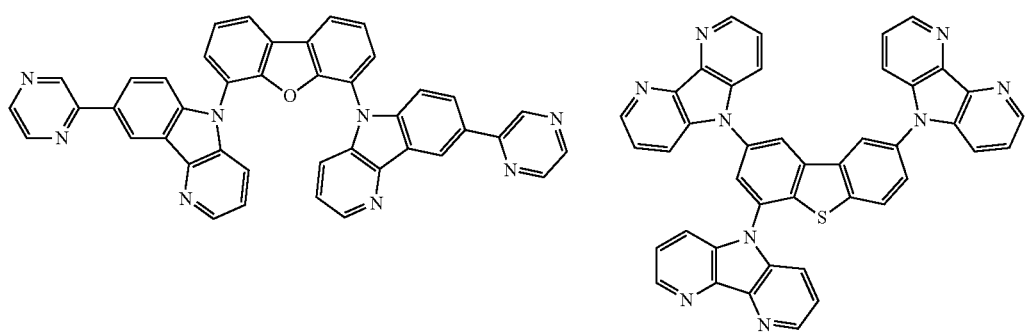
II-33
II-34
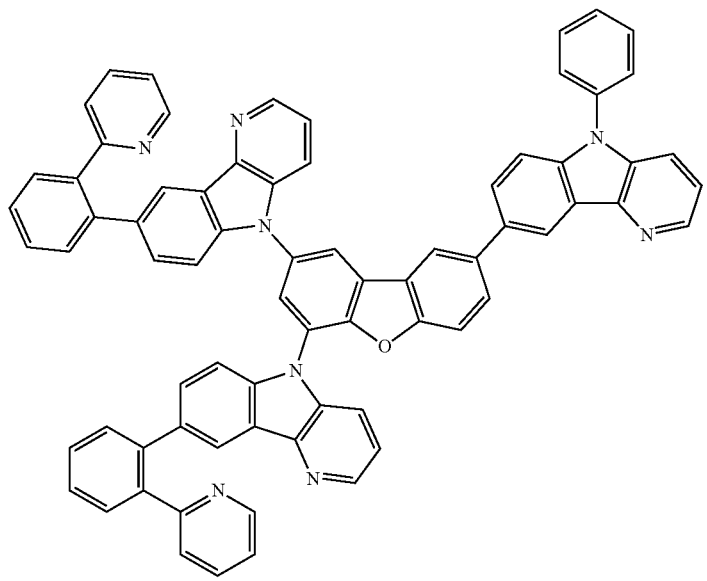
II-35

II-36
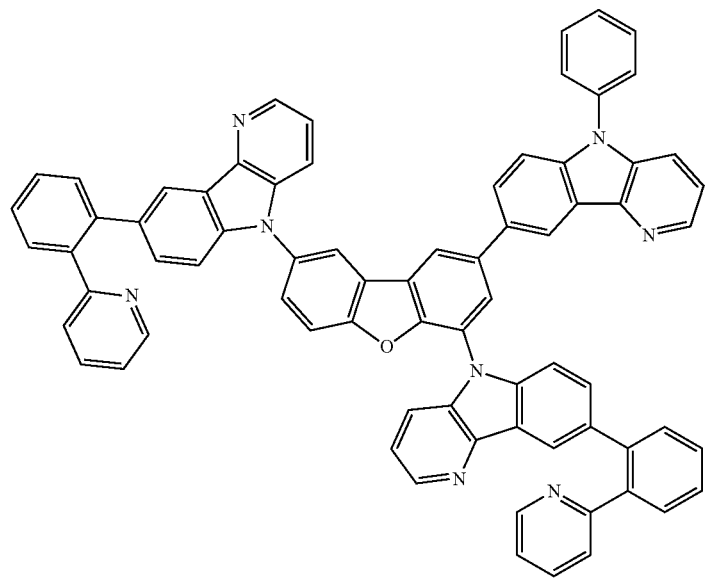
II-37
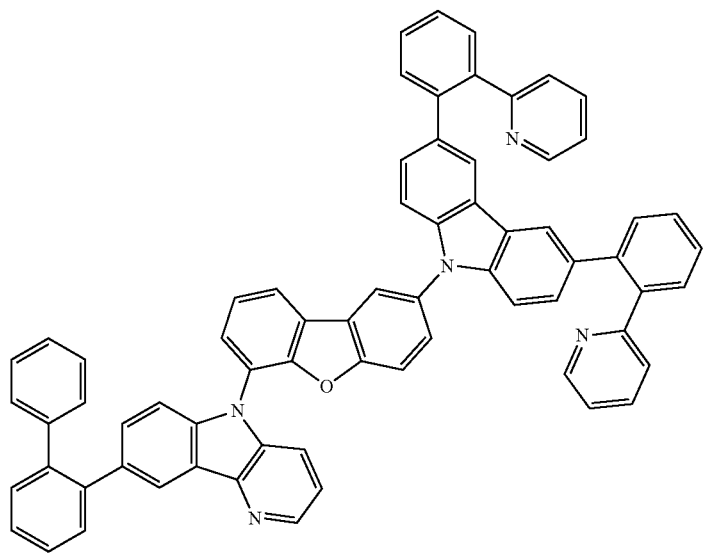
II-38
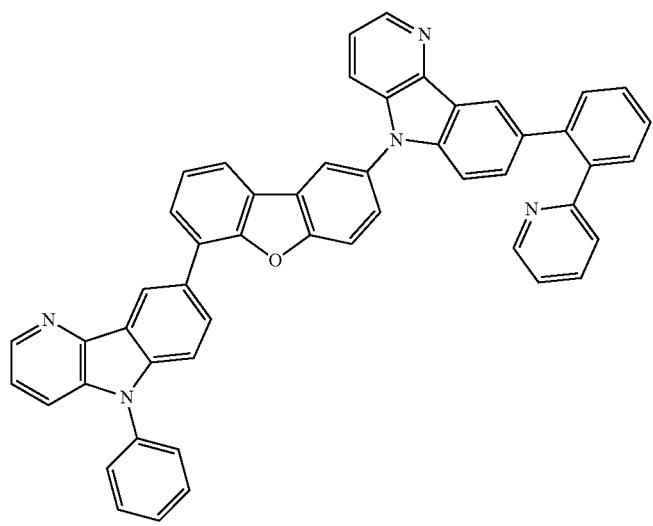

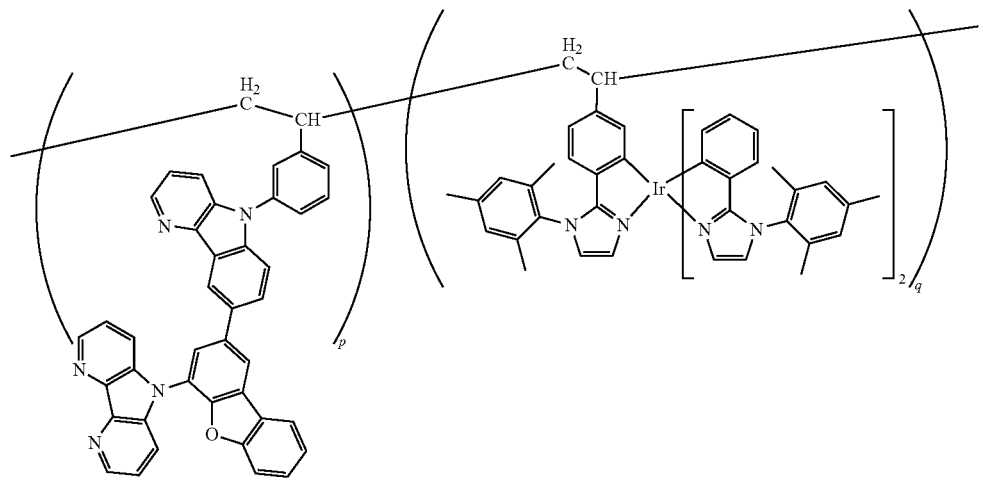
II-39
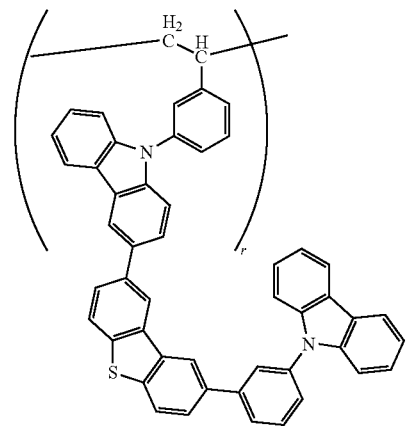
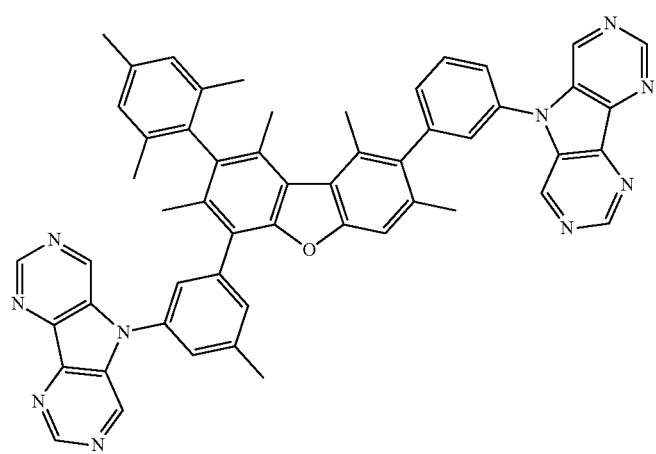
II-40

II-41
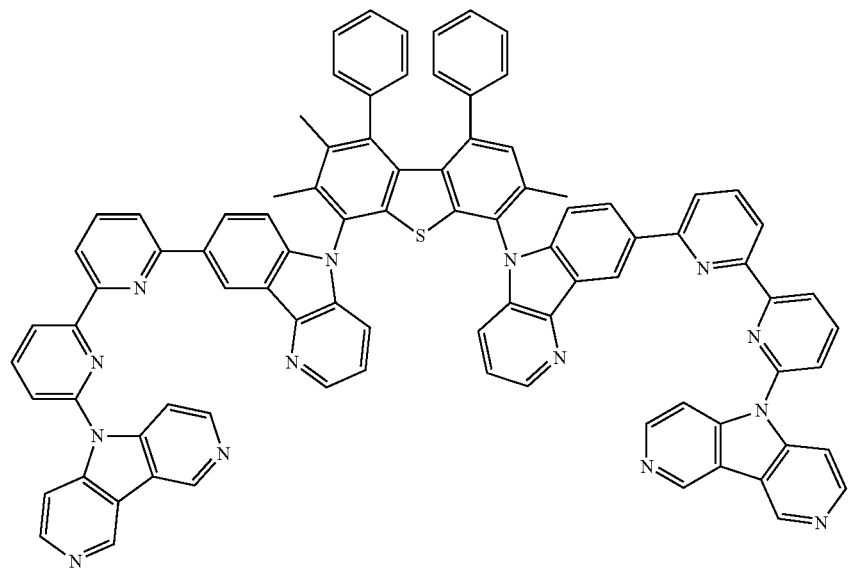
II-42
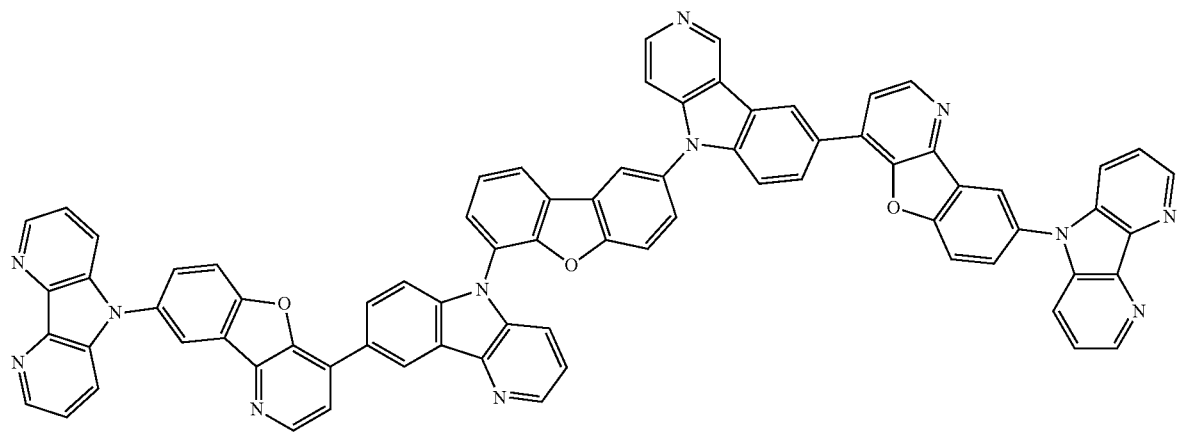
II-43
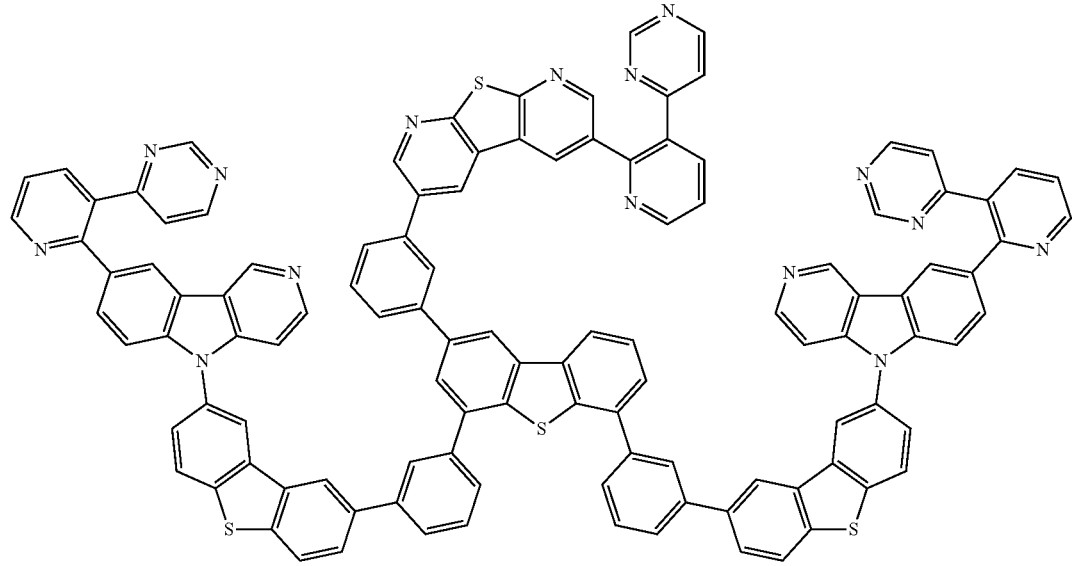

-continued
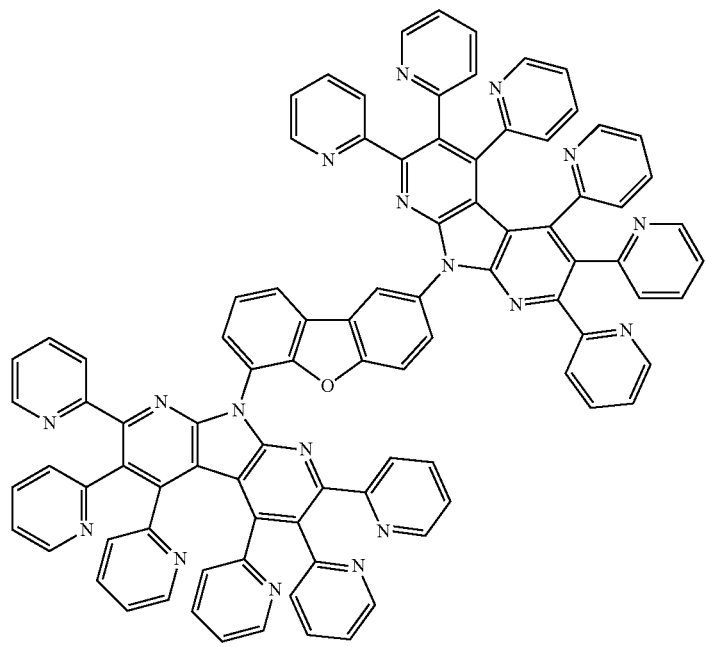
II-44
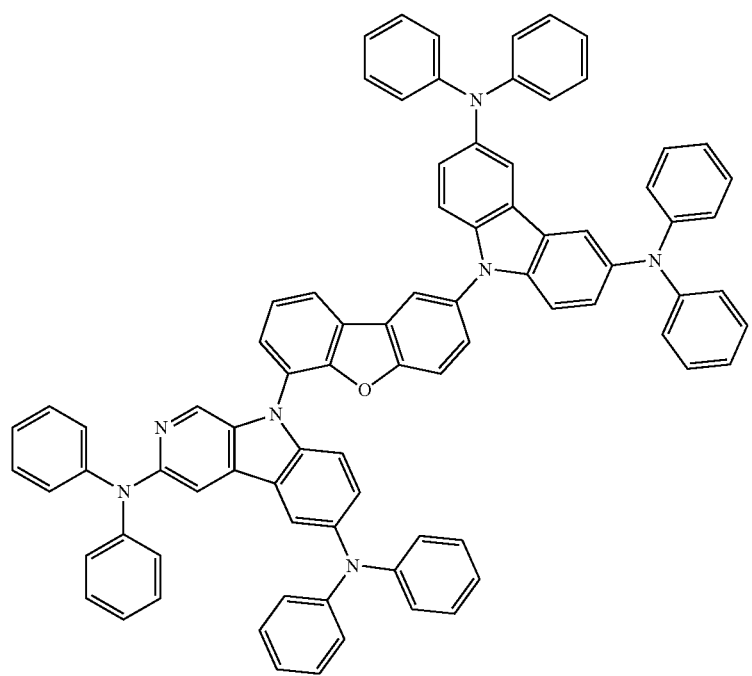
II-45

II-46
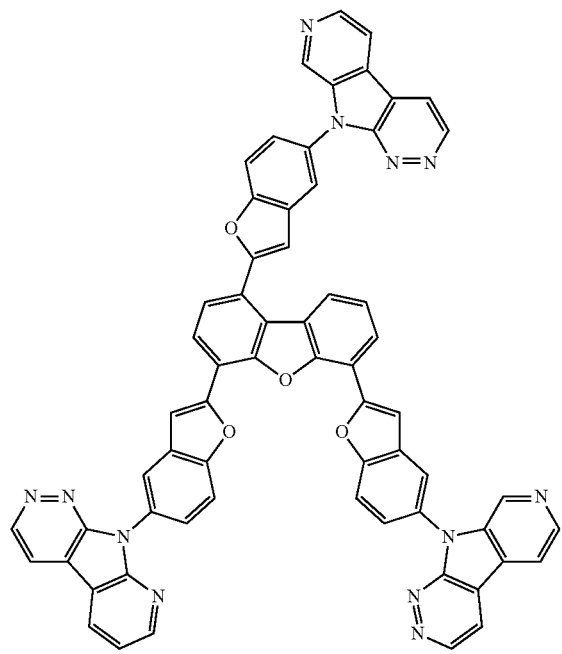
II-47
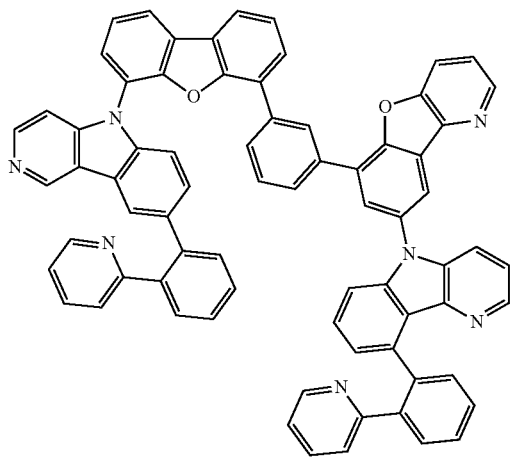
II-48
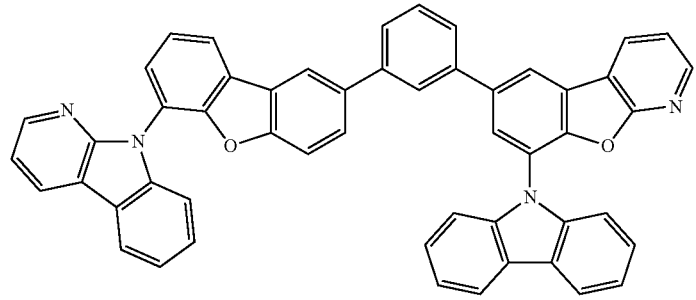
II-49
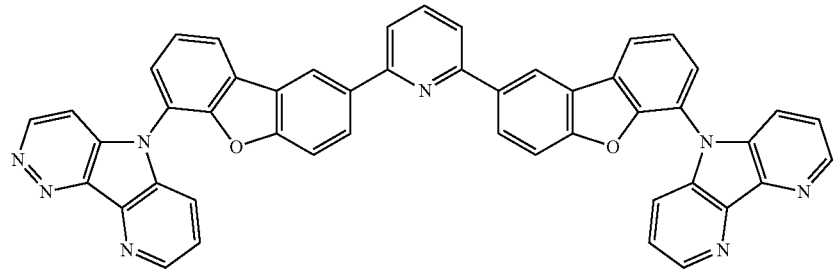
II-50
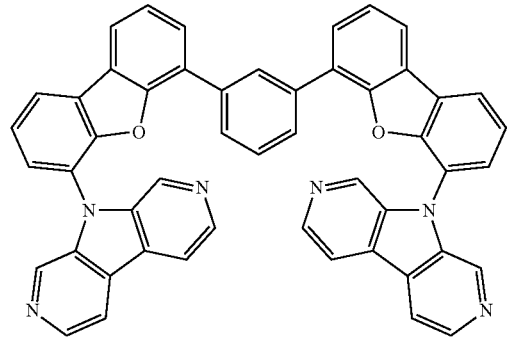

II-51
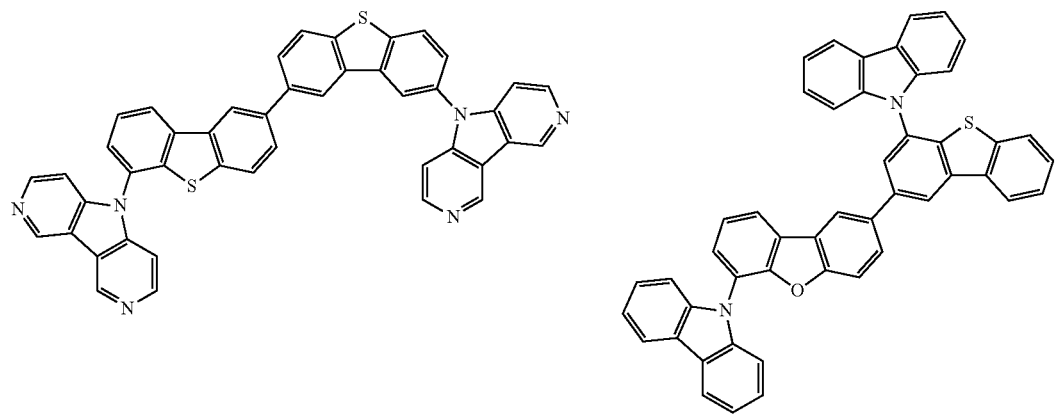
II-52
II-53
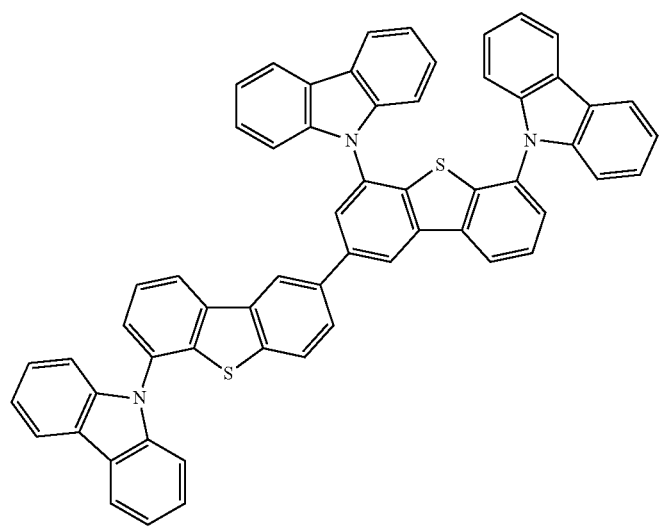
II-54
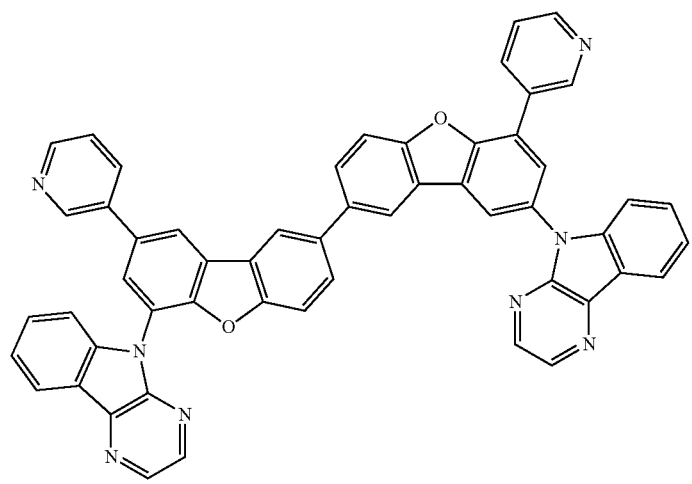

-continued
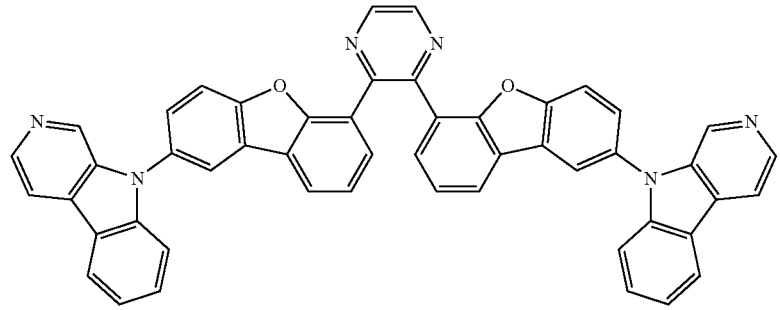
II-55
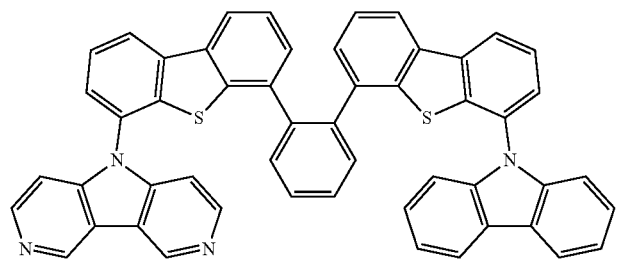
II-56
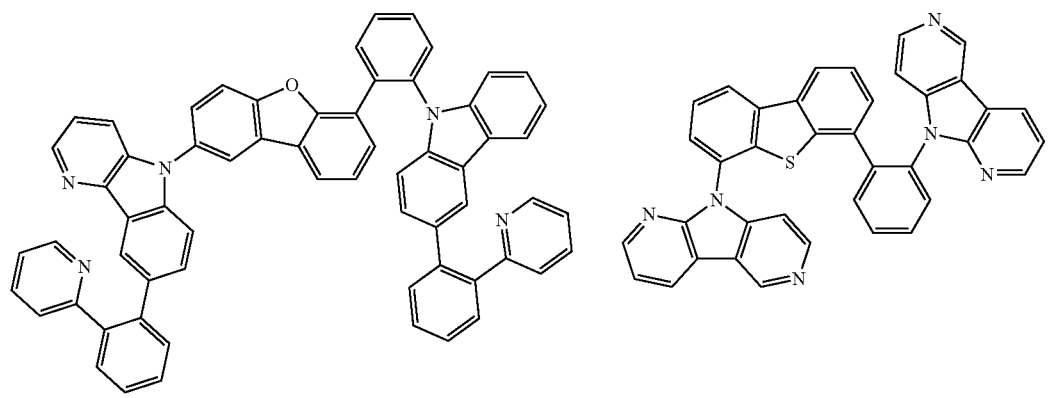
II-57    II-58
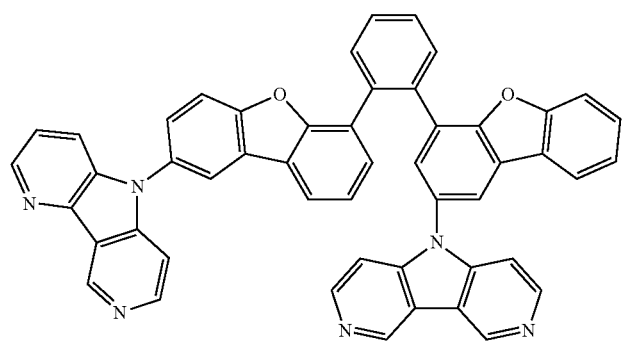
II-59

-continued
II-60
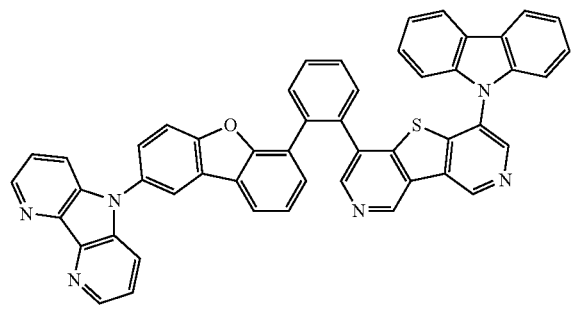
II-61
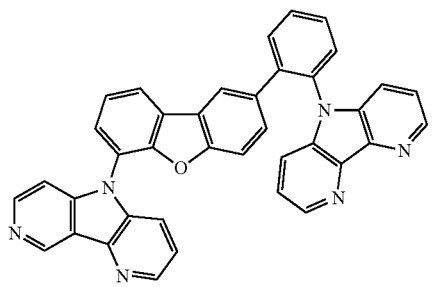
II-62
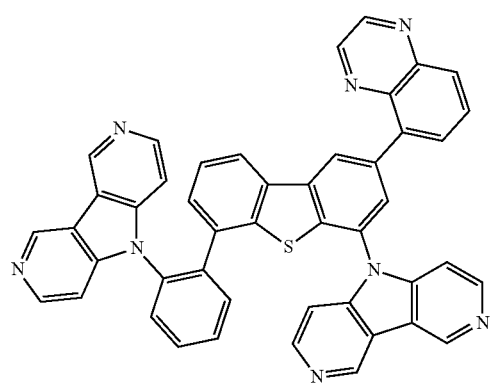
II-63
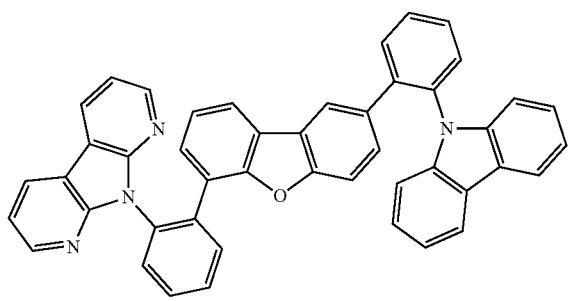
II-64
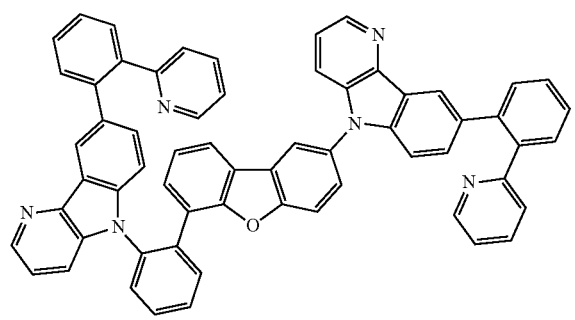
II-65
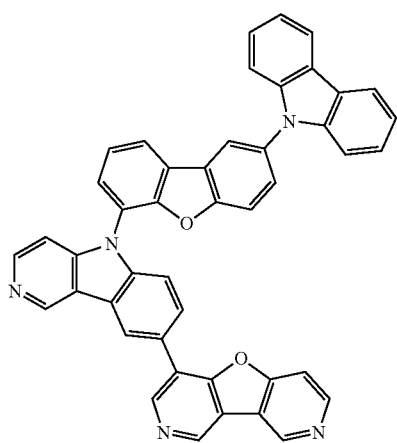

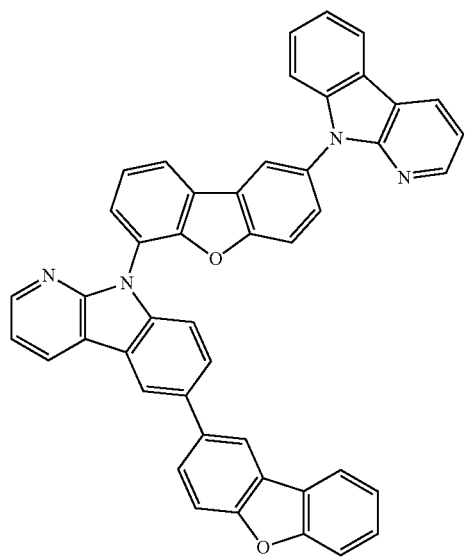
II-66
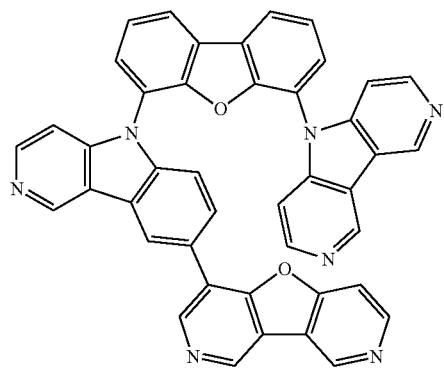
II-67
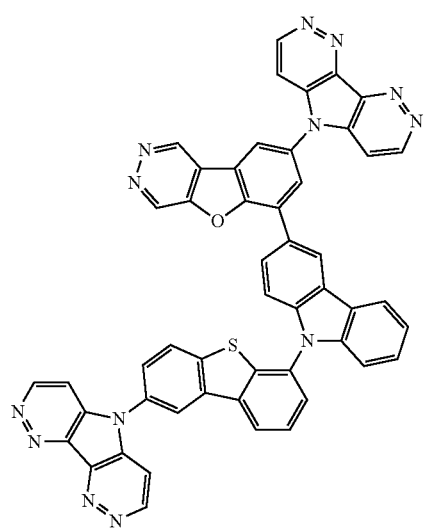
II-68
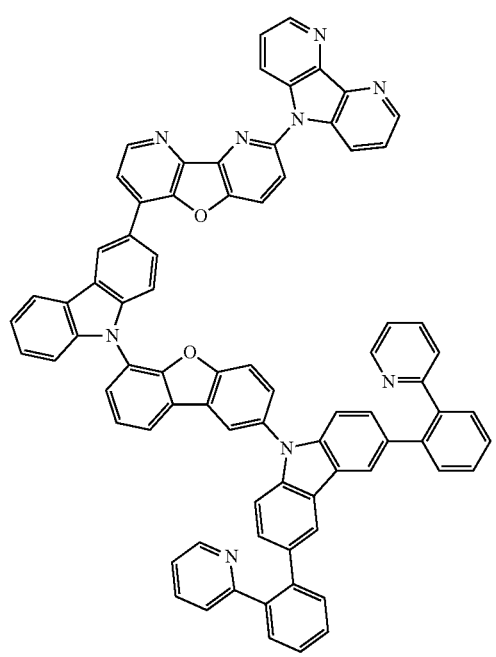
II-69

-continued
II-70
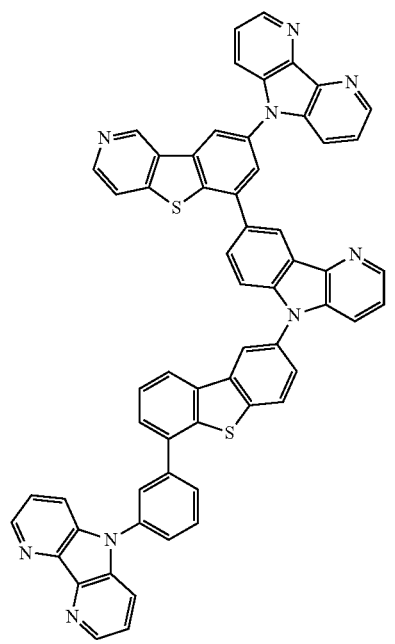
II-71
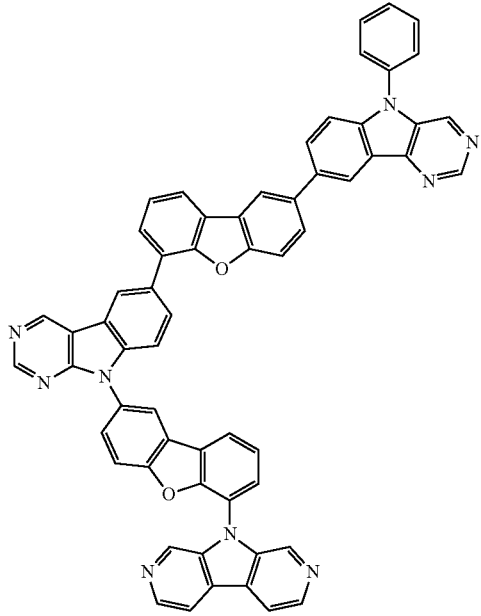
II-72
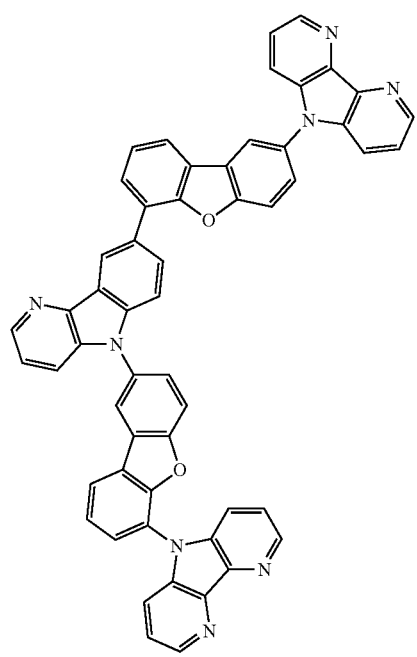
II-73
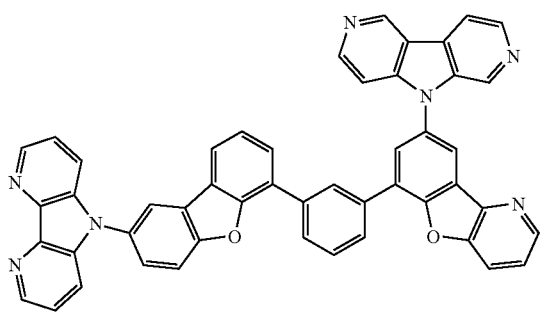
II-74
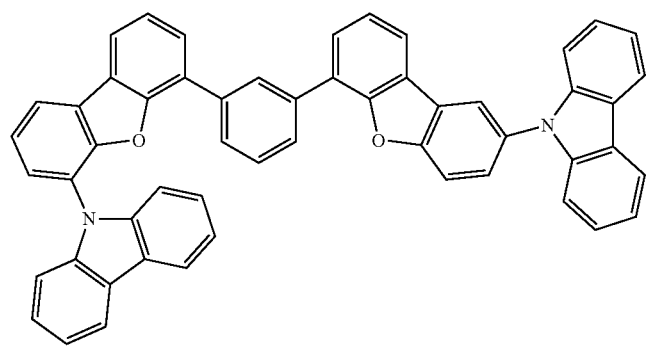

II-75 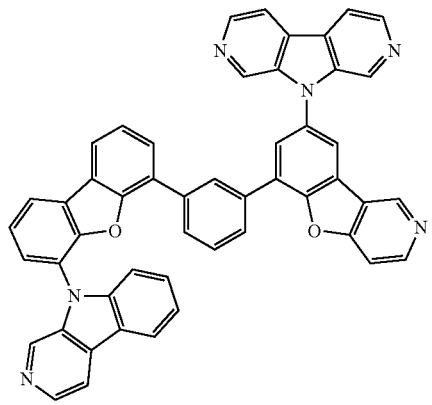
II-76 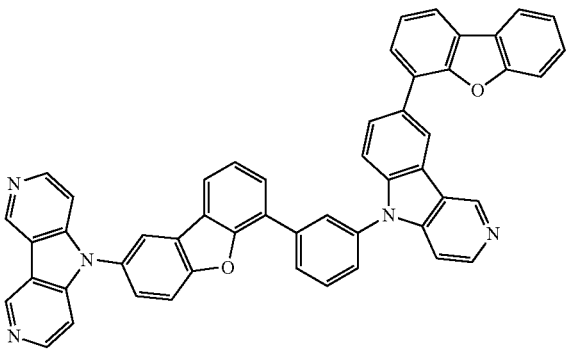
II-77 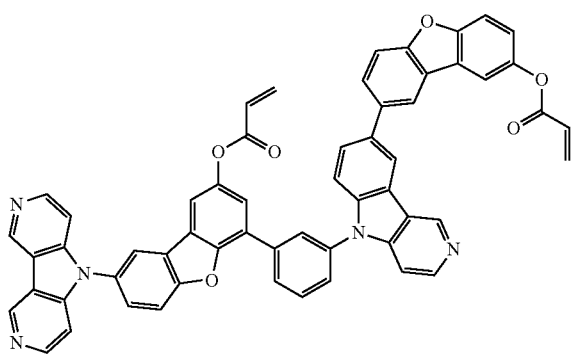
II-78 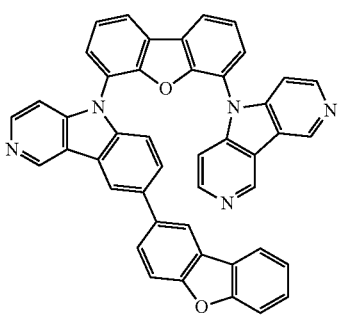
II-79 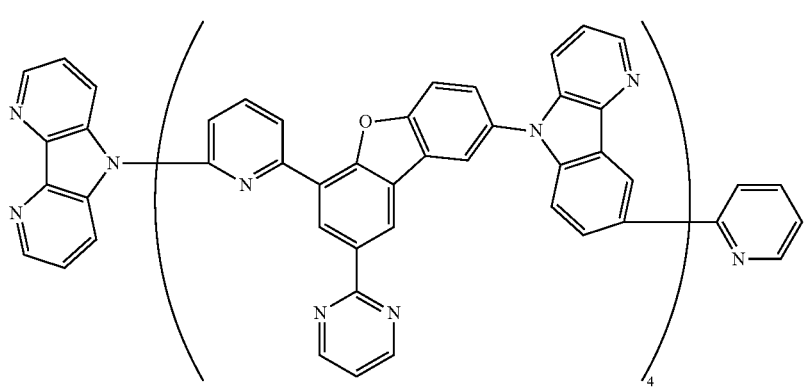

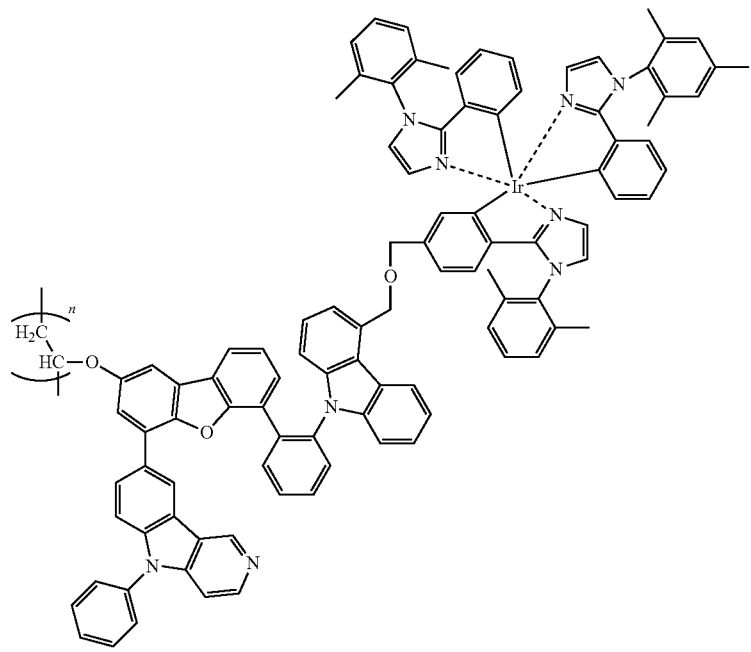
II-80
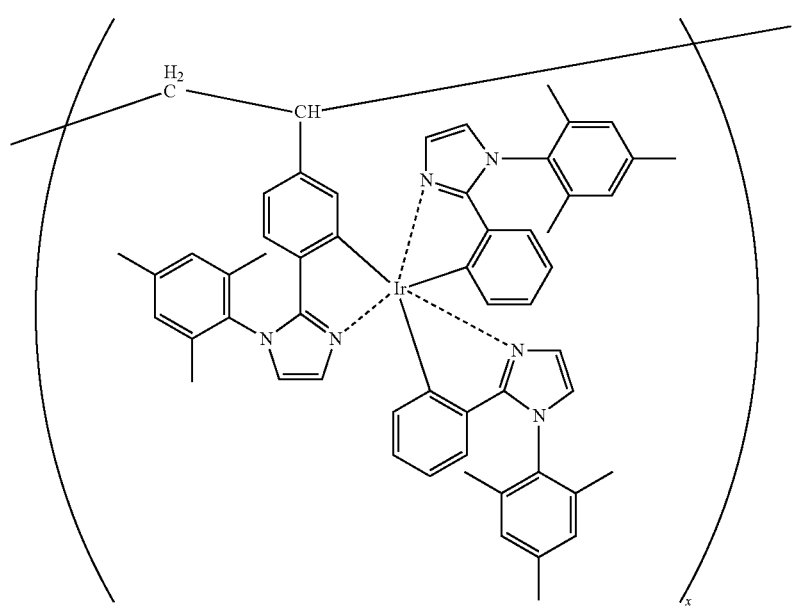
II-81

87 88
-continued
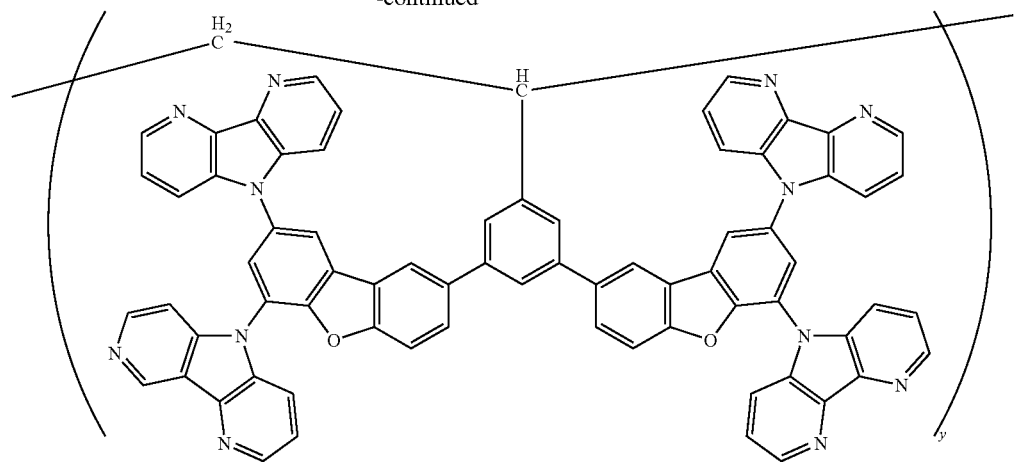
x:y = 1:4
random co-polymer
II-82 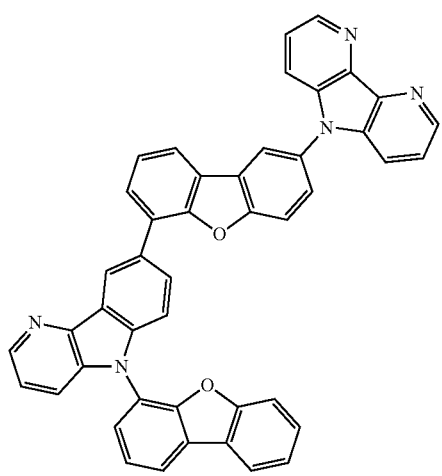
II-83 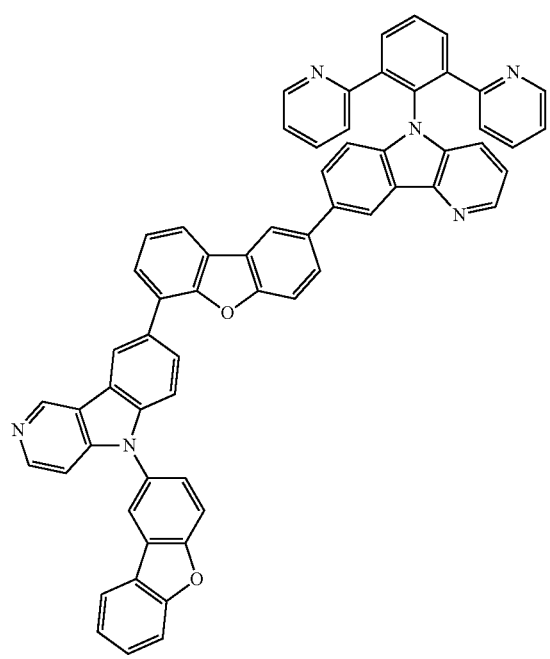
III-1 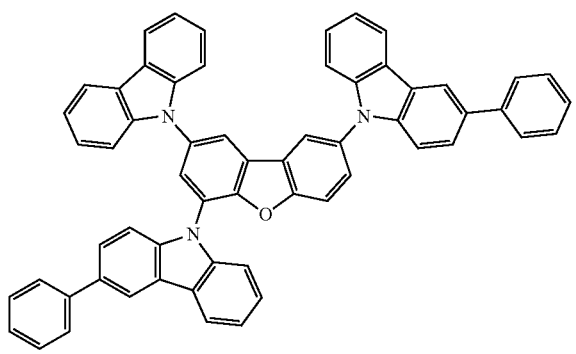
III-2 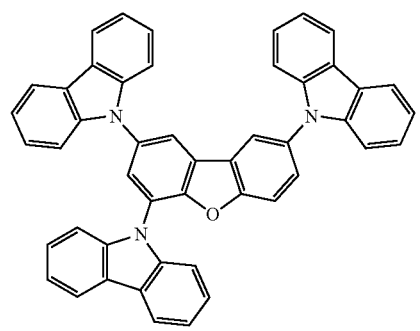

-continued
III-3
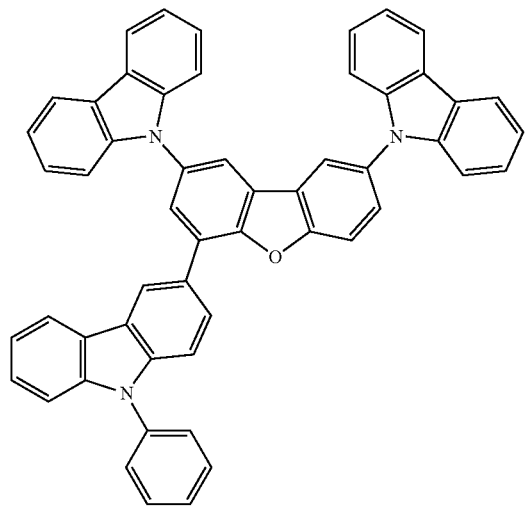
III-4
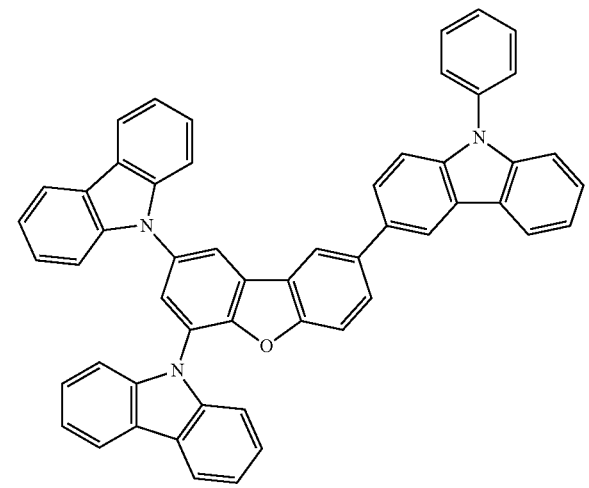
III-5
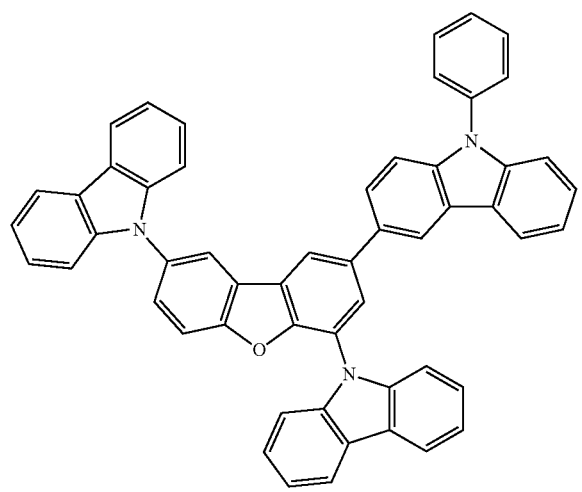
III-6
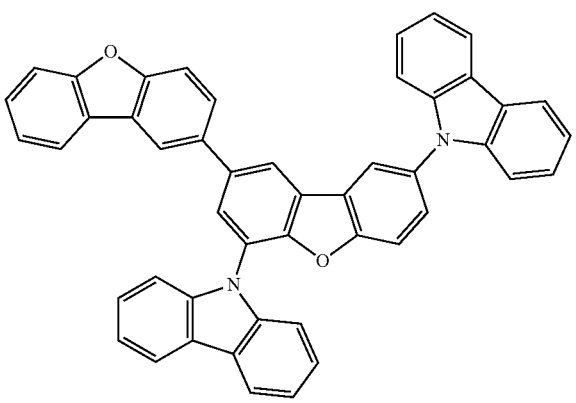
III-7
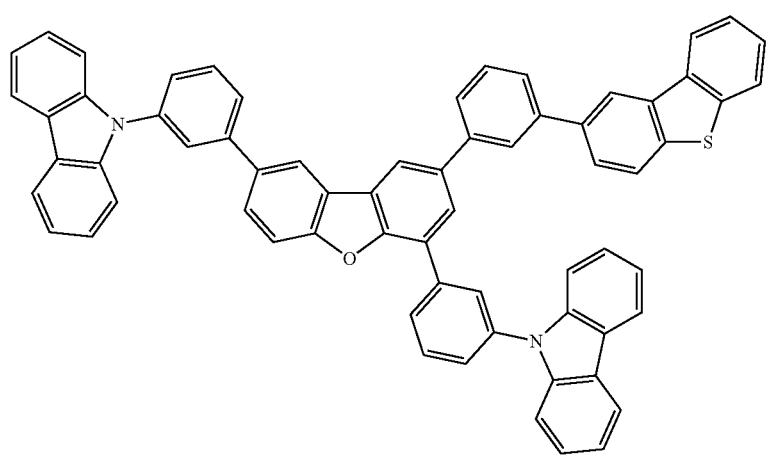

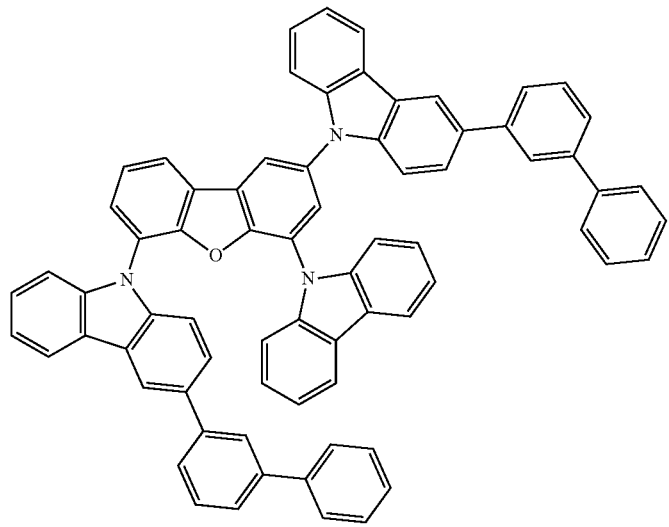
III-8
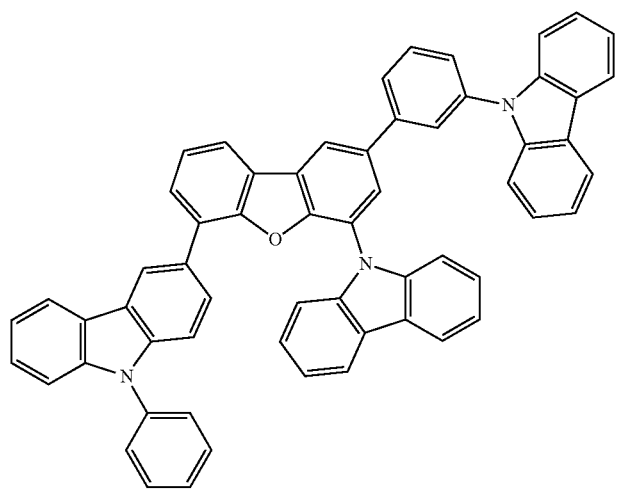
III-9
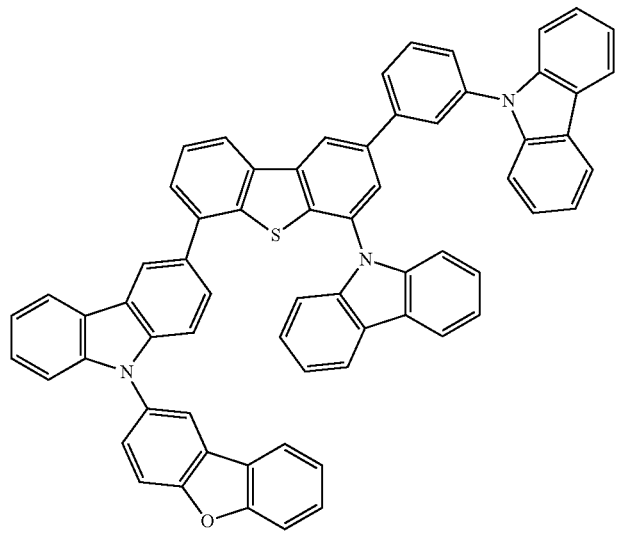
III-10

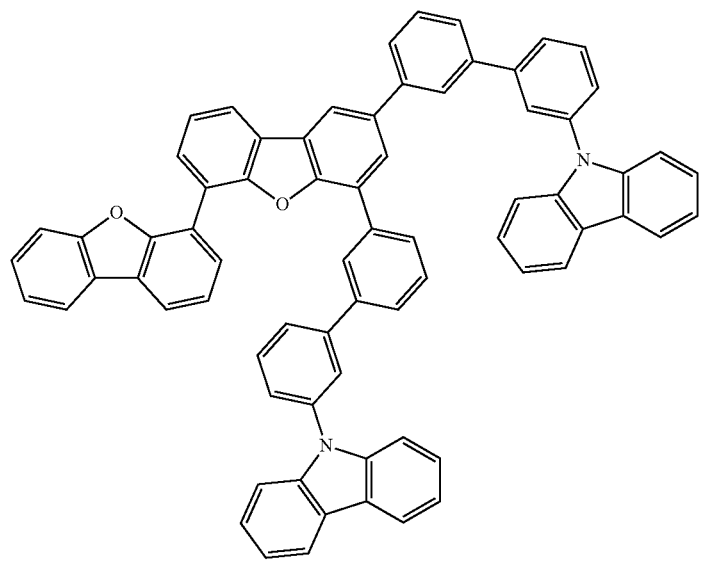
III-11
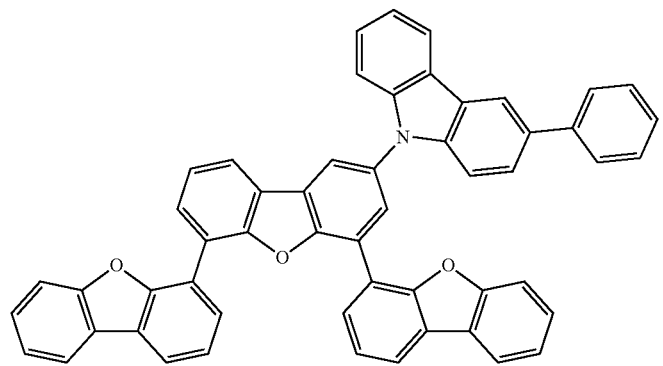
III-12
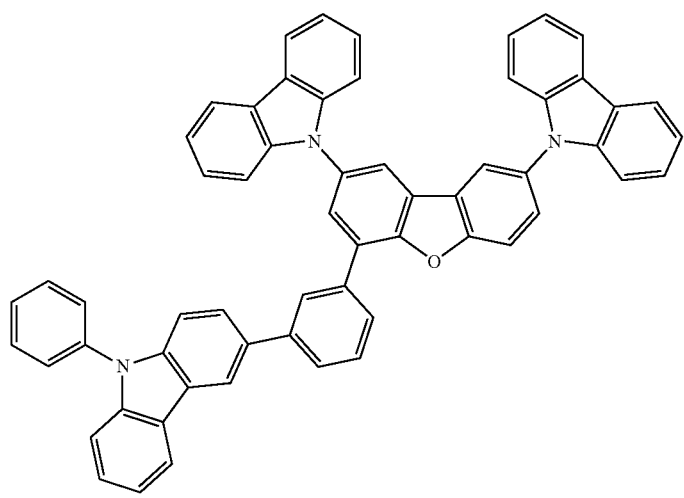
III-13

III-14
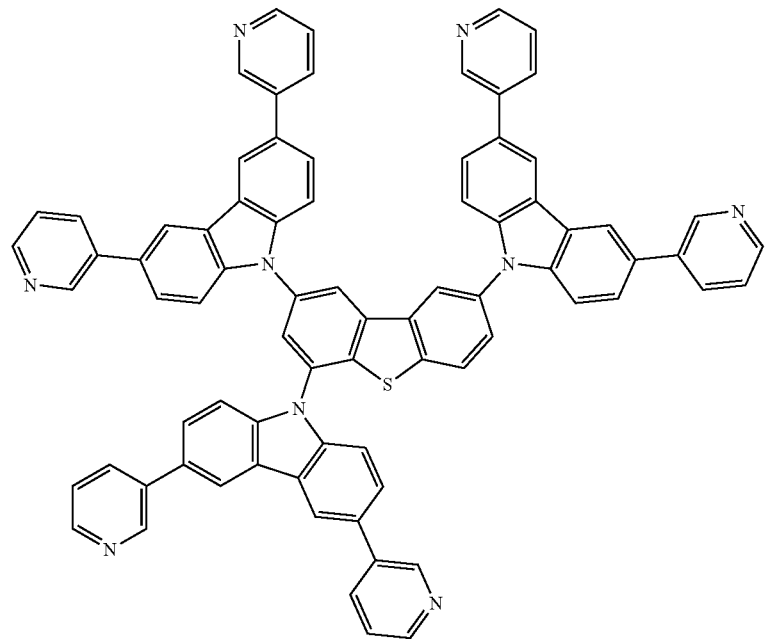
III-15
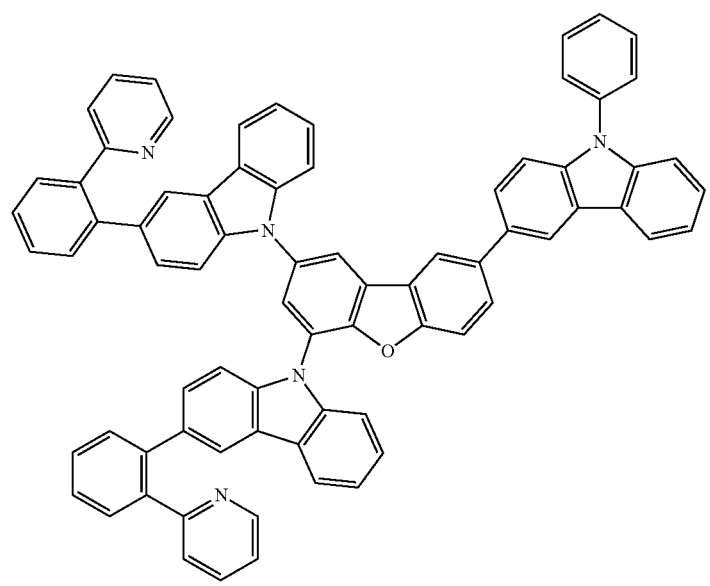

-continued
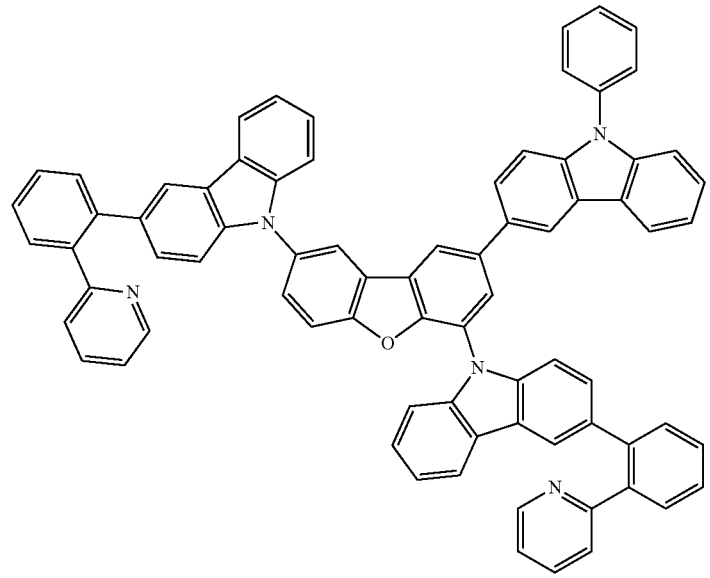
III-16
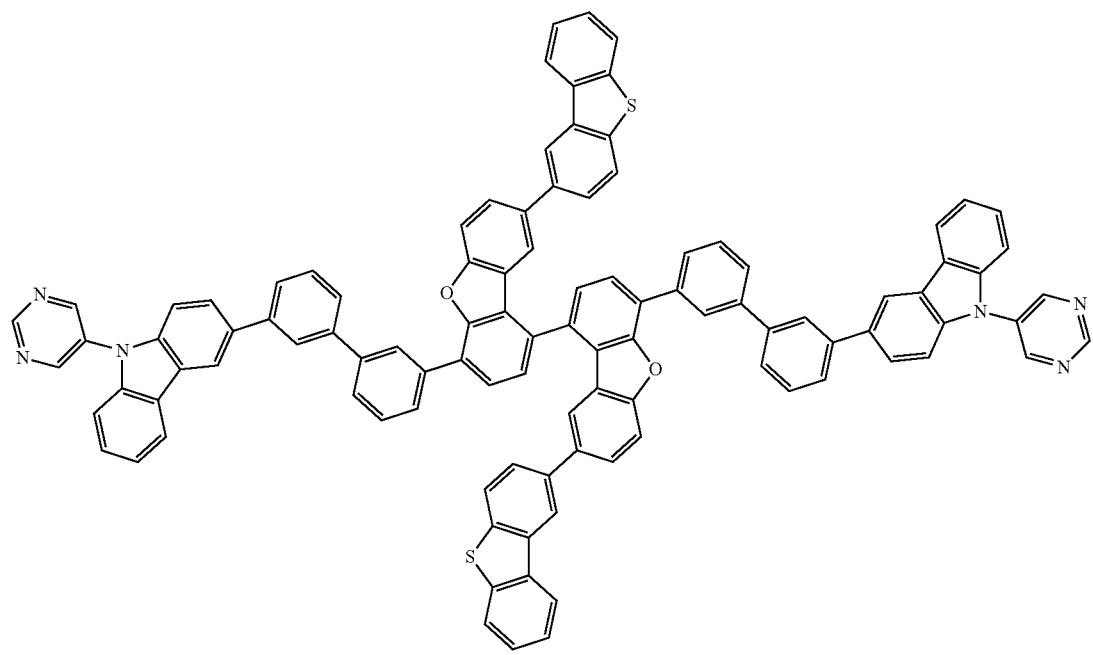
III-17

III-18
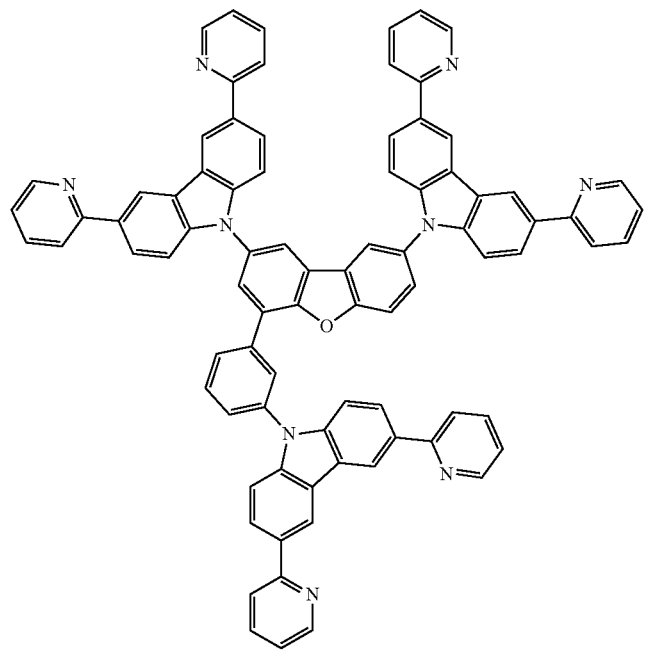
III-19
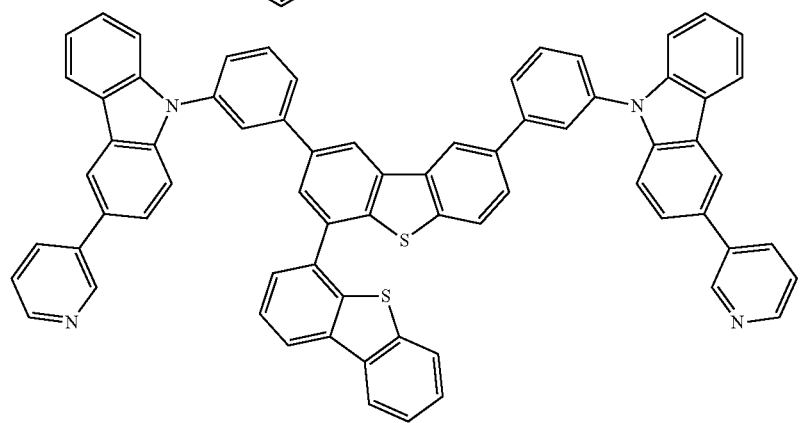
III-20
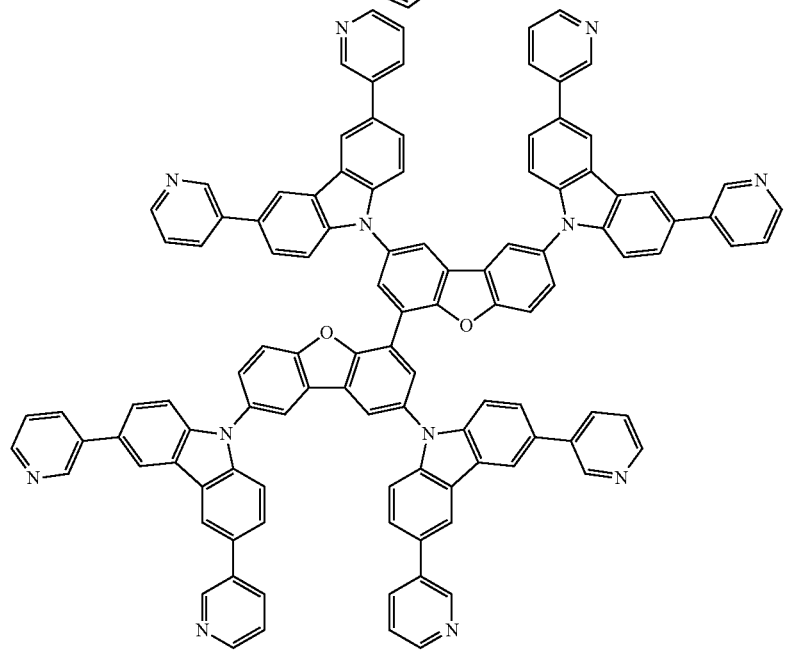

-continued
III-21
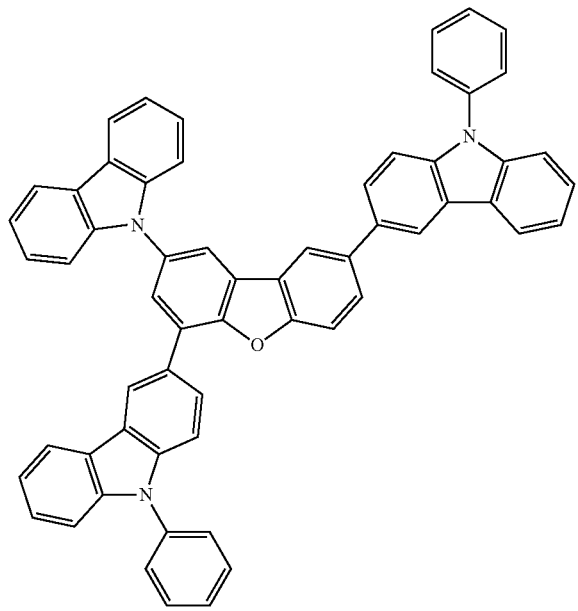
III-22
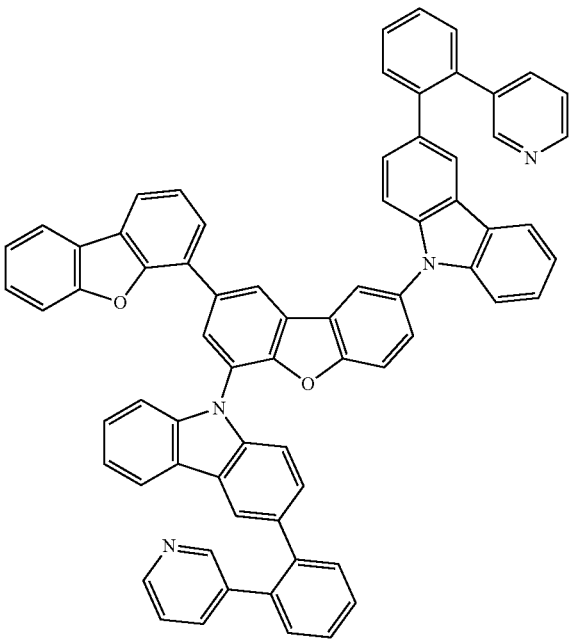
III-23
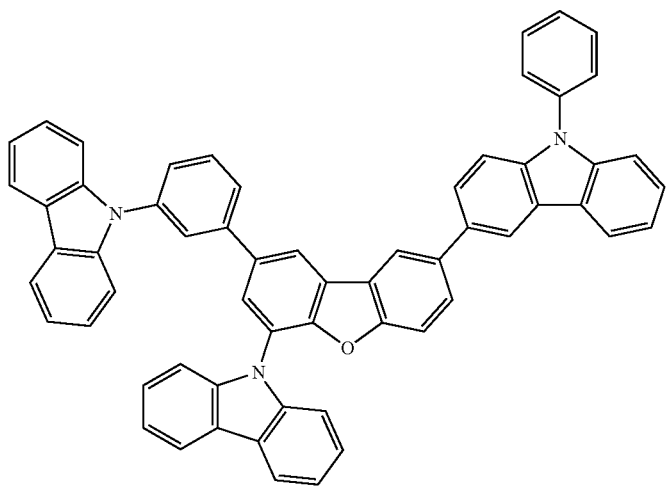
III-24
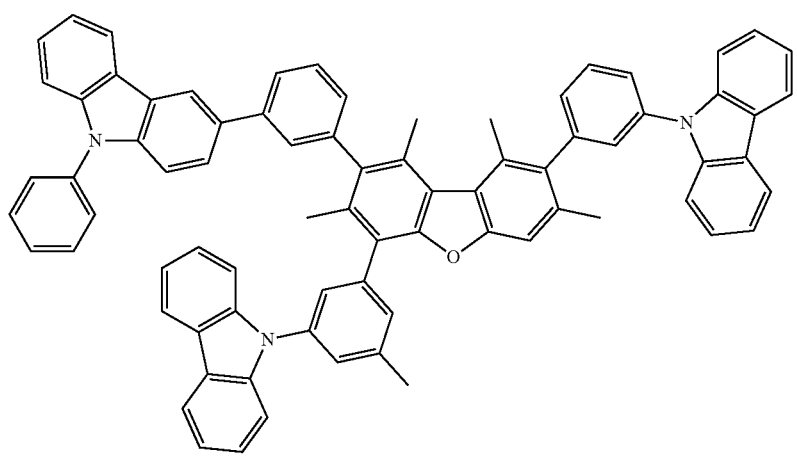

-continued
III-25
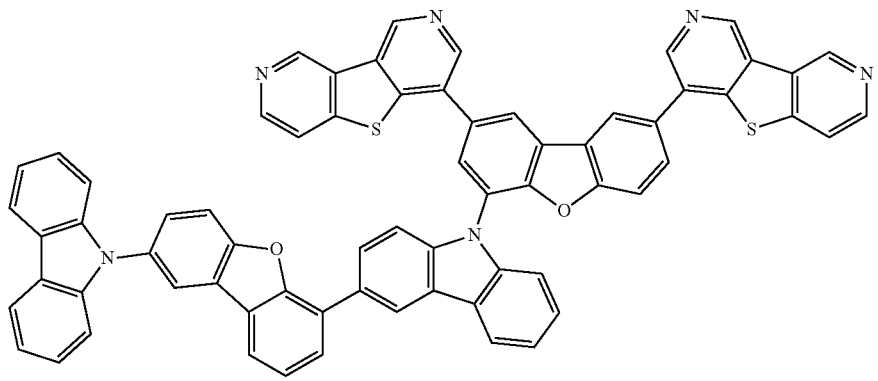
III-26
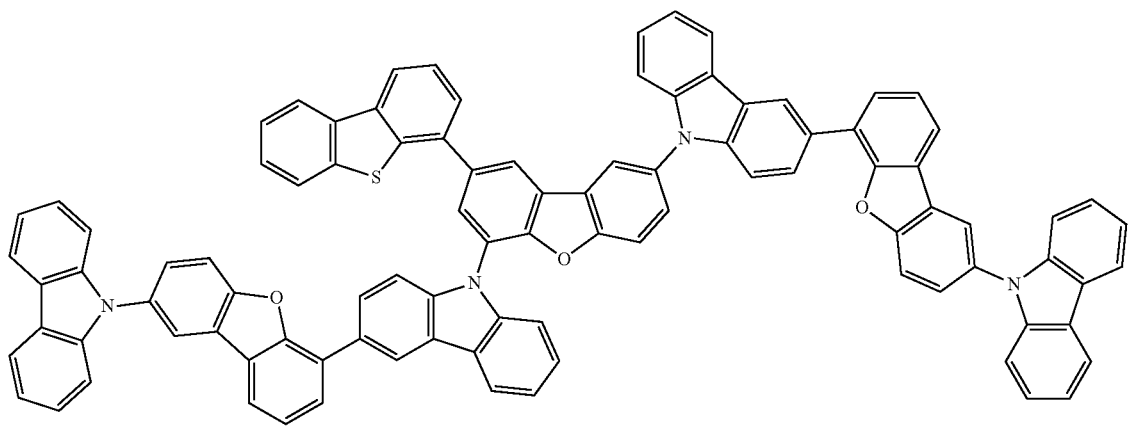
III-27
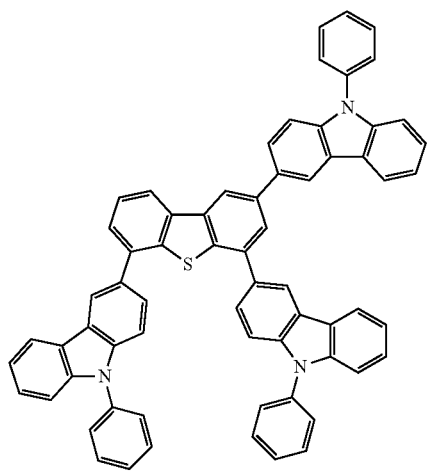
III-28
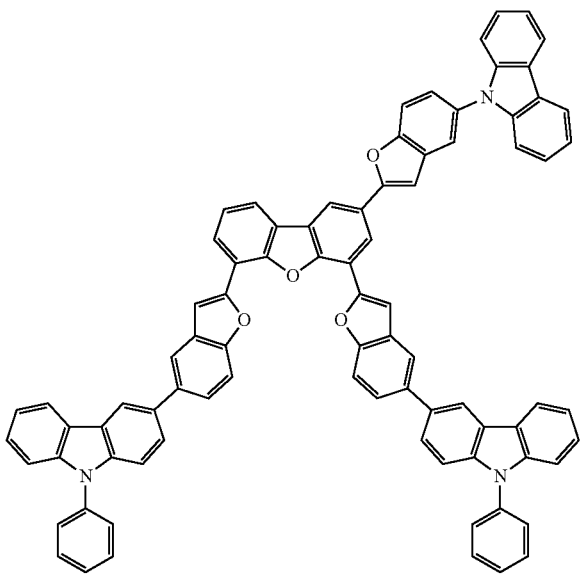

III-29
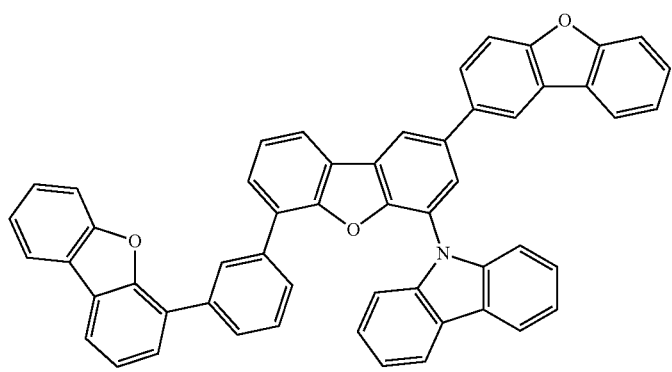
III-30
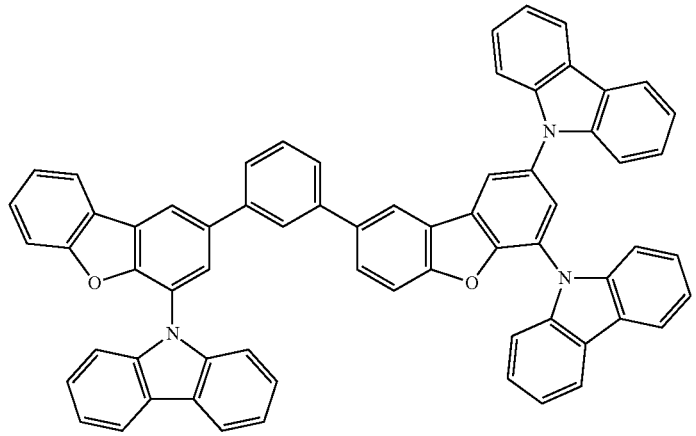
III-31
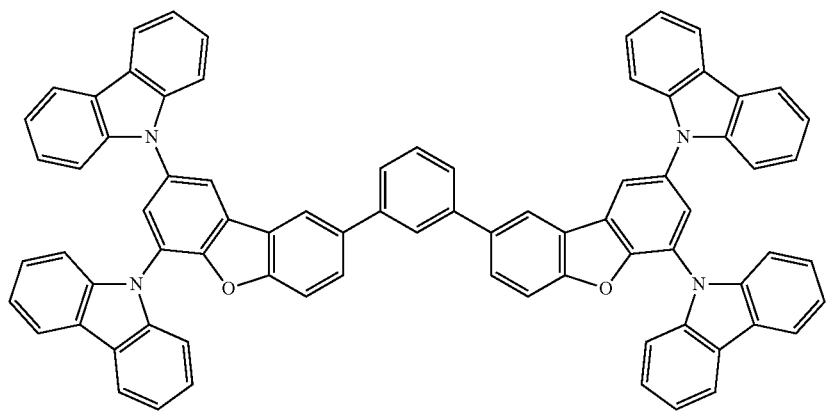
III-32
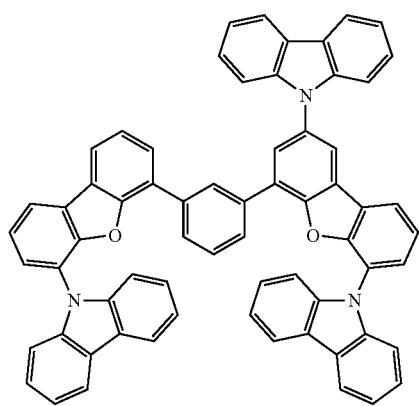
III-33
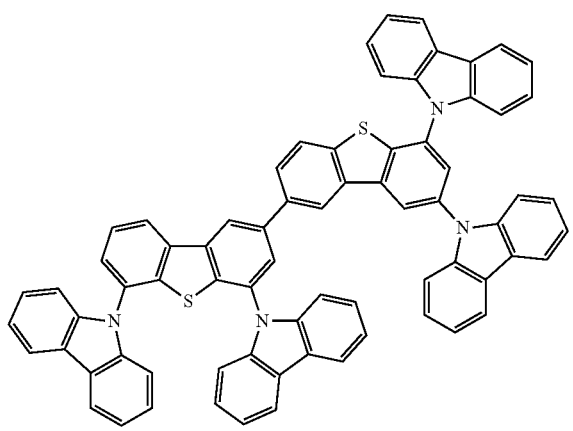

III-34
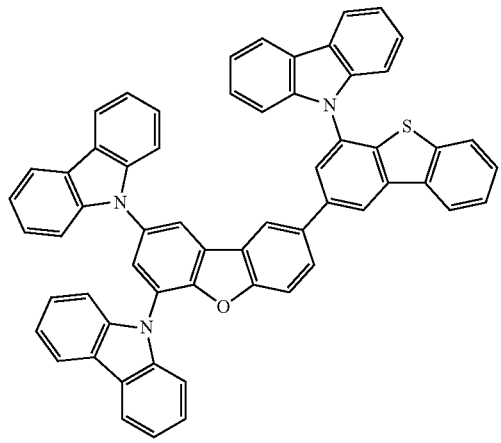
III-35
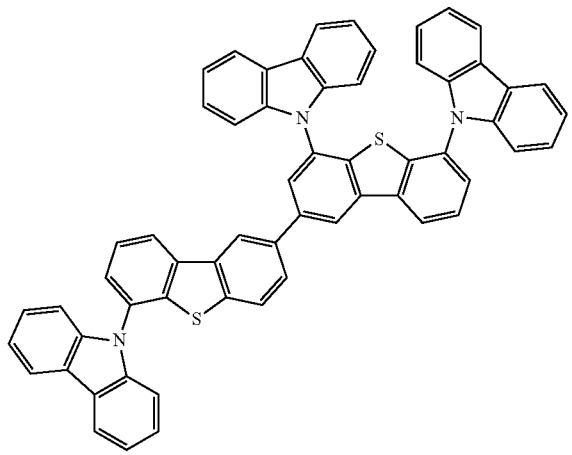
III-36
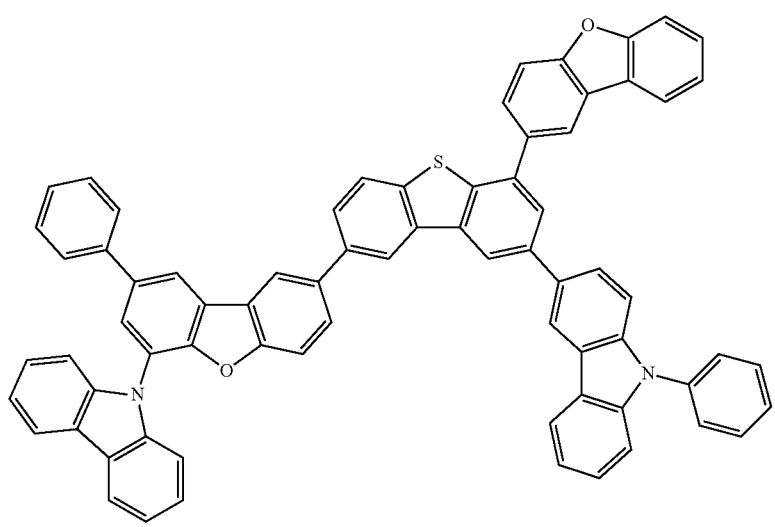
III-37
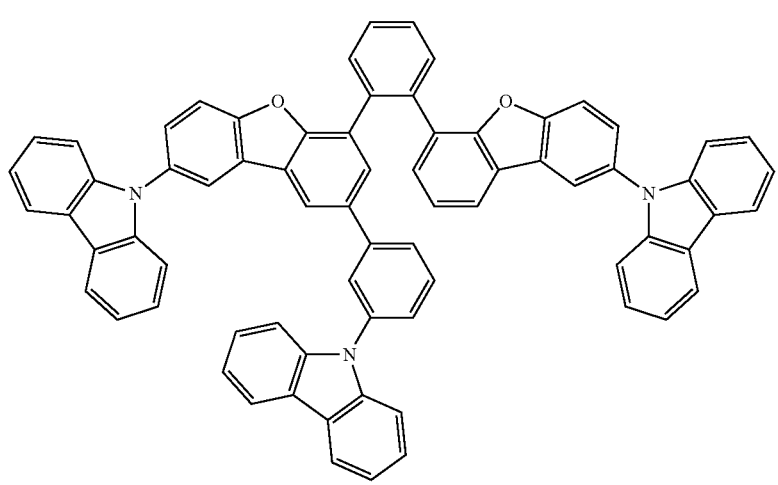

-continued
III-38
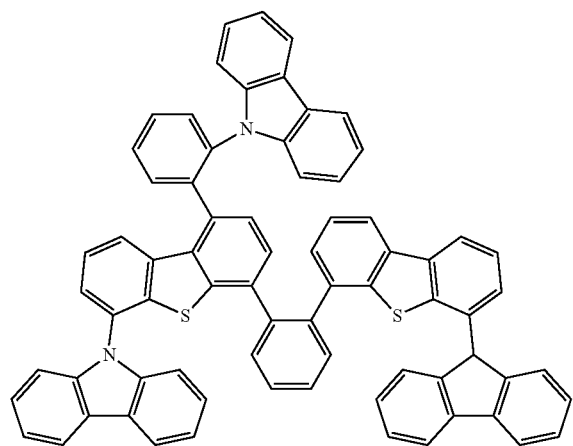
III-39
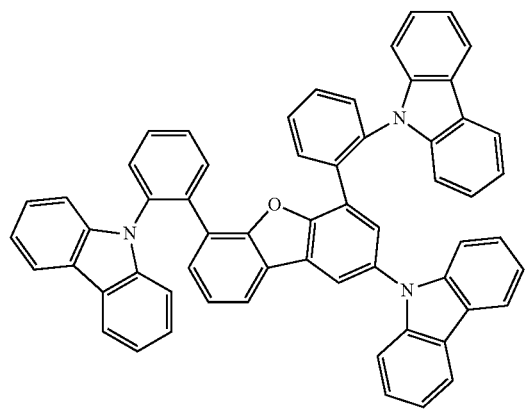
III-40
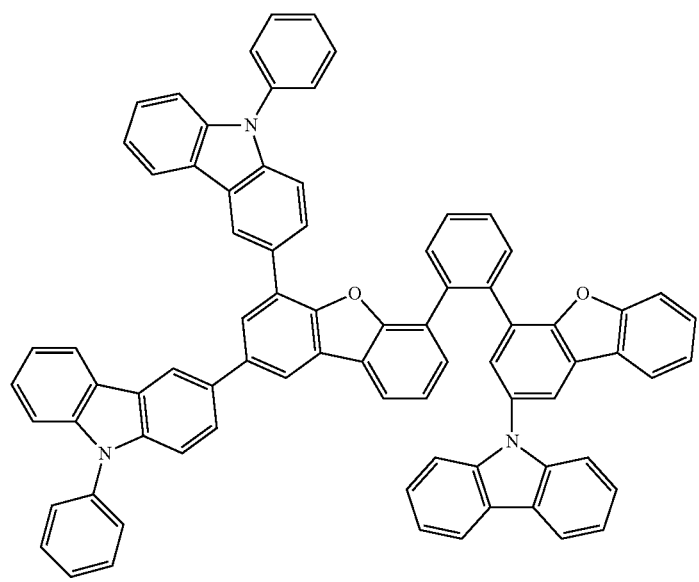
III-41
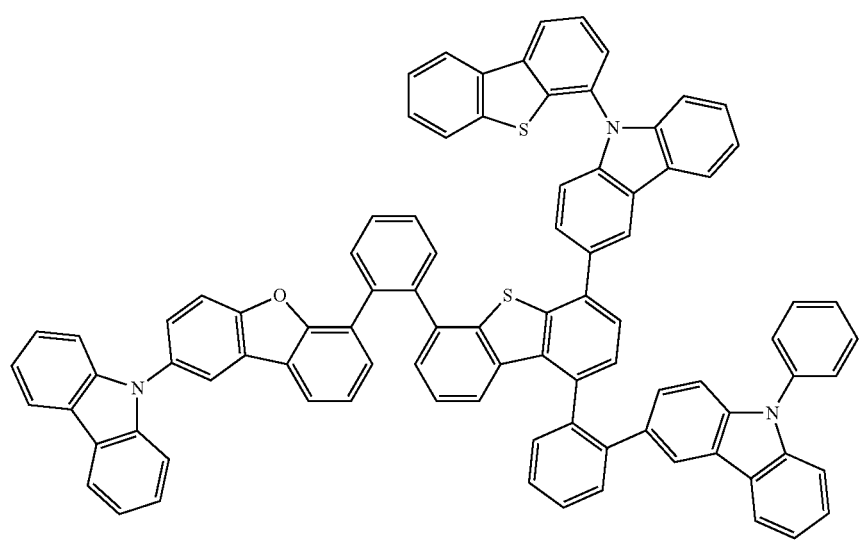

III-42
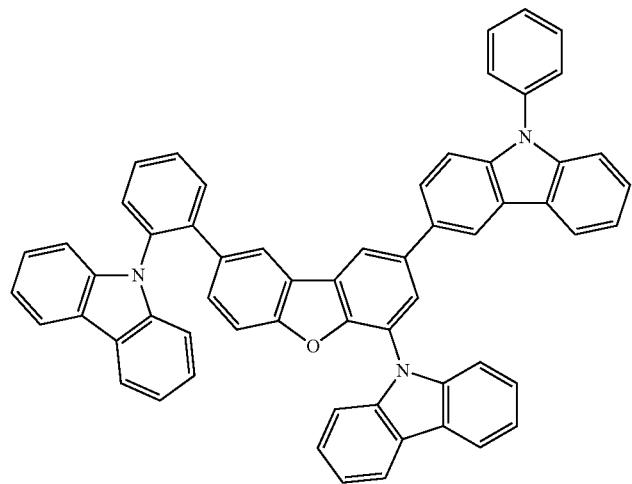
III-43
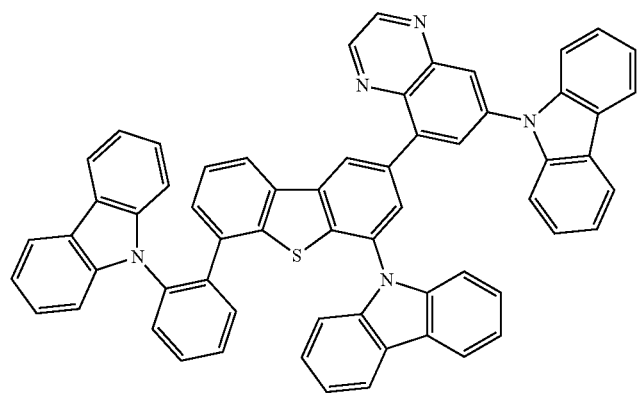
III-44
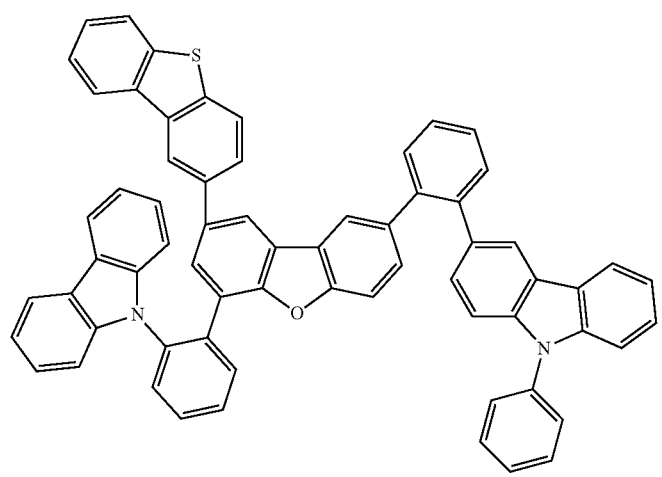

III-45
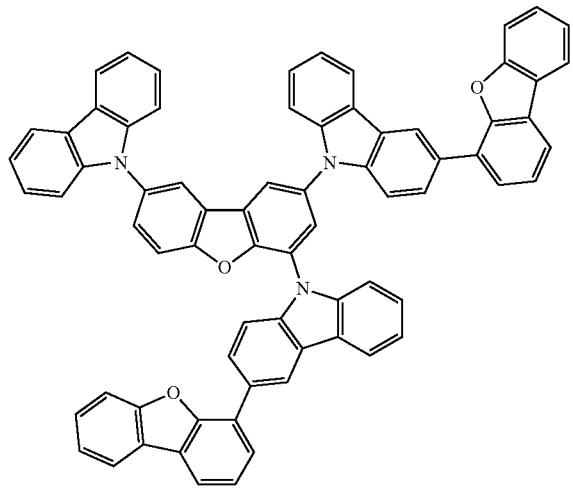
III-46
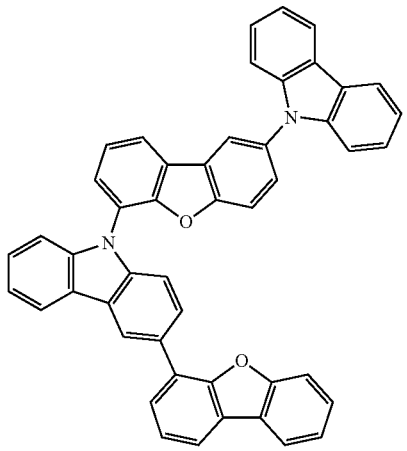
III-47
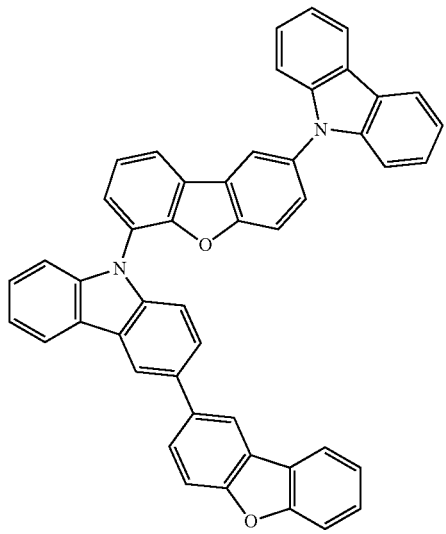
III-48
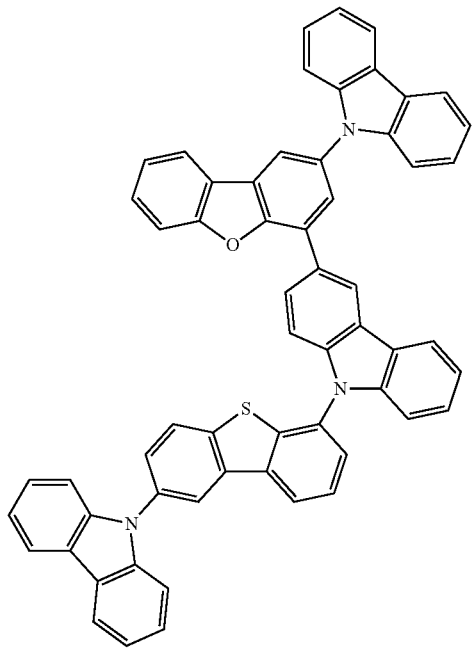

III-49
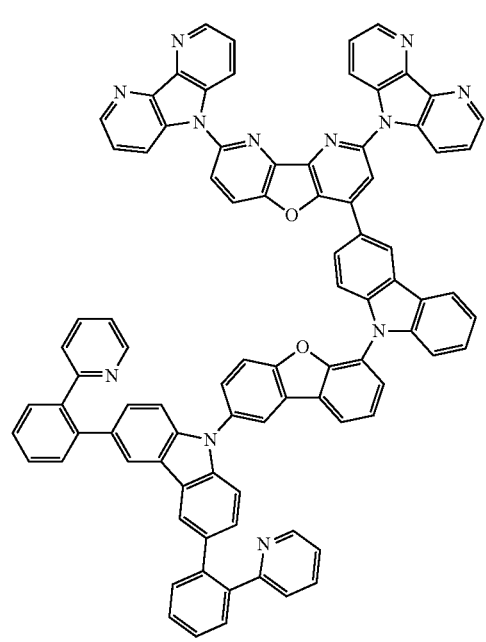
III-50
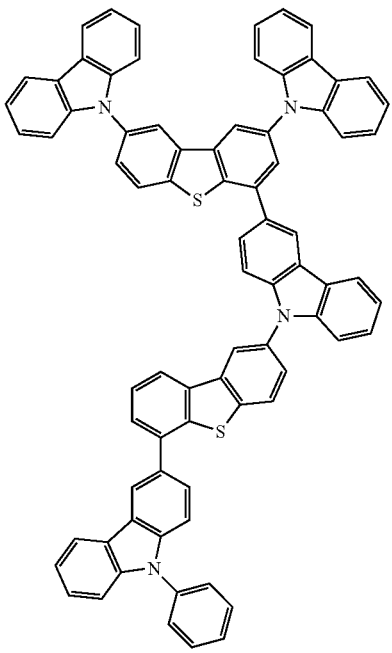
III-51
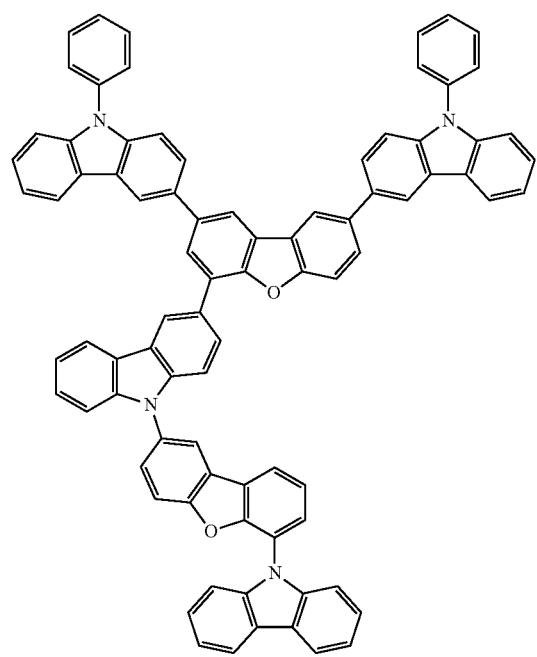
III-52
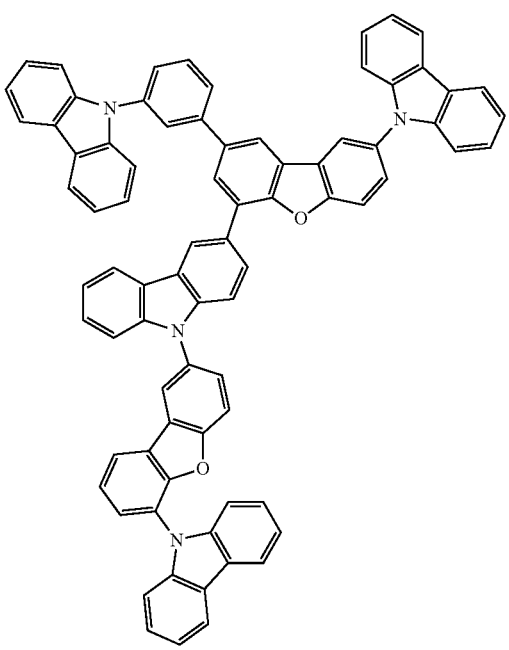

III-53
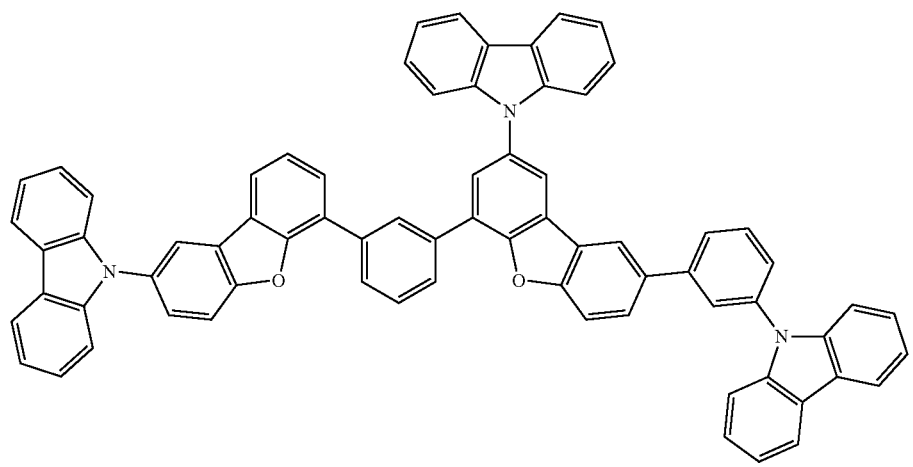
III-54
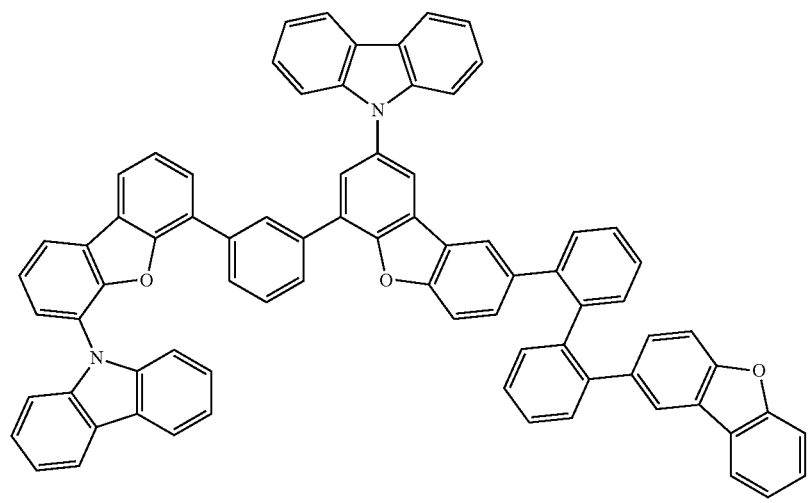
III-55
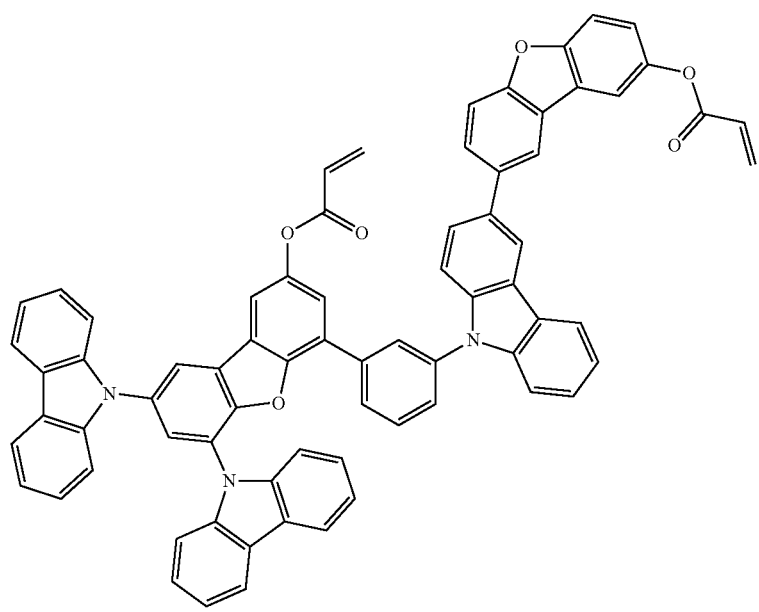

III-56
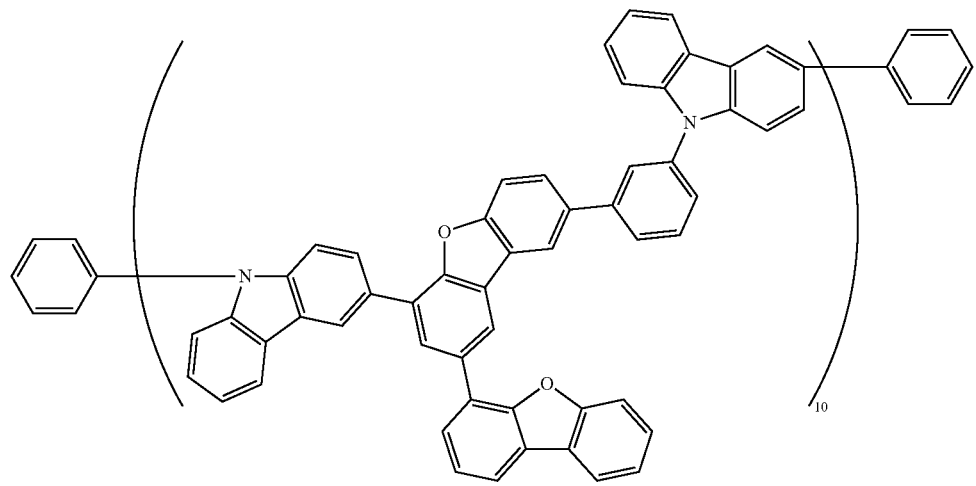
III-57
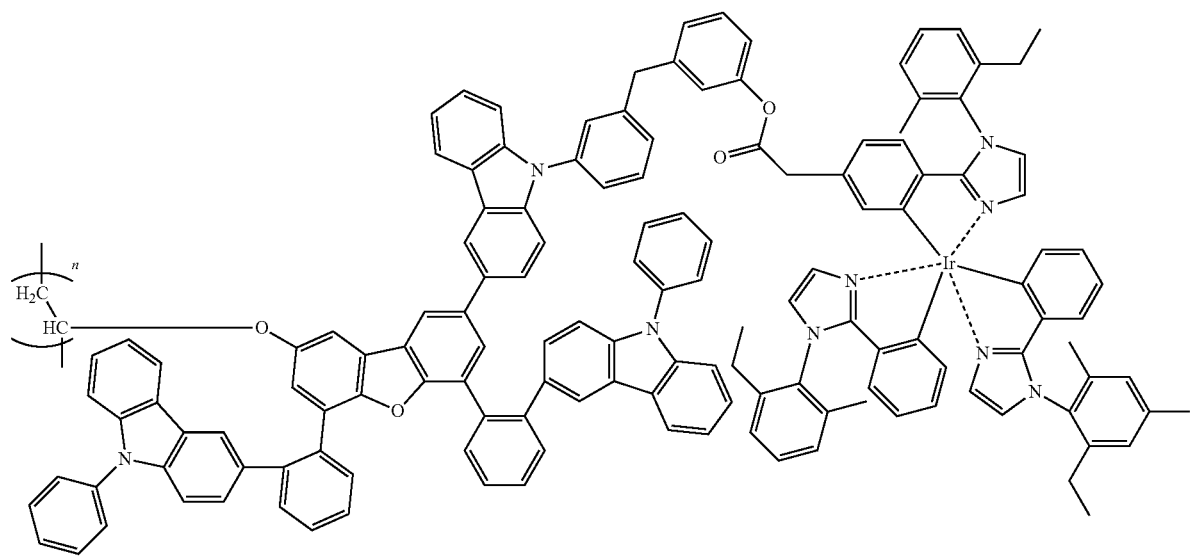
III-58
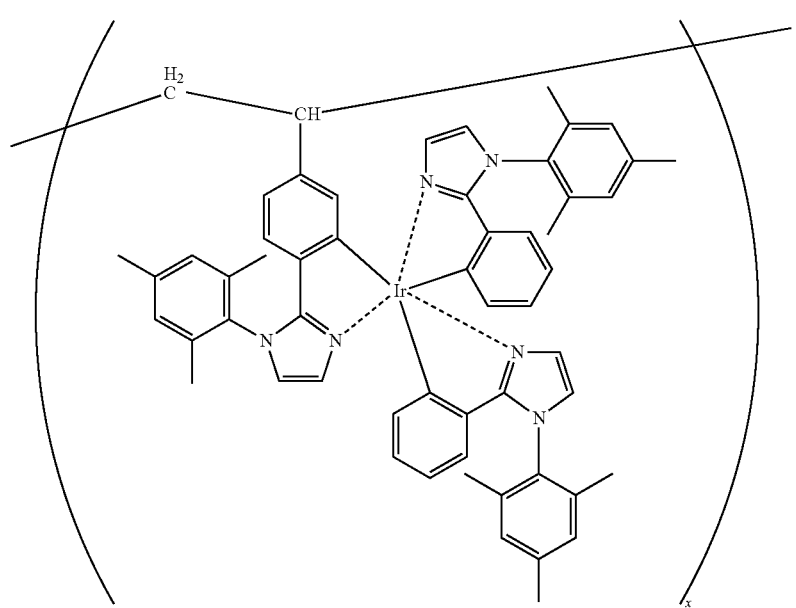

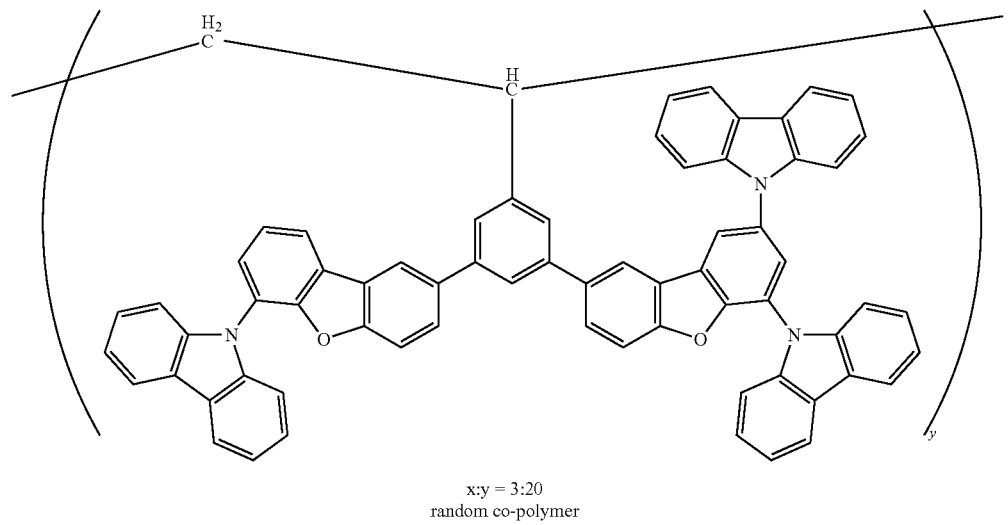
x:y = 3:20
random co-polymer
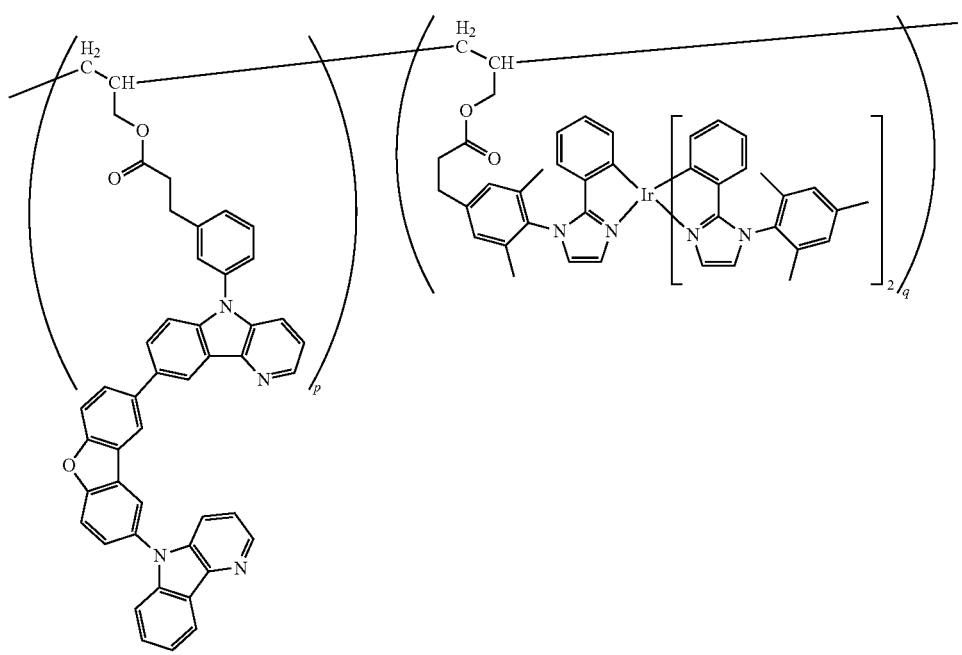
III-59

-continued
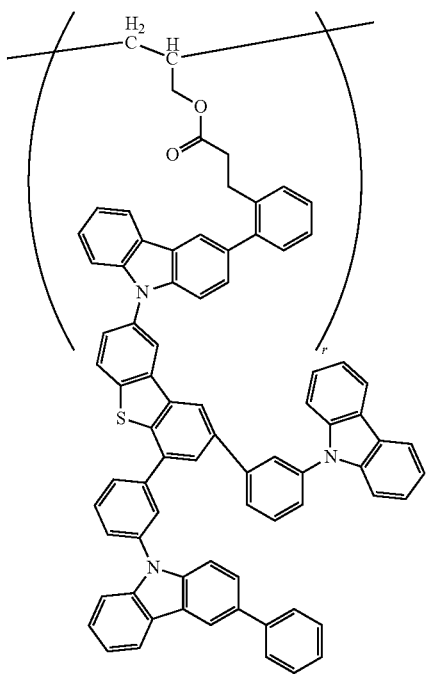
III-60
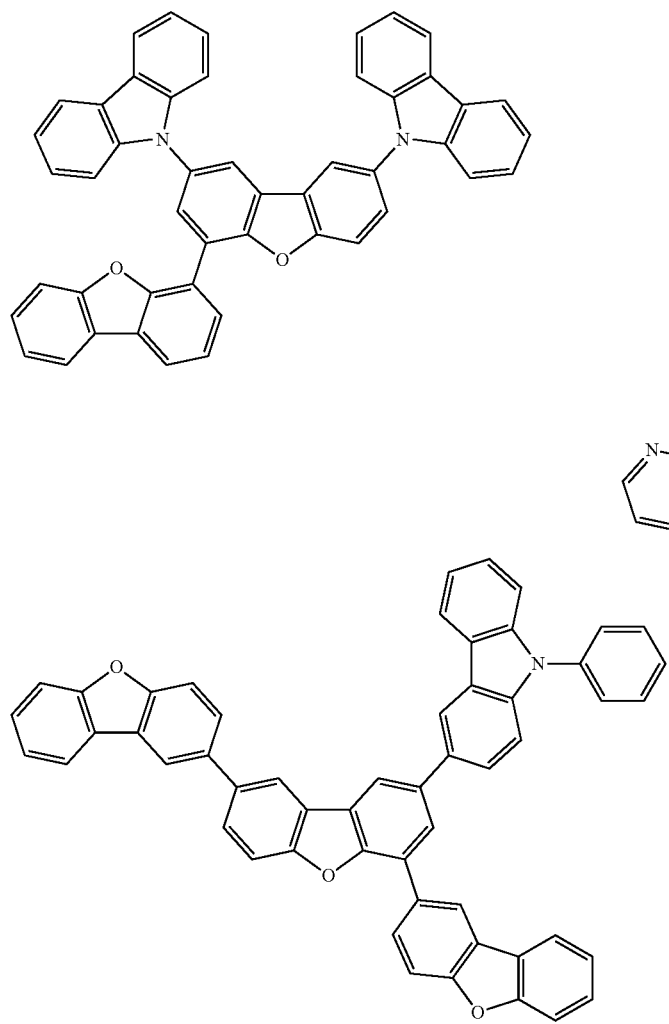
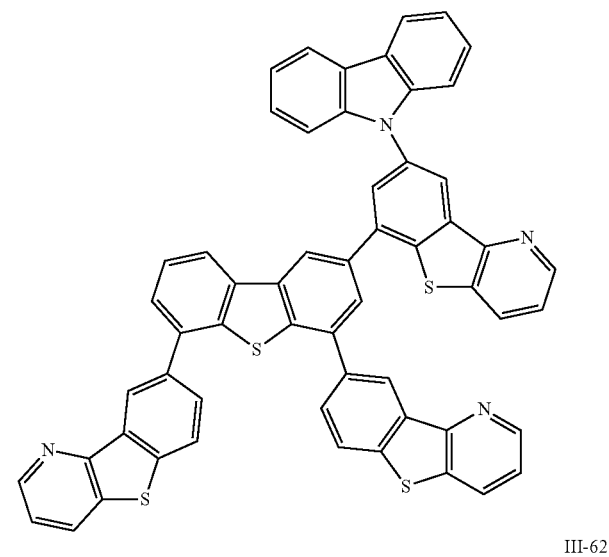
III-61
III-62

-continued
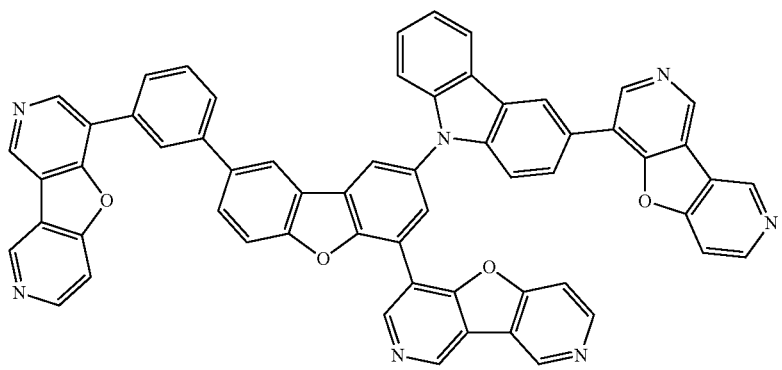
III-63
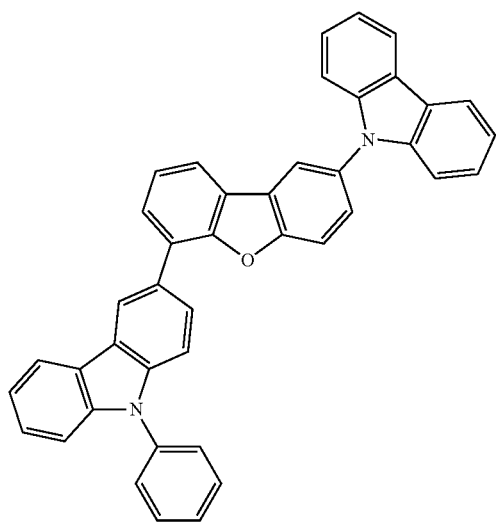
IV-1
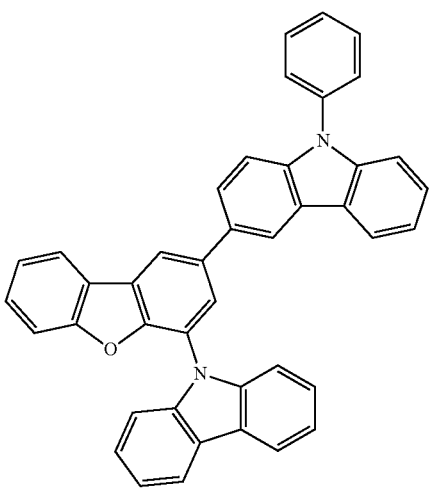
IV-2
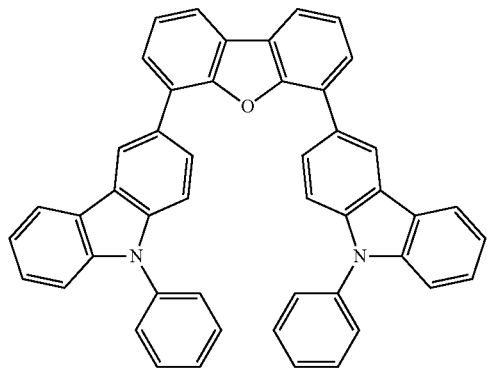
IV-3
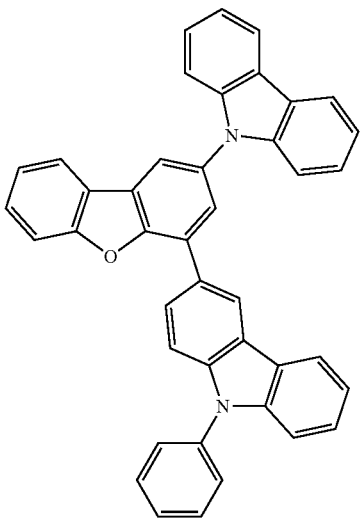
IV-4

-continued
IV-5
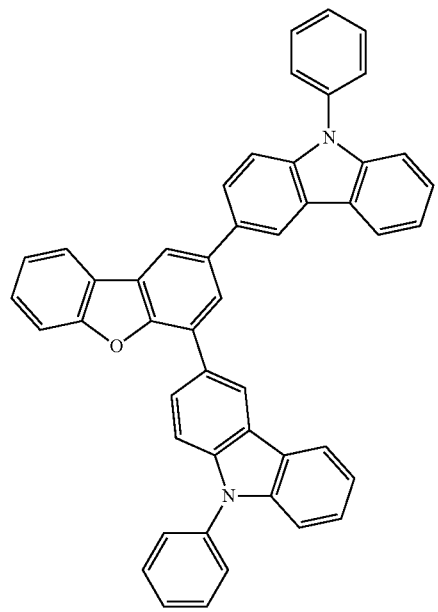
IV-6
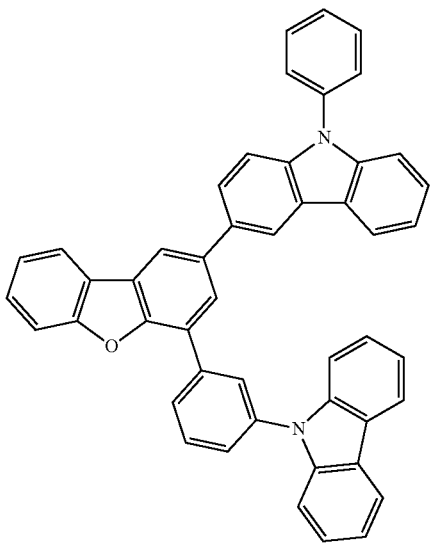
IV-7
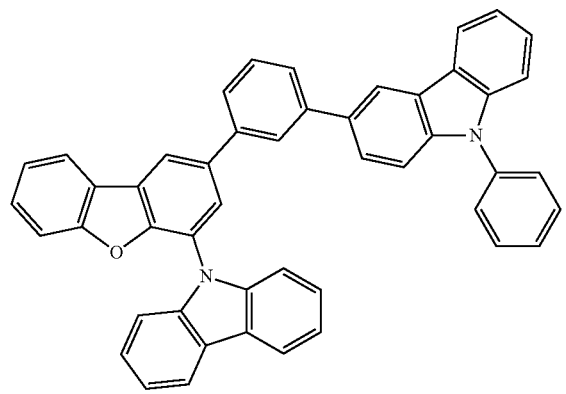
IV-8
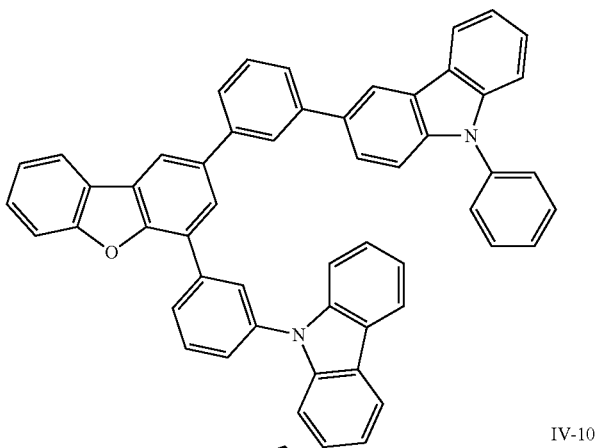
IV-9
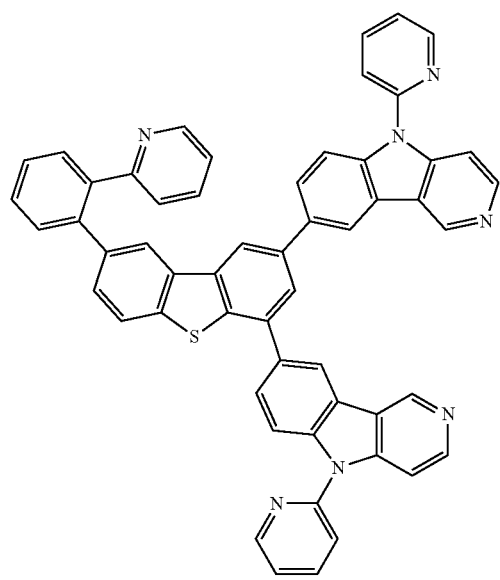
IV-10
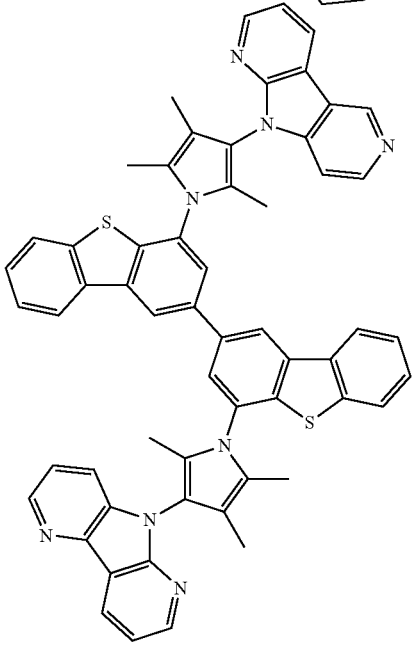

IV-11
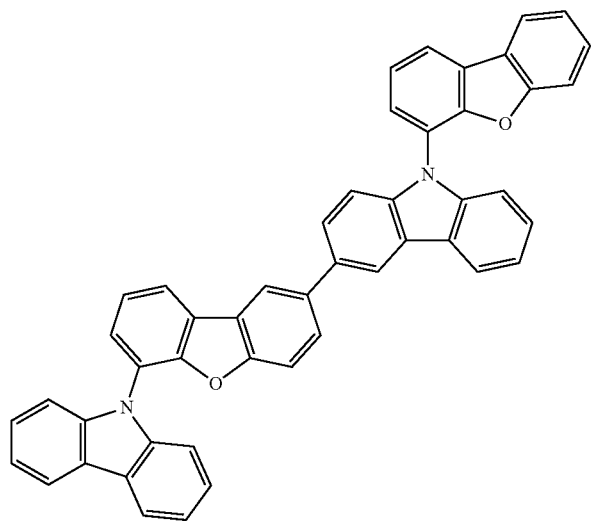
IV-12
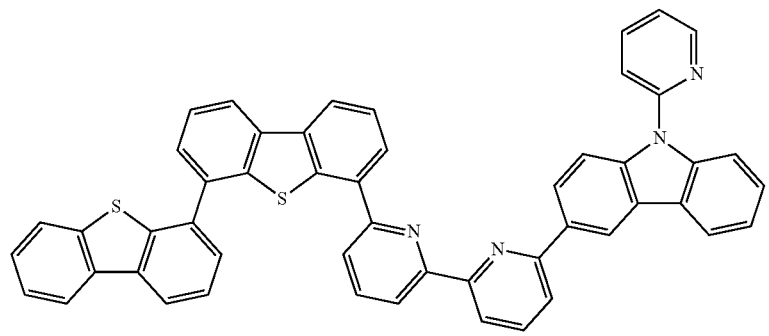
IV-13
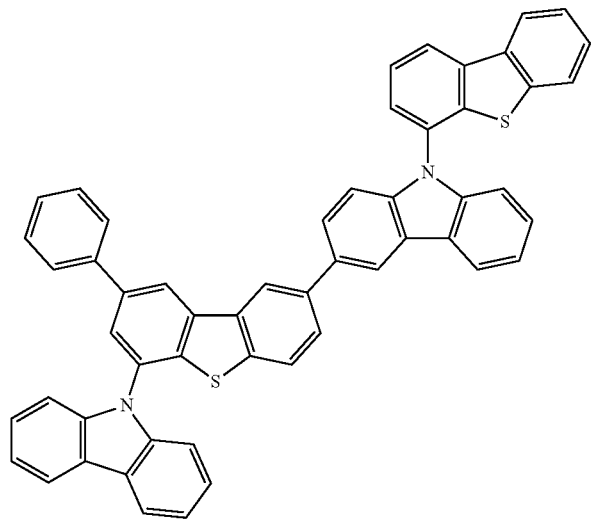

-continued
IV-14
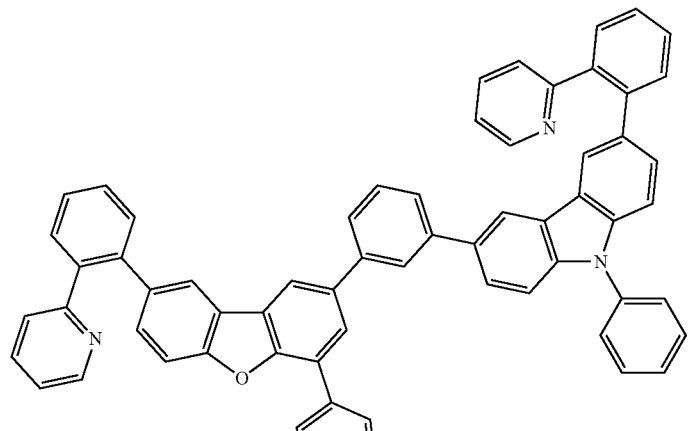
IV-15
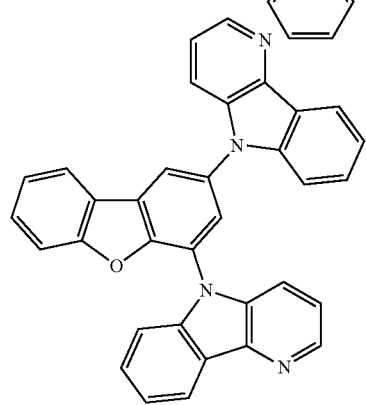
IV-16
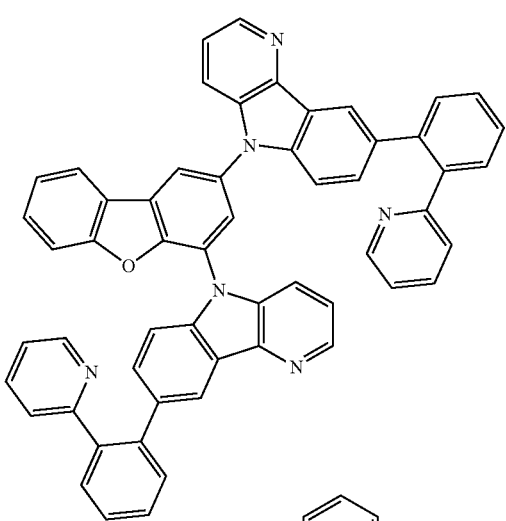
IV-17
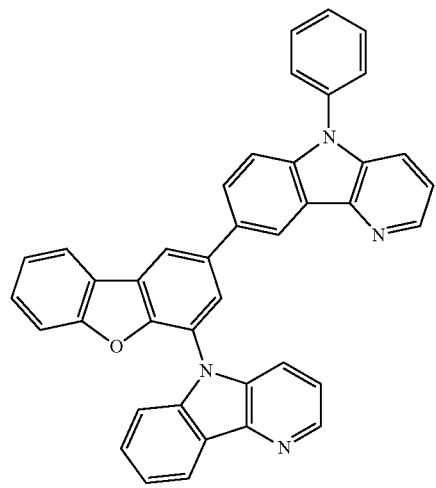
IV-18
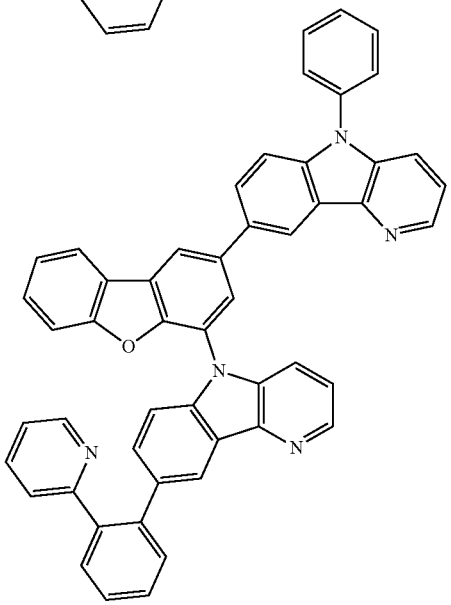

-continued
IV-19
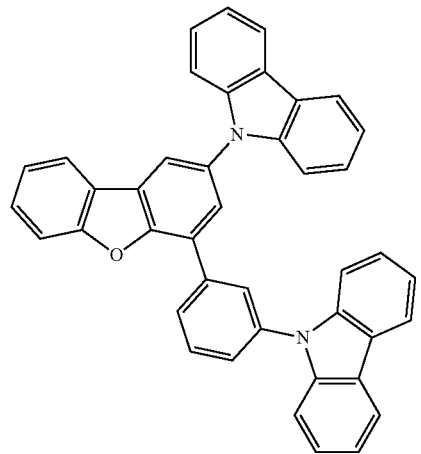
IV-20
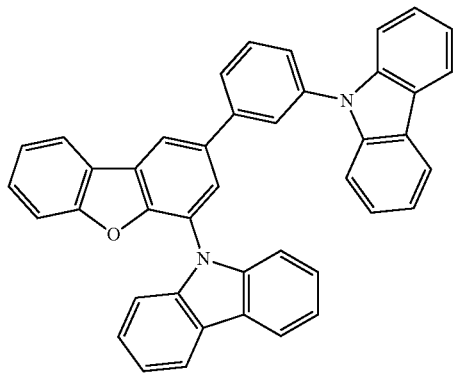
IV-21
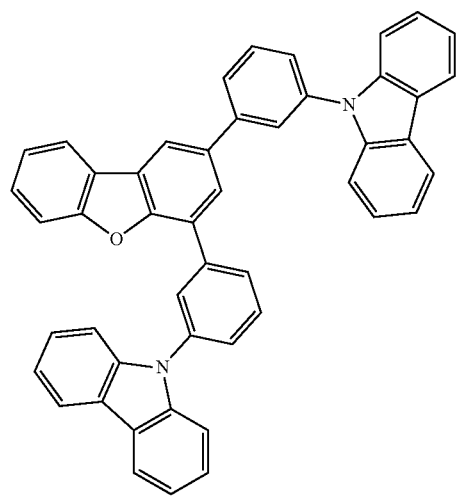
IV-22
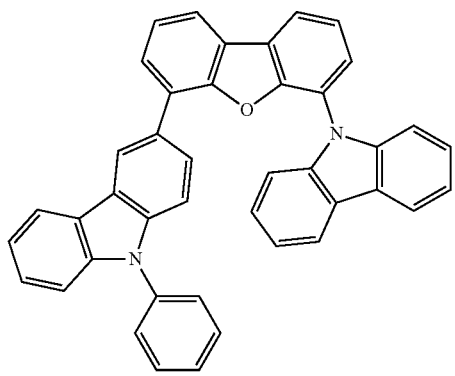
IV-23
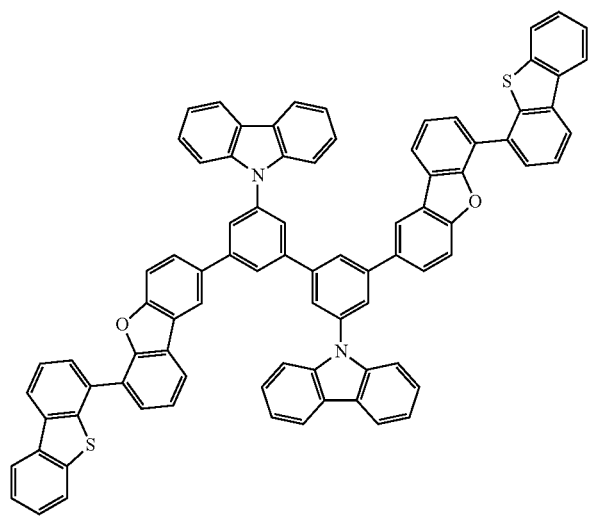
IV-24
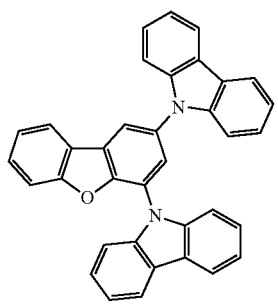

-continued
IV-25
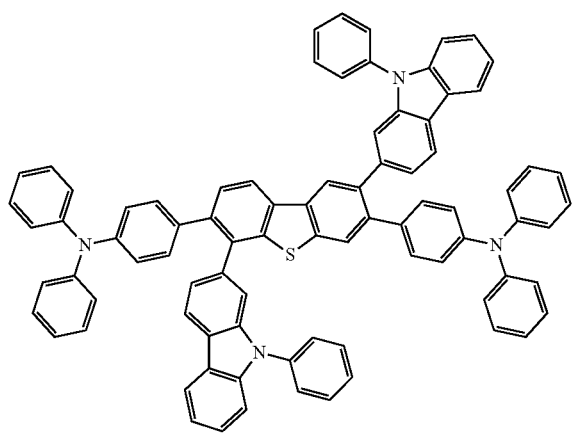
IV-26
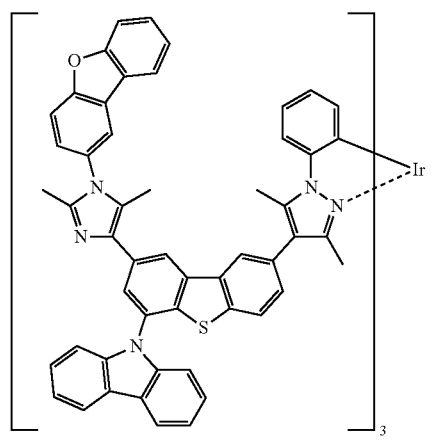
IV-27
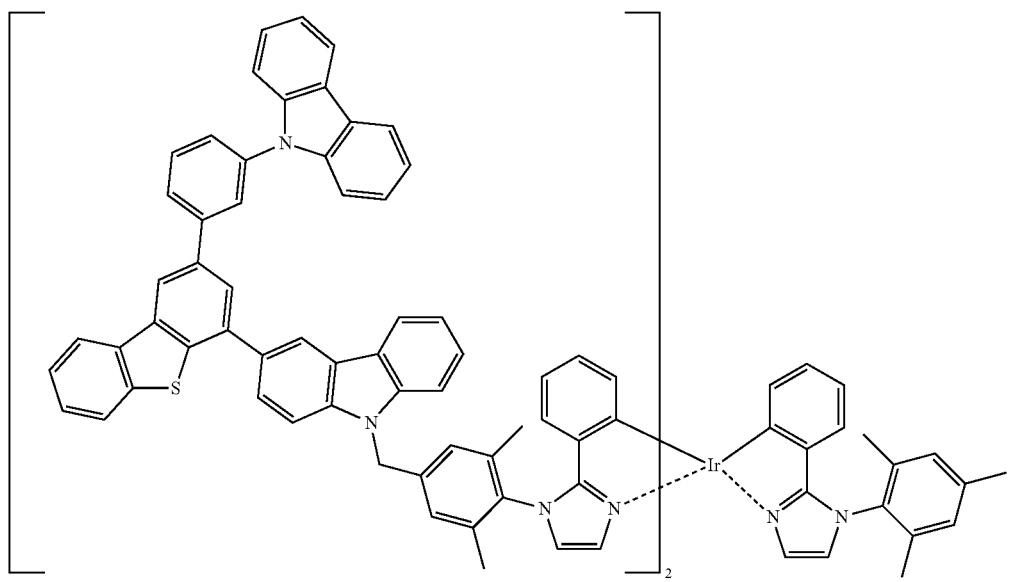
IV-28
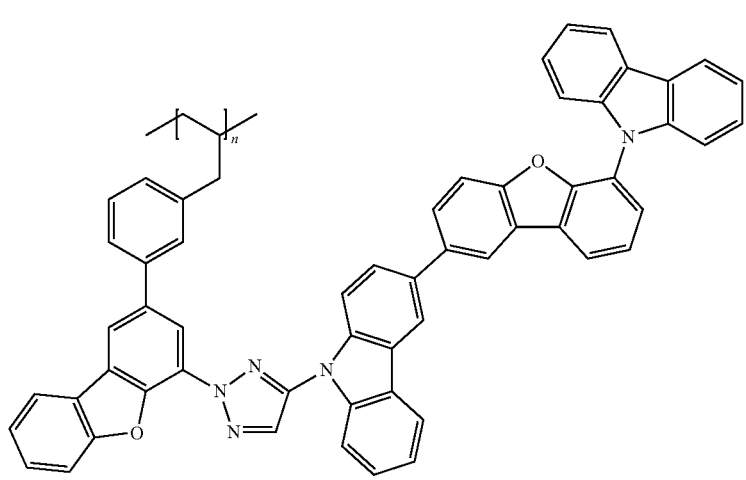

-continued
IV-29
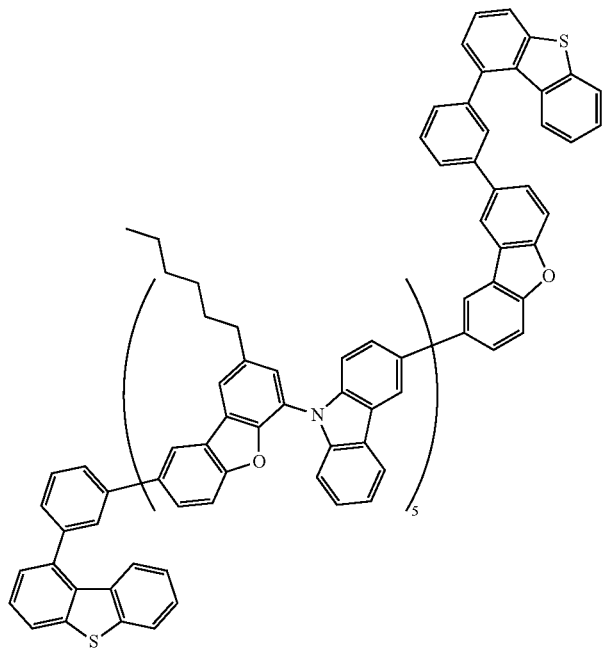
IV-30
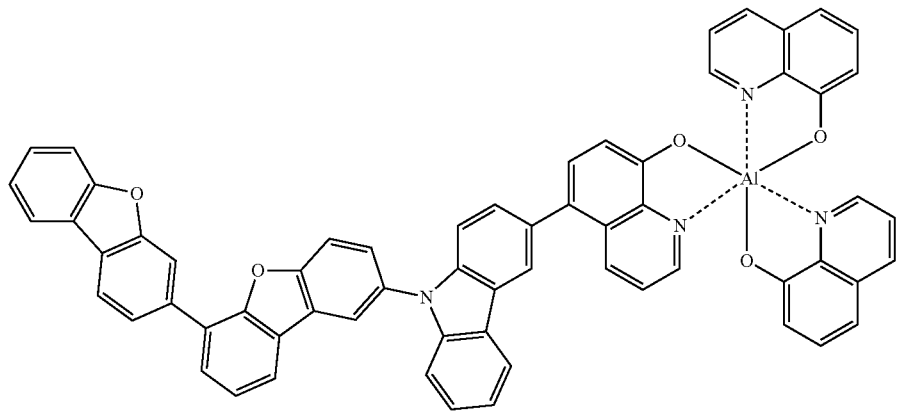
IV-31
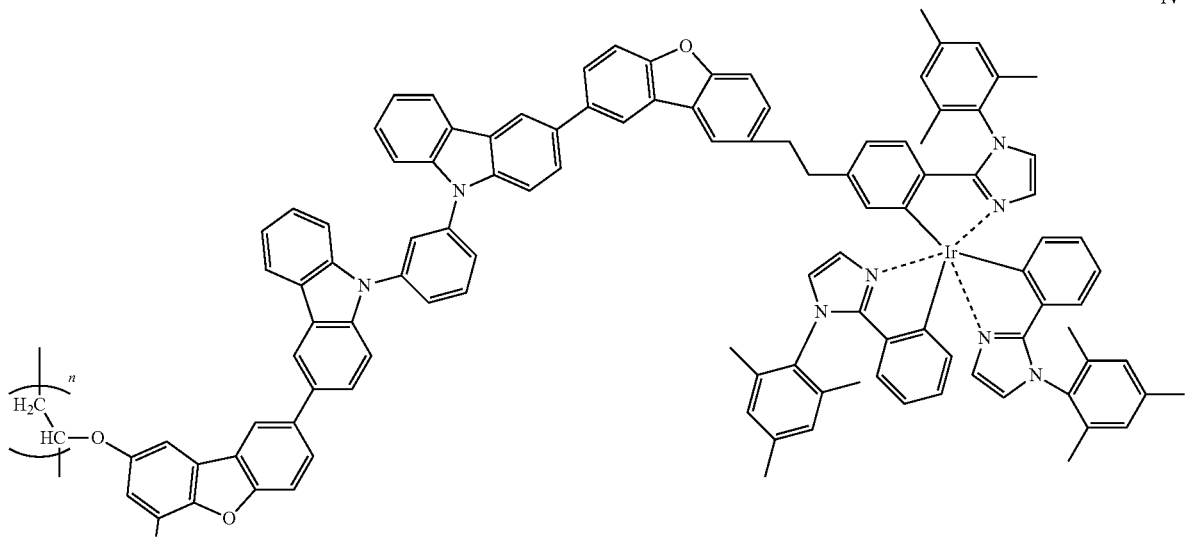

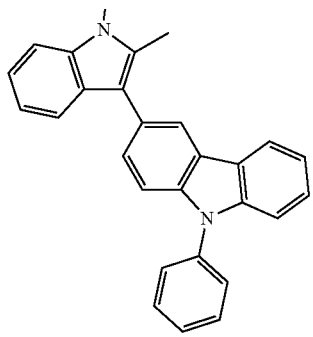
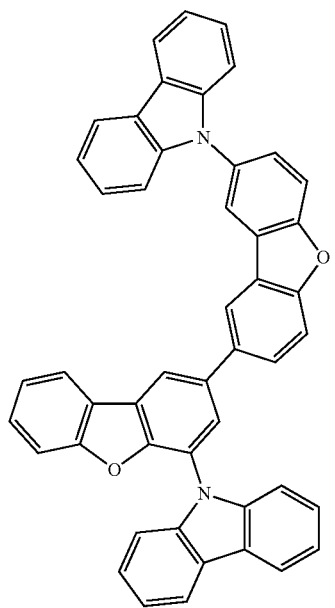
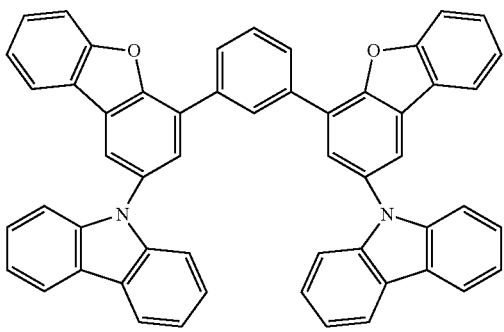
IV-32
IV-33
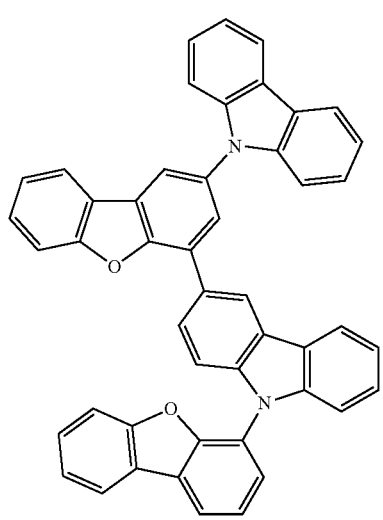
IV-34
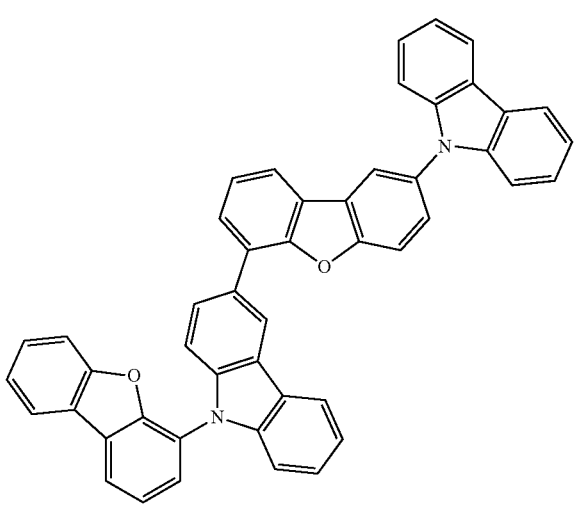
IV-35

IV-36

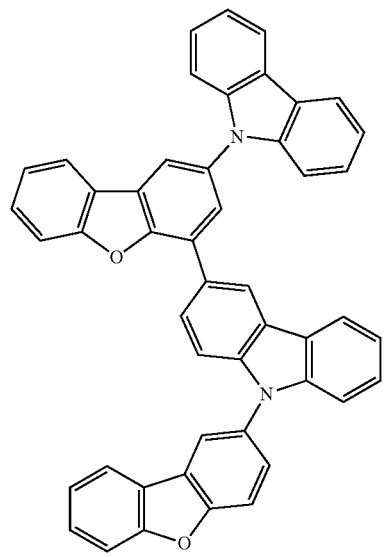

IV-37

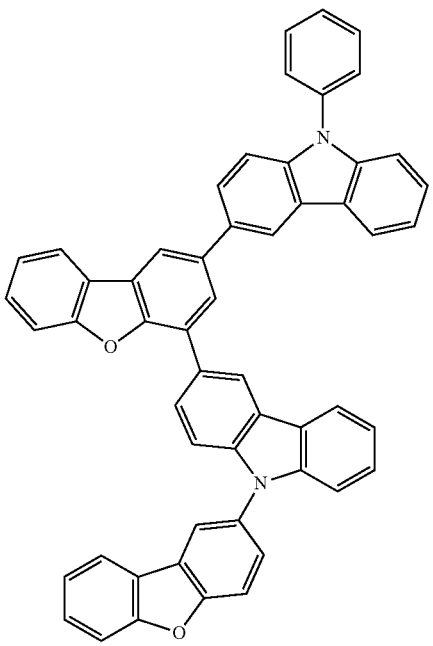

IV-38

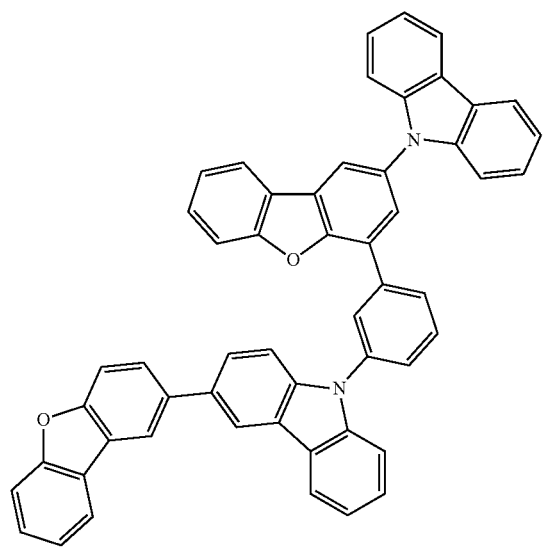

The compound represented by Formula (1) of the present invention can be synthesized with reference to the well-known way of method described in WO 07/111,176, Chem. Mater., 2008, 20, 5951, Experimental Chemistry Lectures, the 5th edition (edited by The Chemical Society of Japan).

A synthetic example of a representative compound is shown below.

<Synthesis of example compound 1>

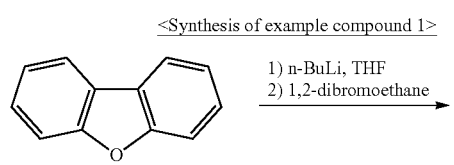

1) n-BuLi, THF
2) 1,2-dibromoethane

-continued

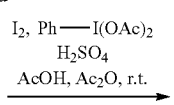

Intermediate 1

I$_2$, Ph—I(OAc)$_2$
H$_2$SO$_4$
AcOH, Ac$_2$O, r.t.

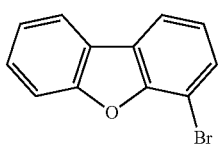

Intermediate 2

Cu
K$_2$CO$_3$
DMAc

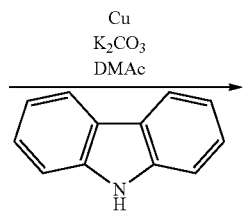

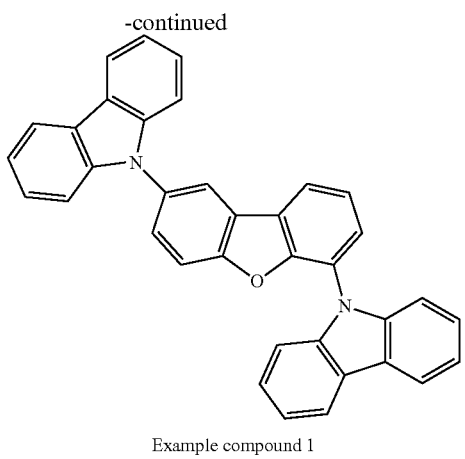

Example compound 1

Step 1: Synthesis of Intermediate 1

0.5 mol of dibenzofuran was added to 800 ml of dehydrated THF under a nitrogen atmosphere. After the solution was cooled to −7° C., 0.5 mol of n-butyl lithium in n-hexane solution (1.6 M/L) was dropped slowly and then the mixture was stirred for three hours. Subsequently, 0.5 mol of 1,2-dibromoethan was added and then the temperature of the solution was raised slowly and the solution was stirred at room temperature for five hours. After completion of reaction, toluene was added to the reaction mixture and the mixture was washed with water three times. After the organic phase was dried with anhydrous magnesium sulfate, the solvent in the organic phase was distilled away under reduced pressure. The obtained residue was purified with silica gel flash chromatography to obtain Intermediate 1 with a yield of 70%.

The structure of the obtain Intermediate 1 was confirmed with a nuclear magnetic resonance spectrum and a mass spectrum.

Step 2: Synthesis of Intermediate 2

0.3 mol of Intermediate 1, 0.15 mol of iodine, 0.15 mol of phenyl iodide diacetate were added to the mixture of 100 ml of acetic acid and 100 ml of acetic anhydride under a nitrogen atmosphere, then added one drop of sulfuric acid. The mixture was stirred at room temperature for ten hours. After completion of reaction, toluene was added to the reaction mixture and the mixture was washed with water three times. After the organic phase was dried with anhydrous magnesium sulfate, the solvent in the organic phase was distilled away under reduced pressure. The obtained residue was purified with silica gel flash chromatography to obtain Intermediate 2 with a yield of 60%.

The structure of the obtain Intermediate 2 was confirmed with a nuclear magnetic resonance spectrum and a mass spectrum.

Step 3: Synthesis of Example compound 1

0.15 mol of Intermediate 2, 0.3 mol of carbazole, 0.45 mol of cupper powder and 0.25 mol of potassium carbonate were added to 50 ml of dimethyl acetoamide (DMAc), then, the mixture was stirred for 24 hours at 130° C. After the reaction mixture was cooled to room temperature, cupper powder was filtered off. 200 ml of toluene was added to the filtrate, then the solution was washed with water three times. After the organic phase was dried with anhydrous magnesium sulfate, the solvent in the organic phase was distilled away under reduced pressure. The obtained residue was purified with silica gel flash chromatography to obtain Example compound 1 with a yield of 80%.

The structure of the obtain Intermediate 2 was confirmed with a nuclear magnetic resonance spectrum and a mass spectrum.

Each of the layers which constitute the organic EL element of the present invention will now be sequentially detailed. Preferred embodiments of the organic EL element of the present invention will be described below, however, the present invention is not limited to these.

(i) anode/light emitting layer/electron transport layer/cathode
(ii) anode/positive hole transport layer/light emitting layer/electron transport layer/cathode
(iii) anode/positive hole transport layer/light emitting layer/positive hole inhibition layer/electron transport layer/cathode
(iv) anode/positive hole transport layer/light emitting layer/positive hole inhibition layer/electron transport layer/cathode buffer layer/cathode
(v) anode/anode buffer layer/positive hole transport layer/light emitting layer/positive hole inhibition layer/electron transport layer/cathode buffer layer/cathode
(vi) anode/positive hole transport layer/anode buffer layer/light emitting layer/positive hole inhibition layer/electron transport layer/cathode buffer layer/cathode
(vii) anode/anode buffer layer/positive hole transport layer/light emitting layer/electron transport layer/cathode buffer layer/cathode The light emitting layer may be a light emitting unit composed of a plurality of light emitting layers.

Further, there may be present a non-light emitting intermediate layer between the light emitting layers. The intermediate layer may contain a charge generating layer. The organic EL element of the present invention have preferably a white light emitting layer, and lighting devices employing these are preferred.

Each of the layers which constitute the organic EL elements of the present invention will now be sequentially detailed.

<Electron Transport Layer>

An electron transport layer is composed of a material having a function to transfer an electron, and an electron injection layer and a positive hole inhibition layer are included in an electron transport layer in a broad meaning. A single layer or plural layers of an electron transport layer may be provided.

Electron transport materials (also including a positive hole inhibition material and an electron injection material) employed in the electron transport layer are only required to have a function of transporting electrons ejected from the cathode to the light emitting layer. As such materials, any of the conventional compounds may be selected and employed.

Examples of the conventional compounds (hereafter they are called as electron transport materials) which can be used in an electron transport layer include: a nitro-substituted fluorene derivative, a diphenylquinone derivative, a thiopyradineoxide derivative, a heterocyclic tetracarboxylic acid anhydride of naphthelene or perylene, carbodiimide, a fluorenylidenemethane derivative, anthraquinonedimethane, an anthrone derivative, an oxadiazole derivative, an azacarbazole derivative including a carboline derivative.

Here, the term "an azacarbazole derivative" indicates a compound having a structure formed by one or more of the carbon atoms which constitute a carbazole ring are replaced with the nitrogen atom.

Further, a thiadiazole derivative in which an oxygen atom in the oxadiazole ring of the above-described oxadiazole derivative is substituted by a sulfur atom, and a quinoxaline derivative having a quinoxaline ring which is known as an electron attracting group can be utilized as an electron transport material.

Polymer materials, in which these materials are introduced in a polymer chain or these materials form the main chain of polymer, can be also utilized.

Further, a metal complex of a 8-quinolinol derivative such as tris(8-quinolinol) aluminum (Alq$_3$), tris(5,7-dichloro-8-quinolinol)aluminum, tris(5,7-dibromo-8-quinolinol)aluminum, tris(2-methyl-8-quinolinol)aluminum, tris(5-methyl-8-quinolinol)aluminum and bis(8-quinolinol)zinc (Znq); and metal complexes in which a central metal of the aforesaid metal complexes is substituted by In, Mg, Cu, Ca, Sn, Ga or Pb, can be also utilized as an electron transport material.

Further, metal-free or metal phthalocyanine, or those the terminal of which is substituted by an alkyl group and a sulfonic acid group, can be preferably utilized as an electron transport material.

Moreover, similarly to the case of a positive hole injection layer and to the case of a positive hole transfer layer, an inorganic semiconductor such as an n-type-Si and an n-type-SiC can be also utilized as an electron transport material.

The electron transport layer can be preferably prepared by forming a thin layer made of the above-described electron transport material with a vacuum evaporation method or a wet preparation method. A wet preparation method is also called as a wet process, and examples of this include: a spin coating method, a cast method, a die coating method, a blade coating method, a roll coating method, an inkjet method, a printing method, a spray coating method, a curtain coating method, and a LB method (Langmuir Blodgett method).

The preparation method of the constituting layers of the organic EL element will be described in detain in the portion of preparation of an organic EL element.

The layer thickness of the electron transport layer of the present invention is not specifically limited; however, it is generally 5 nm-5,000 nm, and preferably it is 5 nm-200 nm. This electron transport layer may be a single layer structure containing of one or more types of the above described materials.

Further, it is possible to employ an electron transport layer doped with impurities, which exhibits high n property. Examples thereof include those, described in JP-A Nos. 4-297076, 10-270172, 2000-196140, 2001-102175, as well as J. Appl. Phys., 95, 5773 (2004).

Next, there will be listed specific example compounds known in the art and preferably used in the electron transport layer of the white light emitting organic EL element. However, the present invention is not limited to them.

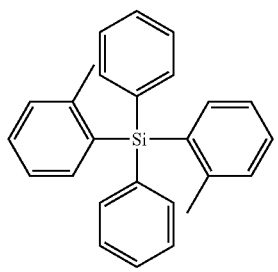

ET-1

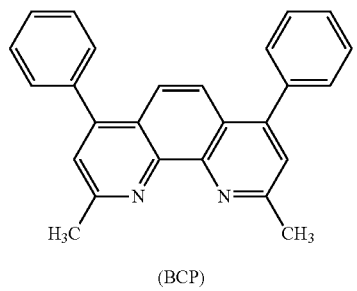

(BCP)

ET-2

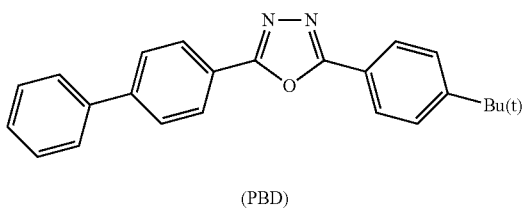

(PBD)

ET-3

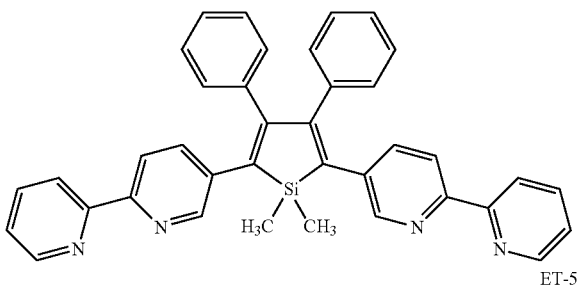

ET-4

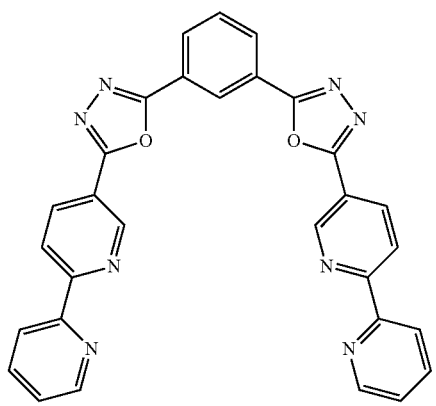

ET-5

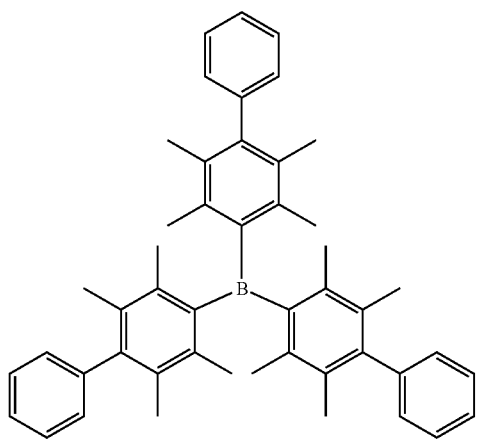

ET-6

-continued

ET-7

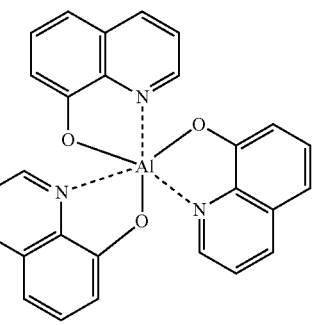

(Alq3)

ET-8

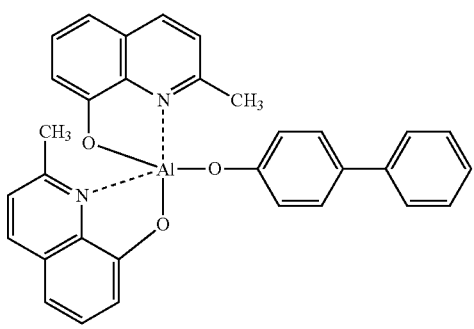

(BAlq)

ET-9

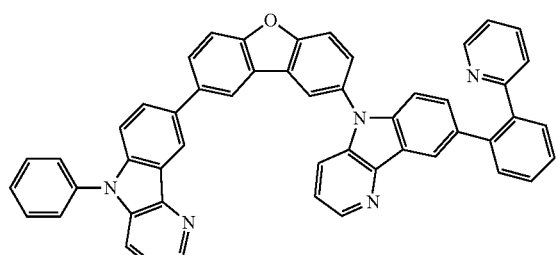

ET-10

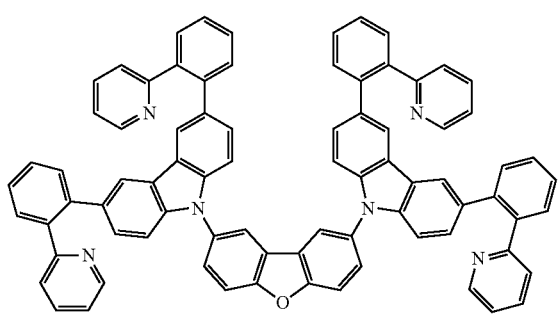

ET-11

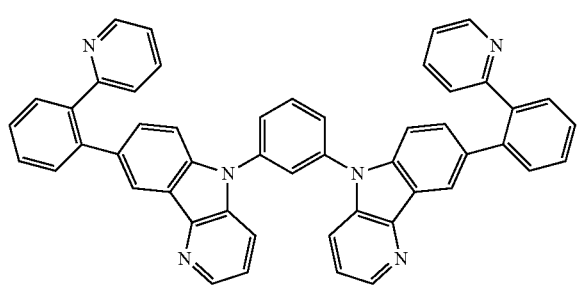

Particularly preferable compounds as an electron transport material used for the organic EL element of the present invention are compounds mentioned above and represented by the Formula (1) or Formula (2) of the present invention. Specific examples are exemplified compounds 1 to 79 which were shown above.

<Light Emitting Layer>

The light emitting layer of the present invention is a layer, which emits light via recombination of electrons and positive holes injected from an electrode or a layer such as an electron transport layer or a positive hole transport layer. The light emission portion may be present either within the light emitting layer or at the interface between the light emitting layer and an adjacent layer thereof.

The total thickness of the light emitting layer is not particularly limited. However, in view of the layer homogeneity, the minimization of application of unnecessary high voltage during light emission, and the stability enhancement of the emitted light color against the drive electric current, the layer thickness is regulated preferably in the range of 2 nm-5 µm, more preferably in the range of 2 nm-200 nm, but most preferably in the range of 5 nm-100 nm.

The light emitting layer can be prepared by forming a thin layer made of a light emitting dopant and a host compound, which will be described later, with a vacuum evaporation method or a wet preparation method. A wet preparation method is also called as a wet process, and examples of this include: a spin coating method, a cast method, a die coating method, a blade coating method, a roll coating method, an inkjet method, a printing method, a spray coating method, a curtain coating method, and a LB method (Langmuir Blodgett method).

When using the compound of the present invention for a light emitting layer, preparation with a wet process is preferable.

It is preferable that the light emitting layer of the organic EL element of the present invention incorporates at least two kinds of compounds: one is a light emitting dopant (a phosphorescent emitting dopant (or it is called as a phosphorescence dopant or a phosphorescence emitting dopant group) or a fluorescent dopant) and the other is a light emitting host compound.

(Light Emitting Dopant Compound)

The light emitting dopant compound (it may be called as the light emitting dopant) of the present invention will now be described.

As light emitting dopants according to the present invention, it can be employed fluorescent dopants (also referred to as fluorescent compounds) and phosphorescent dopants (also referred to as phosphorescent emitting materials, phosphorescent compounds or phosphorescence emitting compounds).

(Phosphorescent Dopant (Also Referred to as Phosphorescence Emitting Dopant))

A phosphorescence dopant of the present invention will be described.

The phosphorescent dopant of the present invention is a compound, wherein emission from an excited triplet state thereof is observed, specifically, emitting phosphorescence at room temperature (25° C.) and exhibiting a phosphorescence quantum yield of at least 0.01 at 25° C. The phosphorescence quantum yield is preferably at least 0.1.

The phosphorescence quantum yield can be determined via a method described in page 398 of Bunko II of Dai 4 Han Jikken Kagaku Koza 7 (Spectroscopy II of 4th Edition Lecture of Experimental Chemistry 7) (1992, published by Maruzen Co., Ltd.). The phosphorescence quantum yield in a solution can be determined using appropriate solvents. However, it is only necessary for the phosphorescent dopant of the present invention to exhibit the above phosphorescence quantum yield using any of the appropriate solvents.

Two kinds of principles regarding emission of a phosphorescent dopant are cited. One is an energy transfer-type, wherein carriers recombine on a host compound on which the carriers are transferred to produce an excited state of the host compound, and then via transfer of this energy to a phosphorescent dopant, emission from the phosphorescence-emitting dopant is realized. The other is a carrier trap-type, wherein a phosphorescence-emitting dopant serves as a carrier trap and then carriers recombine on the phosphorescent dopant to generate emission from the phosphorescent dopant. In each case, the excited state energy of the phosphorescent dopant is required to be lower than that of the host compound.

The light emitting layer of the present invention may further incorporate the compounds described in the following patent documents.

The patent documents are: WO 00/70655 pamphlet, JP-A Nos. 2002-280178, 2001-181616, 2002-280179, 2001-181617, 2002-280180, 2001-247859, 2002-299060, 2001-313178, 2002-302671, 2001-345183 and 2002-324679, WO 02/15645 pamphlet, JP-A Nos. 2002-332291, 2002-50484, 2002-322292 and 2002-83684, Japanese Translation of PCT International Application Publication No. 2002-540572, JP-A Nos. 2002-117978, 2002-338588, 2002-170684 and 2002-352960, WO 01/93642 pamphlet, JP-A Nos. 2002-50483, 2002-100476, 2002-173674, 2002-359082, 2002-175884, 2002-363552, 2002-184582 and 2003-7469, Japanese Translation of PCT International Application Publication No. 2002-525808, JP-A 2003-7471, Japanese Translation of PCT International Application Publication No. 2002-525833, JP-A Nos. 2003-31366, 2002-226495, 2002-234894, 2002-235076, 2002-241751, 2001-319779, 2001-319780, 2002-62824, 2002-100474, 2002-203679, 2002-343572 and 2002-203678.

(Fluorescent Dopants (Also Referred to as Fluorescent Compounds))

As fluorescent dopants, listed are compounds exhibiting a high fluorescent quantum efficiency such as: coumarin based dyes, pyran based dyes, cyanine based dyes, croconium based dyes, squarylium based dyes, oxobenzanthracene based dyes, fluorescein based dyes, Rhodamine based dyes, pyrylium based dyes, perylene based dyes, stilbene based dyes, polythiophene based dyes, rare earth complex based fluorescent materials, or laser dyes.

Moreover, two or more sorts of compounds may be combined together and used for the light emitting dopants of the present invention. It is possible to use in combination with phosphorescence dopants each having a different structure or to use in combination of a fluorescence dopant and a phosphorescence dopant.

In the present invention, a dopant compound is preferably a compound represented by the following Formula (3), and it is more preferably a compound represented by the following Formula (4)

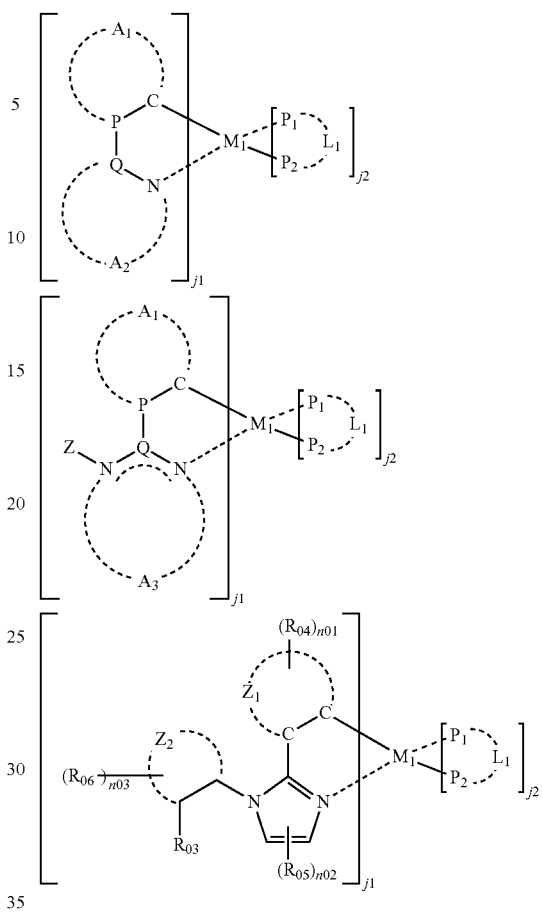

In Formula (3), P and Q each respectively represent a carbon atom or a nitrogen atom, and $A_1$ represents an atomic group which forms an aromatic hydrocarbon ring or an aromatic heterocycle with P—C. $A_2$ represents an atomic group which forms an aromatic heterocycle with Q-N. $P_1$-$L_1$-$P_2$ represents a bidentate ligand, and $P_1$ and $P_2$ each respectively represent a carbon atom, a nitrogen atom, or an oxygen atom. $L_1$ represents an atomic group which forms a bidentate ligand with $P_1$ and $P_2$. Although $j_1$ represents an integer of 1 to 3 and $j_2$ represents an integer of 0 to 2, $j_1$+$j_2$ is an integer of 2 or 3. $M_1$ represents the transition metal element of the $8^{th}$ group to $10^{th}$ group in the periodic table of the elements.

In Formula (3), examples of an aromatic hydrocarbon ring which is formed by $A_1$ combined with P—C include: a benzene ring, a biphenyl ring, a naphthalene ring, an azulene ring, an anthracene ring, a phenanthrene ring, a pyrene ring, a chrysene ring, a naphthacene ring, a triphenylene ring, α-terphenyl ring, m-terphenyl ring, p-terphenyl ring, an acenaphthene ring, a coronene ring, a fluorene ring, a fluoanthrene ring, a naphthacene ring, a pentacene ring, a perylene ring, a pentaphene ring, a picene ring, a pyrene ring, a pyranthrene ring and an anthraanthrene ring.

These rings may further have a substituent represented by $Y_1$ to $Y_3$ in Formula (1).

In Formula (3), examples of an aromatic heterocycle which is formed by $A_1$ combined with P—C include: a furan ring, a thiophene ring, an oxazole ring, a pyrrole ring, a pyridine ring, a pyridazine ring, a pyrimidine ring, a pyrazine ring, a triazine ring, a benzimidazole ring, an oxadiazole ring, a triazole ring, an imidazole ring, a pyrazole ring, a triazole ring, an indole ring, a benzimidazole ring, a benzothiazole ring, a benzooxazole ring, a quinoxaline ring, a quinazoline ring, a phthalazine ring, a carbazole ring and an azacarbazole ring.

Here, an azacarbazole ring indicates a ring structure in which one or plural carbon atoms constituting the aforesaid carbazole ring is replaced with one or plural nitrogen atoms.

These rings may further have a substituent represented by $Y_1$ to $Y_3$ in Formula (1).

In Formula (3), examples of an aromatic heterocycle which is formed by $A_2$ combined with Q-N include: an oxazole ring, an oxadiazole ring, an oxatriazole ring, an isoxazole ring, a tetrazole ring, a thiadiazole ring, a thiatriazole ring, an isothiazole ring, a pyrrole ring, a pyridine ring, a pyridazine ring, a pyrimidine ring, a pyrazine ring, a triazine ring, an imidazole ring, a pyrazole ring and a triazole ring.

These rings may further have a substituent represented by $Y_1$ to $Y_3$ in Formula (1).

In Formula (3), examples of a bidentate ligand represented by $P_1$-$L_1$-$P_2$ include: phenylpyridine, phenylpyrazole, phenylimidazole, phenyltriazole, phenyltetrazole, pyrazabol, acetylacetone and picolinic acid.

In Formula (3), although $j_1$ represents an integer of 1 to 3 and $j_2$ represents an integer of 0 to 2, $j_1+j_2$ is 2 or 3. In particular, $j_2$ is preferably 0.

In Formula (3), $M_1$ represents a transition metal element of the $8^{th}$ group to $10^{th}$ group (simply it is called as a transition metal) in the periodic table of the elements. In particular, $M_1$ is preferably iridium.

Among the compounds represented by Formula (3) of the present invention, the compounds represented by Formula (4) are preferable.

In Formula (4), Z represents a hydrocarbon ring group or a heterocycle group. P, Q, $A_1$, $P_1$, $P_2$, $j_1$, $j_2$, and $M_1$ are abovementioned Formula (3). $P_1$-$L_1$-$P_2$ represents a bidentate ligand, and $j_1+j_2$ is an integer of 2 or 3.

$A_3$ represents —C($R_{01}$)=C($R_{01}$)—, —N=C($R_{02}$)—, —C($R_{01}$)=N—, or —N=N—, and $R_{01}$ and $R_{01}$ each respectively represent a hydrogen atom or a substituent.

In Formula (4), as a hydrocarbon ring group represented by Z, a non aromatic hydrocarbon ring group and an aromatic hydrocarbon ring group are cited. And as a non aromatic hydrocarbon ring group, a cyclopropyl group, a cyclopentyl group and a cyclohexyl group are cited. These groups may have no substituent or may have a substituent later mentioned.

Moreover, as an aromatic hydrocarbon ring group (it is called an aromatic hydrocarbon group or an aryl group), examples include: a phenyl group, p-chlorophenyl group, a mesityl group, a tolyl group, a xylyl group, a naphthyl group, an anthryl group, a azulenyl group, a acenaphthenyl group, a fluorenyl group, a phenanthryl group, an indenyl group, a pyrenyl group and a biphenylyl group.

These groups may have no substituent or may have a substituent represented by $Y_1$ to $Y_3$ in Formula (1).

In Formula (4), examples of a heterocycle represented by Z include: an epoxy ring, an aziridine ring, a thiirane ring, an oxetane ring, an azethidine ring, a thiethane ring, a tetrahydrofuran ring, a dioxolane ring, a pyrrolidine ring, a pyrazolidine ring, an imidazolidine ring, an oxazolidine ring, a tetrahydrothiophene ring, a sulfolane ring, a thiazolidine ring, an ε-caprolactone ring, an ε-caprolactam ring, a piperidine ring, a hexahydropyridazine ring, a hexahydropyrimidine ring, a piperazine ring, a morpholine ring, a tetrahydropyran ring, a 1,3-dioxane rings, a 1,4-dioxane ring, a trioxane ring, a tetrahydrothiopyran ring, a thiomorpholine ring, a thiomorpholine 1,1-dioxide ring, a pyranose ring and a diazabicyclo[2,2,2]-octane ring.

These rings may have no substituent, or they may have a substituent represented by $Y_1$ to $Y_3$ in Formula (1).

Examples of an aromatic heterocycle include: a pyridyl group, a pyrimidinyl group, a furyl group, a pyrrolyl group, an imidazolyl group, a benzimidazolyl group, a pyrazolyl group, a pyrazinyl group, a triazolyl group (for example, 1,2,4-triazole-1-yl group, 1,2,3-triazole-1-yl group), an oxazolyl group, a benzoxazolyl group, a thiazolyl group, an isooxazolyl group, an isothiazolyl group, a furazanyl group, a thienyl group, a quinolyl group, a benzofuryl group, a dibenzofuryl group, a benzothienyl group, a dibenzothienyl group, an indolyl group, a carbazolyl group, an azacarbazolyl group (here, "an azacarbazolyl group" indicates a ring structure in which one or plural carbon atoms constituting the aforesaid carbazolyl group is replaced with one or plural nitrogen atoms), a quinoxalinyl group, a pyridazinyl group, a triazinyl group, a quinazolinyl group and a phthalazinyl group.

These groups may have no substituent or may have a substituent represented by $Y_1$ to $Y_3$ in Formula (1).

The group represented by Z is preferably an aromatic hydrocarbon ring group or an aromatic heterocycle group.

Preferable examples of Z in Formula (4) are shown below, however, Z may have no substituent or may have further a substituent. Z is not limited to these examples. In addition, "*" indicated a linking position.

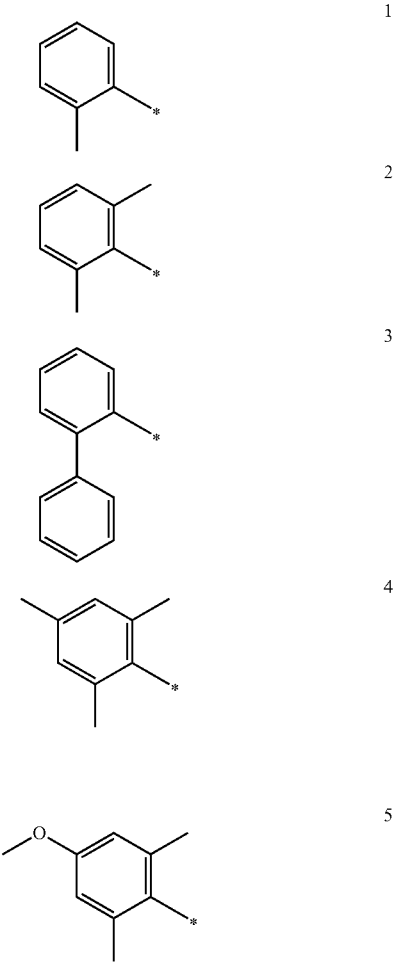

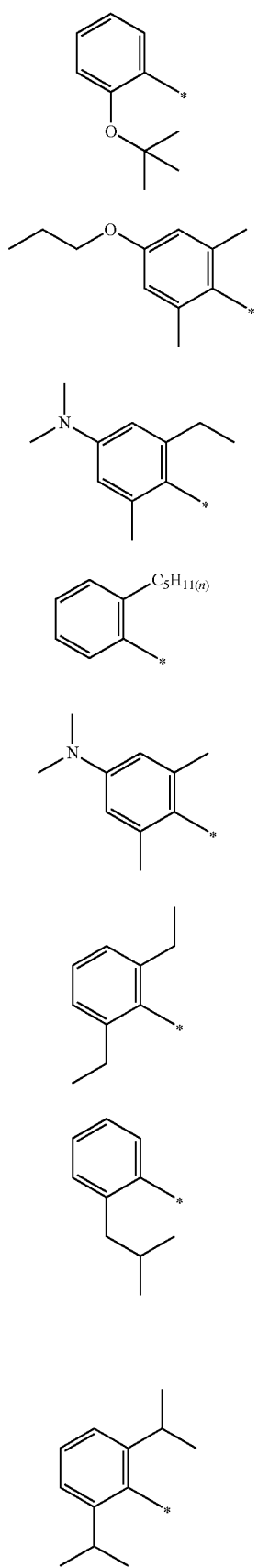
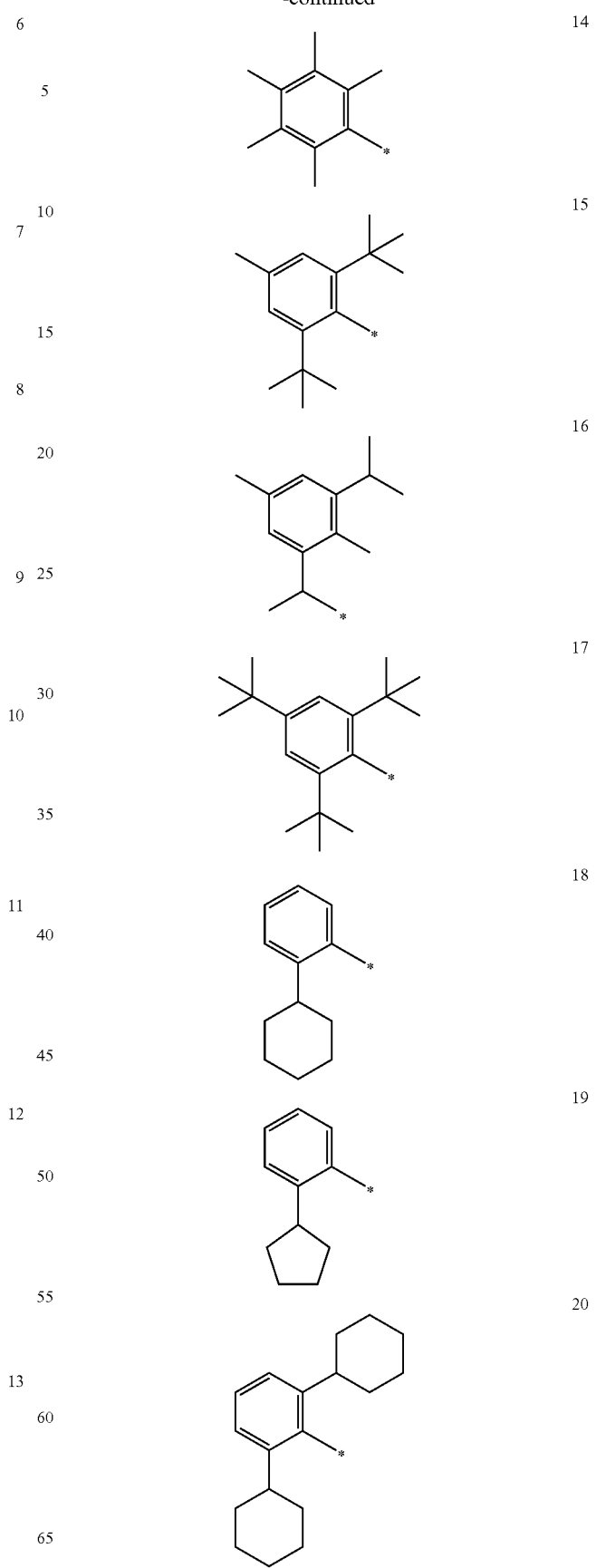

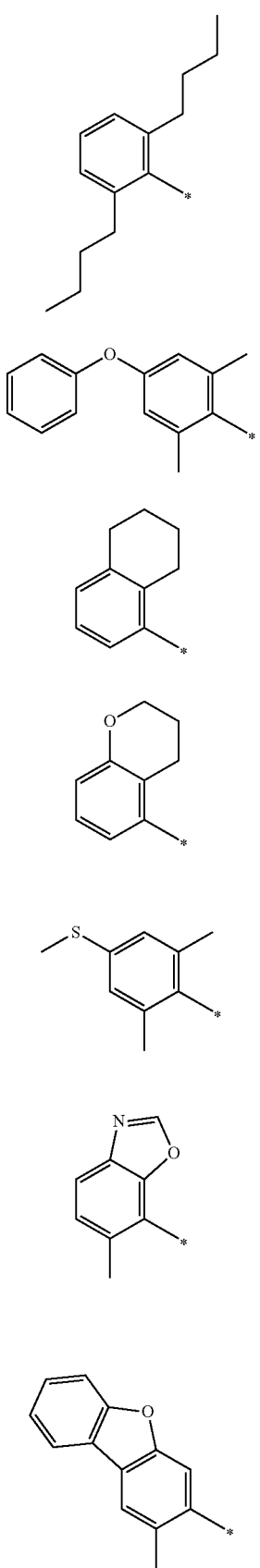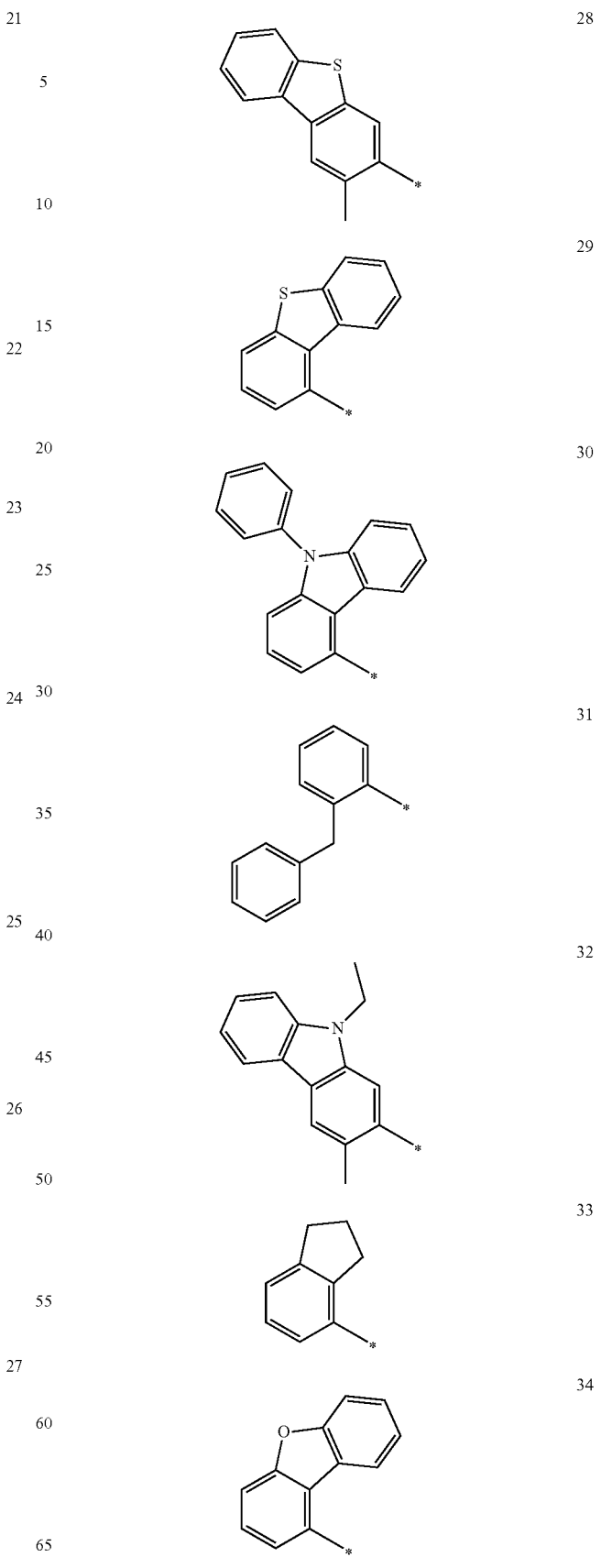

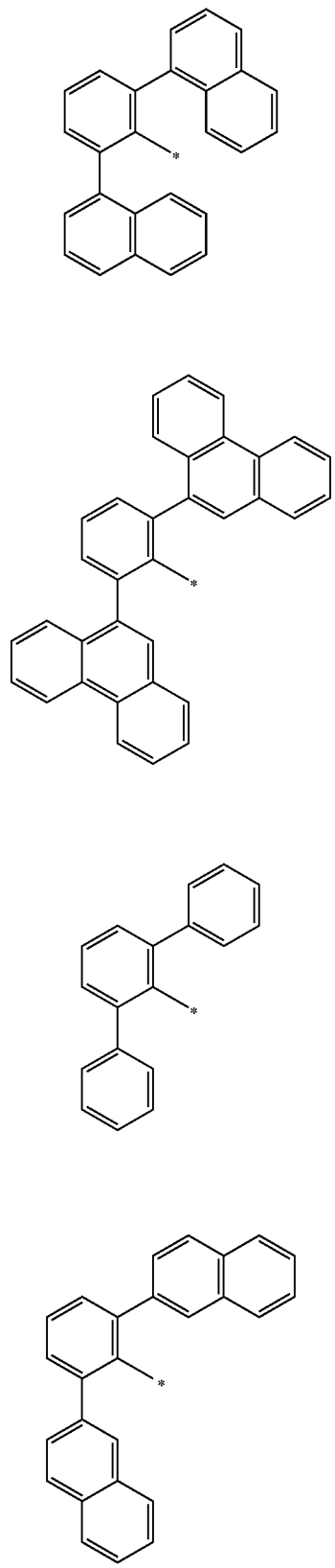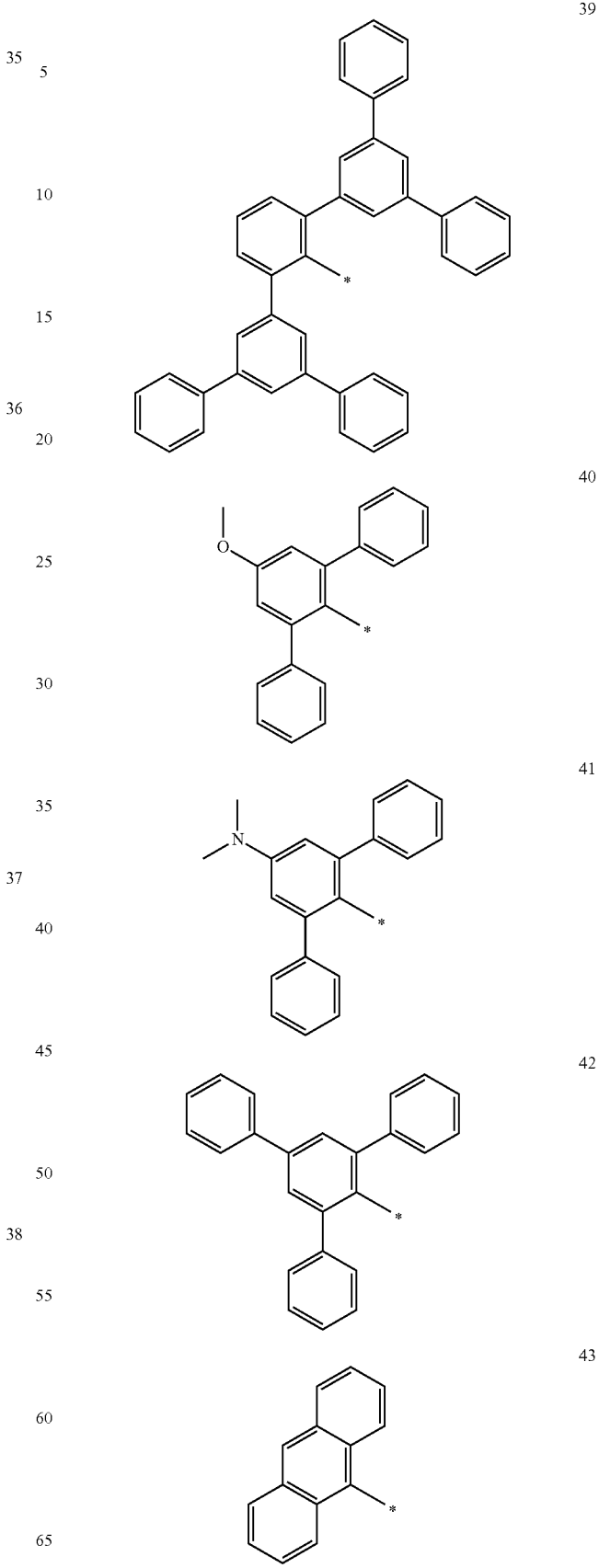

-continued
44
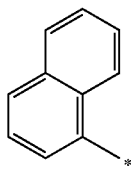
45
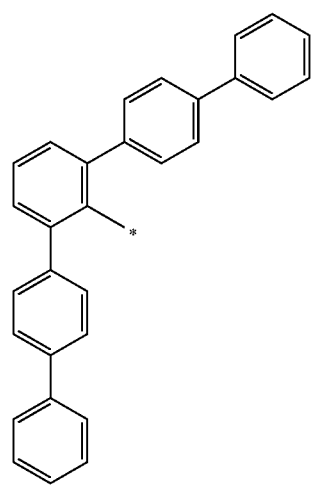
46
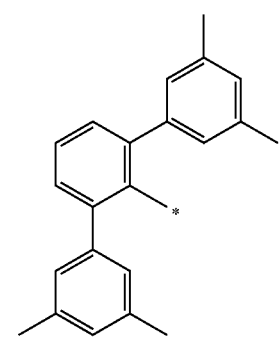
47
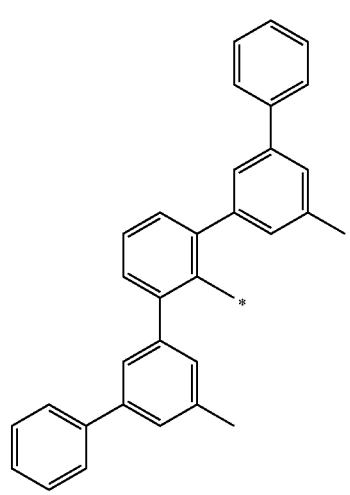
-continued
48
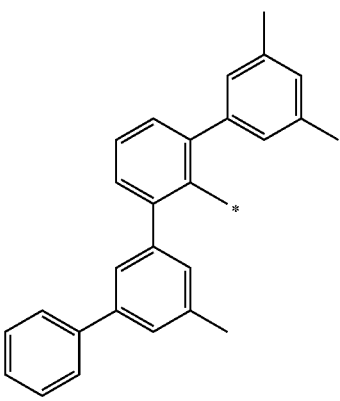
49
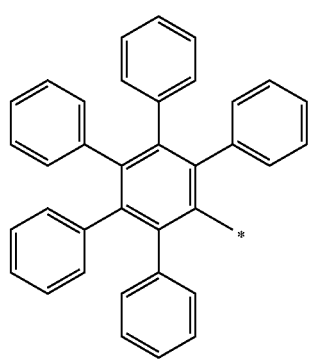
50
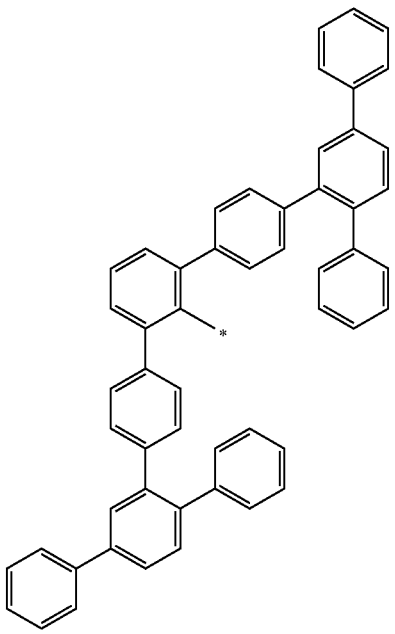

161
-continued
51
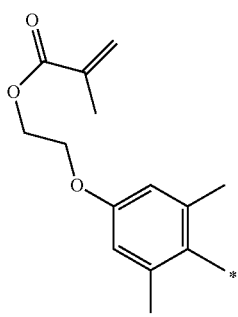
52
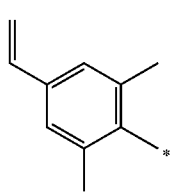
53
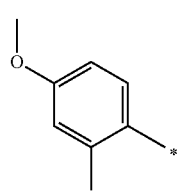
54
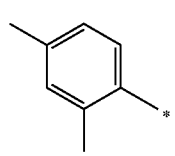
55
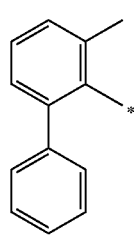
56
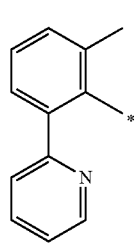
57
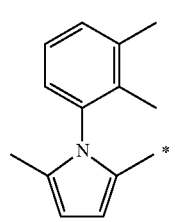
162
-continued
58
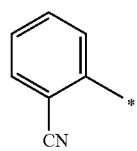
59
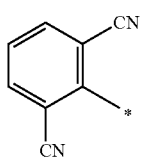
60
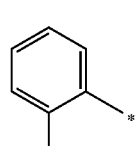
61
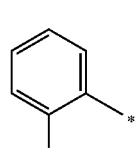
62
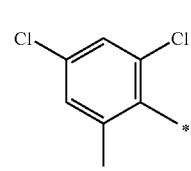
63
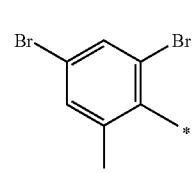
64
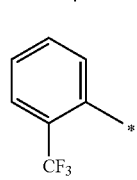
65
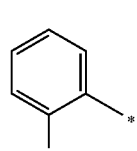
66
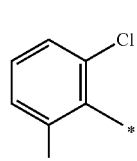
67
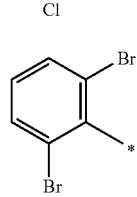

-continued
| | | | |
|---|---|---|---|
| 68 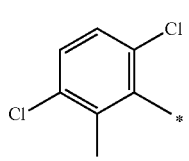 | | 77 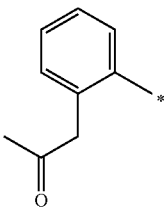 | |
| 69 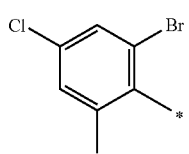 | | 78 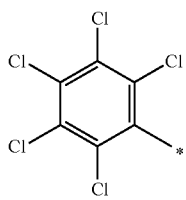 | |
| 70 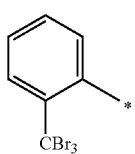 | | 79 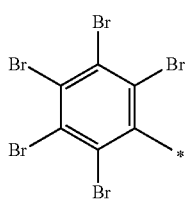 | |
| 71 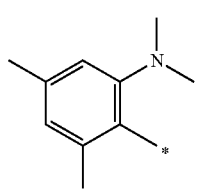 | | 80 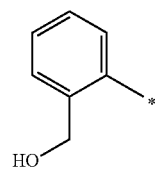 | |
| 72 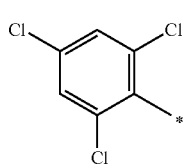 | | 81 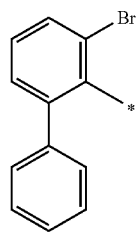 | |
| 73 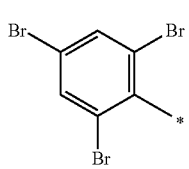 | | 82 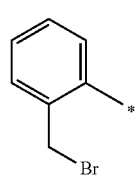 | |
| 74 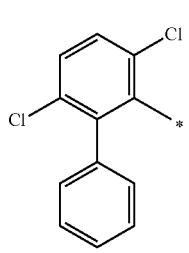 | | 83 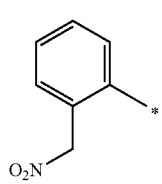 | |
| 75 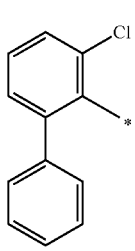 | | 84 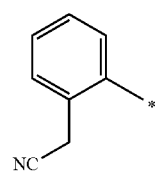 | |
| 76 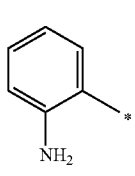 | | | |

-continued
| | |
|---|---|
| 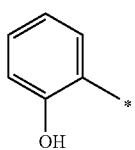 | 85 |
| 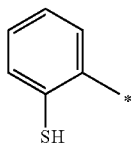 | 86 |
| 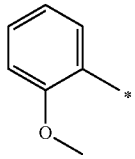 | 87 |
| 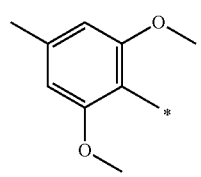 | 88 |
| 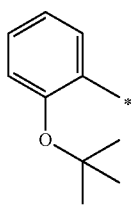 | 89 |
| 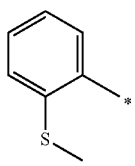 | 90 |
| 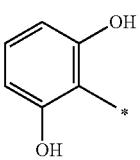 | 91 |
| 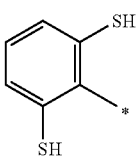 | 92 |
| 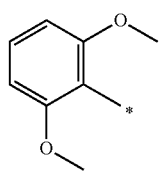 | 93 |
-continued
| | |
|---|---|
| 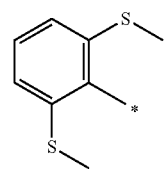 | 94 |
| 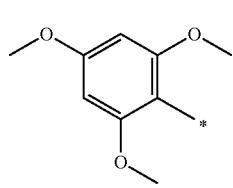 | 95 |
| 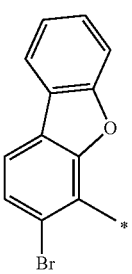 | 96 |
| 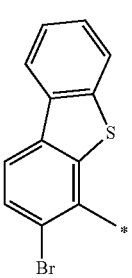 | 97 |
| 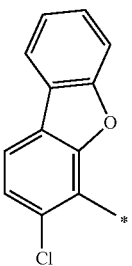 | 98 |
| 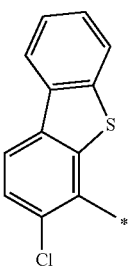 | 99 |

100 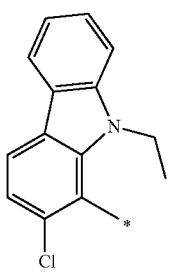
101 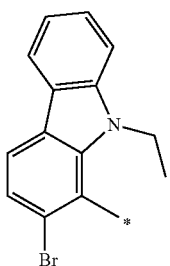
102 
103 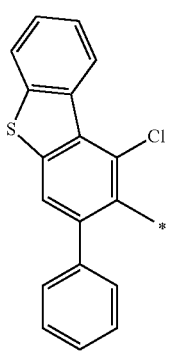
104 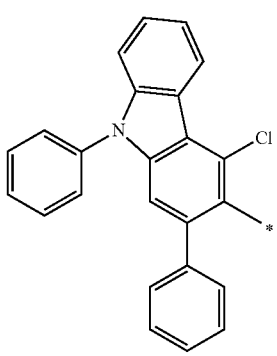
105 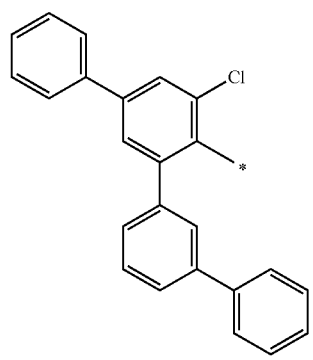
106 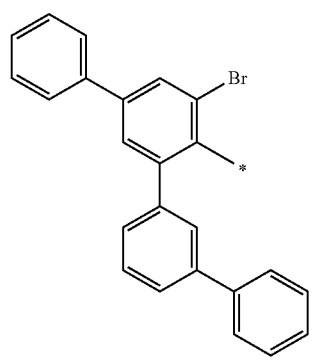
107 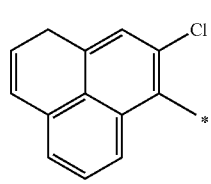
108 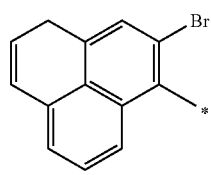
109 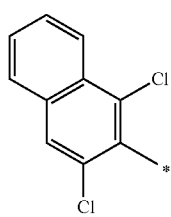
110 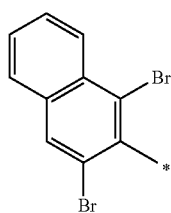

169
-continued
111 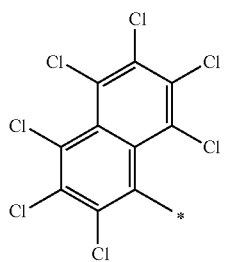
112 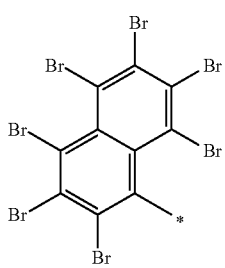
113 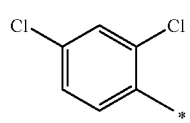
114 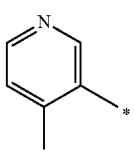
115 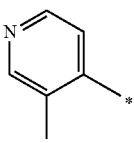
116 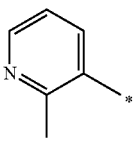
117 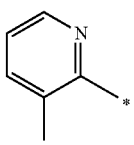
118 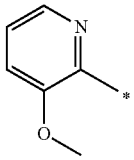
119 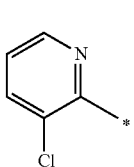
170
-continued
120 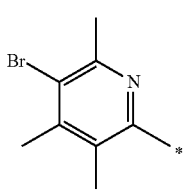
121 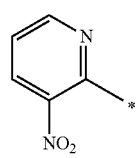
122 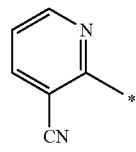
123 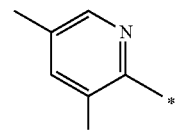
124 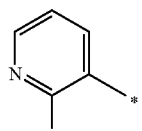
125 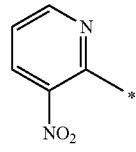
126 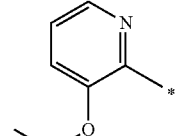
127 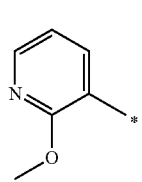
128 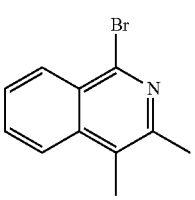

-continued
| | |
|---|---|
| 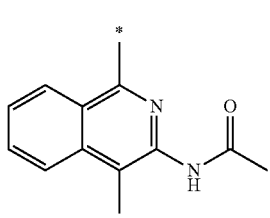 | 129 |
| 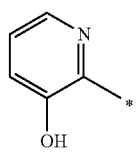 | 130 |
| 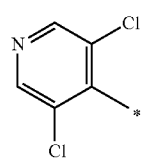 | 131 |
| 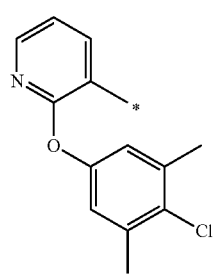 | 132 |
| 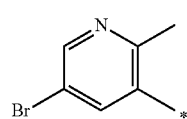 | 133 |
| 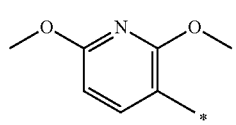 | 134 |
| 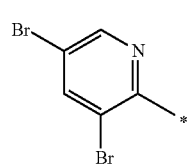 | 135 |
| 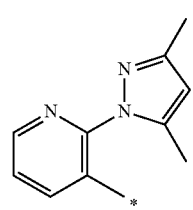 | 136 |
| 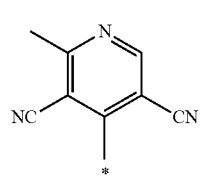 | 137 |
-continued
| | |
|---|---|
| 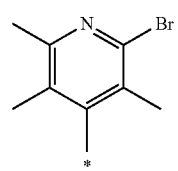 | 138 |
| 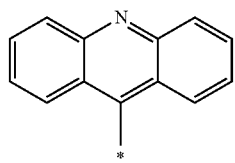 | 139 |
| 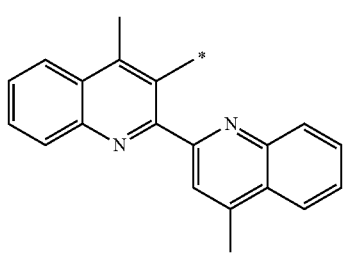 | 140 |
| 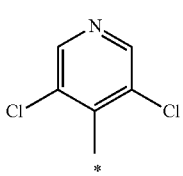 | 141 |
| 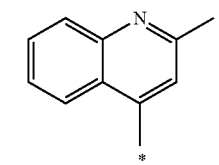 | 142 |
| 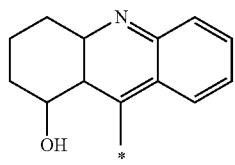 | 143 |
| 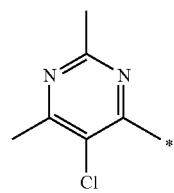 | 144 |
| 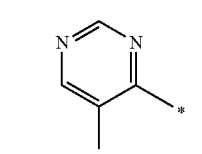 | 145 |

-continued
| | |
|---|---|
| 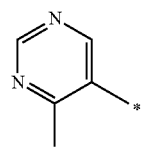 | 146 |
| 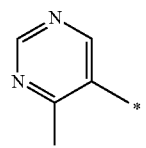 | 147 |
| 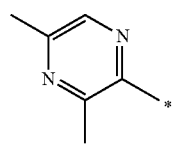 | 148 |
| 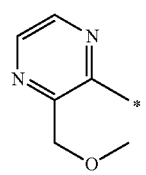 | 149 |
| 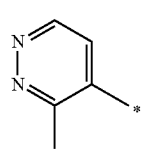 | 150 |
| 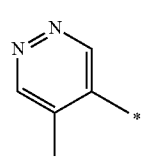 | 151 |
| 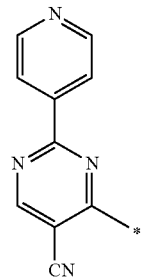 | 152 |
| 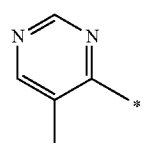 | 153 |
| 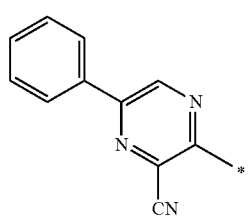 | 154 |
-continued
| | |
|---|---|
| 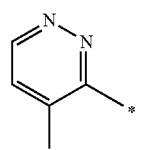 | 155 |
| 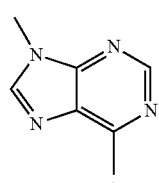 | 156 |
| 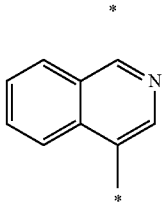 | 157 |
| 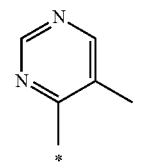 | 158 |
| 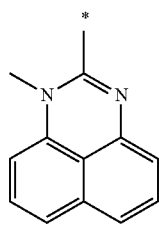 | 159 |
| 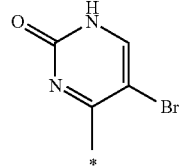 | 160 |
| 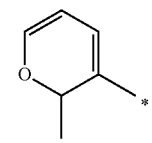 | 161 |
| 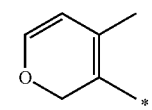 | 162 |
| 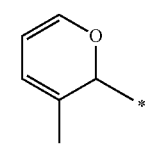 | 163 |

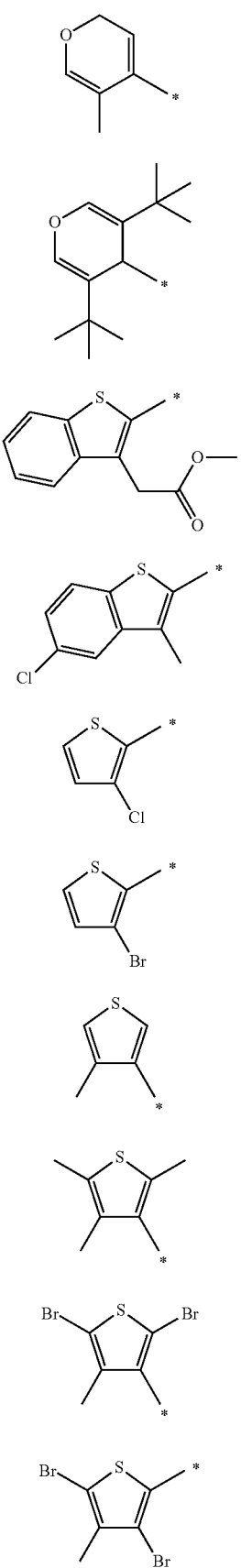

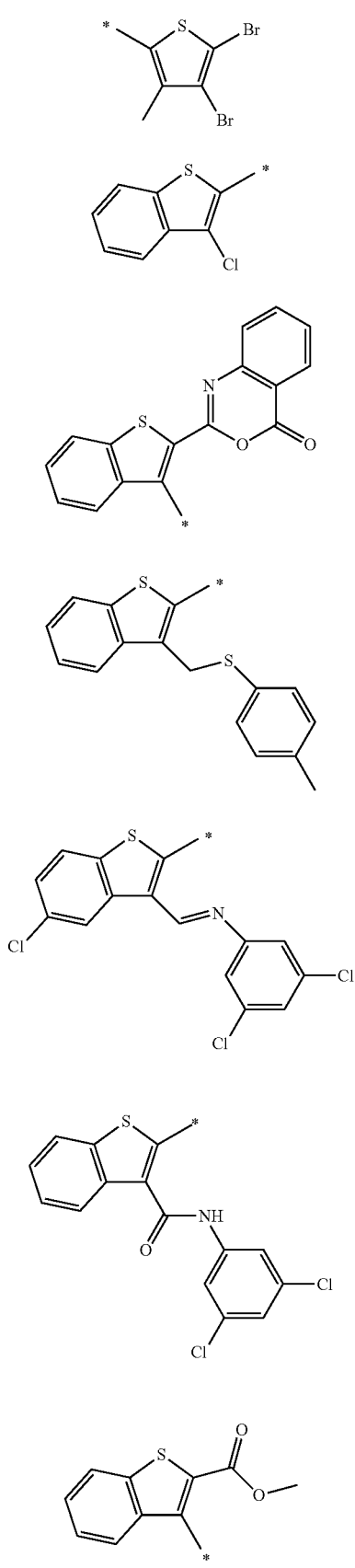
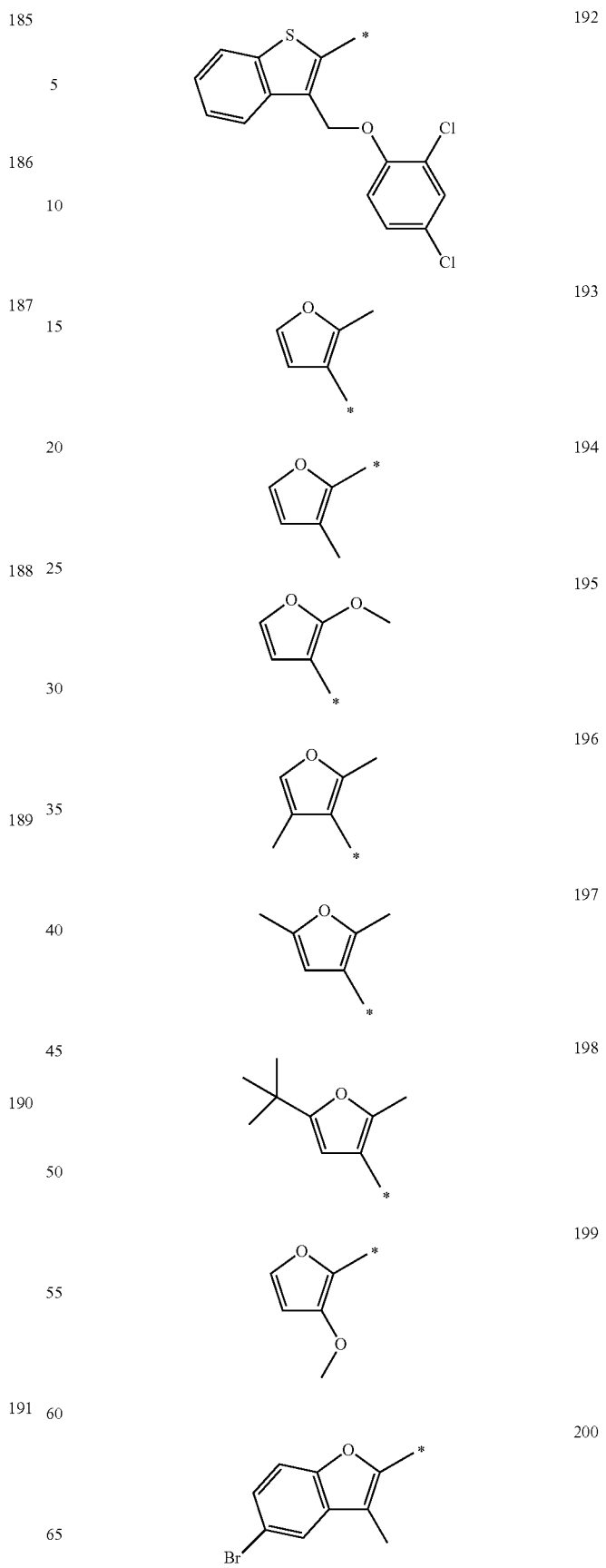

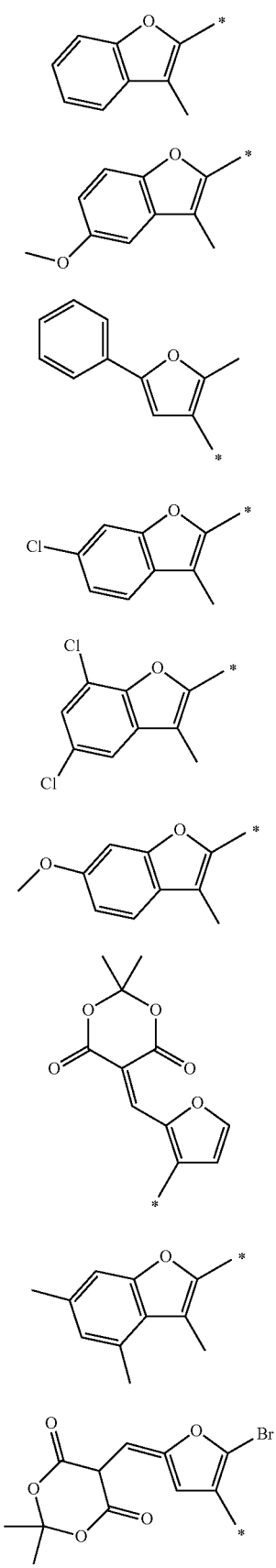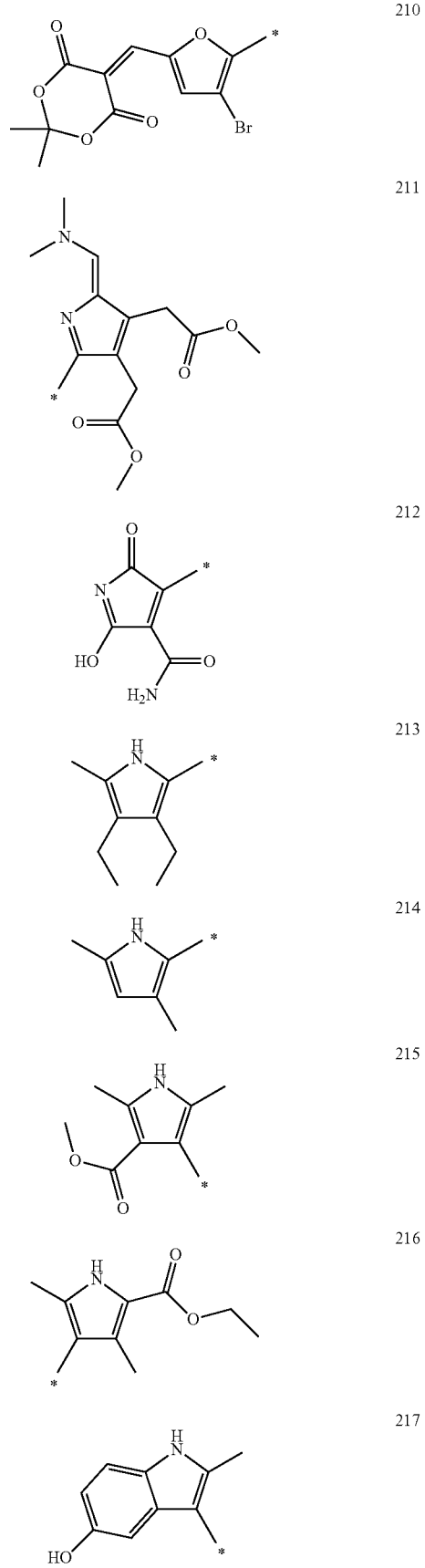

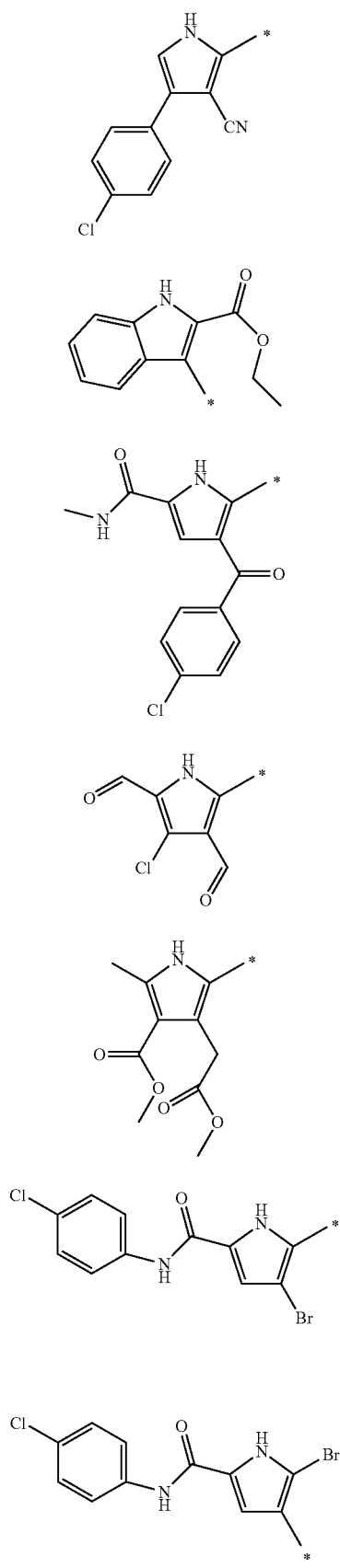

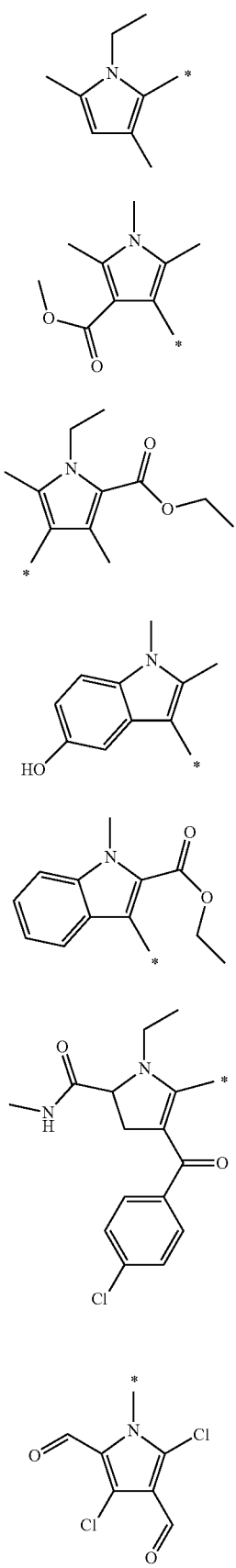
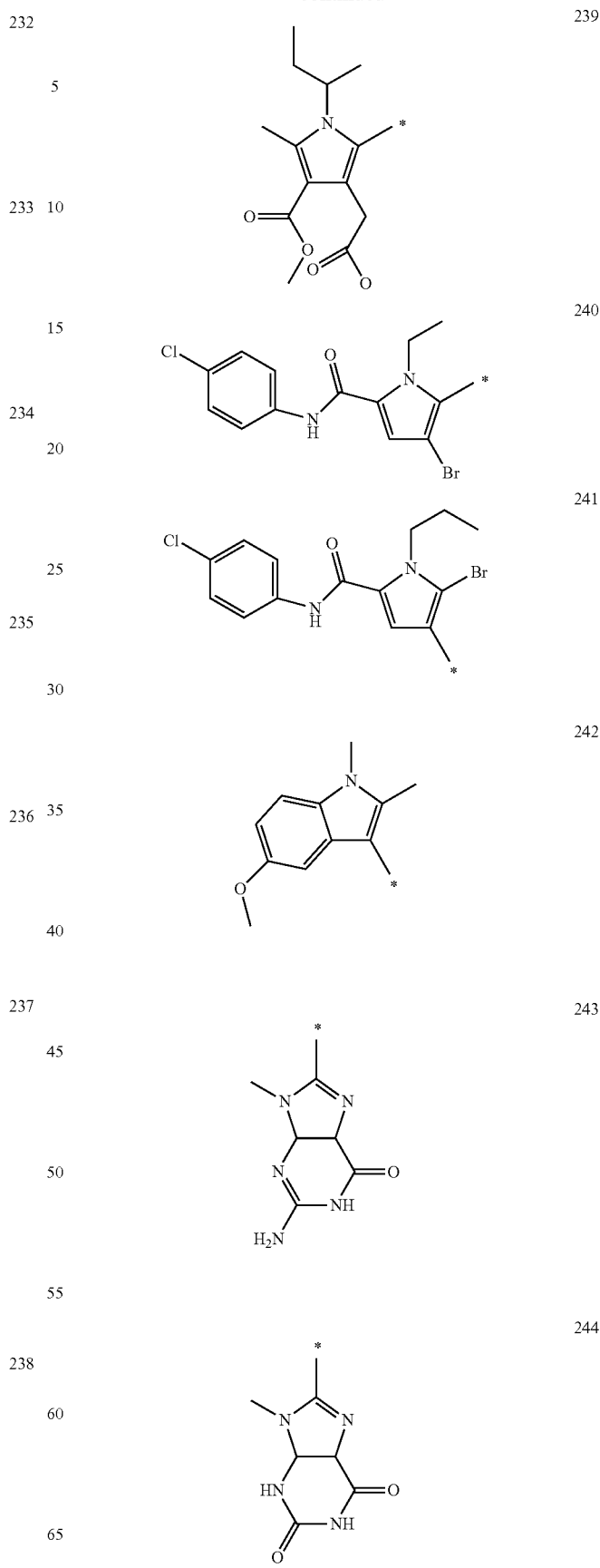

185
-continued
245
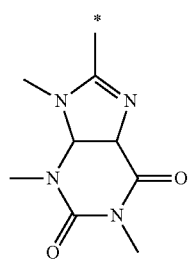
246
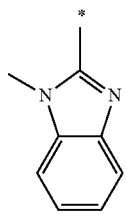
247
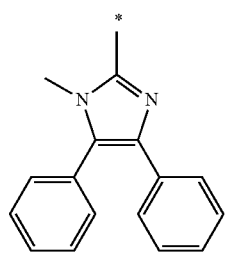
248
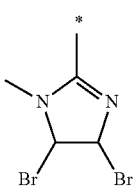
249
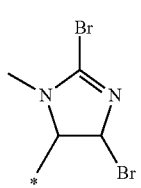
250
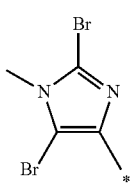
251
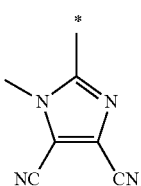
186
-continued
252
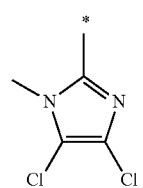
253
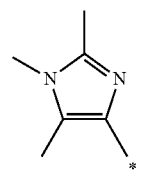
254
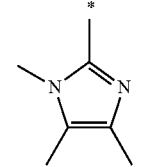
255
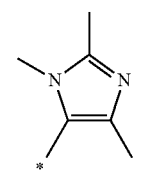
256
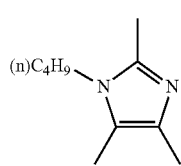
257
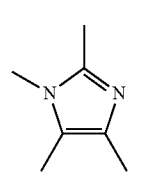
258
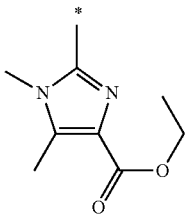
259
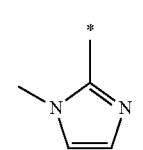

| 187 | 188 |
|---|---|
| -continued | -continued |
260 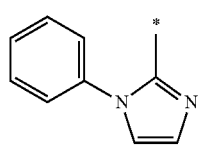
261 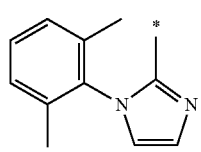
262 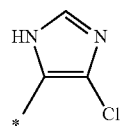
263 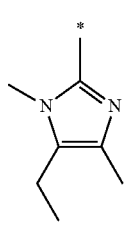
264 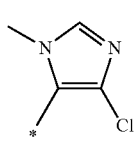
265 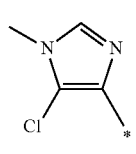
266 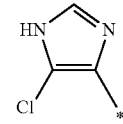
267 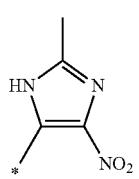
268 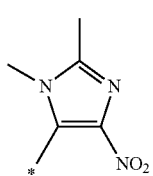
269 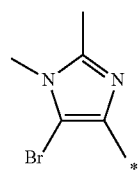
270 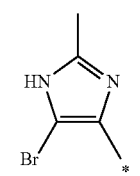
271 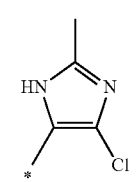
272 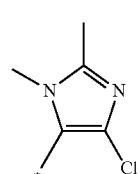
273 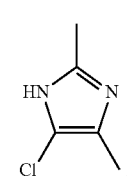
274 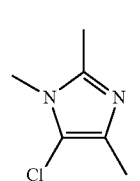
275 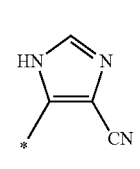
276 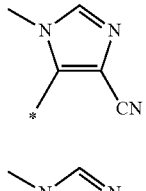
277 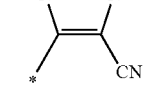

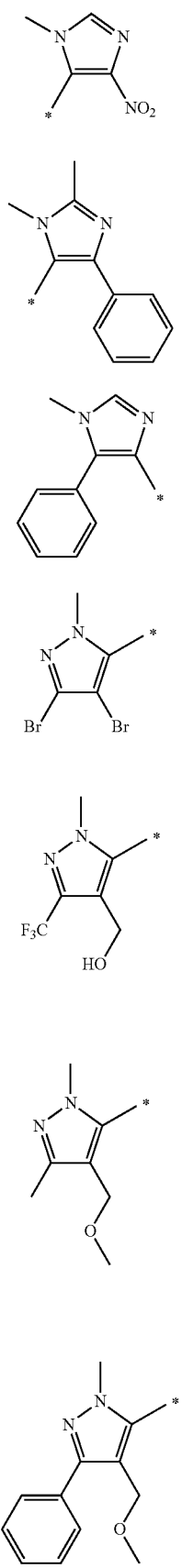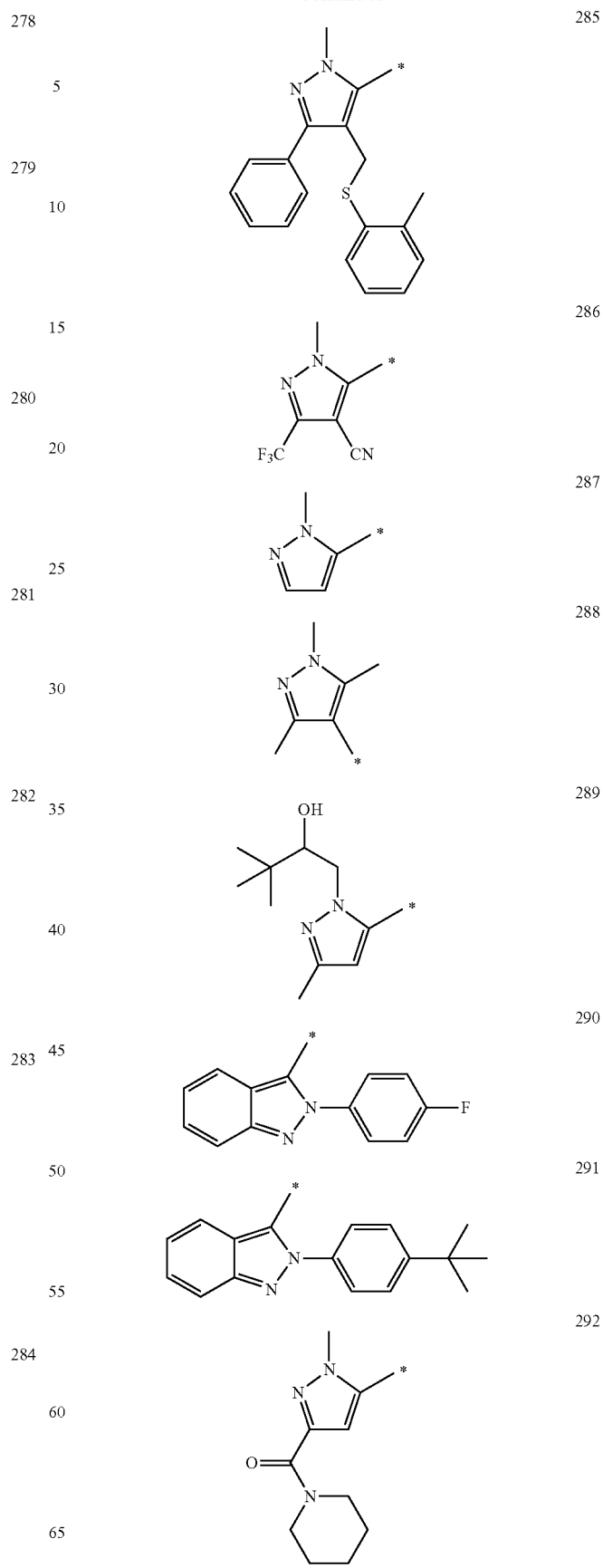

293 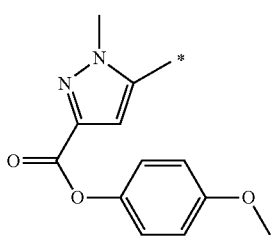
294 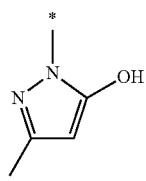
295 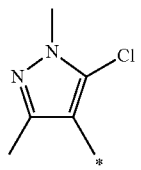
296 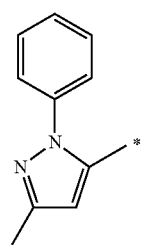
297 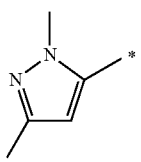
298 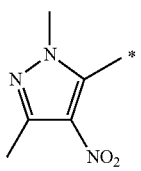
299 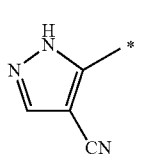
300 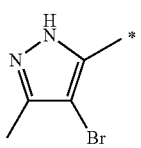
301 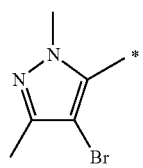
302 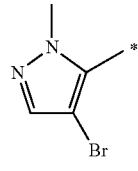
303 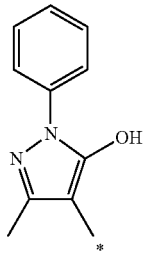
304 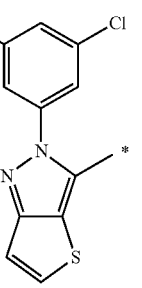
305 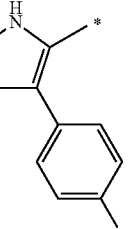
306 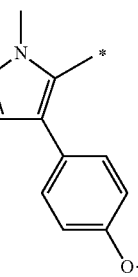
307 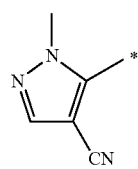

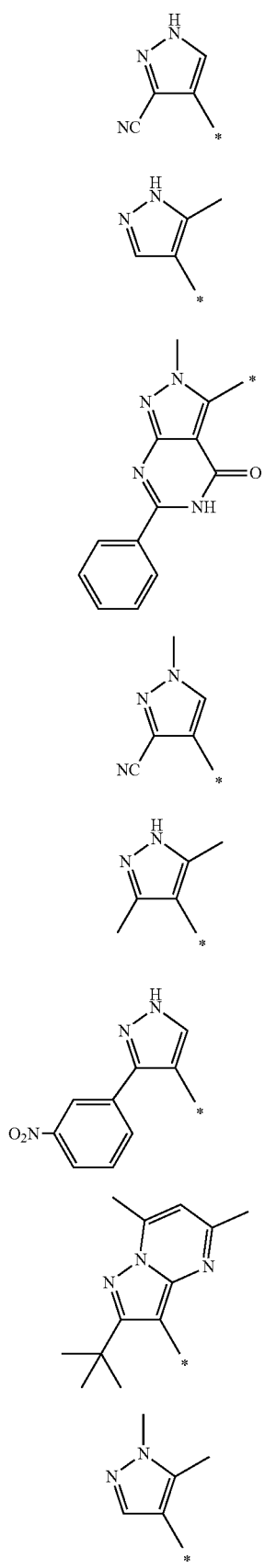

| 195 -continued | | 196 -continued | |
|---|---|---|---|
| 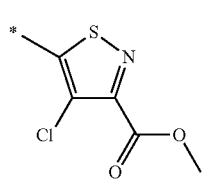 | 324 | 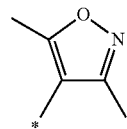 | 331 |
| 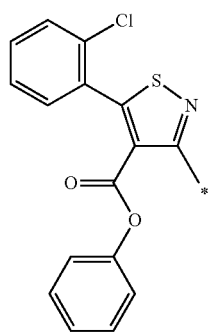 | 325 | 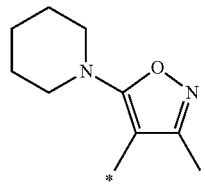 | 332 |
| 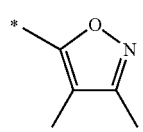 | 326 | 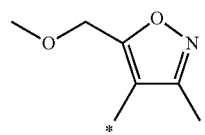 | 333 |
| 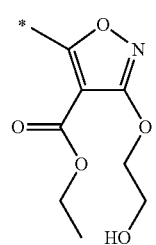 | 327 | 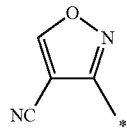 | 334 |
| 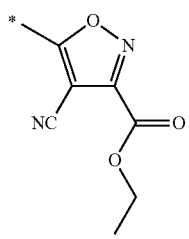 | 328 | 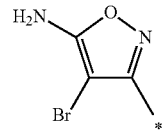 | 335 |
| 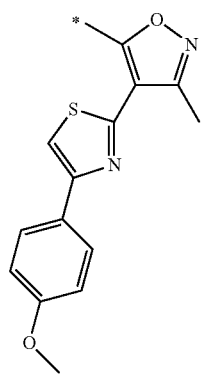 | 329 | 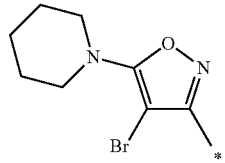 | 336 |
| 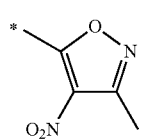 | 330 | 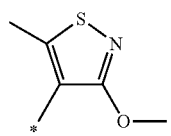 | 337 |
| | | 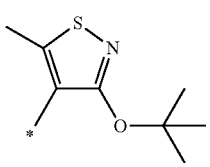 | 338 |
| | | 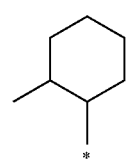 | 339 |

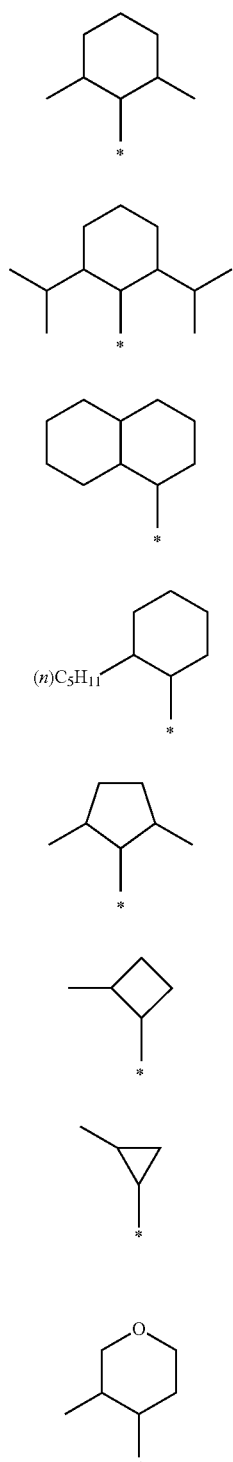
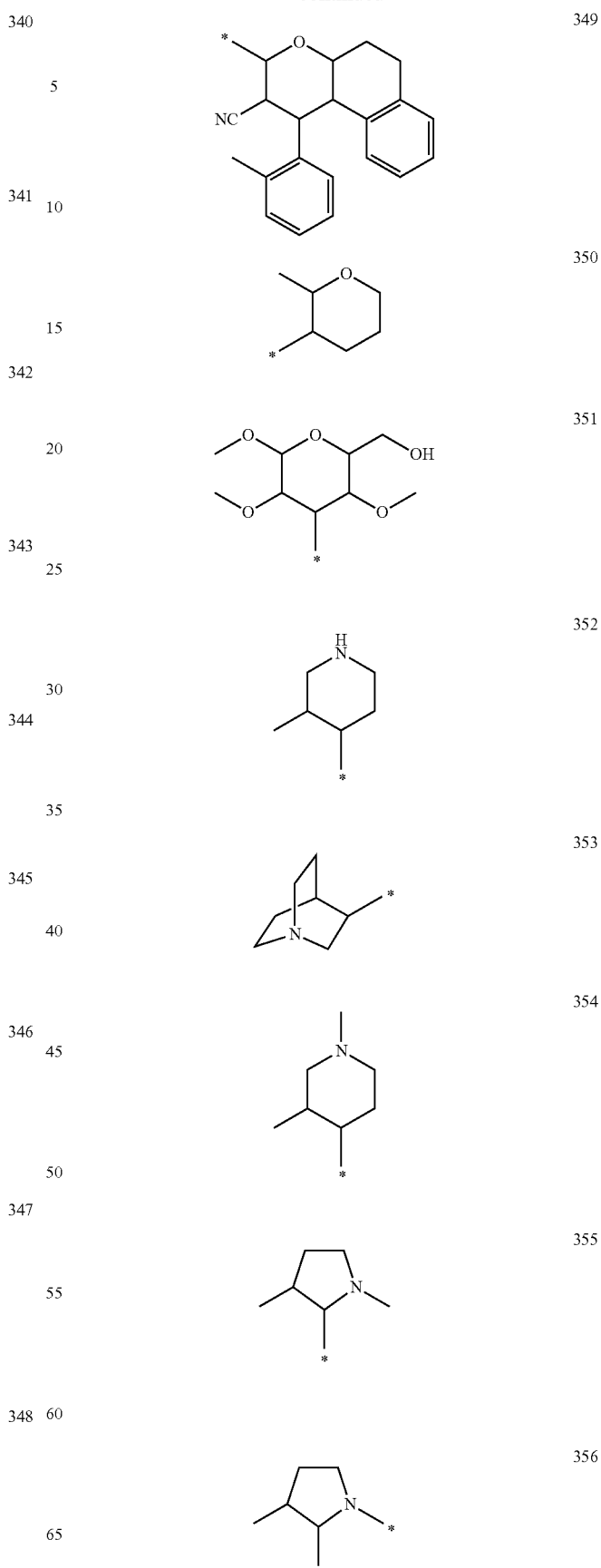

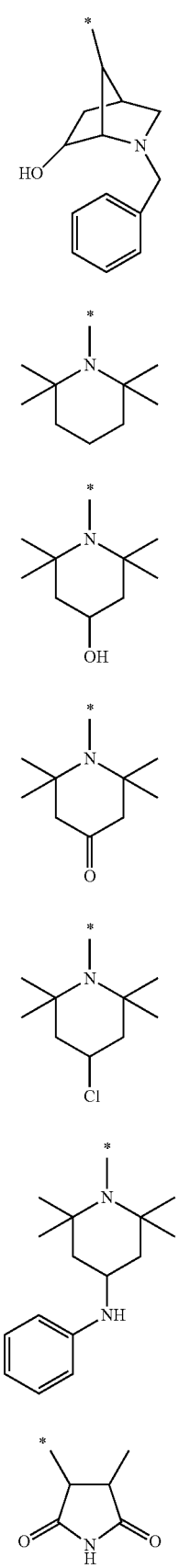
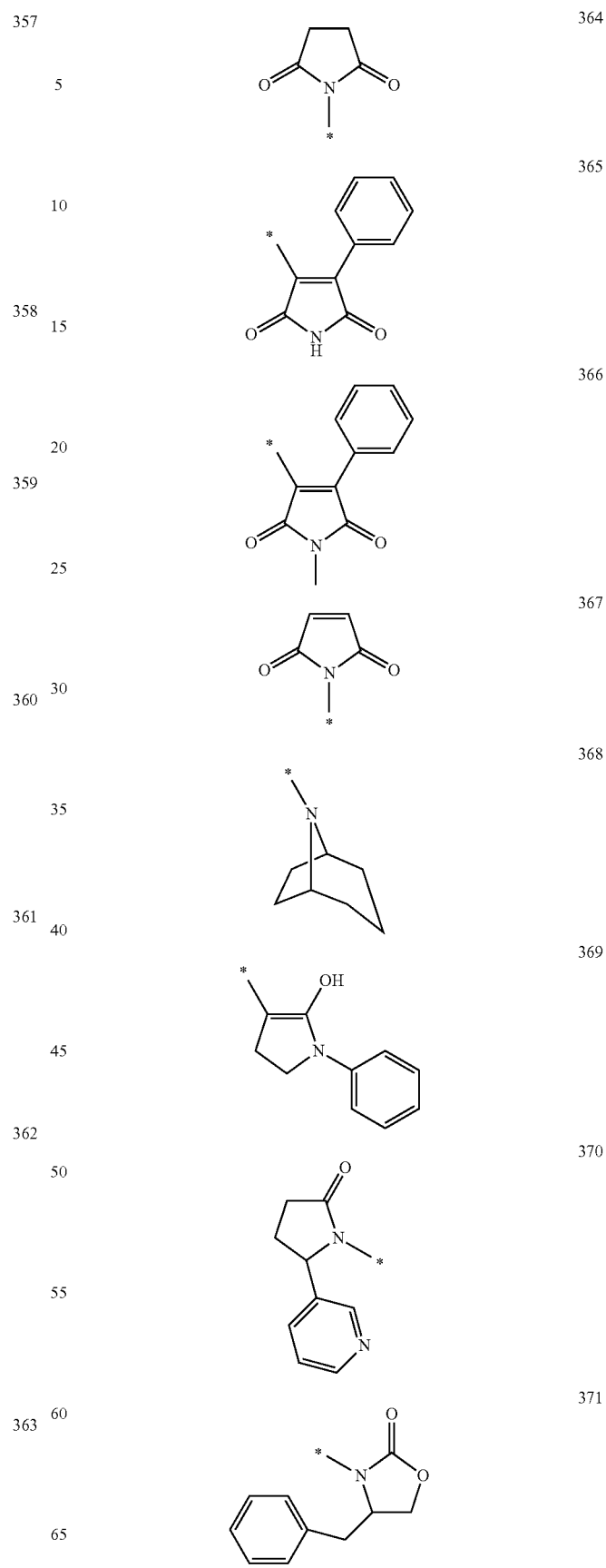

| 201 -continued | | 202 -continued | |
|---|---|---|---|
| 372 | 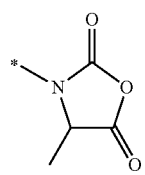 | 380 | 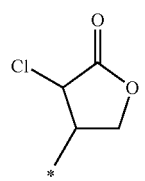 |
| 373 | 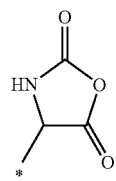 | 381 | 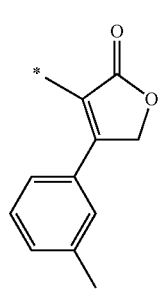 |
| 374 | 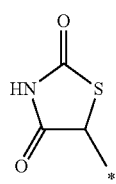 | 382 | 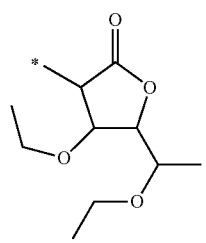 |
| 375 | 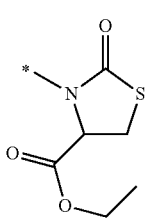 | 383 | 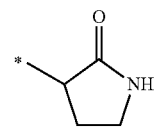 |
| 376 | 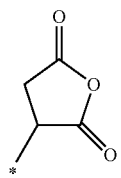 | 384 | 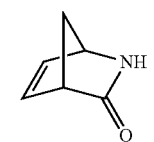 |
| 377 | 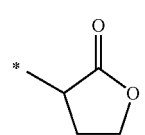 | 385 | 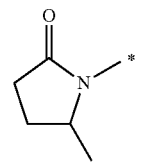 |
| 378 | 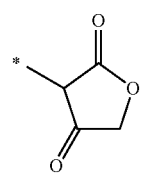 | 386 | 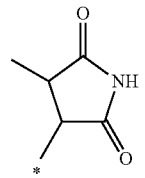 |
| 379 | 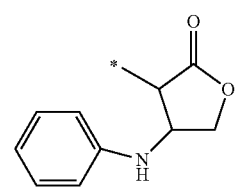 | 387 | 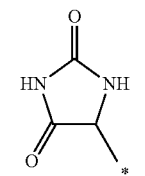 |

388 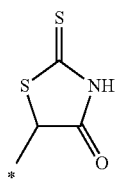

389 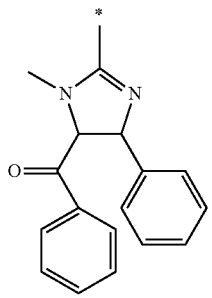

390 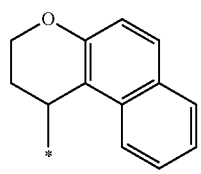

391 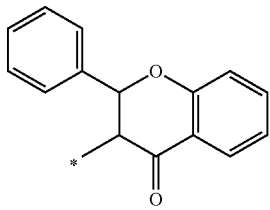

392 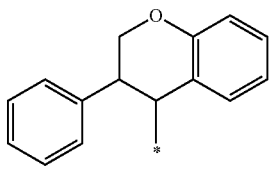

As one of the preferable embodiments of a compound represented by the above-mentioned Formula (4), the compound represented by the above-mentioned Formula (5) is cited.

In Formula (5), $R_{03}$ represents a substituent, $R_{04}$ represents a hydrogen atom or a substituent, a plurality of $R_{04}$ may be combined with each other to form a ring. $n_{01}$ represents an integer of 1 to 4.

$R_{05}$ represents a hydrogen atom or a substituent, a plurality of $R_{05}$ may be combined with each other to form a ring. $n_{02}$ represents an integer of 1 or 2. $R_{06}$ represents a hydrogen atom or a substituent, a plurality of $R_{06}$ may be combined with each other to form a ring. $n_{03}$ represents an integer of 1 to 4. $Z_1$ represents an atomic group required to form a 6 membered aromatic heterocycle or a 5 to 6 membered aromatic hydrocarbon ring with C—C. $Z_2$ represents an atomic group required to form a hydrocarbon ring group or a heterocyclic group. $P_1, P_2, j_1, j_2,$ and $M_1$ are synonymous with $P_1, P_2, j_1, j_2,$ and $M_1$ of the above-mentioned Formula (3). $P_1$-$L_1$-$P_2$ represents a bidentate ligand, and $j_1+j_2$ is an integer of 2 or 3. $R_{03}$ and $R_{06}$, $R_{04}$ and $R_{06}$, and $R_{05}$ and $R_{06}$ each may be combined with each other to form the ring.

In Formula (5), each substituent represented by $R_{03}$, $R_{04}$, $R_{05}$, and $R_{06}$ may be further substituted with a substituent represented by $Y_1$ to $Y_3$ in Formula (1).

In Formula (5), a phenyl ring is preferable as a 6 membered aromatic hydrocarbon ring which is formed by $Z_1$ with C—C. This ring may have further a substituent represented by $Y_1$ to $Y_3$ in Formula (1).

In Formula (5), examples of an aromatic heterocycle which is formed by $Z_2$ combined with C—C include: an oxazole ring, an oxadiazole ring, an oxatriazole ring, an isoxazole ring, a tetrazole ring, a thiadiazole ring, a thiatriazole ring, an isothiazole ring, a thiophene ring, a furan ring, a pyrrole ring, a pyridine ring, a pyridazine ring, a pyrimidine ring, a pyrazine ring, a triazine ring, an imidazole ring, a pyrazole ring and a triazole ring.

These rings may have further a substituent represented by $Y_1$ to $Y_3$ in Formula (1).

In Formula (5), the bidentate ligand represented by $P_1$-$L_1$-$P_2$ represents ligand is synonymous with the bidentate represented by $P_1$-$L_1$-$P_2$ in Formula (3).

In Formula (5), the transition metal element of the $8^{th}$ group to $10^{th}$ group in the periodic table of the elements represented by $M_1$ is synonymous with the transition metal element of the $8^{th}$ group to $10^{th}$ group in the periodic table of the elements represented by $M_1$ in Formula (3).

The compounds respectively represented by Formulas (3), (4) and (5) of the present invention can be synthesized by referring to the following ways: by allowing to react a nitrogen containing compound or an imidazole compound with a corresponding halogenated compound as described in Eur. J. Chem., 2005, 1637-1643; and by allowing to react a corresponding amine and glyoxal, and an aldehyde with ammonium chloride as described in SYNTHESIS 2003, 17, 2661-2666.

Example of a dopant compound which can be preferably used in the present invention are shown below, however, the present invention is not limited to these.

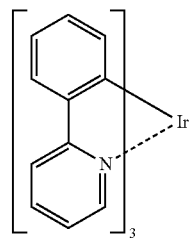

D-1

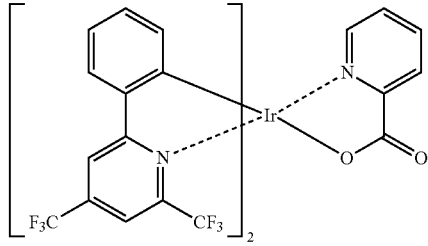

D-2

-continued
D-3
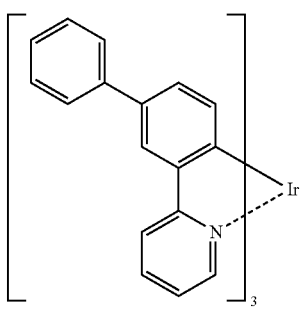
D-4
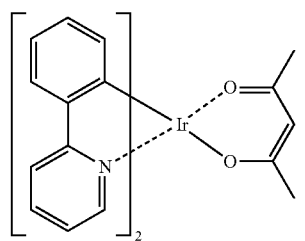
D-5
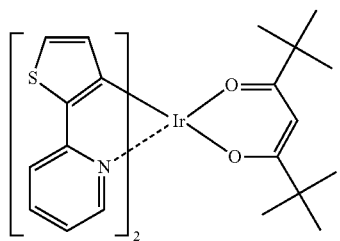
D-6
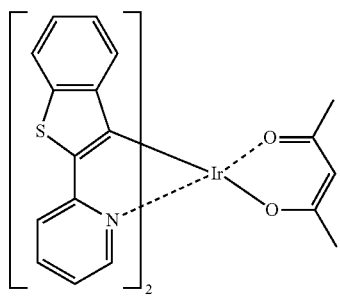
D-7
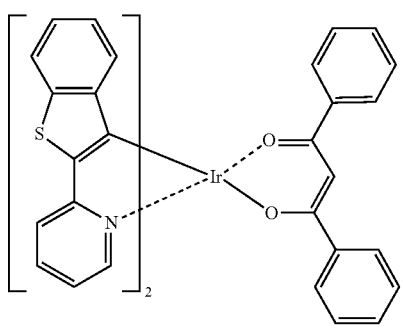
-continued
D-8
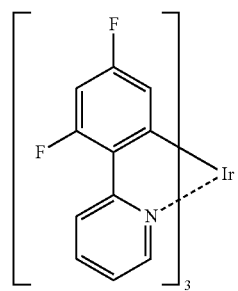
D-9
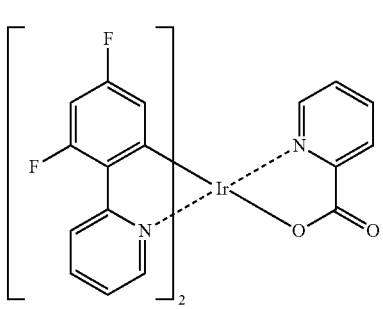
D-10
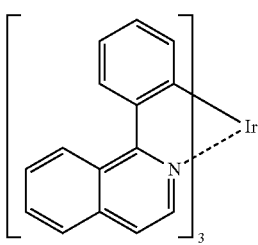
D-11
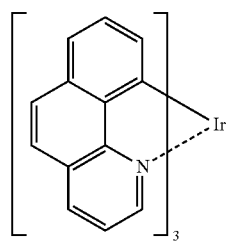
D-12
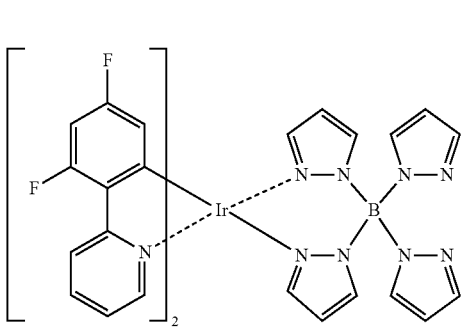

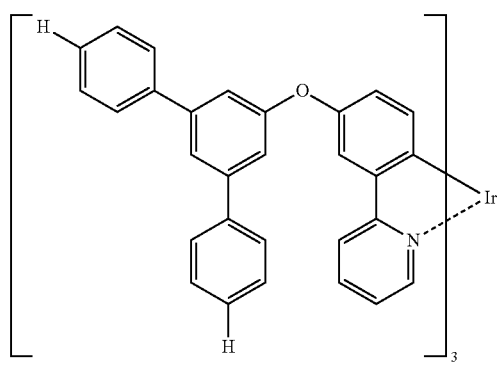
D-13
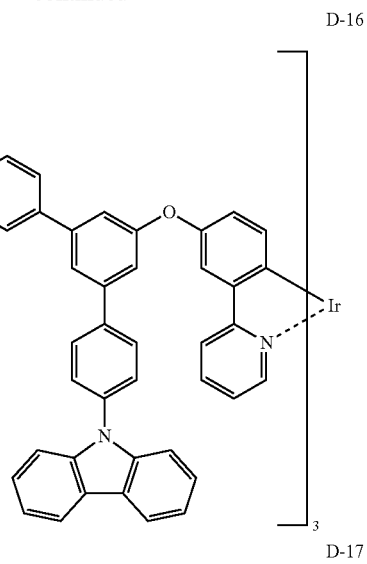
D-16
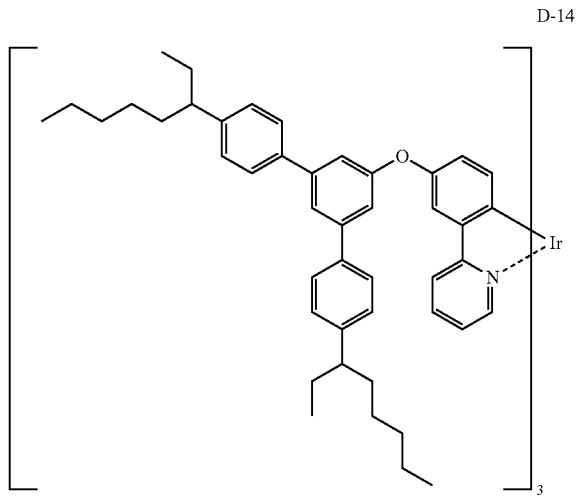
D-14
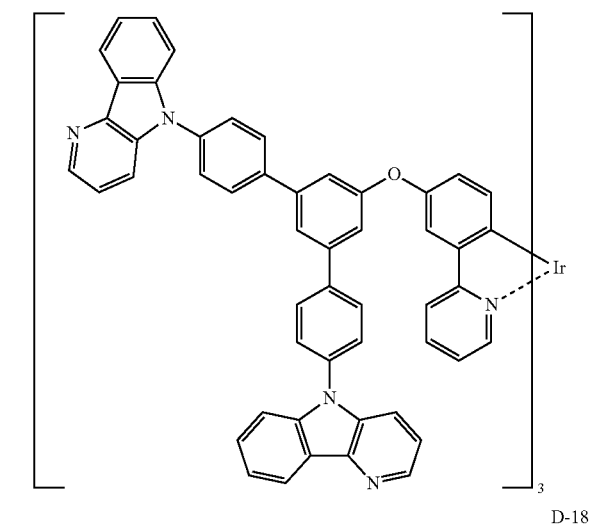
D-17
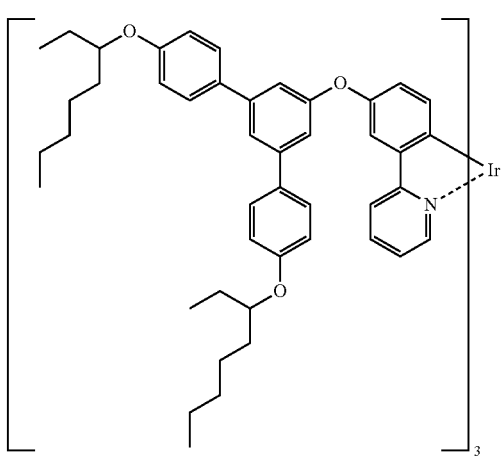
D-15
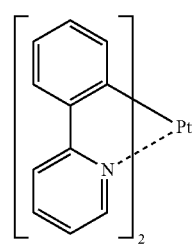
D-18
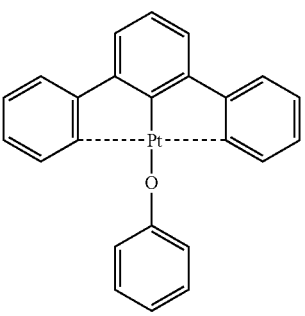
D-19

D-20 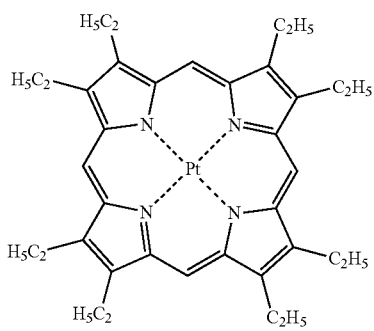
D-21 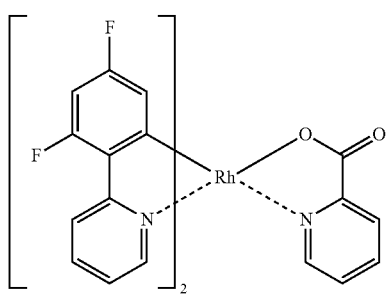
D-26 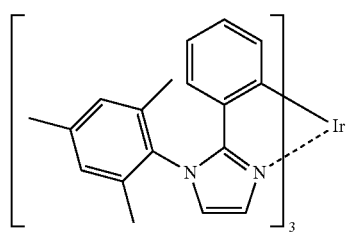
D-27 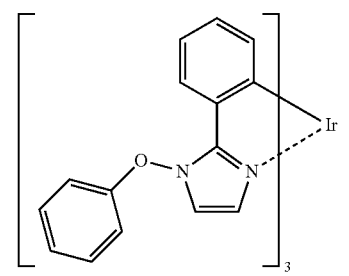
D-22 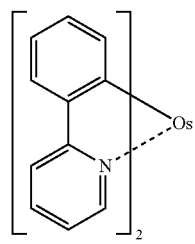
D-28 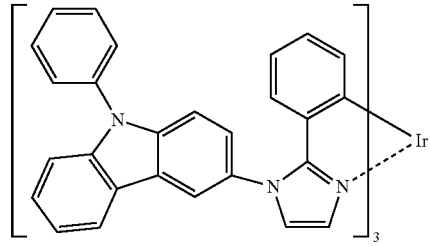
D-23 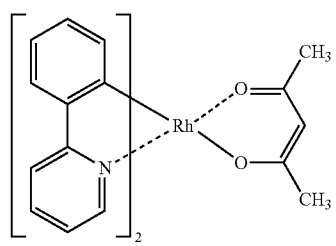
D-24 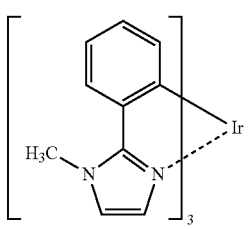
D-29 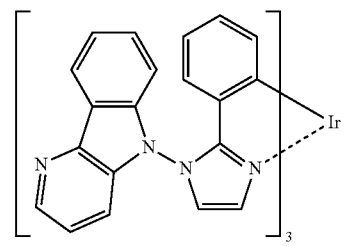
D-25 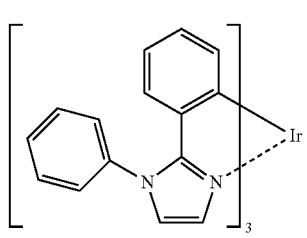
D-30 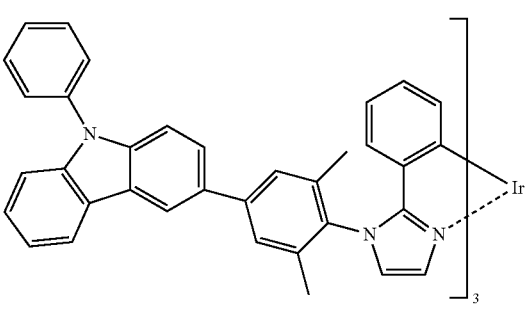

-continued
D-31
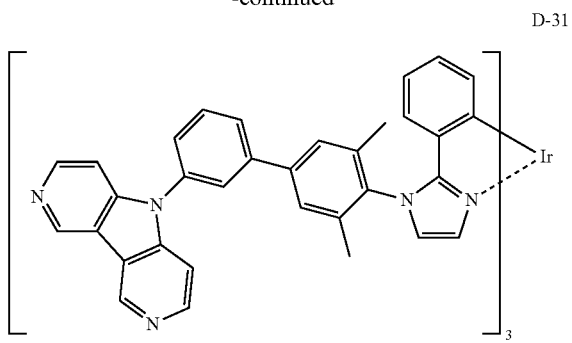
D-32
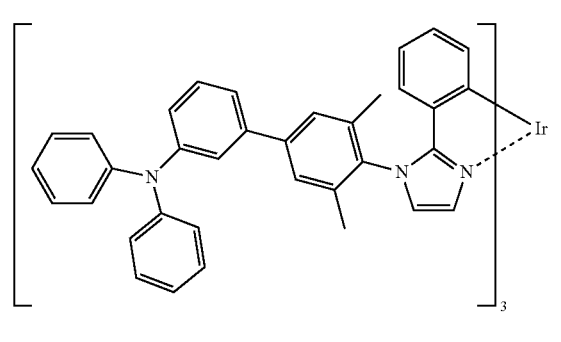
D-33
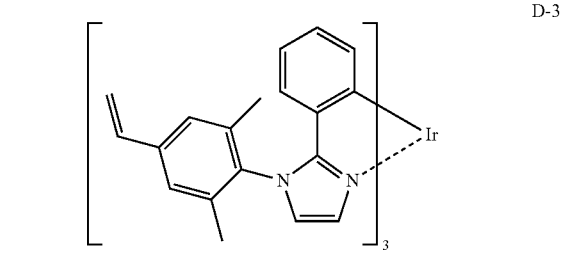
D-34
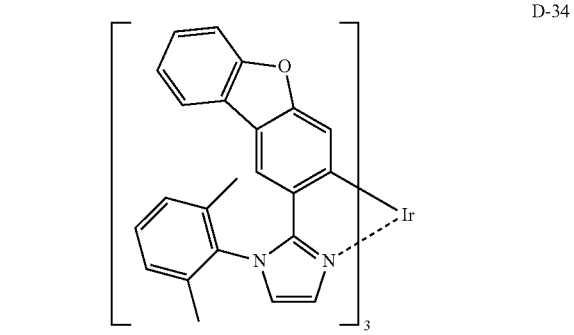
D-35
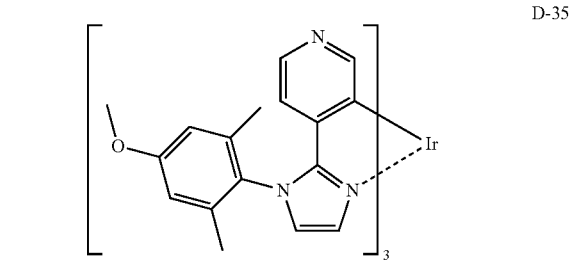
-continued
D-36
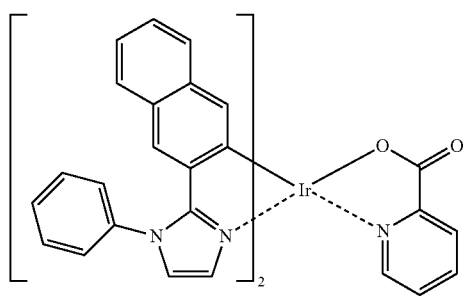
D-37
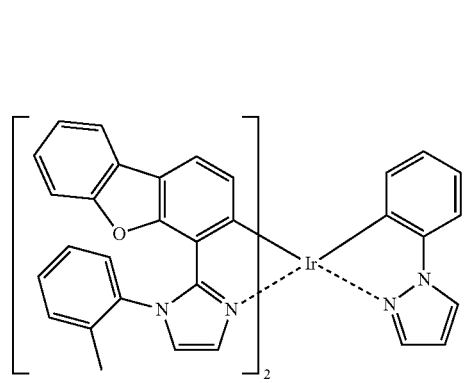
D-38
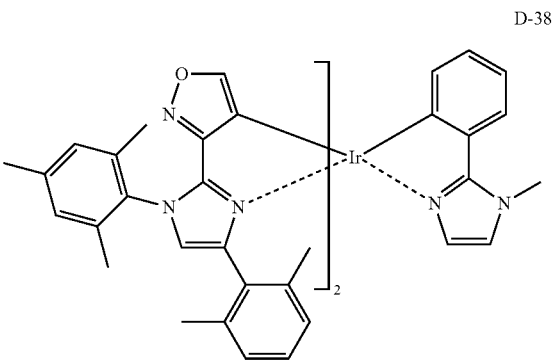
D-39
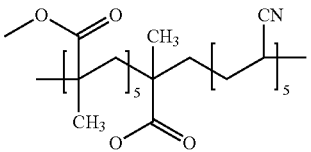

D-40
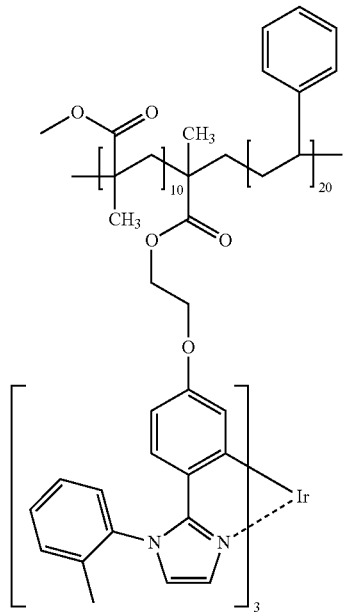
D-41
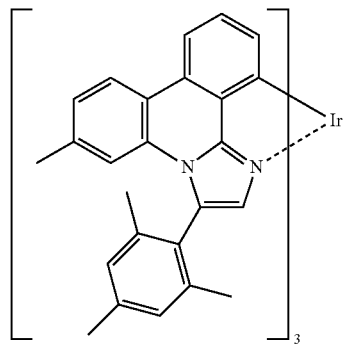
D-42
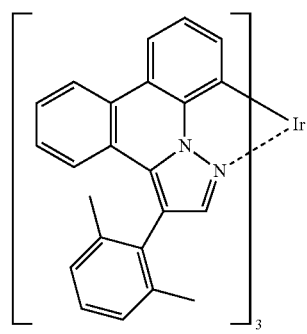
D-43
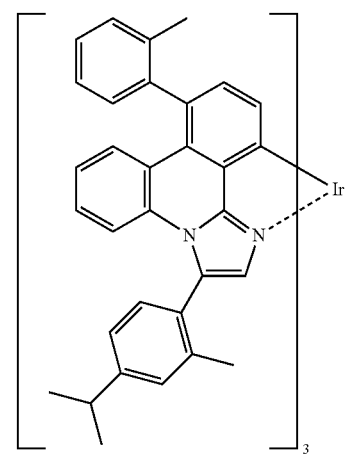
D-44
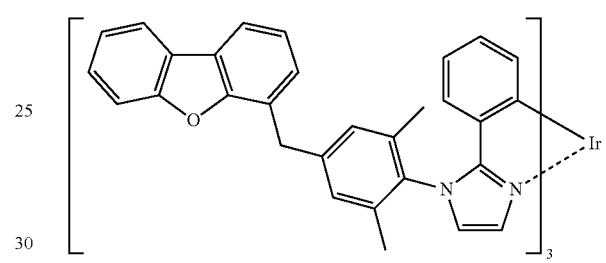
D-45
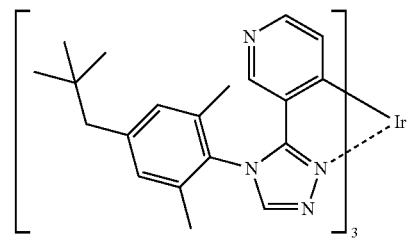
D-46
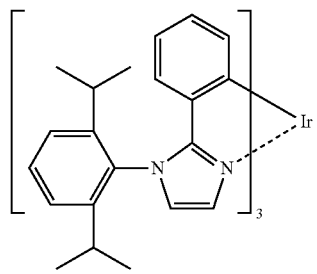
D-47
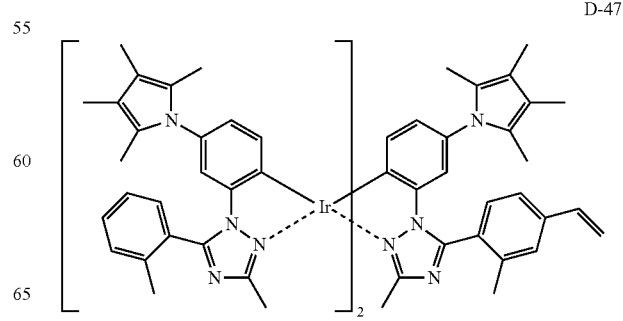

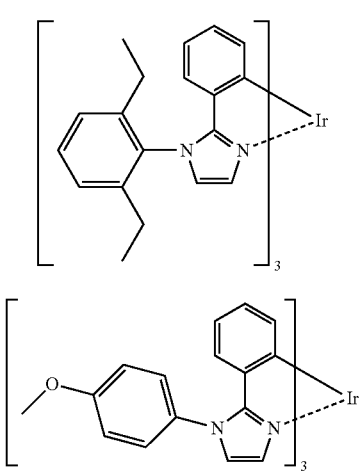

(Light Emitting Host Compounds (Also Referred to as Light Emitting Hosts or Host Compounds)

"Host compounds", as described in the present invention, are defined as compounds, incorporated in a light emitting layer, which result in a weight ratio of at least 20% in the above layer and also result in a phosphorescent quantum yield of the phosphorescence emission of less than 0.1. Further, of compounds incorporated in the light emitting layer, it is preferable that the weight ratio in the aforesaid layer is at least 20%.

Structures of the light emitting host employed in the present invention are not particularly limited. The conventionally known host compounds in organic EL elements can be used. Representative compounds include those having a basic skeleton such as carbazole derivatives, triarylamine derivatives, aromatic compound derivatives, nitrogen-containing heterocyclic compounds, thiophene derivatives, furan derivatives, oligoarylene compounds, carboline derivatives, or diazacarbazole derivatives (here, "a diazacarbazole derivative" indicates a ring structure in which at least one of the carbon atoms constituting the carboline ring is replaced with a nitrogen atom).

A known light emitting host (or emission host) which may be used in the present invention is preferably a compound having a positive hole transporting ability and an electron transporting ability, as well as preventing elongation of an emission wavelength and having a high Tg (a glass transition temperature).

It may be used an emission host compound of the present invention singly or it may be used in combination with plural host compounds, which may be other host compound of the present invention or a known host compound.

It is possible to control the transfer of charges by making use of a plurality of host compounds, which results in high efficiency of an organic EL element.

In addition, it is possible to mix a different emission lights by making use of a plurality of known phosphorescent dopants as described above. Any required emission color can be obtained thereby.

Further, an emission host used in the present invention may be either a low molecular weight compound or a polymer compound having a repeating unit, in addition to a low molecular weight compound provided with a polymerizing group such as a vinyl group and an epoxy group (an evaporation polymerizing emission host). These compounds may be used singly or in combination of two or more compounds.

As specific examples of an emission host compounds, the compounds described in the following Documents are preferable.

For example, JP-A Nos. 2001-257076, 2002-308855, 2001-313179, 2002-319491, 2001-357977, 2002-334786, 2002-8860, 2002-334787, 2002-15871, 2002-334788, 2002-43056, 2002-334789, 2002-75645, 2002-338579, 2002-105445, 2002-343568, 2002-141173, 2002-352957, 2002-203683, 2002-363227, 2002-231453, 2003-3165, 2002-234888, 2003-27048, 2002-255934, 2002-260861, 2002-280183, 2002-299060, 2002-302516, 2002-305083, 2002-305084 and 2002-308837.

Examples of the conventionally known compounds used as an emission host in the light emitting layer of the organic EL element of the present invention are given below, however, the present invention is not limited to these.

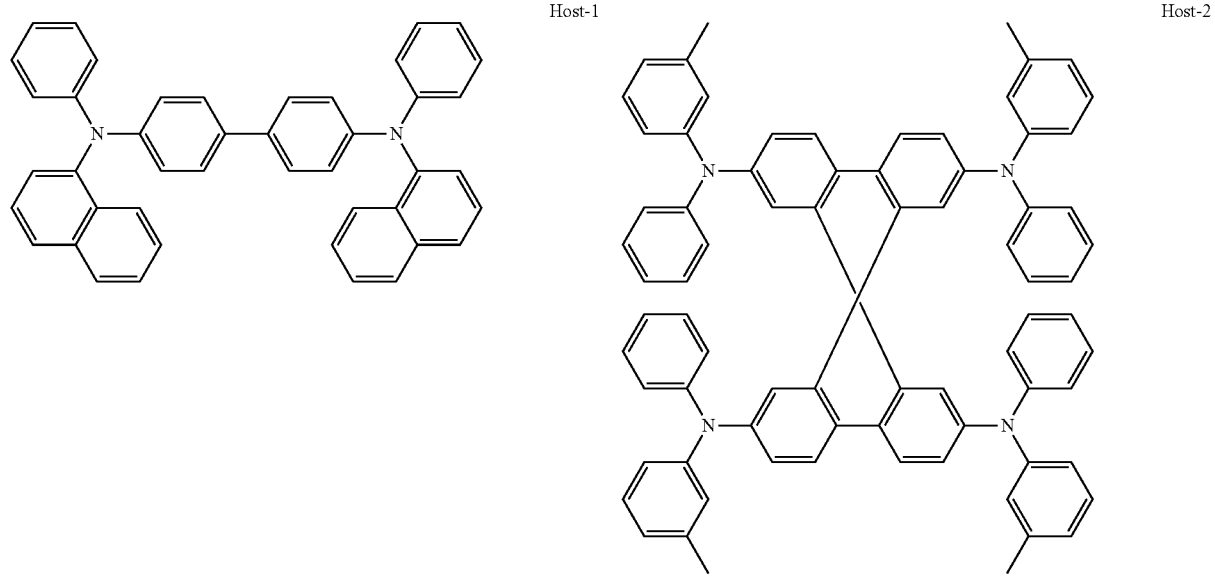

-continued
Host-3
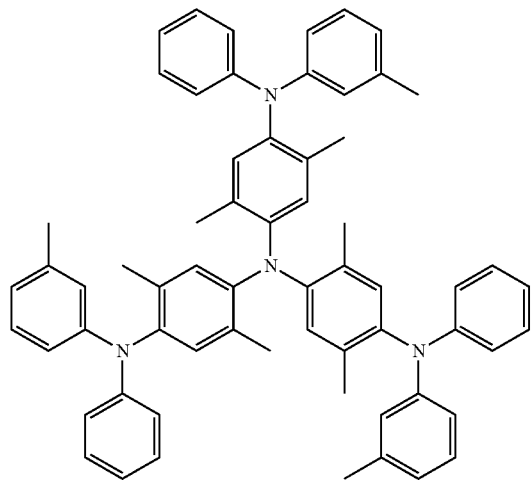
Host-4
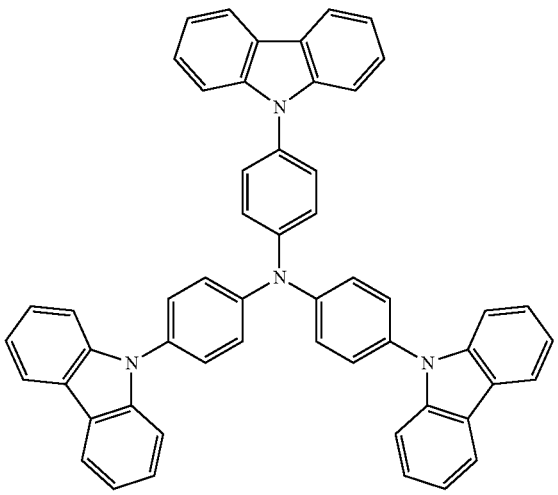
Host-5
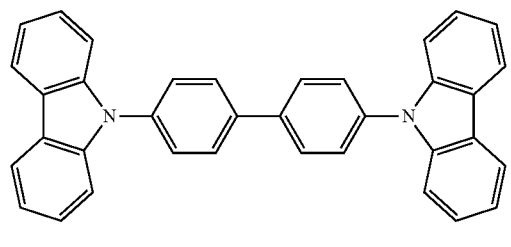
Host-6
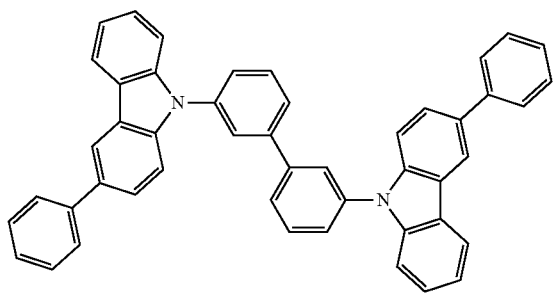
Host-7
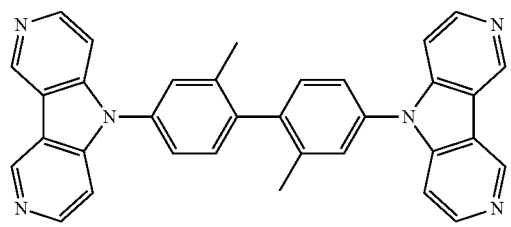
Host-8
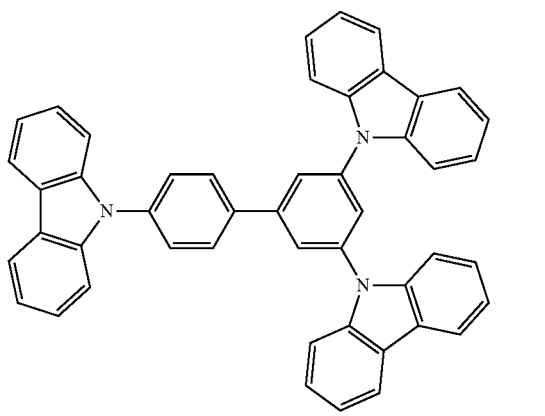
Host-9
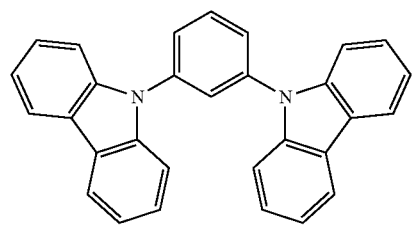
Host-10
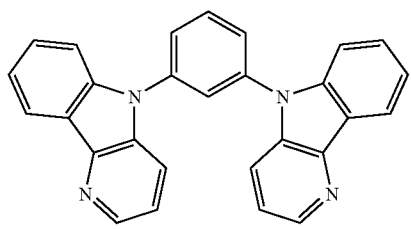

-continued
Host-11
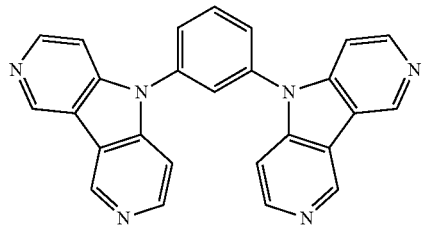
Host-12
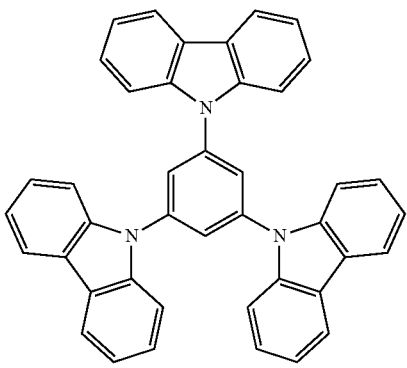
Host-13
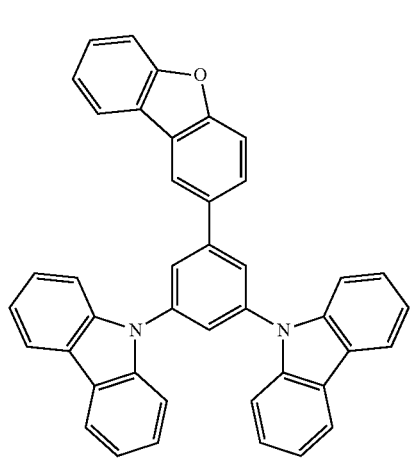
Host-14
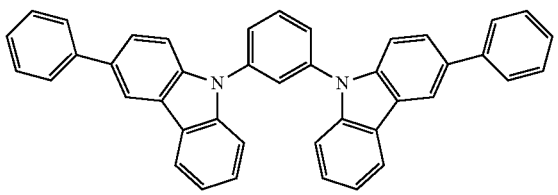
Host-15
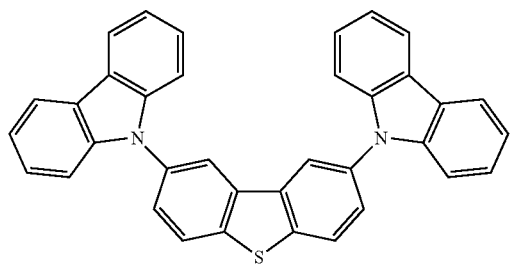
Host-16
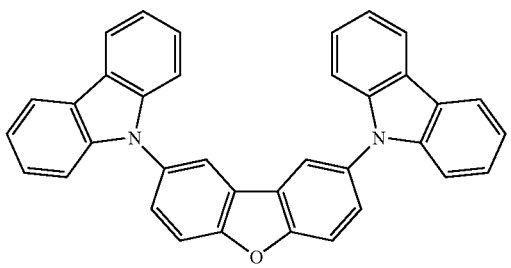
Host-17
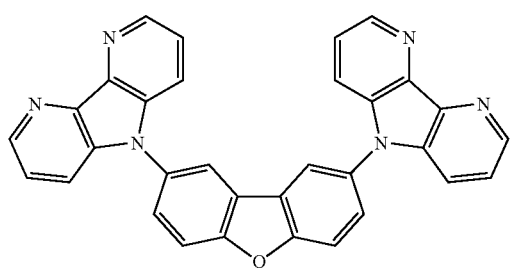
Host-18
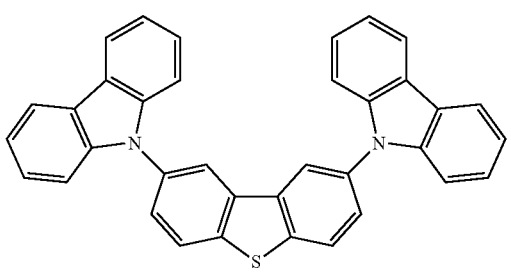

Host-19
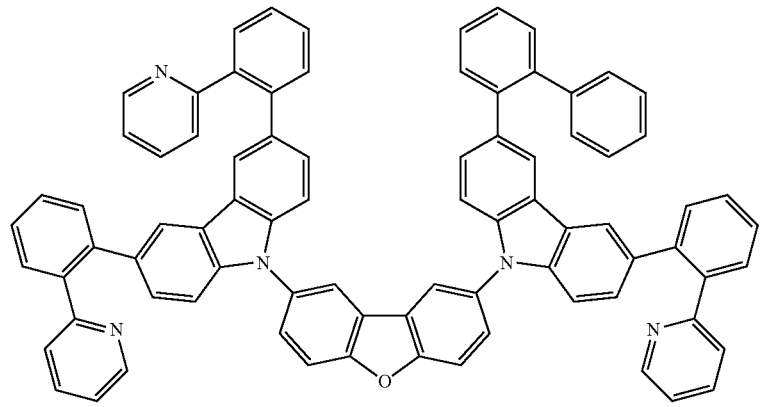
Host-20
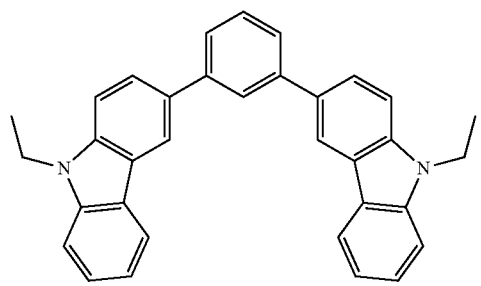
Host-21
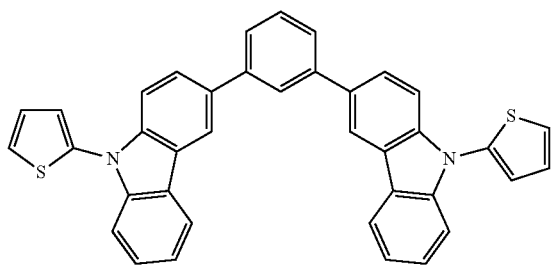
Host-22
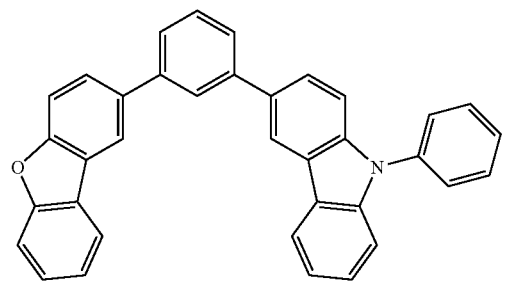
Host-23
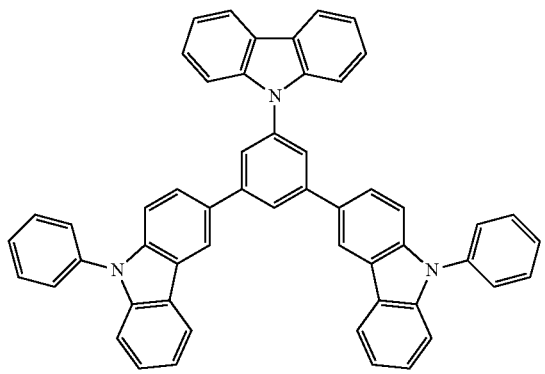
Host-24
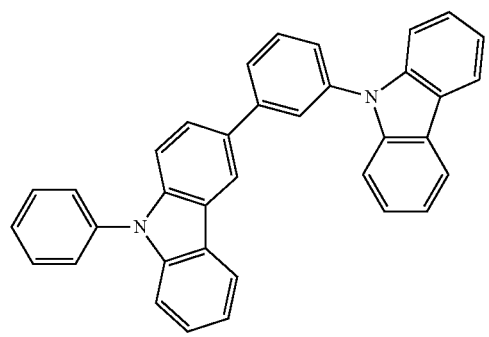
Host-25
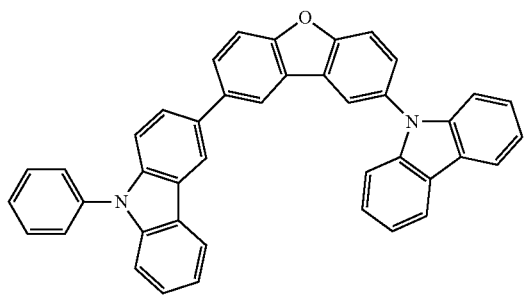

-continued
Host-26
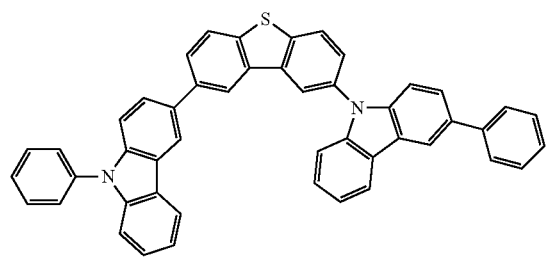
Host-27
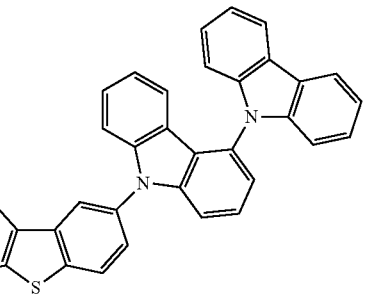
Host-28
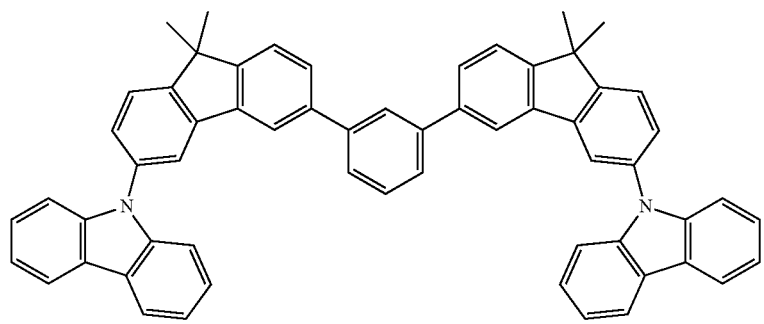
Host-29
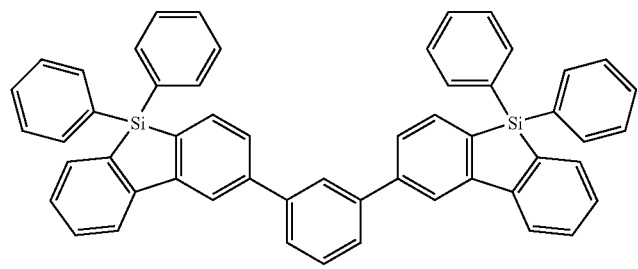
Host-30
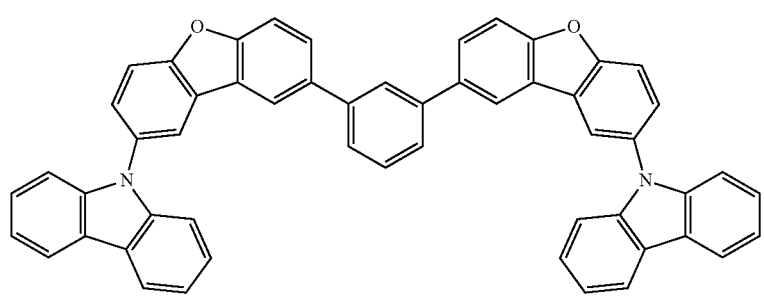
Host-31
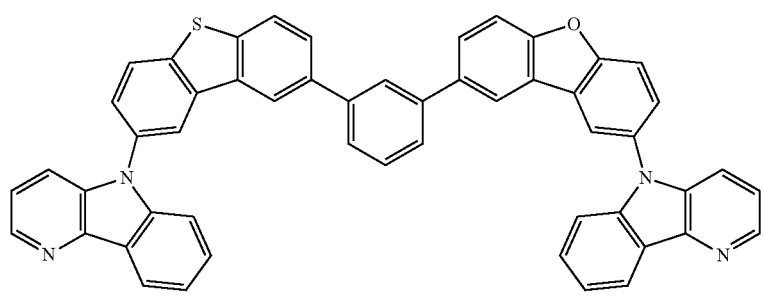

-continued
Host-32
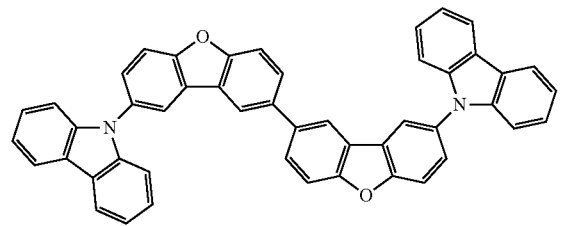
Host-33
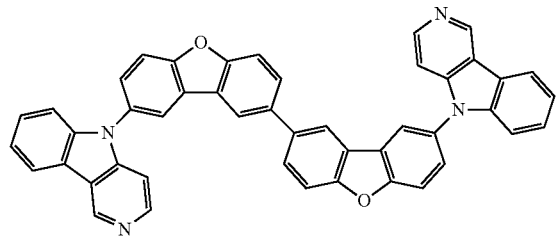
Host-34
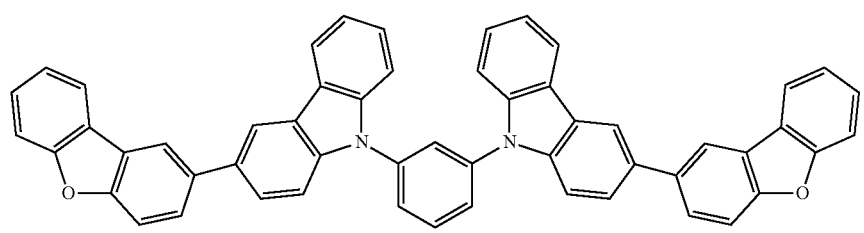
Host-35
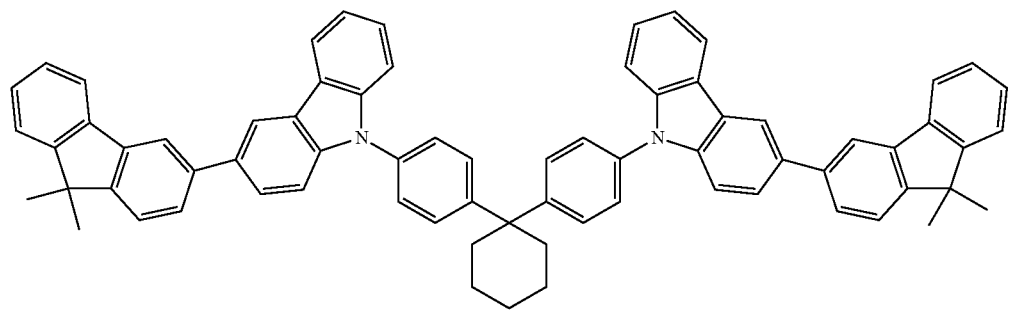
Host-36
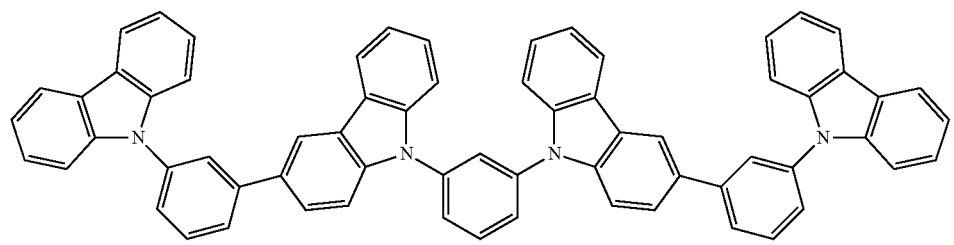
Host-37
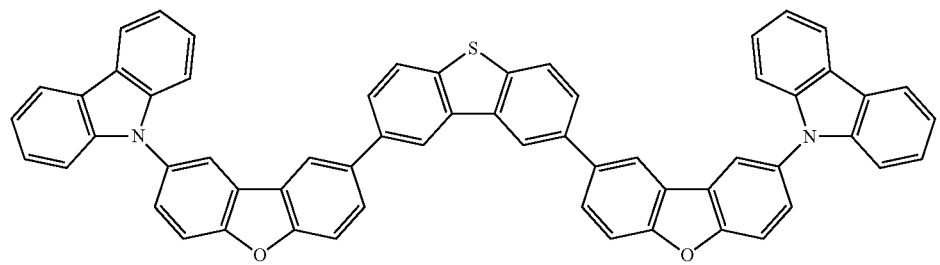

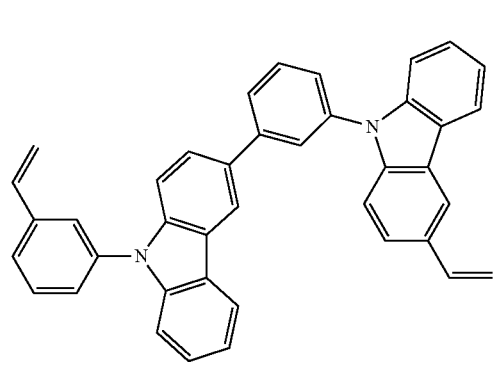
Host-38
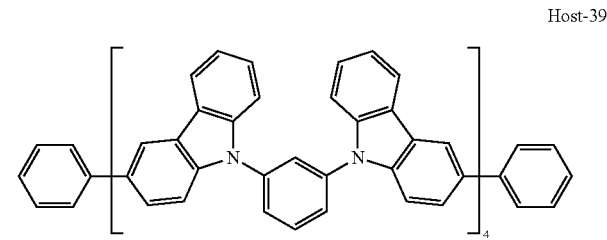
Host-39
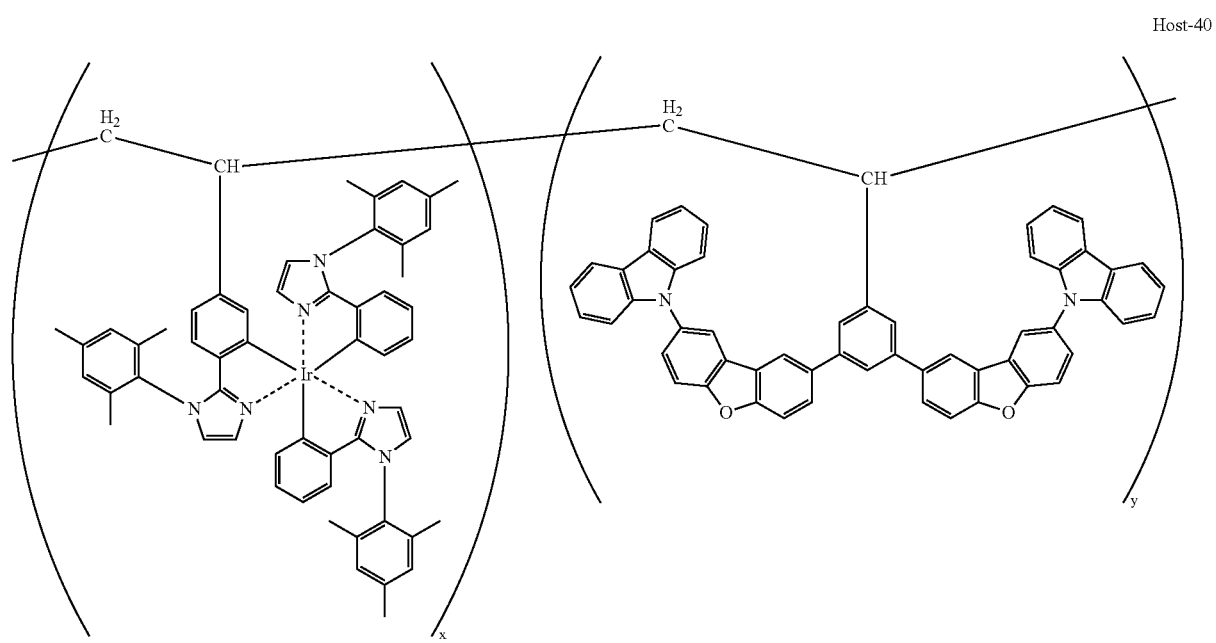
Host-40
x:y = 1:10
random co-polymer -continued
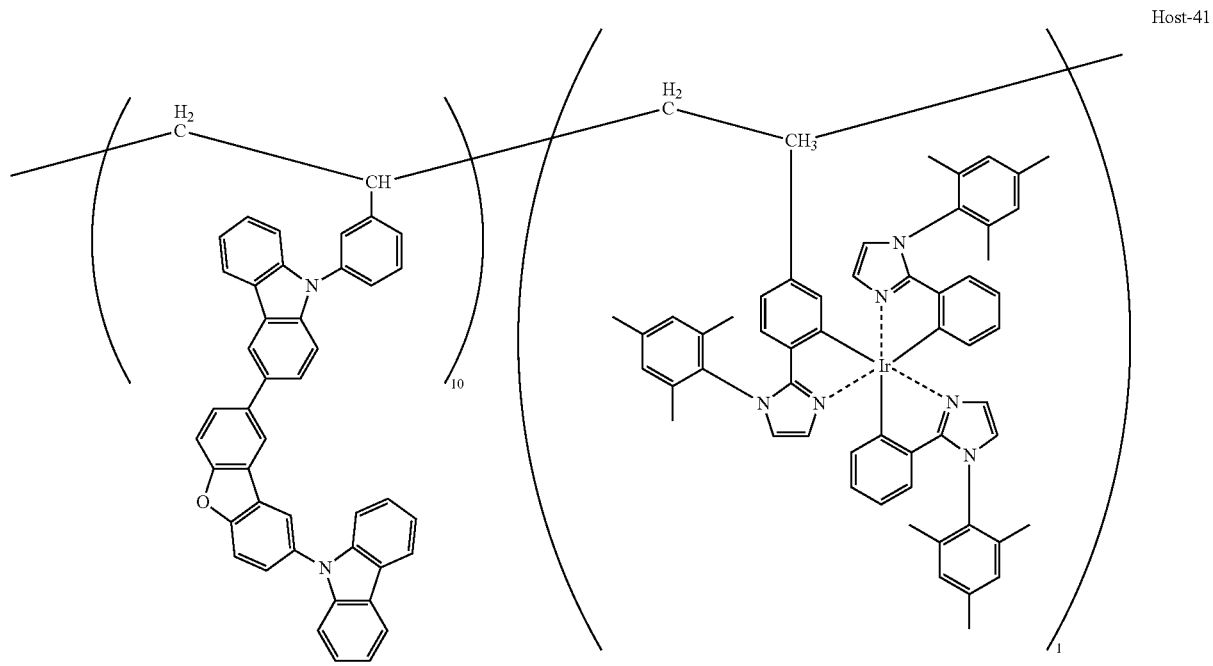
Host-41
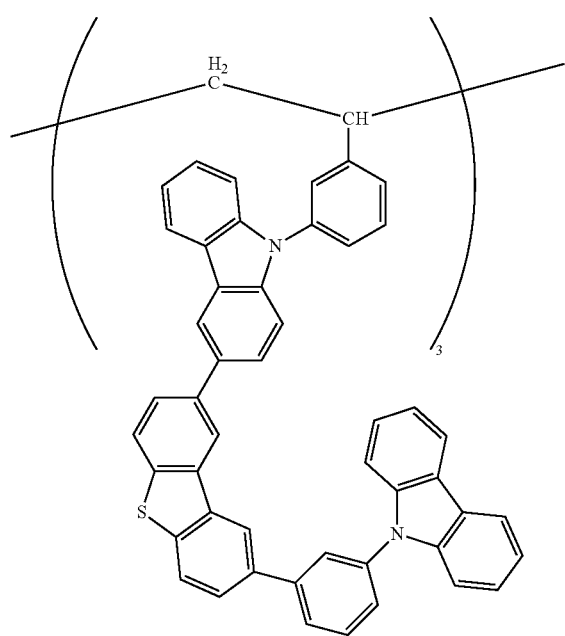

-continued
Host-42
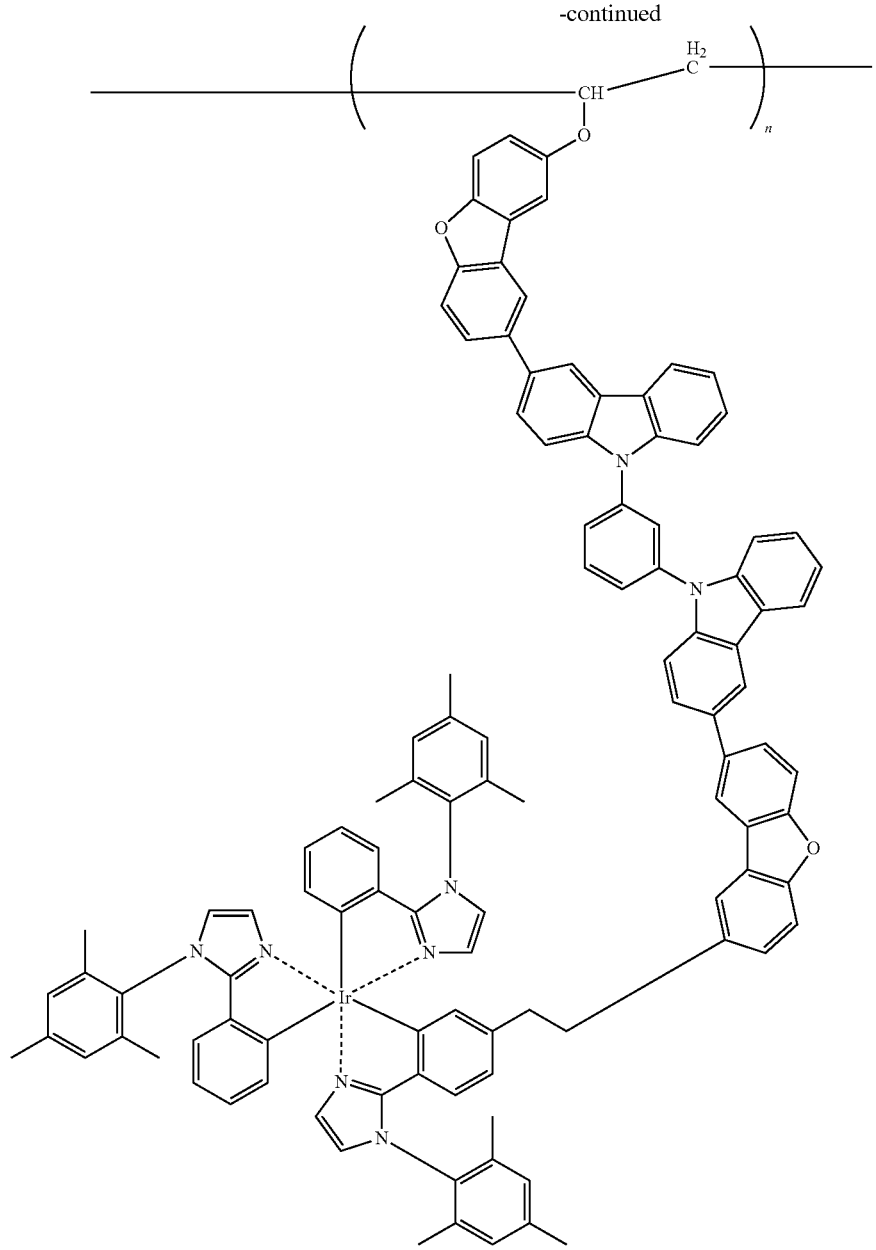
Mw(weight average molecularweight) = 40,000
Host-43
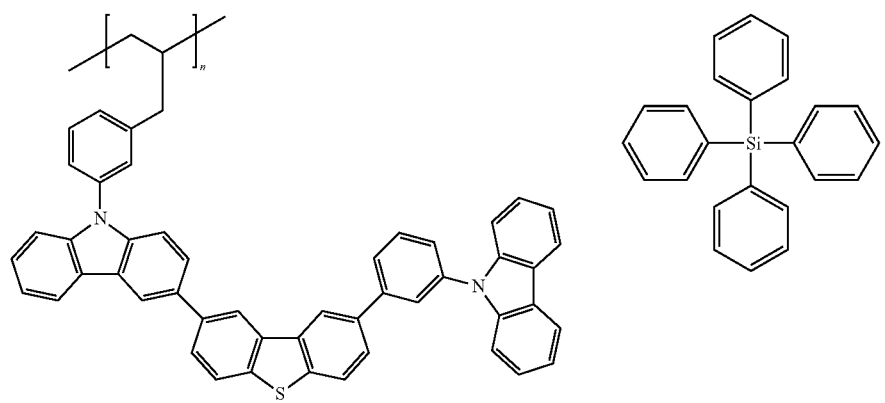
Mw(weight average molecularweight) = 100,000
Host-44

Host-45
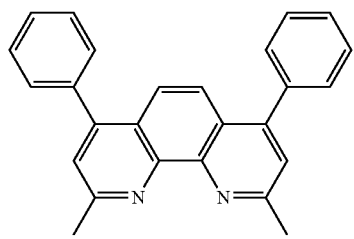
Host-46
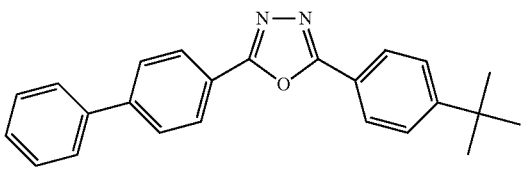
Host-47
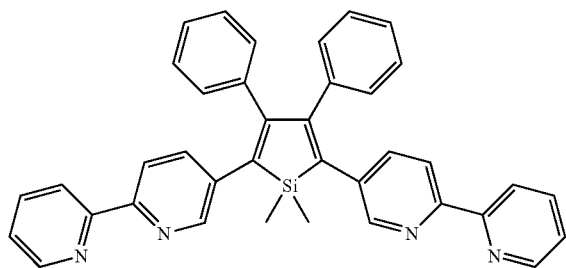
Host-48
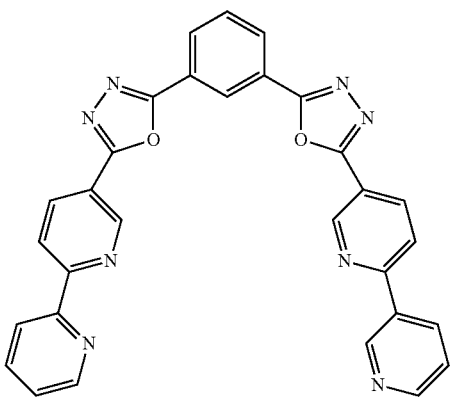
Host-49
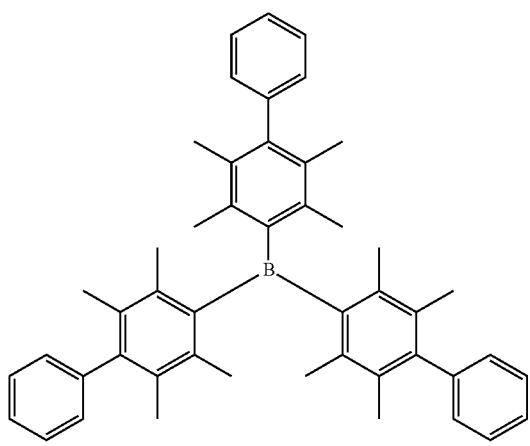
Host-50
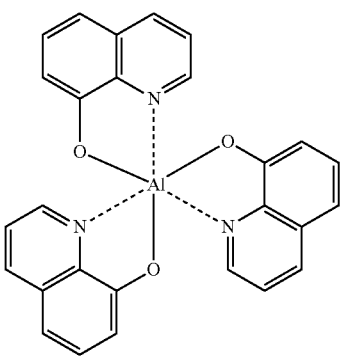
Host-51
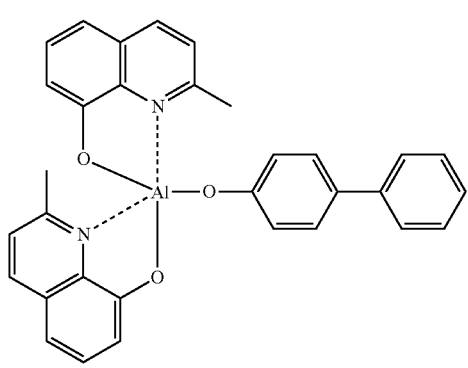

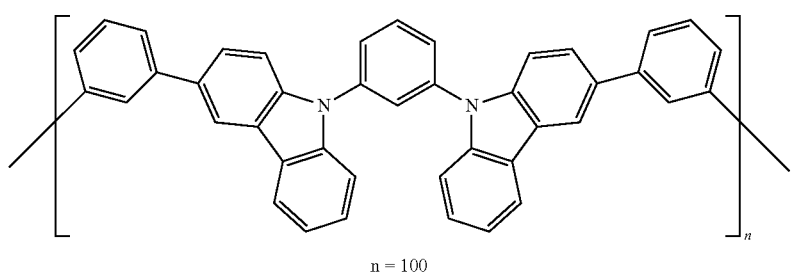

Host-52

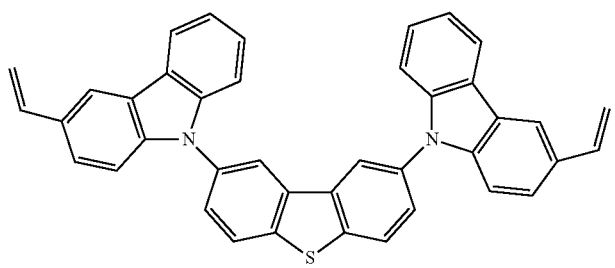

Host-53

Specifically preferable emission host compounds for the light emitting layer of the organic EL element of the present invention are the compounds represented by Formula (1) and Formula (2) as described above. Specific examples are the afore-mentioned compounds 1 to 79.

<Positive Hole Transport Layer>

A positive hole transport layer contains a material having a function of transporting a positive hole, and in a broad meaning, a positive hole injection layer and an electron inhibition layer are also included in a positive hole transport layer. A single layer of or plural layers of a positive hole transport layer may be provided.

A positive hole transport material is those having any one of a property to inject or transport a positive hole or a barrier property to an electron, and may be either an organic substance or an inorganic substance. For example, listed are a triazole derivative, an oxadiazole derivative, an imidazole derivative, a polyarylalkane derivative, a pyrazolone derivative, a phenylenediamine derivative, an arylamine derivative, an amino substituted chalcone derivative, an oxazole derivatives, a styrylanthracene derivative, a fluorenone derivative, a hydrazone derivative, a stilbene derivative, a silazane derivative, an aniline type copolymer, or conductive polymer oligomer and specifically preferably such as thiophene oligomer.

As a positive hole transport material, those described above can be utilized, however, it is preferable to utilized a porphyrin compound, an aromatic tertiary amine compound and a styrylamine compound, and specifically preferably an aromatic tertiary amine compound.

Typical examples of an aromatic tertiary amine compound and a styrylamine compound include: N,N,N',N'-tetraphenyl-4,4'-diaminophenyl; N,N'-diphenyl-N,N'-bis(3-methylphenyl)-(1,1'-biphenyl)-4,4'-diamine (TDP); 2,2-bis(4-di-p-tolylaminophenyl)propane; 1,1-bis(4-di-p-tolylaminophenyl)cyclohexane; N,N,N',N'-tetra-p-tolyl 4,4'-diaminobiphenyl; 1,1-bis(4-di-p-tolylaminophenyl)-4-phenylcyclohexane; bis(4-dimethylamino-2-methyl)phenylmethane; bis(4-di-p-tolylaminophenyl)phenylmethane; N,N'-diphenyl-N, N'-di(4-methoxyphenyl)-4,4'-diaminobiphenyl; N,N,N',N'-tetraphenyl-4,4'-diaminophenylether; 4,4'-bis(diphenylamino)quadriphenyl; N,N,N-tri(p-tolyl)amine; 4-(di-p-tolylamino)-4'-[4-(di-p-tri-amino)styryl]stilbene; 4-N, N-diphenylamino-(2-diphenylvinyl)benzene; 3-methoxy-4'-N,N-diphenylaminostilbene; and N-phenylcarbazole, in addition to those having two condensed aromatic rings in a molecule described in U.S. Pat. No. 5,061,569, such as 4,4'-bis[N-(1-naphthyl)-N-phenylamino]biphenyl (NDP), and 4,4',4"-tris[N-(3-methylphenyl)-N-phenylamino]triphenylamine (MDTDATA), in which three of triphenylamine units are bonded in a star burst form, described in JP-A No. 4-308688.

Polymer materials, in which these materials are introduced in a polymer chain or constitute the main chain of polymer, can be also utilized.

Further, an inorganic compound such as a p type-Si and a p type-SiC can be utilized as a positive hole injection material and a positive hole transport material Further, it is possible to employ so-called p type positive hole transport materials, as described in Japanese Patent Publication Open to Public Inspection (referred to as JP-A) No. 11-251067, and J. Huang et al. reference (Applied Physics Letters 80 (2002), p. 139). In the present invention, since high efficiency light emitting elements are prepared, it is preferable to employ these materials.

This positive hole transport layer can be prepared by forming a thin layer made of the above-described positive hole transport material according to a method well known in the art such as a vacuum evaporation method, a spin coating method, a cast method, an inkjet method and a LB method.

The layer thickness of a positive hole transport layer is not specifically limited, however, it is generally 5 nm-5 μm, and preferably 5 nm-200 nm. This positive transport layer may have a single layer structure comprised of one or not less than two types of the above described materials.

Further, it is possible to employ a positive hole transport layer of a higher p property which is doped with impurities. As its example, listed are those described in each of JP-A Nos. 4-297076, 2000-196140, 2001-102175, as well as in J. Appl. Phys., 95, 5773 (2004).

In the present invention, it is preferable to employ a positive hole transport layer of such a high p property, since it is possible to produce an element of lower electric power consumption.

There are given examples of the compound preferably used for formation of the positive hole transporting layer of the organic EL element of the present invention. However, the present invention is not limited to these.
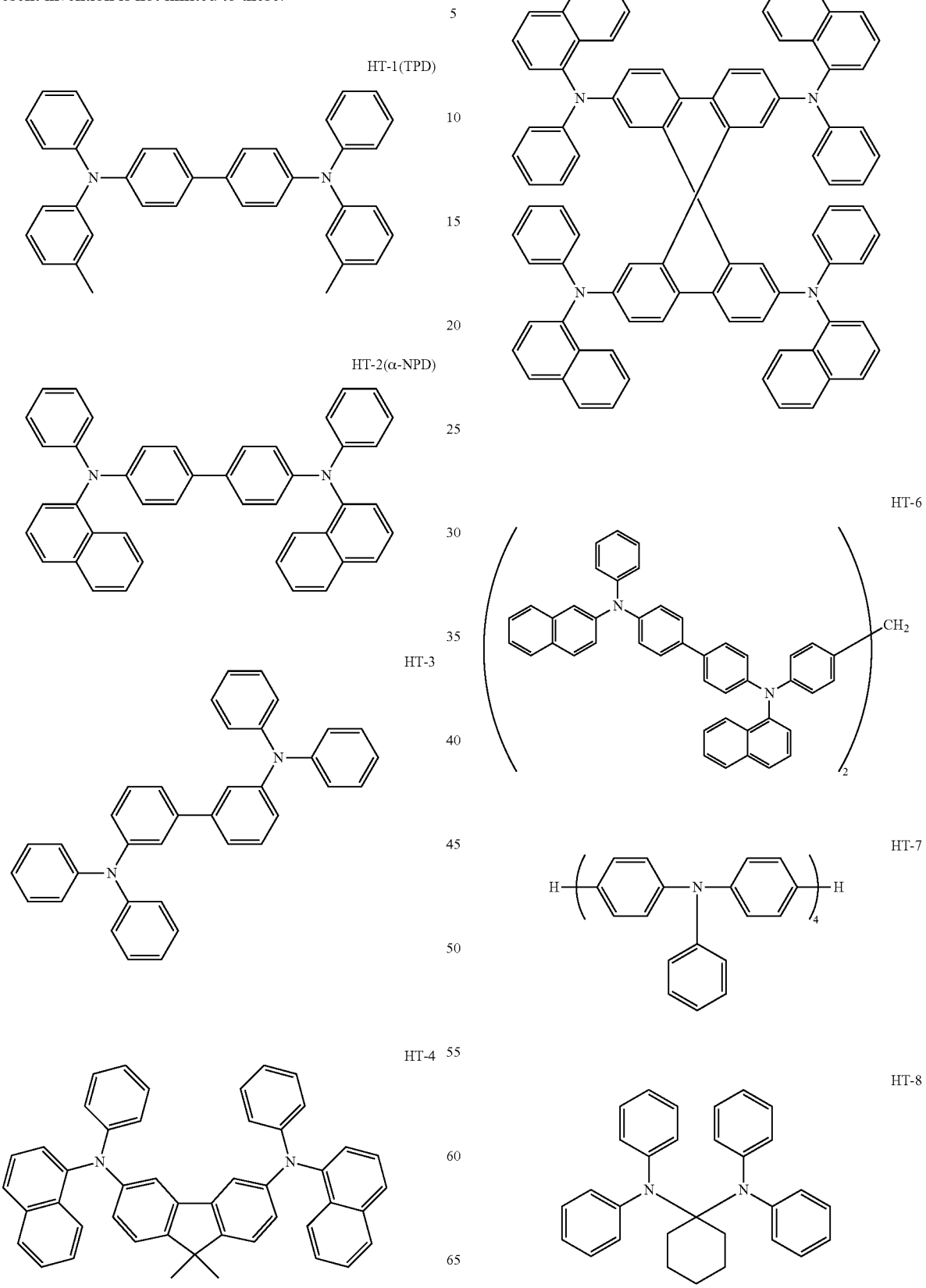

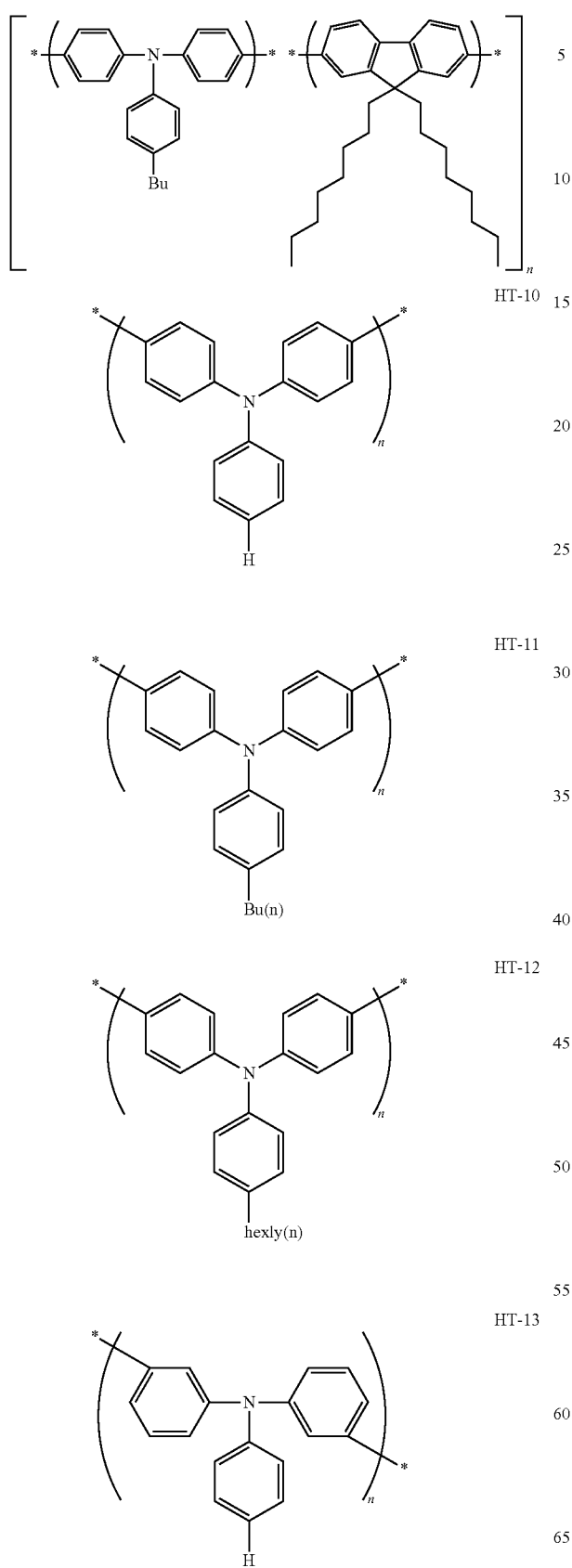
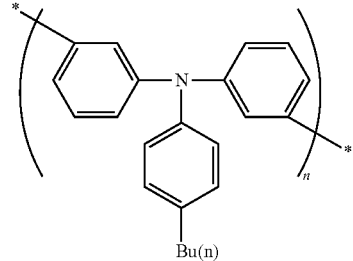
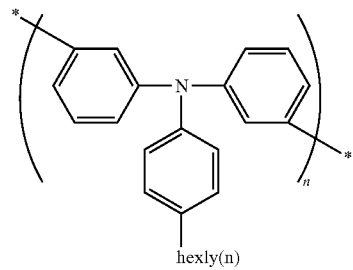
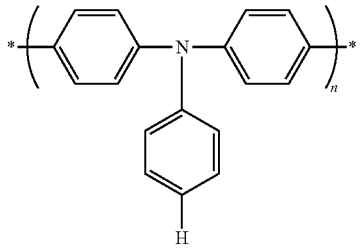
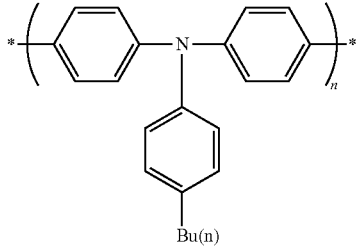
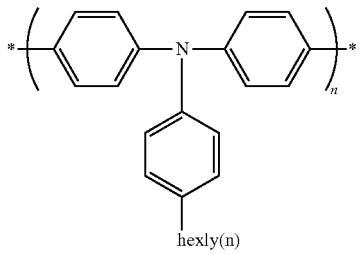
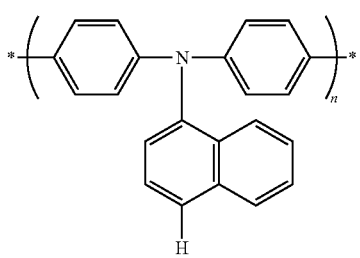

HT-20 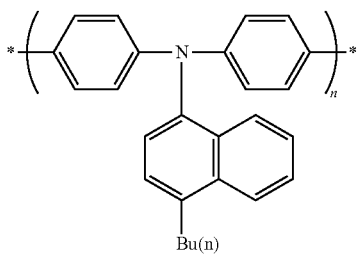

HT-21 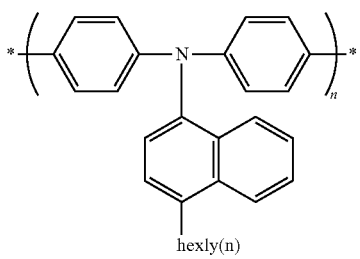

HT-22 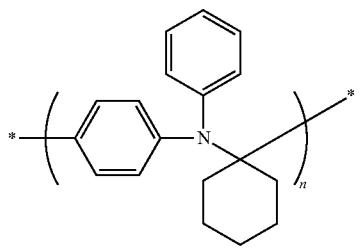

HT-23 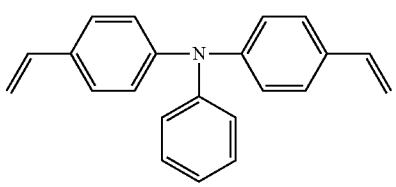

HT-24 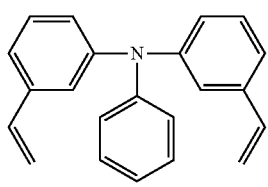

HT-25 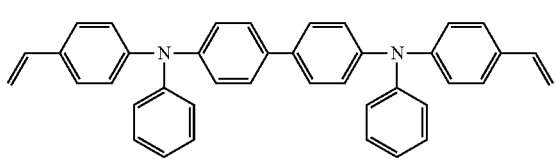

HT-26 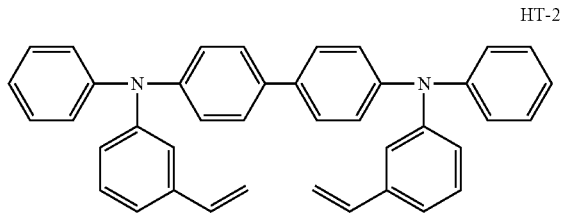

HT-27 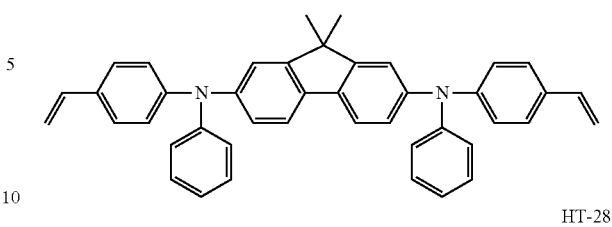

HT-28 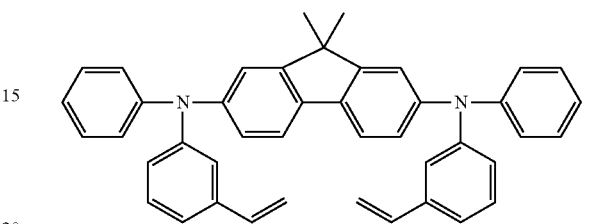

HT-29 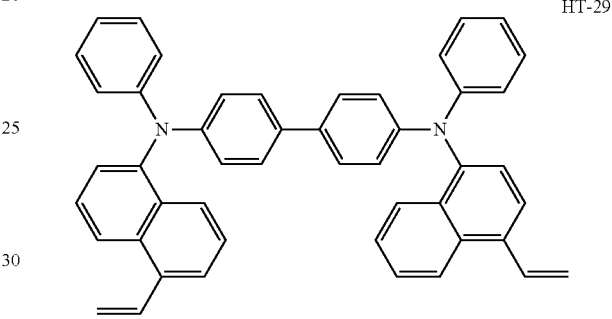

<Inhibition Layer: Positive Hole Inhibition Layer, Electron Inhibition Layer>

An inhibition layer is appropriately provided in addition to the basic constitution layers composed of organic thin layers as described above. Examples are described in such as JP-A Nos. 11-204258 and 11-204359 and p. 273 of "Organic EL Elements and Industrialization Front Thereof (Nov. 30 (1998), published by N. T. S Corp.)" is applicable to a positive hole inhibition (hole block) layer according to the present invention.

A positive hole inhibition layer, in a broad meaning, is provided with a function of electron transport layer, being comprised of a material having a function of transporting an electron but a very small ability of transporting a positive hole, and can improve the recombination probability of an electron and a positive hole by inhibiting a positive hole while transporting an electron.

Further, a constitution of an electron transport layer described above can be appropriately utilized as a positive hole inhibition layer according to the present invention.

The positive hole inhibition layer of the organic EL element of the present invention is preferably arranged adjacent to the light emitting layer.

It is preferable that the positive hole inhibition layer incorporates a carbazole derivative, or a azacarbazole derivative (here, "a azacarbazole derivative" indicates a compound in which at least one of the carbon atoms constituting the carbazole ring is replaced with a nitrogen atom) listed as a host compound as described above.

Further, in the present intention, in the case in which a plurality of light emitting layers which differ in a plurality of different emitted light colors, it is preferable that the light emitting layer which results in the shortest wavelength of the emitted light maximum wavelength is nearest to the anode in all light emitting layers. However, in such a case, it is preferable to additionally arrange the positive hole inhibition layer between the aforesaid shortest wavelength layer and the light emitting layer secondly near the anode. Further, at least 50% by weight of the compounds incorporated in the positive hole inhibition layer arranged in the aforesaid position preferably exhibits the ionization potential which is greater by at least 0.3 eV than that of the host compounds of the aforesaid shortest wavelength light emitting layer.

The ionization potential is defined as energy which is necessary to release electrons in the HOMO (being the highest occupied molecular orbital) to the vacuum level, and may be determined via, for example, the method described below.

(1) By employing Gaussian98 (Gauaaian98, Revision A. 11. 4, M. J. Frisch, et al. Gaussian 98 (Gaussian98, Revision A. 11. 4, M. J. Frisch, et al, Gaussian, Inc., Pittsburgh Pa., 2002), which is a molecular orbital calculation software, produced by Gaussian Co. in the United State of America, and by employing B3LYP/6-31G* as a key word, the value (in terms of corresponding eV unit) was computed, and it is possible to obtain the ionization potential by rouging off the second decimal point. The background, in which the resulting calculated values are effective, is that the calculated values obtained by the above method exhibit high relationship with the experimental values.

(2) It is possible to determine the ionization potential via a method in which ionization potential is directly determined employing a photoelectron spectrometry. For example, by employing a low energy electron spectrophotometer "Model AC-1", produced by Riken Keiki Co., or appropriately employ a method known as an ultraviolet light electron spectrometry.

On the other hand, the electron inhibition layer, as described herein, has a function of the positive hole transport layer in a broad sense, and is composed of materials having markedly small capability of electron transport, while having capability of transporting positive holes and enables to enhance the recombination probability of electrons and positive holes by inhibiting electrons, while transporting electrons.

Further, it is possible to employ the constitution of the positive hole transport layer, described below, as an electron inhibition layer when needed. The thickness of the positive hole inhibition layer and the electron transport layer according to the present invention is preferably 3-100 nm, but is more preferably 3-30 nm.

<Injection Layer: Electron Injection Layer (Cathode Buffer Layer), Positive Hole Injection Layer>

An injection layer is appropriately provided and includes an electron injection layer and a positive hole injection layer, which may be arranged between an anode and an emitting layer or a positive transfer layer, and between a cathode and an emitting layer or an electron transport layer, as described above.

An injection layer is a layer which is arranged between an electrode and an organic layer to decrease an operating voltage and to improve an emission luminance, which is detailed in volume 2, chapter 2 (pp. 123-166) of "Organic EL Elements and Industrialization Front thereof (Nov. 30, 1998, published by N. T. S corp.)", and includes a positive hole injection layer (an anode buffer layer) and an electron injection layer (a cathode buffer layer).

An anode buffer layer (a positive hole injection layer) is also detailed in such as JP-A Nos. 9-45479, 9-260062 and 8-288069, and specific examples include such as a phthalocyanine buffer layer comprising such as copper phthalocyanine, an oxide buffer layer comprising such as vanadium oxide, an amorphous carbon buffer layer, and a polymer buffer layer employing conductive polymer such as polyaniline (or called as emeraldine) or polythiophene.

A cathode buffer layer (an electron injection layer) is also detailed in such as JP-A Nos. 6-325871, 9-17574 and 10-74586, and specific examples include a metal buffer layer comprising such as strontium and aluminum, an alkali metal compound buffer layer comprising such as lithium fluoride, an alkali earth metal compound buffer layer comprising such as magnesium fluoride, and an oxide buffer layer comprising such as aluminum oxide. The above-described buffer layer (injection layer) is preferably a very thin layer, and the layer thickness is preferably in a range of 0.1 nm 5 μm although it depends on a raw material.

The materials used for an anode buffer layer and a cathode buffer layer can be used in combination with other materials. For example, they can be used in a positive hole transport layer or in an electron transport layer.

<Anode>

As an anode according to an organic EL element of the present invention, those comprising metal, alloy, a conductive compound, which is provided with a large work function (not less than 4 eV), and a mixture thereof as an electrode substance are preferably utilized. Specific examples of such an electrode substance include a conductive transparent material such as metal like Au, CuI, indium tin oxide (ITO), $SnO_2$ and ZnO.

Further, a material such as IDIXO ($In_2O_3$—ZnO), which can prepare an amorphous and transparent electrode, may be also utilized. As for an anode, these electrode substances may be made into a thin layer by a method such as evaporation or spattering and a pattern of a desired form may be formed by means of photolithography, or in the case of requirement of pattern precision is not so severe (not less than 100 μm), a pattern may be formed through a mask of a desired form at the time of evaporation or spattering of the above-described substance.

Alternatively, when coatable materials such as organic electrically conductive compounds are employed, it is possible to employ a wet system filming method such as a printing system or a coating system. When emission is taken out of this anode, the transmittance is preferably set to not less than 10% and the sheet resistance as an anode is preferably not more than a few hundreds Ω/□. Further, although the layer thickness depends on a material, it is generally selected in a range of 10 nm-1,000 nm and preferably of 10 nm-200 nm.

<Cathode>

On the other hand, as a cathode according to the present invention, metal, alloy, a conductive compound and a mixture thereof, which have a small work function (not more than 4 eV), are utilized as an electrode substance. Specific examples of such an electrode substance includes such as sodium, sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture and rare earth metal.

Among them, with respect to an electron injection property and durability against such as oxidation, preferable are a mixture of electron injecting metal with the second metal which is stable metal having a work function larger than electron injecting metal, such as a magnesium/silver mixture, a magnesium/aluminum mixture, a magnesium/indium mixture, an aluminum/aluminum oxide ($Al_2O_3$) mixture and a lithium/aluminum mixture, and aluminum.

As for a cathode, these electrode substances may be made into a thin layer by a method such as evaporation or spattering. Further, the sheet resistance as a cathode is preferably not more than a few hundreds Ω/□ and the layer thickness is generally selected in a range of 10 nm-5 μm and preferably of 50 nm-200 nm. Herein, to transmit emission, either one of an anode or a cathode of an organic EL element is preferably transparent or translucent to improve the emission luminance.

Further, after forming, on the cathode, the above metals at a film thickness of 1 nm-20 nm, it is possible to prepare a transparent or translucent cathode in such a manner that electrically conductive transparent materials are prepared thereon. By applying the above, it is possible to produce an element in which both anode and cathode are transparent.

<Substrate>

A substrate according to an organic EL element of the present invention is not specifically limited with respect to types of such as glass and plastics. They me be transparent or opaque. However, a transparent substrate is preferable when the emitting light is taken from the side of substrate. Substrates preferably utilized includes such as glass, quartz and transparent resin film. A specifically preferable substrate is resin film capable of providing an organic EL element with a flexible property.

Resin film includes such as: polyesters such as polyethylene terephthalate (PET) and polyethylene naphthalate (PEN); polyethylene, polypropyrene; cellulose esters or their derivatives such as cellophane, cellulose diacetate, cellulose triacetate, cellulose acetate butylate, cellulose acetate propionate (CAP), cellulose acetate phthalate (TAC) and cellulose nitrate; polyvinylidene chloride, polyvinyl alcohol, polyethylene vinyl alcohol, syndiotactic polystyrene, polycarbonate, norbornene resin, polymethylpentene, polyether ketone, polyimide, polyether sulfone (PES), polyphenylene sulfide, polysulfones, polyetherimide, polyether ketone imide, polyamide, fluororesin, Nylon, polymethylmethacrylate, acrylic resin, polyacrylate; and cycloolefine resins such as ARTON (produced by JSR Co. Ltd.) and APEL (produce by Mitsui Chemicals, Inc.)

On the surface of a resin film, it may be formed a film incorporating an inorganic or an organic compound or a hybrid film incorporating both compounds. Barrier films are preferred at a water vapor permeability (25±0.5° C., and relative humidity (90±2)% RH) of at most 0.01 g/(m$^2$·24 h), determined based on JIS K 7129-1992. Further, high barrier films are preferred at an oxygen permeability of at most $1\times10^{-3}$ ml/(m$^2$·24 h·MPa), and at a water vapor permeability of at most $10^{-5}$ g/(m$^2$·24 h), determined based on JIS K 7126-1987.

As materials forming a barrier film, employed may be those which retard penetration of moisture and oxygen, which deteriorate the element. For example, it is possible to employ silicon oxide, silicon dioxide, and silicon nitride. Further, in order to improve the brittleness of the aforesaid film, it is more preferable to achieve a laminated layer structure of inorganic layers and organic layers. The laminating order of the inorganic layer and the organic layer is not particularly limited, but it is preferable that both are alternatively laminated a plurality of times.

Barrier film forming methods are not particularly limited, and examples of employable methods include a vacuum deposition method, a sputtering method, a reactive sputtering method, a molecular beam epitaxy method, a cluster ion beam method, an ion plating method, a plasma polymerization method, a plasma CVD method, a laser CVD method, a thermal CVD method, and a coating method. Of these, specifically preferred is a method employing an atmospheric pressure plasma polymerization method, described in JP-A No. 2004-68143.

Examples of opaque support substrates include metal plates such aluminum or stainless steel, films, opaque resin substrates, and ceramic substrates.

The external extraction efficiency of light emitted by the organic EL element of the present invention is preferably at least 1% at room temperature, but is more preferably at least 5%.

External extraction quantum yield (%)=(the number of photons emitted by the organic EL element to the exterior/the number of electrons fed to organic EL element)×100

Further, even by simultaneously employing color hue improving filters such as a color filter, simultaneously employed may be color conversion filters which convert emitted light color from the organic EL element to multicolor by employing fluorescent materials. When the color conversion filters are employed, it is preferable that λmax of light emitted by the organic EL element is at least 480 nm.

<Preparation Method of Organic EL Element>

As one example of the preparation method of the organic EL element of the present invention, there will be described the preparation method of the organic EL element composed of: anode/positive hole injection layer/positive hole transport layer/light emitting layer/positive hole inhibition layer/electron transport layer/cathode buffer layer (electron injection layer)/cathode.

Initially, a thin film composed of desired electrode substances, for example, anode substances is formed on an appropriate base material to reach a thickness of at most 1 μm, but preferably 10 nm-200 nm, whereby an anode is prepared.

Subsequently, on the above, formed are organic compound thin layers including a positive hole injection layer, a positive hole transport layer, a light emitting layer, a positive hole inhibition layer, an electron transport layer, and a cathode buffer layer, which contain organic materials.

With respect to the layers in the phosphorescence emitting organic EL element of the present invention, at least a cathode and an electron transport layer which is adjacent to the cathode are coated with a wet process and the layers are formed.

Examples of a wet process include: a spin coating method, a cast method, a die coating method, a blade coating method, a roll coating method, an inkjet method, a printing method, a spray coating method, a curtain coating method, and a LB method. From the viewpoint of enabling to form a precise thin layer with a high productivity, a die coating method, a roll coating method, an inkjet method and a spray coating method are preferably used. These methods are suitable for applying to a roll to roll production method. It may be possible to use a different film production method for every layer.

As liquid media which are employed to dissolve or disperse organic metal complexes according to the present invention, employed may be, for example, ketones such as methyl ethyl ketone or cyclohexanone, fatty acid esters such as ethyl acetate, halogenated hydrocarbons such as dichlorobenzene, aromatic hydrocarbons such as toluene, xylene, mesitylene, and cyclohexylbenzene, aliphatic hydrocarbons such as cyclohexane, decaline, and dodecane, and organic solvents such as DMF or DMSO.

Further, with regard to dispersion methods, it is possible to achieve dispersion employing dispersion methods such as ultrasonic waves, high shearing force dispersion or media dispersion.

After forming these layers, a thin layer composed of cathode materials is formed on the above layers so that the film thickness reaches at most 1 μm, but is preferably in the range of 50-200 nm, whereby a cathode is arranged, and the desired organic EL element is prepared.

Further, by reversing the preparation order, it is possible to achieve preparation in order of a cathode, a cathode buffer layer, an electron injection layer, an electron transport layer, a light emitting layer, a positive hole transport layer, a positive hole injection layer, and an anode.

When direct current voltage is applied to the multicolor display device prepared as above, the anode is employed as "+" polarity, while the cathode is employed as "−" polarity. When 2-40 V is applied, it is possible to observe light emission. Further, alternating current voltage may be applied. The wave form of applied alternating current voltage is not specified.

It is preferable to produce an organic EL element of the present invention with one vacuum operation, from formation of a positive hole injection layer to formation of a cathode without interruption. However, it may be possible to interrupt the operation and take out the intermediate product in order to apply a different film forming method. In that case, working under a dry inert gas atmosphere is preferable.

<Sealing>

As sealing means employed in the present invention, listed may be, for example, a method in which sealing members, electrodes, and a supporting substrate are subjected to adhesion via adhesives.

The sealing members may be arranged to cover the display region of an organic EL element, and may be an engraved plate or a flat plate. Neither transparency nor electrical insulation is limited.

Specifically listed are glass plates, polymer plate-films, metal plates, and films. Specifically, it is possible to list, as glass plates, soda-lime glass, barium-strontium containing glass, lead glass, aluminosilicate glass, borosilicate glass, bariumborosilicate glass, and quartz.

Further, listed as polymer plates may be polycarbonate, acryl, polyethylene terephthalate, polyether sulfide, and polysulfone. As a metal plate, listed are those composed of at least one metal selected from the group consisting of stainless steel, iron, copper, aluminum magnesium, nickel, zinc, chromium, titanium, molybdenum, silicon, germanium, and tantalum, or alloys thereof.

In the present invention, since it is possible to convert the element to a thin film, it is possible to preferably employ a metal film.

Further, the oxygen permeability of the polymer film is preferably at most $1\times10^{-3}$ ml/(m$^2$·24 h·MPa), determined by the method based on JIS K 7126-1987, while its water vapor permeability (at 25±0.5° C. and relative humidity (90±2)%) is at most $10^{-5}$ g/(m$^2$·24 h), determined by the method based on JIS K 7129-1992.

Conversion of the sealing member into concave is carried out employing a sand blast process or a chemical etching process.

In practice, as adhesives, listed may be photo-curing and heat-curing types having a reactive vinyl group of acrylic acid based oligomers and methacrylic acid, as well as moisture curing types such as 2-cyanoacrylates. Further listed may be thermal and chemical curing types (mixtures of two liquids) such as epoxy based ones. Still further listed may be hot-melt type polyamides, polyesters, and polyolefins. Yet further listed may be cationically curable type ultraviolet radiation curable type epoxy resin adhesives.

In addition, since an organic EL element is occasionally deteriorated via a thermal process, those are preferred which enable adhesion and curing between room temperature and 80° C. Further, desiccating agents may be dispersed into the aforesaid adhesives. Adhesives may be applied onto sealing portions via a commercial dispenser or printed on the same in the same manner as screen printing.

Further, it is appropriate that on the outside of the aforesaid electrode which interposes the organic layer and faces the support substrate, the aforesaid electrode and organic layer are covered, and in the form of contact with the support substrate, inorganic and organic material layers are formed as a sealing film. In this case, as materials forming the aforesaid film may be those which exhibit functions to retard penetration of those such as moisture or oxygen which results in deterioration. For example, it is possible to employ silicon oxide, silicon dioxide, and silicon nitride.

Still further, in order to improve brittleness of the aforesaid film, it is preferable that a laminated layer structure is formed, which is composed of these inorganic layers and layers composed of organic materials. Methods to form these films are not particularly limited. It is possible to employ, for example, a vacuum deposition method, a sputtering method, a reactive sputtering method, a molecular beam epitaxy method, a cluster ion beam method, an ion plating method, a plasma polymerization method, an atmospheric pressure plasma polymerization method, a plasma CVD method, a thermal CVD method, and a coating method.

In a gas phase and a liquid phase, it is preferable to inject inert gases such as nitrogen or argon, and inactive liquids such as fluorinated hydrocarbon or silicone oil into the space between the sealing member and the surface region of the organic EL element. Further, it is possible to form vacuum. Still further, it is possible to enclose hygroscopic compounds in the interior.

Examples of hygroscopic compounds include metal oxides (for example, sodium oxide, potassium oxide, calcium oxide, barium oxide, magnesium oxide, and aluminum oxide); sulfates (for example, sodium sulfate, calcium sulfate, magnesium sulfate, and cobalt sulfate); metal halides (for example, calcium chloride, magnesium chloride, cesium fluoride, tantalum fluoride, cerium bromide, magnesium bromide, barium iodide, and magnesium iodide); perchlorates (for example, barium perchlorate and magnesium perchlorate). In sulfates, metal halides, and perchlorates, suitably employed are anhydrides.

<Protective Film and Protective Plate>

The aforesaid sealing film on the side which nips the organic layer and faces the support substrate or on the outside of the aforesaid sealing film, a protective or a protective plate may be arranged to enhance the mechanical strength of the element. Specifically, when sealing is achieved via the aforesaid sealing film, the resulting mechanical strength is not always high enough, whereby it is preferable to arrange the protective film or the protective plate described above. Usable materials for these include glass plates, polymer plate-films, and metal plate-films which are similar to those employed for the aforesaid sealing. However, in terms of light weight and a decrease in thickness, it is preferable to employ polymer films.

<Light Extraction>

It is generally known that an organic EL element emits light in the interior of the layer exhibiting the refractive index (being about 1.7-about 2.1) which is greater than that of air, whereby only about 15-about 200 of light generated in the light emitting layer is extracted.

This is due to the fact that light incident to an interface (being an interface of a transparent substrate to air) at an angle of θ which is at least critical angle is not extracted to the exterior of the element due to the resulting total reflection, or light is totally reflected between the transparent electrode or the light emitting layer and the transparent substrate, and light is guided via the transparent electrode or the light emitting layer, whereby light escapes in the direction of the element side surface.

Means to enhance the efficiency of the aforesaid light extraction include, for example, a method in which roughness is formed on the surface of a transparent substrate, whereby total reflection is minimized at the interface of the transparent substrate to air (U.S. Pat. No. 4,774,435), a method in which efficiency is enhanced in such a manner that a substrate results in light collection (JP-A No. 63-314795), a method in which a reflection surface is formed on the side of the element (JP-A No. 1-220394), a method in which a flat layer of a middle refractive index is introduced between the substrate and the light emitting body and an antireflection film is formed (JP-A No. 62-172691), a method in which a flat layer of a refractive index which is equal to or less than the substrate is introduced between the substrate and the light emitting body (JP-A No 2001-202827), and a method in which a diffraction grating is formed between the substrate and any of the layers such as the transparent electrode layer or the light emitting layer (including between the substrate and the outside) (JP-A No. 11-283751).

In the present invention, it is possible to employ these methods while combined with the organic EL element of the present invention. Of these, it is possible to appropriately employ the method in which a flat layer of a refractive index which is equal to or less than the substrate is introduced between the substrate and the light emitting body and the method in which a diffraction grating is formed between the substrate and any of the layers such as the transparent electrode layer or the light emitting layer (including between the substrate and the outside), By combining these means, the present invention enables the production of elements which exhibit higher luminance or excel in durability.

When a low refractive index medium of a thickness, which is greater than the wavelength of light, is formed between the transparent electrode and the transparent substrate, the extraction efficiency of light emitted from the transparent electrode to the exterior increases as the refractive index of the medium decreases.

As materials of the low refractive index layer, listed are, for example, aerogel, porous silica, magnesium fluoride, and fluorine based polymers. Since the refractive index of the transparent substrate is commonly about 1.5-about 1.7, the refractive index of the low refractive index layer is preferably at most approximately 1.5, but is more preferably at most 1.35.

Further, thickness of the low refractive index medium is preferably at least two times the wavelength in the medium. The reason is that when the thickness of the low refractive index medium reaches nearly the wavelength of light so that electromagnetic waves oozed via evernescent enter into the substrate, effects of the low refractive index layer are lowered.

The method in which the interface which results in total reflection or a diffraction grating is introduced in any of the media is characterized in that light extraction efficiency is significantly enhanced.

The above method works as follows. By utilizing properties of the diffraction grating capable of changing the light direction to the specific direction different from diffraction via so-called Bragg diffraction such as primary diffraction or secondary diffraction of the diffraction grating, of light emitted from the light emitting layer, light, which is not emitted to the exterior due to total reflection between layers, is diffracted via introduction of a diffraction grating between any layers or in a medium (in the transparent substrate and the transparent electrode) so that light is extracted to the exterior.

It is preferable that the introduced diffraction grating exhibits a two-dimensional periodic refractive index. The reason is as follows. Since light emitted in the light emitting layer is randomly generated to all directions, in a common one-dimensional diffraction grating exhibiting a periodic refractive index distribution only in a certain direction, light which travels to the specific direction is only diffracted, whereby light extraction efficiency is not sufficiently enhanced.

However, by changing the refractive index distribution to a two-dimensional one, light, which travels to all directions, is diffracted, whereby the light extraction efficiency is enhanced.

As noted above, a position to introduce a diffraction grating may be between any layers or in a medium (in a transparent substrate or a transparent electrode). However, a position near the organic light emitting layer, where light is generated, is desirous.

In this case, the cycle of the diffraction grating is preferably about ½-about 3 times the wavelength of light in the medium. The preferable arrangement of the diffraction grating is such that the arrangement is two-dimensionally repeated in the form of a square lattice, a triangular lattice, or a honeycomb lattice.

<Light Collection Sheet>

Via a process to arrange a structure such as a micro-lens array shape on the light extraction side of the organic EL element of the present invention or via combination with a so-called light collection sheet, light is collected in the specific direction such as the front direction with respect to the light emitting element surface, whereby it is possible to enhance luminance in the specific direction.

In an example of the micro-lens array, square pyramids to realize a side length of 30 μm and an apex angle of 90 degrees are two-dimensionally arranged on the light extraction side of the substrate. The side length is preferably 10 μm-100 μm. When it is less than the lower limit, coloration results due to generation of diffraction effects, while when it exceeds the upper limit, the thickness increases undesirably.

It is possible to employ, as a light collection sheet, for example, one which is put into practical use in the LED backlight of liquid crystal display devices. It is possible to employ, as such a sheet, for example, the luminance enhancing film (BEF), produced by Sumitomo 3M Limited.

As shapes of a prism sheet employed may be, for example, A shaped stripes of an apex angle of 90 degrees and a pitch of 50 μm formed on a base material, a shape in which the apex angle is rounded, a shape in which the pitch is randomly changed, and other shapes.

Further, in order to control the light radiation angle from the light emitting element, simultaneously employed may be a light diffusion plate-film. For example, it is possible to employ the diffusion film (LIGHT-UP), produced by Kimoto Co., Ltd.

<Application>

It is possible to employ the organic EL element of the present invention as display devices, displays, and various types of light emitting sources. Examples of light emitting sources include, but are not limited to lighting apparatuses (home lighting and car lighting), clocks, backlights for liquid crystals, sign advertisements, signals, light sources of light memory media, light sources of electrophotographic copiers, light sources of light communication processors, and light sources of light sensors.

It is effectively employed especially as backlights of liquid crystal display devices and lighting sources.

If needed, the organic EL element of the present invention may undergo patterning via a metal mask or an ink-jet printing method during film formation. When the patterning is carried out, only an electrode may undergo patterning, an electrode and a light emitting layer may undergo patterning, or all element layers may undergo patterning. During preparation of the element, it is possible to employ conventional methods.

Figure 4:
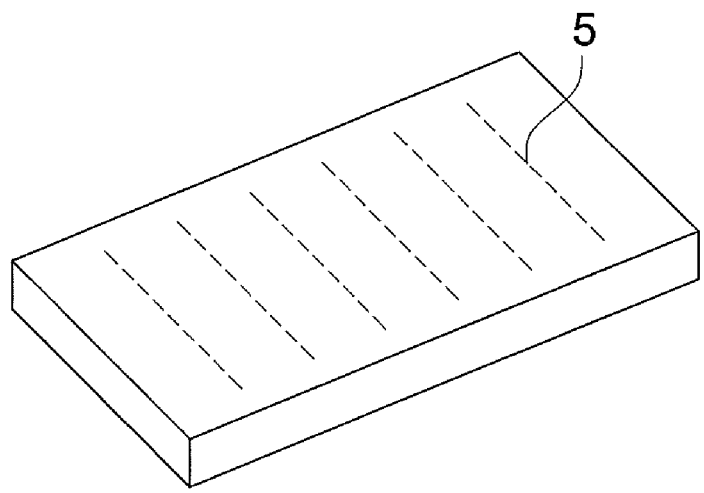
FIG. 4 is a schematic drawing of a full color display device according to a passive matrix mode.
Figure 4:
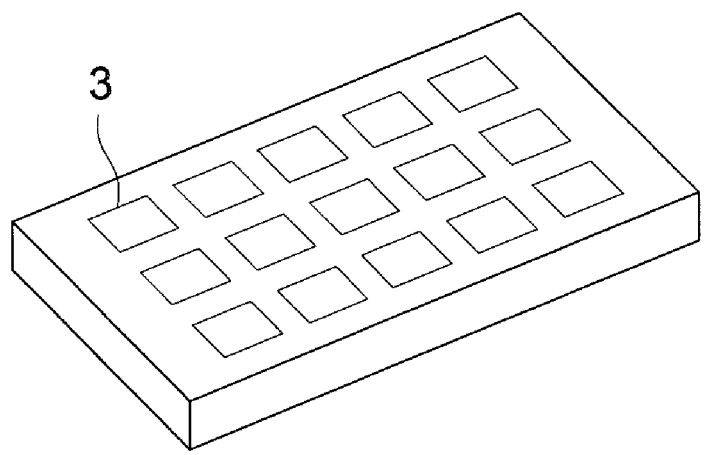
Figure 4:
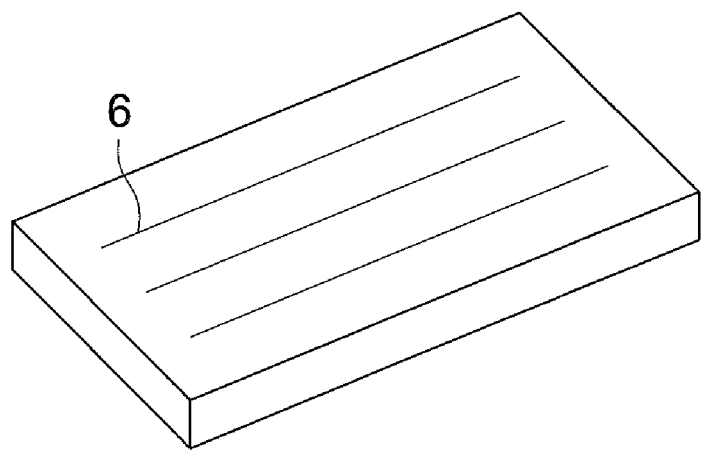

Color of light emitted by the organic EL element of the present invention and compounds according to the present invention is specified as follows. In FIG. 4.16 on page 108 of "Shinpen Shikisai Kagaku Handbook (New Edition Color Science Handbook)" (edited by The Color Science Association of Japan, Tokyo Daigaku Shuppan Kai, 1985), values determined via a spectroradiometric luminance meter CS-1000 (produced by Konica Minolta Sensing Inc.) are applied to the CIE chromaticity coordinate, whereby the color is specified.

Further, when the organic EL element of the present invention is a white element, "white", as described herein, means that when 2-degree viewing angle front luminance is determined via the aforesaid method, chromaticity in the CIE 1931 Color Specification System is within the region of X=0.33±0.07 and Y=0.33±0.07.

<Display Device>

A display device of the present invention will now be explained. The display device of the present invention includes the above-described organic EL element.

A display device of the present invention may be either monochromatic or multi-colored. Here explained will be a multicolor display device. In the case of a multicolor display device, a shadow mask is provided only at the time of emission layer formation, and layers can be formed all over the surface by such as an evaporation method, a cast method, a spin coat method, an inkjet method and a printing method.

When patterning is performed only for producing a light emitting layer, the method is not specifically limited; however, preferable are an evaporation method, an inkjet method, a spin coating method and a printing method.

The constitution of the organic EL element used for a display device can be selected from the embodiments of the organic EL element as described above, in accordance with the requirement.

The production method of the organic EL element was described above for one of the embodiments of the organic EL element of the present invention.

When a direct current voltage is applied on the multicolor display device thus prepared, emission can be observed by application of a voltage of approximately 2-40 V setting an anode to + polarity and a cathode to − polarity. Further, no current flows and no emission generate at all even when a voltage is applied with a reversed polarity. Further, in the case of alternate current voltage being applied, emission generates only in a state of an anode being + and a cathode being −. Herein, the wave shape of alternate current may be arbitrary.

A multicolor display device can be utilized as a display device, a display and various types of emission light sources. In a display device and a display, full-colored display is possible by employing three types of organic EL elements providing blue, red and green emissions.

A display device and a display include a TV, a personal computer, a mobile instrument, an AV instrument, a character broadcast display and an information display in a car. Particularly, the display device and the display may be also utilized as a display to playback still images and moving images, and may adopt either a simple matrix (a passive matrix) mode or an active matrix mode when being utilized as a display device for moving image playback.

An illumination light source includes a home use illumination, a car room illumination, a backlight of a watch or a liquid crystal, a panel advertisement, a signal, a light source of an optical memory medium, a light source for an electrophotographic copier, a light source for an optical telecommunication processor and a light source for a photo-sensor, however, the present invention is not limited thereto.

In the following, one example of a display device provided with an organic EL element of the present invention will be explained with reference to figures.

FIG. 1 is a schematic drawing to show an example of a display device constituted of an organic EL element. It is a schematic drawing of a display, which displays image information by emission of an organic EL element, such as a mobile phone.

Display 1 is constituted of display section A having plural number of pixels and control section B which performs image scanning of display section A based on image information.

Control section B, which is electrically connected to display section A, sends a scanning signal and an image data signal to plural number of pixels based on image information from the outside and pixels of each scanning line successively emit depending on the image data signal by a scanning signal to perform image scanning, whereby image information is displayed on display section A.

Figure 2:
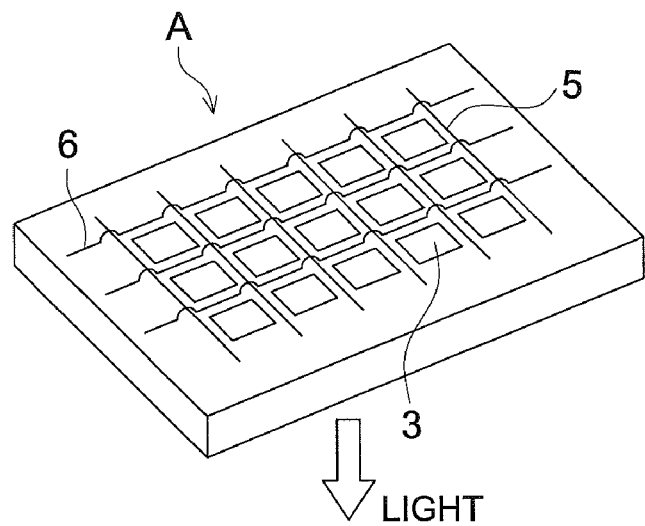
FIG. 2 is a schematic drawing of display section A.

FIG. 2 is a schematic drawing of display section A.

Display section A is provided with such as a wiring part, which contains plural scanning lines 5 and data lines 6, and plural pixels 3 on a substrate. Primary part materials of display section A will be explained in the following.

In the drawing, shown is the case that light emitted by pixel 3 is taken out along the white allow (downward).

Scanning lines 5 and plural data lines 6 in a wiring part each are comprised of a conductive material, and scanning lines 5 and data lines 6 are perpendicular in a grid form and are connected to pixels 3 at the right-angled crossing points (details are not shown in the drawing).

Pixel 3 receives an image data from data line 6 when a scanning signal is applied from scanning line 5 and emits according to the received image data.

Full-color display device is possible by appropriately arranging pixels having an emission color in a red region, pixels in a green region and pixels in a blue region, side by side on the same substrate.

Next an emission process of a pixel will be explained.

Figure 3:
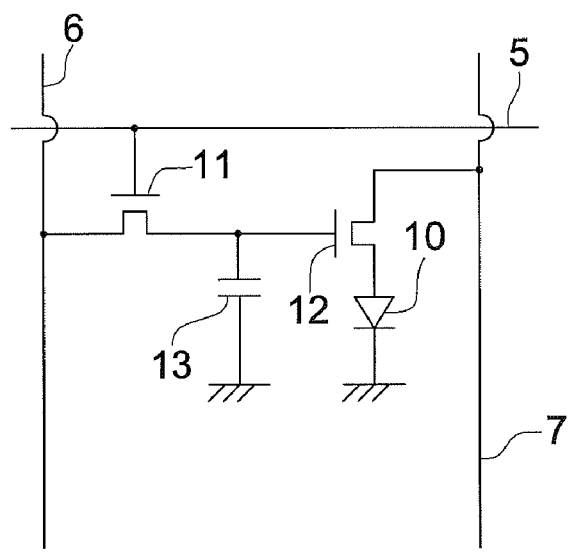
FIG. 3 is an equivalent circuit diagram of an image pixel.

FIG. 3 is a schematic drawing of a pixel.

A pixel is equipped with such as organic EL element 10, switching transistor 11, operating transistor 12 and capacitor 13. Red, green and blue emitting organic EL elements are utilized as organic EL element 10 for plural pixels, and full-color display device is possible by arranging these side by side on the same substrate.

In FIG. 3, an image data signal is applied on the drain of switching transistor 11 via data line 6 from control section B. Then, when a scanning signal is applied on the gate of switching transistor 11 via scanning line 5 from control section B, operation of switching transistor is on to transmit the image data signal applied on the drain to the gates of capacitor 13 and operating transistor 12.

Operating transistor 12 is on, simultaneously with capacitor 13 being charged depending on the potential of an image data signal, by transmission of an image data signal. In operating transistor 12, the drain is connected to electric source line 7 and the source is connected to the electrode of organic EL element 10, and an electric current is supplied from electric source line 7 to organic EL element 10 depending on the potential of an image data applied on the gate.

When a scanning signal is transferred to next scanning line 5 by successive scanning of control section B, operation of switching transistor 11 is off. However, since condenser 13 keeps the charged potential of an image data signal even when operation of switching transistor 11 is off, operation of operating transistor 12 is kept on to continue emission of organic EL element 10 until the next scanning signal is applied. When the next scanning signal is applied by successive scanning, operating transistor 12 operates depending on the potential of an image data signal synchronized to the scanning signal and organic EL element 10 emits.

That is, emission of each organic EL element 10 of plural pixels 3 is performed by providing switching transistor 11 and operating transistor 12 against each organic EL element 10 of plural pixels 3. Such an emission method is called as an active matrix mode.

Herein, emission of organic EL element 10 may be either emission of plural gradations based on a multiple-valued image data signal having plural number of gradation potentials or on and off of a predetermined emission quantity based on a binary image data signal. Further, potential hold of capacitor 13 may be either continuously maintained until the next scanning signal application or discharged immediately before the next scanning signal application.

In the present invention, emission operation is not necessarily limited to the above-described active matrix mode but may be a passive matrix mode in which organic EL element is emitted based on a data signal only when a scanning signal is scanned.

FIG. 4 is a schematic drawing of a display device based on a passive matrix mode. In FIG. 4, plural number of scanning lines 5 and plural number of image data lines 6 are arranged grid-wise, opposing to each other and sandwiching pixels 3.

When a scanning signal of scanning line 5 is applied by successive scanning, pixel 3 connected to scanning line 5 applied with said signal emits depending on an image data signal.

Since pixel 3 is provided with no active element in a passive matrix mode, decrease of manufacturing cost is possible.

<Lighting Device>

A lighting device of the present invention will now be explained. The lighting device of the present invention includes the above-described organic EL element.

An organic EL element of the present invention can be utilized as an organic EL element provided with a resonator structure, and a utilization purpose of such an organic EL element provided with a resonator structure includes such as a light source for an optical memory medium, a light source for an electrophotographic copier, a light source for a optical telecommunication processor and a light source for a photosensor, however, is not limited thereto. Further, the organic EL element may be utilized for the above-described applications by being made to perform laser emission.

Further, an organic EL element of the present invention may be utilized as one type of a lamp like an illumination and an exposure light, and may be also utilized as a display device of a projector of an image projecting type and a display device (a display) of a type to directly view still images and moving images.

An operating mode in the case of being utilized as a display device for playback of moving images may be either a simple matrix (a passive matrix) mode or an active matrix mode. In addition, a full-color display device can be prepared by utilizing at least two types of organic EL elements of the present invention which emit different emitting colors.

An organic EL element material of the present invention can be also applied to an organic EL element to generate emission of practically white color as a lighting device.

Plural emission colors are simultaneously emitted by plural number of emission materials to obtain white light by mixing colors. A combination of plural emission colors may be either the one, in which three emission maximum wavelengths of three primary colors of blue, green and red are contained, or the other, in which two emission maximum wavelengths, utilizing a relationship of complimentary colors such as blue and yellow, or blue and orange, are contained.

Further, a combination of emission materials to obtain plural number of emission colors may be either a combination comprising plural number of materials which emit phosphoresce or fluorescence, or a combination of a material which emits phosphoresce or fluorescence and a dye material which emits by light from an emission material as exiting light, however, in a white organic electroluminescence element according to the present invention, it is enough only to mix plural emission dopants in combination.

A mask is provided only at the time of forming such as an emission layer, a positive hole transport layer or an electron transport layer, to only simply arrange the plural emission dopants such as by separately painting through the mask, while other layers are commonly utilized to require no patterning such as a mask. Therefore, such as an electrode can be formed all over the plane by such as an evaporation method, a cast method, a spin coat method, an inkjet method and a printing method, resulting in improvement of productivity.

According to this method, different from a white organic EL device in which plural colors of emission elements are arranged parallel in an alley form, an element itself is white emitting.

An emission material utilized in an emission layer is not specifically limited, and in the case of a backlight of a liquid crystal display element, any combination by arbitrary selection among platinum complexes according to the present invention or emission materials well known in the art can be utilized so as to be fitted to the wavelength range corresponding to CF (color filter) characteristics, whereby white emission can be obtained.

<One Embodiment of Lighting Device of the Present Invention>

The non-light emitting surface of the organic EL element of the present invention was covered with a glass case, and a 300 μm thick glass substrate was employed as a sealing substrate. An epoxy based light curable type adhesive (LUX-TRACK LC0629B produced by Toagosei Co., Ltd.) was employed in the periphery as a sealing material. The resulting one was superimposed on the aforesaid cathode to be brought into close contact with the aforesaid transparent support substrate, and curing and sealing were carried out via exposure of UV radiation onto the glass substrate side, whereby the lighting device shown in FIGS. 5 and 6 was formed.

Figure 5:
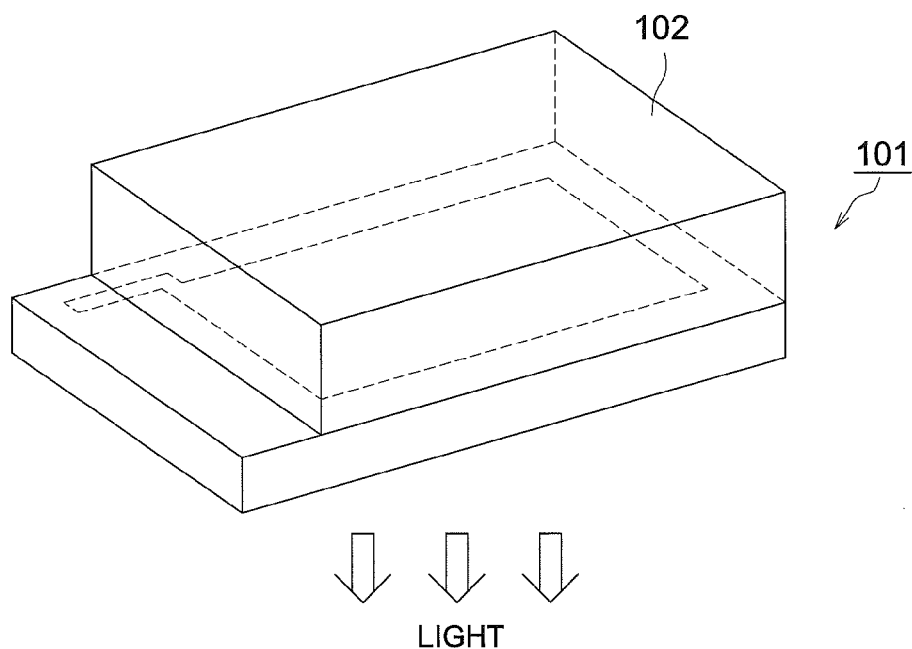
FIG. 5 is a schematic drawing of a lighting device.

FIG. 5 is a schematic view of a lighting device and Organic EL element 101 is covered with glass cover 102 (incidentally, sealing by the glass cover was carried out in a globe box under nitrogen ambience (under an ambience of high purity nitrogen gas at a purity of at least 99.999%) so that Organic EL Element 101 was not brought into contact with atmosphere.

Figure 6:
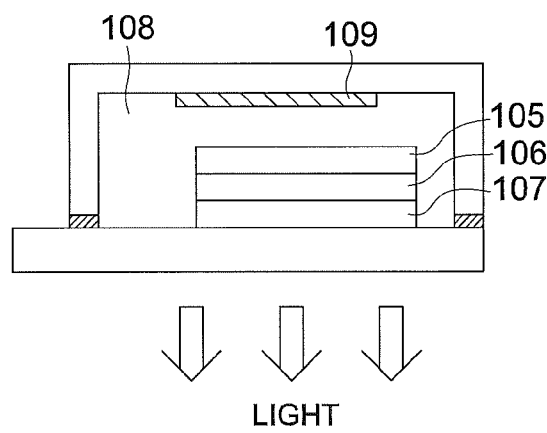
FIG. 6 is a cross-sectional drawing of a lighting device.
Figure 7A:
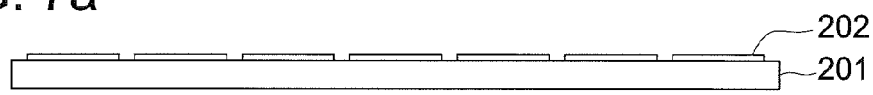
FIGS. 7a to 7e are schematic structural drawings of a full color organic EL display device.
Figure 7B:
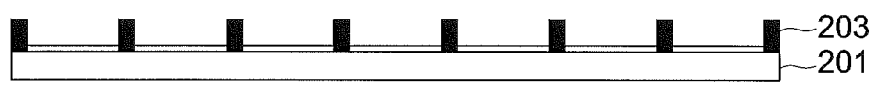
Figure 7C:
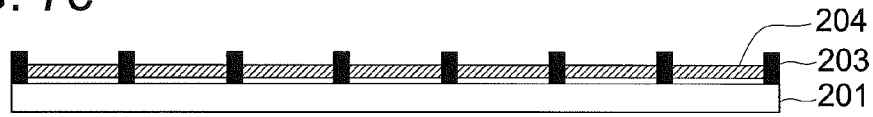
Figure 7D:
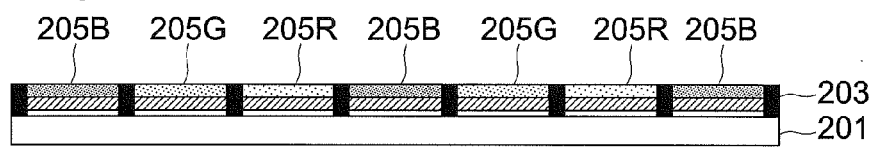
Figure 7E:
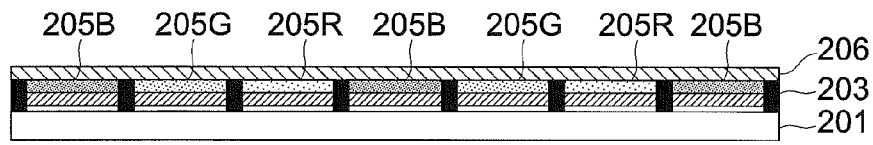

FIG. 6 is a cross-sectional view of a lighting device, and in FIG. 6, 105 represents a cathode, 106 represents an organic EL layer, and 107 represents a glass substrate fitted with a transparent electrode. Further, the interior of glass cover 102 is filled with nitrogen gas 108 and water catching agent 109 is provided.

EXAMPLES

The present invention will now be described with reference to examples, however the present invention is not limited thereto.

The chemical structures of the compounds used in Examples are shown in the followings.

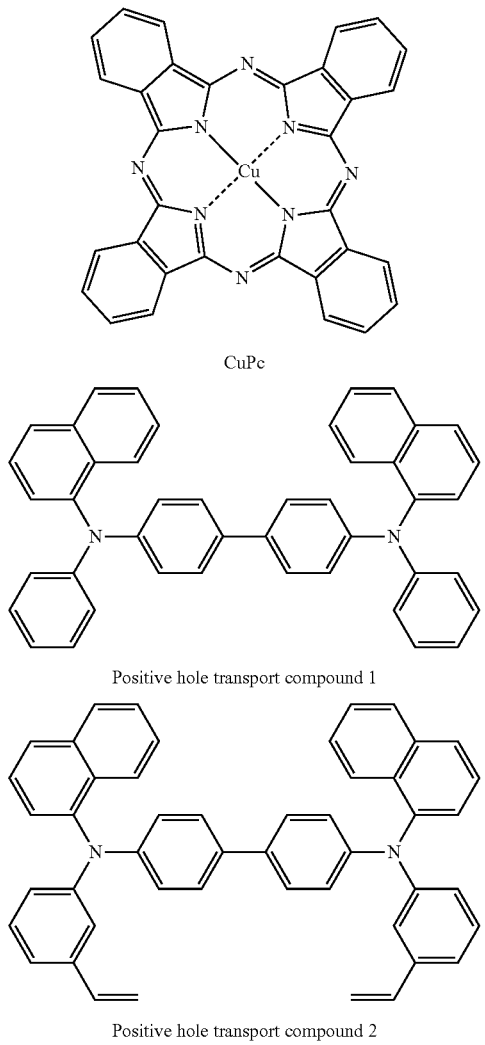

CuPc

Positive hole transport compound 1

Positive hole transport compound 2

Positive hole transport compound 3

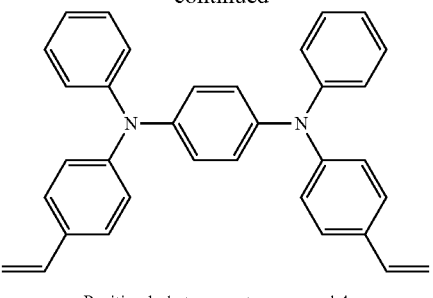

Positive hole transport compound 4

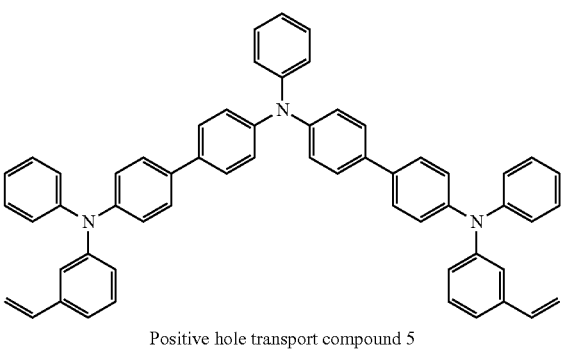

Positive hole transport compound 5

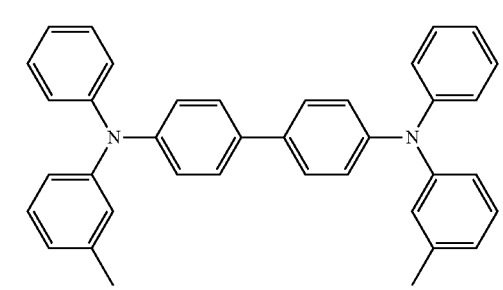

Positive hole transport compound 6

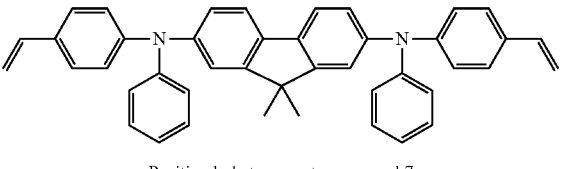

Positive hole transport compound 7

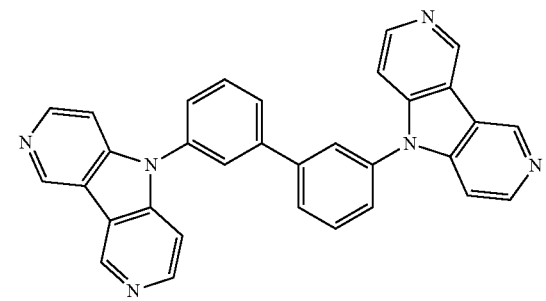

Electron transport compound 1

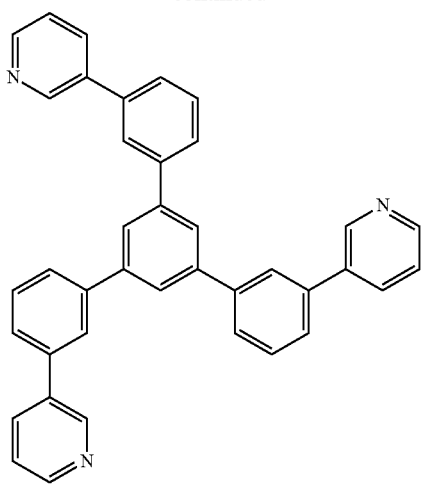
Electron transport compound 2
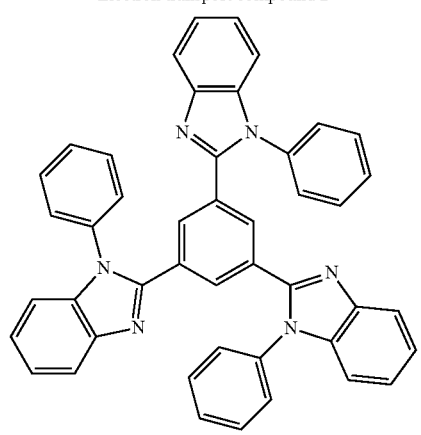
Electron transport compound 3
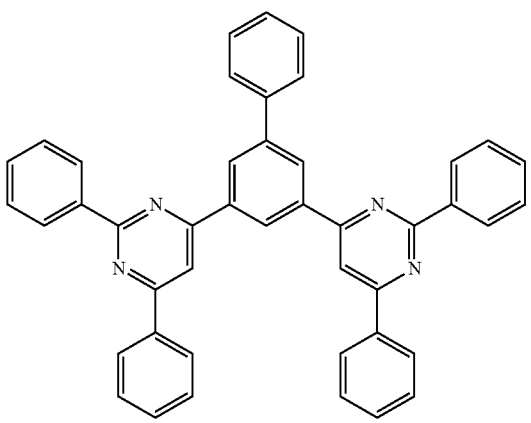
Electron transport compound 4
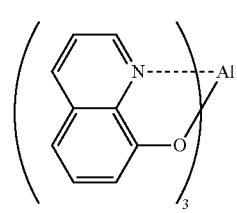
Electron transport compound 5
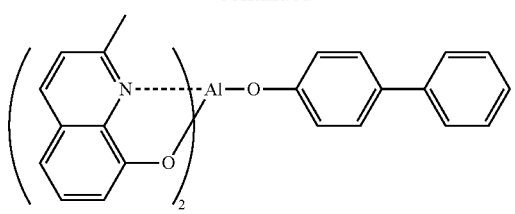
Electron transport compound 6
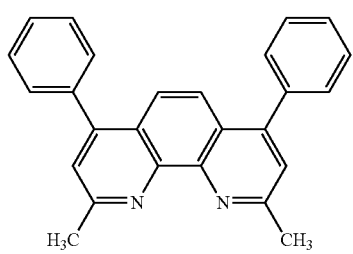
Electron transport compound 7
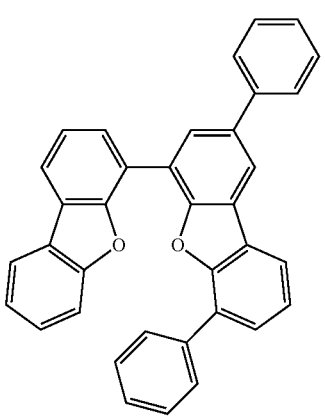
Comparative compound 1
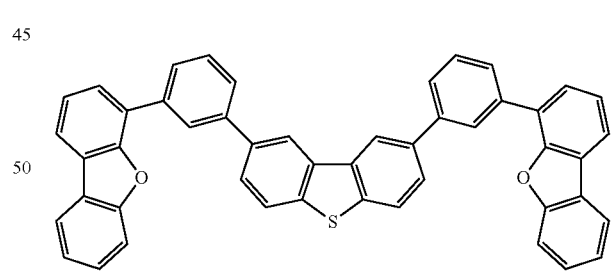
Comparative compound 2
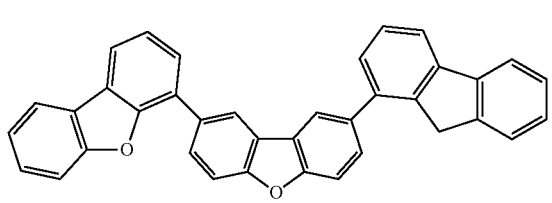
Comparative compound 3

-continued

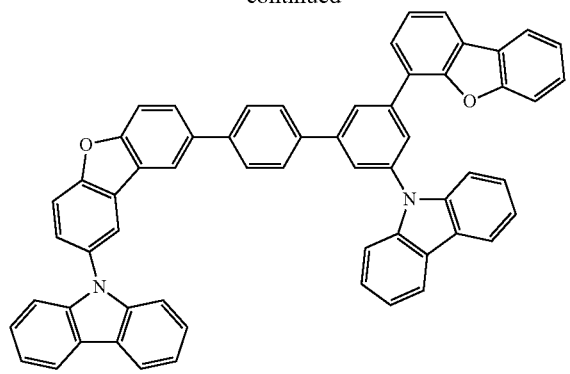

Comparative compound 4

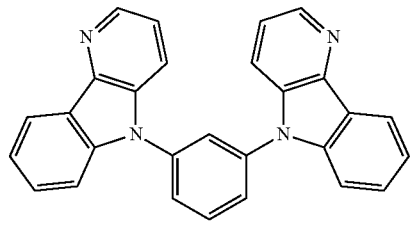

Comparative compound 5

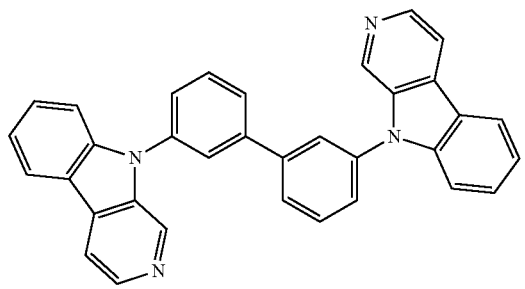

Comparative compound 6

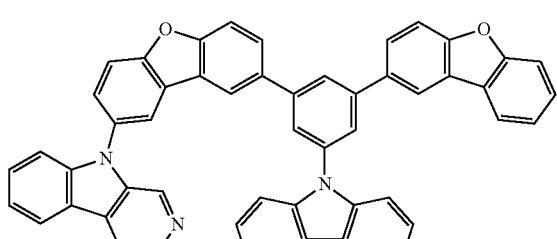

Comparative compound 7

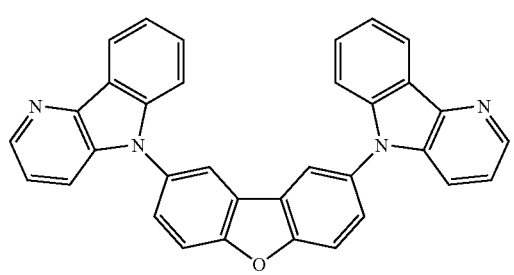

Comparative compound 8

-continued

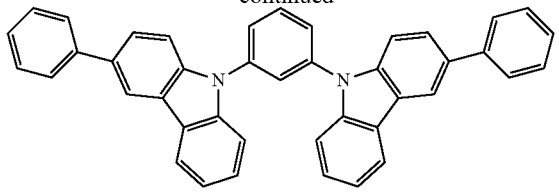

Comparative compound 9

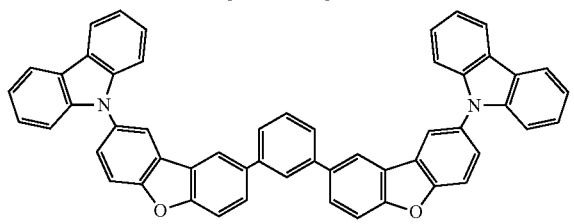

Host compound 1

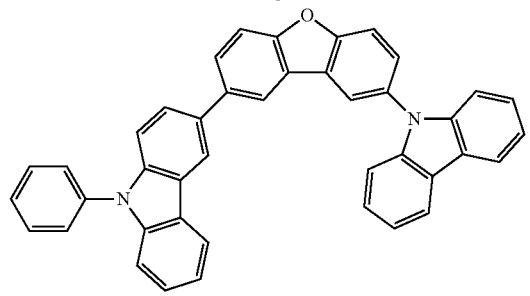

Host compound 2

Example 1

Preparation of Organic EL Element 1-1

An anode was prepared by making patterning to a glass substrate of 100 mm×100 mm×1.1 mm (NA45 produced by NH Techno Glass Corp.) on which a 100 nm film of ITO (indium tin oxide) was formed. Thereafter, the above transparent support substrate provided with the ITO transparent electrode was subjected to ultrasonic washing with isopropyl alcohol, followed by drying with desiccated nitrogen gas, and was subjected to UV ozone washing for 5 minutes.

The resulting transparent support substrate was fixed to the substrate holder of a commercial vacuum deposition apparatus. Separately, 200 mg of copper phthalocyanine (CuPc) was placed in a molybdenum resistance heating boat, 200 mg of Positive hole transport compound 1 was placed in another molybdenum resistance heating boat, 200 mg of Comparative compound 1 as a host compound was placed in further another molybdenum resistance heating boat, 100 mg of Dopant compound D-9 was placed in yet another molybdenum resistance heating boat, 200 mg of Electron transport compound 1 was placed in yet another molybdenum resistance heating boat, and 200 mg of Electron transport compound 6 was placed in still yet another molybdenum resistance heating boat, and the resulting boats were fitted in the vacuum deposition apparatus.

Subsequently, after reducing the pressure of the vacuum tank to $4\times10^{-4}$ Pa, the aforesaid heating boat, in which CuPc was placed, was heated via application of electric current and deposition was carried out onto the transparent support substrate at a deposition rate of 0.1 nm/second, whereby a 20 nm thick positive hole injection layer was arranged.

Further, the aforesaid heating boat containing Positive hole transport compound 1 was heated via application of electric current and deposition was carried out onto the positive hole injection layer at a deposition rate of 0.1 nm/second, whereby a 20 nm thick positive hole transport layer was arranged.

Further, the aforesaid heating boats each respectively containing Comparative compound 1 and D-9 were heated via application of electric current and co-deposition was carried out onto the aforesaid positive hole transport layer at a respective deposition rate of 0.1 nm/second and 0.006 nm/second, whereby a 20 nm thick light emitting layer was arranged.

Further, the aforesaid heating boat containing Positive hole transport compound 1 was heated via application of electric current and deposition was carried out onto the aforesaid light emitting layer at a deposition rate of 0.1 nm/second, whereby a 30 nm thick $1^{st}$ electron transport layer was arranged.

Further, the aforesaid heating boat containing Positive hole transport compound 6 was heated via application of electric current and deposition was carried out onto the aforesaid $1^{st}$ electron transport layer at a deposition rate of 0.1 nm/second, whereby a 30 nm thick $2^{nd}$ electron transport layer was arranged. Here, the temperature of the substrate during the deposition was room temperature.

Subsequently, 0.5 nm thick lithium fluoride was deposited to form a cathode buffer layer, then 110 nm thick aluminum was deposited to form a cathode, whereby Organic EL element 1-1 was prepared.

Preparation of Organic EL Elements 1-2 to 1-4

Organic EL elements 1-2 to 1-4 were prepared in the same manner as preparation of Organic EL element 1-1, except that Comparative compound 1 was replaced with the compounds as are listed in Table 1.

Evaluation of Organic EL Elements 1-2 to 1-4

In order to evaluate the obtained organic EL elements, the following processes were done to them. The non-light emitting surface of each of the organic EL elements was covered with a glass cover. As a sealing material, an epoxy based light curable type adhesive (LUXTRACK LC0629B produced by Toagosei Co., Ltd.) was applied to the periphery of the glass cover where the glass cover and the grass substrate prepared thereon Organic EL element were contacted. The resulting one was superimposed on the aforesaid cathode side to be brought into close contact with the aforesaid transparent support substrate, and curing and sealing were carried out via exposure of UV radiation onto the glass substrate side, whereby the lighting device shown in FIGS. 5 and 6 was formed. The organic EL elements were evaluated using the lighting devices. The following evaluations were made.

(Electric Power Efficiency)

Front luminance and angle dependency of each organic EL element was measured using a spectroradiometric luminance meter CS-1000 (produced by Konica Minolta Sensing Inc.). Electric power efficiency at front luminance of 1,000 cd/m$^2$ was determined. Here, the electric power efficiency was presented as a relative value when the electric power efficiency of Organic EL element 1-1 was set to be 100.

(Aging Stability)

Each Organic EL element was kept at aging condition of 60° C. and 70% RH for one month. Electric power efficiencies of before aging and after aging were measured according to the following formula. This value was used for evaluating aging stability.

Aging stability (%)=(Electric power efficiency after kept at aging condition/Electric power efficiency before kept at aging condition)×100

TABLE 1

| Organic EL element | Host Compound | Electric power efficiency (%) | Aging stability (%) | Remarks |
|---|---|---|---|---|
| 1-1 | Comparative compound 1 | 100 | 60 | Comparison |
| 1-2 | I-14 | 123 | 65 | Invention |
| 1-3 | I-13 | 140 | 73 | Invention |
| 1-4 | I-4 | 152 | 80 | Invention |

As is clearly shown in Table 1, Organic EL elements of the present invention were exhibited to be excellent in aging stability compared with a comparative organic EL element.

Example 2

Preparation of Organic EL Element 2-1

An anode was prepared by making patterning to a glass substrate of 100 mm×100 mm×1.1 mm (NA45 produced by NH Techno Glass Corp.) on which a 100 nm film of ITO (indium tin oxide) was formed. Thereafter, the above transparent support substrate provided with the ITO transparent electrode was subjected to ultrasonic washing with isopropyl alcohol, followed by drying with desiccated nitrogen gas, and was subjected to UV ozone washing for 5 minutes.

On the transparent support substrate thus prepared was applied a 70% a solution of poly(3,4-ethylenedioxythiphene)-polystyrene sulfonate (PEDOT/PSS, Baytron P Al 4083 made by Bayer AG.) diluted with water by using a spin coating method at 3,000 rpm for 30 seconds to form a film and then it was dried at 200° C. for one hour. A positive hole transport layer having a thickness of 20 nm was prepared.

The aforesaid substrate was transferred under an atmosphere of nitrogen, and a solution containing 50 mg of Positive hole transport compound 2 dissolved in 10 ml of toluene was applied on the aforesaid positive hole transport layer by using a spin coating method at 1,500 rpm for 30 seconds to form a film. The film was irradiated with UV rays for 180 seconds so as to achieve photopolymerization and cross-linking. A $2^{nd}$ positive hole transport layer having a thickness of 20 nm was thus prepared.

One the $2^{nd}$ positive hole transport layer was applied a solution containing 100 mg of Comparative compound 2 and 10 mg of Dopant D-24 dissolved in 10 ml of toluene by using a spin coating method at 600 rpm for 30 seconds to form a film. The film was subjected to a vacuum drying at 60° C. for one hour to obtain a light emitting layer having a thickness of 70 nm.

One the light emitting layer was applied a solution containing 50 mg of Electron transport compound 2 dissolved in 10 ml of hexafluoroisopropanol (HFIP) by using a spin coating method at 1,000 rpm for 30 seconds to form a film. The film was subjected to a vacuum drying at 60° C. for one hour to obtain an electron transport layer having a thickness of 30 nm.

Subsequently, the substrate was fixed to the substrate holder of the vacuum deposition apparatus, and the pressure of the vacuum tank was reduced to $4 \times 10^{-4}$ Pa. Then, 0.4 nm thick lithium fluoride was deposited to form a cathode buffer layer, then 110 nm thick aluminum was deposited to form a cathode, whereby Organic EL element 2-1 was prepared.

Preparation of Organic EL Elements 2-2 to 2-6

Organic EL elements 2-2 to 2-6 were prepared in the same manner as preparation of Organic EL element 2-1, except that the materials used in the light emitting layer and in the electron transport layer were replaced with the compounds as are listed in Table 2.

Evaluation of Organic EL Elements 2-1 to 2-6

In order to evaluate the obtained organic EL elements 2-1 to 2-6, the same sealing processes was done as done to Organic EL elements 1-1 to 1-4 in Example 1, whereby the lighting device shown in FIGS. 5 and 6 was formed. The organic EL elements were evaluated using the lighting devices. The following evaluations were made.

(External Extraction Quantum Efficiency)

Each organic EL element was allowed to emit a light with a constant electric current of 2.5 mA/cm² at room temperature (at about 23 to 25° C.). The external extraction quantum efficiency (η) was determined by measuring the luminance (L) (cd/m²) measured immediately after starting to emit light.

The measurement of luminance was done with a spectro-radiometric luminance meter CS-1000 (produced by Konica Minolta Sensing Inc.). The external extraction quantum efficiency was represented by the relative value when the external extraction quantum efficiency of Organic EL element 2-1 was set to be 100.

(Driving Voltage)

Each organic EL element was driven with a constant electric current of 2.5 mA/cm² at room temperature (at about 23 to 25° C.), and each voltage was measured. The measurement results were represented as below by the relative value when the driving voltage of Organic EL element 2-1 was set to be 100.

Driving voltage ratio=(Driving voltage of each organic EL element/Driving voltage of Organic EL element 2-1)×100

Here, the smaller voltage ratio indicates that the driving voltage of a sample is smaller than the comparative sample and it is preferable.

(Emission Lifetime)

Organic EL element was driven with a constant electric current of 2.5 mA/cm² at room temperature (at about 23 to 25° C.) to continuously emit a light. The time required for a decease in one half of the luminance of immediately after the initiation of light emission (being the initial luminance) was determined, and the resulting value was employed as an index of the lifetime in terms of a half lifetime ($\tau_{1/2}$). The emission lifetime was represented as a relative value when the lifetime of Organic EL element 2-1 was set to be 100.

The obtained results are shown in Table 2.

TABLE 2

| Organic EL element | Light emitting layer | Electron transport layer | External extraction quantum efficiency | Driving voltage ratio | Emission lifetime | Remarks |
|---|---|---|---|---|---|---|
| 2-1 | Comparative compound 2 D-24 | Electron transport compound 2 | 100 | 100 | 100 | Comp. |

TABLE 2-continued

| Organic EL element | Light emitting layer | Electron transport layer | External extraction quantum efficiency | Driving voltage ratio | Emission lifetime | Remarks |
|---|---|---|---|---|---|---|
| 2-2 | I-10 D-24 | Electron transport compound 2 | 118 | 88 | 130 | Inv. |
| 2-3 | I-11 D-24 | Electron transport compound 2 | 125 | 81 | 170 | Inv. |
| 2-4 | I-1 D-24 | Electron transport compound 2 | 129 | 72 | 200 | Inv. |
| 2-5 | I-1 D-46 | Electron transport compound 2 | 142 | 71 | 930 | Inv. |
| 2-6 | I-1 D-46 | II-18 | 149 | 60 | 1100 | Inv. |

Comp.: Comparison, Inv.: Invention

As is clearly shown in Table 2, organic EL elements of the present invention were exhibited to be excellent in external extraction quantum efficiency, driving voltage and emission lifetime compared with the comparative organic EL element.

Example 3

Preparation of Organic EL Element 3-1

Organic EL element 3-1 was prepared in the same manner as preparation of Organic EL element 2-1, except that the following changes were made: Positive hole transport compound 2 was replaced with a commercially available compound ADS254BE (made by American Dye Source, Inc.) and it was spin coated at 2500 rpm for 30 seconds; a combination of Comparative compound 2 with D-24 was replaced with a mixed solution composed of 100 mg of Host compound 2 with 14 mg of D-26 dissolved in 10 ml of butyl acetate; and Electron transport compound 2 was replaced with Comparative compound 4.

Preparation of Organic EL Elements 3-2 to 3-5

Organic EL elements 3-2 to 3-5 were prepared in the same manner as preparation of Organic EL element 3-1, except that Comparative compound 4 was replaced with the compounds as are listed in Table 3.

Evaluation of Organic EL Elements 3-1 to 3-5

In order to evaluate the obtained Organic EL elements 3-1 to 3-5, the same sealing processes was done as done to Organic EL elements 1-1 to 1-4 in Example 1, whereby the lighting device shown in FIGS. 5 and 6 was formed. The organic EL elements were evaluated using the lighting devices. The following evaluations were made.

(Electric Power Efficiency)

Electric power efficiency was evaluated in the same manner as done in Example 1. Electric power efficiency was indicates as a relative value when the electric power efficiency of Organic EL element 3-1 was set to be 100.

(Emission Lifetime)

Emission lifetime was evaluated in the same manner as done in Example 2.

TABLE 3

| Organic EL element | Electron transport compound | Electric power efficiency | Emission lifetime | Remarks |
|---|---|---|---|---|
| 3-1 | Comparative compound 4 | 100 | 100 | Comparison |
| 3-2 | I-27 | 122 | 420 | Invention |
| 3-3 | I-28 | 145 | 610 | Invention |
| 3-4 | I-29 | 154 | 700 | Invention |

As is clearly shown in Table 3, organic EL elements of the present invention were exhibited to be excellent in electric power efficiency and also in emission lifetime compared with the comparative organic EL element.

Example 4

Preparation of Organic EL Element 4-1

An anode was prepared by making patterning to a glass substrate of 100 mm×100 mm×1.1 mm (NA45 produced by NH Techno Glass Corp.) on which a 100 nm film of ITO (indium tin oxide) was formed. Thereafter, the above transparent support substrate provided with the ITO transparent electrode was subjected to ultrasonic washing with isopropyl alcohol, followed by drying with desiccated nitrogen gas, and was subjected to UV ozone washing for 5 minutes.

On the transparent support substrate thus prepared was applied a 70% solution of poly(3,4-ethylenedioxythiphene)-polystyrene sulfonate (PEDOT/PSS, Baytron P Al 4083 made by Bayer AG.) diluted with water by using a spin coating method at 3,000 rpm for 30 seconds to form a film and then it was dried at 200° C. for one hour. A positive hole transport layer having a thickness of 20 nm was prepared.

The aforesaid substrate was transferred under an atmosphere of nitrogen, and a solution of 45 mg of Positive hole transport compound 2 and 5 mg of Positive hole transport compound 4 dissolved in 10 ml of toluene was applied on the aforesaid positive hole transport layer by using a spin coating method at 1,500 rpm for 30 seconds to form a film. The film was irradiated with UV rays at 120° C. for 90 seconds under an atmosphere of nitrogen so as to achieve photopolymerization and cross-linking. A $2^{nd}$ positive hole transport layer having a thickness of 20 nm was thus prepared.

One the $2^{nd}$ positive hole transport layer was applied a solution containing 100 mg of Host compound 2 and 10 mg of D-46 dissolved in 10 ml of toluene by using a spin coating method at 1,000 rpm for 30 seconds to form a film. The film was subjected to a vacuum drying at 60° C. for one hour to obtain a light emitting layer.

Then, a solution of 50 mg of Comparative compound 3 dissolved in 10 ml of hexafluoroisopropanol (HFIP) was applied on the aforesaid light emitting layer by using a spin coating method at 1,000 rpm for 30 seconds to form a film. The film was subjected to a vacuum drying at 60° C. for one hour to obtain an electron transport layer having a thickness of 30 nm.

Subsequently, the substrate was fixed to the substrate holder of the vacuum deposition apparatus, and the pressure of the vacuum tank was reduced to $4 \times 10^{-4}$ Pa.

Then, 0.4 nm thick lithium fluoride was deposited to form a cathode buffer layer, then 110 nm thick aluminum was deposited to form a cathode, whereby Organic EL element 4-1 was prepared.

Preparation of Organic EL Elements 4-2 to 4-5

Organic EL elements 4-2 to 4-5 were prepared in the same manner as preparation of Organic EL element 4-1, except that Comparative compound 3 was replaced with the compounds as are listed in Table 4.

In preparation of Organic EL element 4-2, it was found that Comparative compound 5 which was used in place of Comparative compound 3 was not completely dissolved in a predetermined amount of hexafluoroisopropanol (HFIP).

Evaluation of Organic EL Elements 4-1 to 4-5

In order to evaluate the obtained Organic EL elements 4-1 to 4-5, the same sealing processes was done as done to Organic EL elements 1-1 to 1-4 in Example 1, whereby the lighting device shown in FIGS. 5 and 6 was formed. The organic EL elements were evaluated using the lighting devices. The following evaluations were made.

(External Extraction Quantum Efficiency and Driving Voltage)

External extraction quantum efficiency and driving voltage were evaluated in the same manner as done in Example 2.

(Aging Stability)

Each Organic EL element was kept at aging condition of 85° C. for 24 hours. Electric power efficiencies of before aging and after aging were measured according to the following formula. This value was used for evaluating aging stability. Electric power efficiency was measured in the same manner as done in Example 1.

Aging stability (%)=(Electric power efficiency after kept at aging condition/Electric power efficiency before kept at aging condition)×100

TABLE 4

| Organic EL element | Electron transport copmpuond | External extraction quantum efficiency | Driving voltage ratio | Aging stability (%) | Remarks |
|---|---|---|---|---|---|
| 4-1 | Comparative compound 3 | 100 | 100 | 130 | Comparison |
| 4-2 | Comparative compound 5 | Unable to measure | Unable to measure | Unable to measure | Comparison |
| 4-3 | II-31 | 114 | 95 | 113 | Invention |
| 4-4 | II-20 | 120 | 88 | 108 | Invention |
| 4-5 | II-18 | 126 | 81 | 105 | Invention |

As is clearly shown in Table 4, Organic EL elements of the present invention were exhibited to be excellent in external extraction quantum efficiency and driving voltage as well as showing good aging stability compared with the comparative organic EL element.

Example 5

Preparation of Organic EL Element 5-1

An anode was prepared by making patterning to a glass substrate of 100 mm×100 mm×1.1 mm (NA45 produced by NH Techno Glass Corp.) on which a 100 nm film of ITO (indium tin oxide) was formed. Thereafter, the above transparent support substrate provided with the ITO transparent electrode was subjected to ultrasonic washing with isopropyl alcohol, followed by drying with desiccated nitrogen gas, and was subjected to UV ozone washing for 5 minutes.

On the transparent support substrate thus prepared was applied a 70% solution of poly(3,4-ethylenedioxythiphene)-polystyrene sulfonate (PEDOT/PSS, Baytron P Al 4083 made by Bayer AG.) diluted with water by using a spin coating method at 3,000 rpm for 30 seconds to form a film and then it was dried at 200° C. for one hour. A positive hole transport layer having a thickness of 20 nm was prepared.

The aforesaid substrate was transferred under an atmosphere of nitrogen, and a solution of 50 mg of Positive hole transport compound 2 dissolved in 10 ml of toluene was applied on the aforesaid positive hole transport layer by using a spin coating method at 2,000 rpm for 30 seconds to form a film. The film was irradiated with UV rays for 180 seconds so as to achieve photopolymerization and cross-linking. A $2^{nd}$ positive hole transport layer having a thickness of 20 nm was thus prepared.

One the $2^{nd}$ positive hole transport layer was applied a solution containing 100 mg of Host compound 1 and 13 mg of D-9 dissolved in 10 ml of toluene by using a spin coating method at 900 rpm for 30 seconds to form a film. The film was subjected to a vacuum drying at 60° C. for one hour to obtain a light emitting layer having a thickness of 50 nm. Then, a solution of 50 mg of Comparative compound 6 dissolved in 10 ml of hexafluoroisopropanol (HFIP) was applied on the aforesaid light emitting layer by using a spin coating method at 1,000 rpm for 30 seconds to form a film. The film was subjected to a vacuum drying at 60° C. for one hour to obtain an electron transport layer having a thickness of 30 nm Subsequently, the substrate was fixed to the substrate holder of the vacuum deposition apparatus, and the pressure of the vacuum tank was reduced to $4 \times 10^{-4}$ Pa.

Then, 0.4 nm thick lithium fluoride was deposited to form a cathode buffer layer, then 110 nm thick aluminum was deposited to form a cathode, whereby Organic EL element 5-1 was prepared.

Preparation of Organic EL Elements 5-2 to 5-5

Organic EL elements 5-2 to 5-5 were prepared in the same manner as preparation of Organic EL element 5-1, except that Dopant and Comparative compound 6 were replaced with the compounds as are listed in Table 5.

Evaluation of Organic EL Elements 5-1 to 5-5

In order to evaluate the obtained organic EL elements 5-1 to 5-5, the same sealing processes was done as done to Organic EL elements 1-1 to 1-4 in Example 1, whereby the lighting device shown in FIGS. 5 and 6 was formed. The organic EL elements were evaluated using the lighting devices. The following evaluations were made.

(External Extraction Quantum Efficiency and Emission Lifetime)

External extraction quantum efficiency and emission lifetime were evaluated in the same manner as done in Example 2.

(Emission Color)

The emission color was evaluated by visual observation for each lighting device emitting light under the constant electric current condition of 2.5 mA/cm².

TABLE 5

| Organic EL element | Dopant | Electron transport compound | External extraction quantum efficiency | Emission lifetime | Emission color | Remarks |
|---|---|---|---|---|---|---|
| 5-1 | D-9 | Comparative compound 6 | 100 | 100 | Blue | Comp. |
| 5-2 | D-9 | II-32 | 131 | 150 | Blue | Inv. |
| 5-3 | D-9 | II-9 | 136 | 190 | Blue | Inv. |
| 5-4 | D-25 | II-9 | 140 | 820 | Blue | Inv. |
| 5-5 | D-26 | II-9 | 148 | 4400 | Blue | Inv. |

Comp.: Comparison, Inv.: Invention

As is clearly shown in Table 5, tested organic EL elements emitted blue light. And the organic EL elements of the present invention were exhibited to be excellent in external extraction quantum efficiency and aging stability compared with the comparative organic EL element.

Example 6

Preparation of Organic EL Element 6-1

An anode was prepared by making patterning to a glass substrate of 100 mm×100 mm×1.1 mm (NA45 produced by NH Techno Glass Corp.) on which a 100 nm film of ITO (indium tin oxide) was formed. Thereafter, the above transparent support substrate provided with the ITO transparent electrode was subjected to ultrasonic washing with isopropyl alcohol, followed by drying with desiccated nitrogen gas, and was subjected to UV ozone washing for 5 minutes.

On the transparent support substrate thus prepared was applied a 70% solution of poly(3,4-ethylenedioxythiphene)-polystyrene sulfonate (PEDOT/PSS, Baytron P Al 4083 made by Bayer AG.) diluted with water by using a spin coating method at 3,000 rpm for 30 seconds to form a film and then it was dried at 200° C. for one hour. A positive hole transport layer having a thickness of 20 nm was prepared.

The aforesaid substrate was transferred under an atmosphere of nitrogen, and a solution of 50 mg of a commercially available compound ADS254BE (made by American Dye Source, Inc.) dissolved in 10 ml of toluene was applied on the aforesaid positive hole transport layer by using a spin coating method at 2,500 rpm for 30 seconds to form a film. The film was subjected to a vacuum drying at 60° C. for one hour to obtain a $2^{nd}$ positive hole transport layer.

One the $2^{nd}$ positive hole transport layer was applied a solution containing 100 mg of Comparative compound 2 and 15 mg of D-49 dissolved in 10 ml of butyl acetate by using a spin coating method at 600 rpm for 30 seconds to form a film. The film was subjected to a vacuum drying at 60° C. for one hour to obtain a light emitting layer having a thickness of 70 nm.

Subsequently, after the substrate was fixed to the substrate holder of the vacuum deposition apparatus and the pressure of the vacuum tank was reduced to $4 \times 10^{-4}$ Pa, the aforesaid heating boat, in which Electron transport compound 6 was placed, was heated via application of electric current and deposition was carried out onto the light emitting layer at a deposition rate of 0.1 nm/second, whereby an electron transport layer having a thickness of 30 nm was arranged. The temperature of the substrate at the time of vapor deposition was room temperature.

Then, 0.5 nm thick lithium fluoride was deposited to form a cathode buffer layer, then 110 nm thick aluminum was deposited to form a cathode, whereby Organic EL element 6-1 was prepared.

Preparation of Organic EL Elements 6-2 to 6-5

Organic EL elements 6-2 to 6-5 were prepared in the same manner as preparation of Organic EL element 6-1, except that Comparative compound 2 and D-49 were replaced with the compounds as are listed in Table 6.

Evaluation of Organic EL Elements 6-1 to 6-5

In order to evaluate the obtained Organic EL elements 6-1 to 6-5, the same sealing processes was done as done to Organic EL elements 1-1 to 1-4 in Example 1, whereby the lighting device shown in FIGS. 5 and 6 was formed. The organic EL elements were evaluated using the lighting devices. The following evaluations were made.
(Electronic Power Efficiency)

Electronic power efficiency was evaluated in the same manner as done in Example 1.
(Emission Lifetime)

Emission lifetime was evaluated in the same manner as done in Example 2.
(Voltage Increasing Ratio)

Organic EL element was driven with a constant electric current of 6 mA/cm$^2$. The initial voltage and the voltage after driving 150 hours each were measured. The relative value of the voltage after 150 hour driving with respect to the initial voltage was defined as a voltage increasing ratio.

TABLE 6

| Organic EL element | Host compound | Dopant | Electronic power effiiency | Emission lifetime | Voltage Increasing ratio | Remarks |
|---|---|---|---|---|---|---|
| 6-1 | Comparative compound 2 | D-49 | 100 | 100 | 127 | Comparison |
| 6-2 | III-12 | D-49 | 123 | 250 | 110 | Invention |
| 6-3 | III-13 | D-49 | 128 | 320 | 108 | Invention |
| 6-4 | III-1 | D-49 | 135 | 400 | 104 | Invention |
| 6-5 | III-1 | D-46 | 140 | 1900 | 103 | Invention |

As is clearly shown in Table 6, Organic EL elements of the present invention were exhibited to be excellent in electronic power efficiency and emission lifetime as well as well as showing a small voltage increasing ratio compared with the comparative organic EL element.

Example 7

Preparation of Organic EL Element 7-1

Organic EL elements 7-1 was prepared in the same manner as preparation of Organic EL element 2-1, except that the following changes were made: Positive hole transport compound 2 was replaced with a mixed solution of 3 mg of Positive hole transport compound 4 and 47 mg of Positive hole transport compound 5 dissolved in 10 ml of toluene; Comparative compound 2 was replaced with Host compound 2; D-24 was replaced with D-26; and Electron transport compound 2 was replaced with Comparative compound 7.

Preparation of Organic EL Elements 7-2 to 7-4

Organic EL elements 7-2 to 7-4 were prepared in the same manner as preparation of Organic EL element 7-1, except that Comparative compound 7 was replaced with the compounds as are listed in Table 7.

Evaluation of Organic EL Elements 7-1 to 7-4

In order to evaluate the obtained organic EL elements 7-1 to 7-4, the same sealing processes was done as done to Organic EL elements 1-1 to 1-4 in Example 1, whereby the lighting device shown in FIGS. 5 and 6 was formed. The organic EL elements were evaluated using the lighting devices. The following evaluations were made.
(External Extraction Quantum Efficiency, Driving Voltage and Emission Lifetime)

External extraction quantum efficiency, driving voltage and emission lifetime were evaluated in the same manner as done in Example 2.

TABLE 7

| Organic EL element | Electron transport compound | External extraction quantum efficiency | Driving voltage ratio | Emission lifetime | Remarks |
|---|---|---|---|---|---|
| 7-1 | Comparative compound 7 | 100 | 100 | 100 | Comparison |
| 7-2 | III-19 | 109 | 91 | 180 | Invention |
| 7-3 | III-18 | 115 | 86 | 320 | Invention |
| 7-4 | III-16 | 125 | 78 | 510 | Invention |

As is clearly shown in Table 7, Organic EL elements of the present invention were exhibited to be excellent in external extraction quantum efficiency, having a small driving voltage and a long emission lifetime compared with comparative Organic EL element.

Example 8

Preparation of Full Color Organic EL Display Device

FIGS. 7a to 7e are schematic structural drawings of a full color organic EL display device. An anode was prepared by making patterning to glass substrate 201 of 100 mm×100 mm×1.1 mm (NA45 produced by NH Techno Glass Corp.) on which 100 nm film of ITO transparent electrode 202 was formed. Thereafter, there were provided dividing walls 203 (20 μm of width, and 2.0 μm of thickness) made of non-photosensitive polyimide between ITO transparent electrodes prepared on the glass substrate via a photolithography.

Between the polyimide dividing walls 203 on the ITO transparent electrodes 202 was injected the following positive hole injection layer composition through an ink-jet head (MJ800C, made by Epson Co., Ltd.). Then, injected composition was irradiating with UV rays for 200 seconds and subjected to drying process at 60° C. for 10 minutes. Thus, positive hole injection layer 204 having a thickness of 40 nm was prepared On the positive hole injection layer 204 were injected the following blue light emitting layer composition, green light emitting layer composition and red light emitting layer composition through the ink-jet head as described above. Then, injected compositions were subjected to drying process at 60° C. for 10 minutes. Thus, light emitting layers (205B, 205G and 205R) each were formed.

Next, 20 nm of Compound II-17 was vacuum vapor-deposited upwards so that the light emission layer might be covered, and also 0.6 nm of lithium fluoride and further 130 nm of aluminum were vacuum deposited to make a cathode 105. Thus, the targeted full color organic EL element was produced.

It was found that the produced organic EL element showed luminescence of blue, green, and red respectively, and can be used as a full color display device by impressing voltage to each electrode.

(Positive Hole Injection Layer Composition)

| | |
|---|---|
| Positive hole transport compound 6 | 20 weight parts |
| Cyclohexylbenzene | 50 weight parts |
| Isopropylbiphenyl | 50 weight parts |

(Blue Light Emitting Layer Composition)

| | |
|---|---|
| Example compound I-2 | 0.7 weight parts |
| D-26 | 0.04 weight parts |
| Cyclohexylbenzene | 50 weight parts |
| Isopropylbiphenyl | 50 weight parts |

(Green Light Emitting Layer Composition)

| | |
|---|---|
| Example compound I-2 | 0.7 weight parts |
| D-1 | 0.04 weight parts |
| Cyclohexylbenzene | 50 weight parts |
| Isopropylbiphenyl | 50 weight parts |

(Red Light Emitting Layer Composition)

| | |
|---|---|
| Example compound I-2 | 0.7 weight parts |
| D-10 | 0.04 weight parts |
| Cyclohexylbenzene | 50 weight parts |
| Isopropylbiphenyl | 50 weight parts |

It was also found that a full color organic EL display device having the similar property as the above-described full color organic EL display device can be achieved when example compound 1-2 was replaced with other example compounds such as example compound III-4.

Example 9

Preparation of White Light Emitting Organic EL Element 9-1

An anode was prepared by making patterning to a glass substrate of 100 mm×100 mm×1.1 mm (NA45 produced by NH Techno Glass Corp.) on which a 100 nm film of ITO (indium tin oxide) was formed. Thereafter, the above transparent support substrate provided with the ITO transparent electrode was subjected to ultrasonic washing with isopropyl alcohol, followed by drying with desiccated nitrogen gas, and was subjected to UV ozone washing for 5 minutes.

On the transparent support substrate thus prepared was applied a 70% solution of poly(3,4-ethylenedioxythiphene)-polystyrene sulfonate (PEDOT/PSS, Baytron P Al 4083 made by Bayer AG.) diluted with water by using a spin coating method at 3,000 rpm for 30 seconds to form a film and then it was dried at 200° C. for one hour. A $1^{st}$ positive hole transport layer having a thickness of 30 nm was prepared.

The aforesaid substrate was transferred under an atmosphere of nitrogen, and a solution containing 70 mg of Positive hole transport compound 3 dissolved in 10 ml of toluene was applied on the aforesaid $1^{st}$ positive hole transport layer by using a spin coating method at 1,500 rpm for 30 seconds to form a film. The film was irradiated with UV rays at 110° C. for 100 seconds so as to achieve photopolymerization and cross-linking. Then it was subjected to a vacuum drying at 60° C. for one hour to obtain a $2^{nd}$ positive hole transport layer having a thickness of 20 nm.

One the $2^{nd}$ positive hole transport layer was applied a solution containing 60 mg of Example compound 1-1, 3.0 mg of D-6 and 3.0 mg of D-46 dissolved in 6 ml of butyl acetate by using a spin coating method at 1,000 rpm for 30 seconds to form a film. The film was subjected to a vacuum drying at 60° C. for one hour to obtain a light emitting layer.

One the light emitting layer was applied a solution containing 30 mg of Example compound II-38 dissolved in 5 ml of hexafluoroisopropanol (HFIP) by using a spin coating method at 1,500 rpm for 30 seconds to form a film. The film was subjected to a vacuum drying at 60° C. for one hour to obtain a $1^{st}$ electron transport layer.

Subsequently, the substrate was fixed to the substrate holder of the vacuum deposition apparatus, and 200 mg of Electron transport compound 5 was placed in a molybdenum resistance heating boat and was fixed to the vacuum deposition apparatus. After the pressure of the vacuum tank was reduced to $4 \times 10^{-4}$ Pa, the aforesaid heating boat including Electron transport compound 5 was heated via application of electric current and deposition was carried out onto the aforesaid $1^{st}$ electron transport layer at an evaporation rate of 0.1 nm/second, whereby a 40 nm thick $2^{nd}$ electron transport layer was further arranged. Here, the temperature of the substrate during the deposition was room temperature.

Subsequently, 0.5 nm thick potassium fluoride was deposited, then 110 nm thick aluminum was deposited to form a cathode, whereby Organic EL element 9-1 was prepared.

When the prepared Organic EL element 9-1 was turned on electricity, the almost white light was obtained, and it was revealed that this organic EL element can be used as a lighting devise. In addition, even if the used compounds were replaced with other example compounds of the present invention, it was found that white luminescence was obtained similarly. For example, by replacing Example compound I-1 with Example compound III-20, and by replacing Example compound II-38 with Example compound I-32 or Example compound III-21, the obtained organic EL element was found to emit a white color light.

Example 10

Preparation of Organic EL Element 10-1(1)

An anode was prepared by making patterning to a glass substrate of 100 mm×100 mm×1.1 mm (NA45 produced by NH Techno Glass Corp.) on which a 100 nm film of ITO (indium tin oxide) was formed. Thereafter, the above transparent support substrate provided with the ITO transparent electrode was subjected to ultrasonic washing with isopropyl alcohol, followed by drying with desiccated nitrogen gas, and was subjected to UV ozone washing for 5 minutes.

On the transparent support substrate thus prepared was applied a 70% solution of poly(3,4-ethylenedioxythiphene)-polystyrene sulfonate (PEDOT/PSS, Baytron P Al 4083 made by Bayer AG.) diluted with water by using a spin coating method at 3,000 rpm for 30 seconds to form a film and then it was dried at 200° C. for one hour. A positive hole transport layer having a thickness of 20 nm was prepared.

The aforesaid substrate was transferred under an atmosphere of nitrogen, and a solution of 50 mg of Positive hole transfer compound 2 dissolved in 10 ml of toluene was applied on the aforesaid positive hole transport layer by using a spin coating method at 2,000 rpm for 30 seconds to form a film. The film was irradiated with UV rays for 180 seconds so as to achieve photopolymerization and cross-linking. A $2^{nd}$ positive hole transport layer having a thickness of 20 nm was thus prepared.

One the $2^{nd}$ positive hole transport layer was applied a solution containing 100 mg of Comparative compound 1 and 12 mg of D-26 dissolved in 10 ml of butyl acetate by using a spin coating method at 2,500 rpm for 30 seconds to form a film. The film was subjected to a vacuum drying at 60° C. for one hour to obtain a light emitting layer having a thickness of 30 nm.

Subsequently, after the substrate was fixed to the substrate holder of the vacuum deposition apparatus and the pressure of the vacuum tank was reduced to $4\times10^{-4}$ Pa, the aforesaid heating boat, in which Electron transport compound 4 was placed, was heated via application of electric current and deposition was carried out onto the aforesaid light emitting layer at a deposition rate of 0.1 nm/second, whereby an electron transport layer having a thickness of 30 nm was arranged. The temperature of the substrate at the time of vapor deposition was room temperature.

Then, after the substrate was fixed to the substrate holder of the vacuum deposition apparatus and the pressure of the vacuum tank was reduced to $4\times10^{-4}$ Pa, 0.4 nm thick lithium fluoride was deposited to form a cathode buffer layer, then 110 nm thick aluminum was deposited to form a cathode, whereby Organic EL element 10-1(1) was prepared.

Preparation of Organic EL Element 10-1(2)

Organic EL element 10-1(2) was prepared in the same manner as preparation of Organic EL element 10-1(1), except that the rotation rate of spin coating to form a light emitting layer was changed so as to form a light emitting layer having a thickness of 55 nm instead of 30 nm.

Preparation of Organic EL Elements 10-2(1) and 10-2(2)

Organic EL elements 10-2(1) and 10-2(2) were prepared in the same manner as preparation of Organic EL elements 10-1 (1) and 10-1(2) respectively, except that Comparative compound 1 was replaced with Example compound 1-4. Thus, there were obtained:

Organic EL element 10-2(1) containing a light emitting layer having a thickness of 30 nm; and Organic EL element 10-2(2) containing a light emitting layer having a thickness of 55 nm.

Evaluation of Organic EL Elements 10-1(1), 10-1(2), 10-2(1) and 10-2(2)

In order to evaluate the obtained Organic EL elements 10-1(1), 10-1(2), 10-2(1) and 10-2(2), the same sealing processes was done as done to Organic EL elements 1-1 to 1-4 in Example 1, whereby the lighting device shown in FIGS. 5 and 6 was formed. The organic EL elements were evaluated using the lighting devices. The following evaluations was made.
(Voltage Increasing Ratio)

Driving voltage of Organic EL elements 10-1 (1), 10-1 (2), 10-2(1) and 10-2(2) were measured in the same manner as in Example 2. A driving voltage increase ratio of a pair of Organic EL elements 10-1(1) and 10-1(2) versus a pair of Organic EL elements 10-2(1) and 10-2(2) were determined using the following formula in order to compare the driving voltage increasing ratio when the thickness of the light emitting layer is increased.

Driving voltage increasing ratio between a pair=(Driving voltage of Organic EL element containing a light emitting layer of 55 nm/Driving voltage of Organic EL element containing a light emitting layer of 30 nm)×100

The evaluation results are shown in Table 8.

TABLE 8

| Pair of Organic EL elements | Host compound | Driving voltage increasing ratio | Remarks |
| --- | --- | --- | --- |
| 10-1(2)/ 10-1(1) | Comparative compound 1 | 151 | Comparison |
| 10-2(2)/ 10-2(1) | I-4 | 110 | Invention |

As is clearly shown in Table 8, Organic EL elements of the present invention exhibited a small amount of driving voltage increase when the light emitting layer was increased compared with the comparative organic EL elements. As a result, it was possible to provide a thick organic EL element which can be driven with a small driving voltage.

Preparation of Organic EL Element 11-1(1)

Organic EL element 11-1(1) was prepared in the same manner as preparation of Organic EL element 10-1(1) until preparation of the light emitting layer.

Then, a solution of 100 mg of Comparative compound 8 dissolved in 10 ml of hexafluoroisopropanol (HFIP) was applied on the aforesaid light emitting layer by using a spin coating method at 3,500 rpm for 30 seconds to form a film. The film was subjected to a vacuum drying at 60° C. for one hour to obtain an electron transport layer having a thickness of 30 nm.

Subsequently, the substrate was fixed to the substrate holder of the vacuum deposition apparatus, and the pressure of the vacuum tank was reduced to $4\times10^{-4}$ Pa. Then, 0.4 nm thick lithium fluoride was deposited to form a cathode buffer layer, then 110 nm thick aluminum was deposited to form a cathode, whereby Organic EL element 11-1(1) was prepared.

Preparation of Organic EL Element 11-1(2)

Organic EL element 11-1(2) was prepared in the same manner as preparation of Organic EL element 11-1 (1), except that the rotation rate of spin coating to form an electron transport layer was changed so as to form an electron transport layer having a thickness of 55 nm instead of 30 nm.

Preparation of Organic EL Elements 11-2(1) and 11-2(2)

Organic EL elements 11-2(1) and 11-2(2) were prepared in the same manner as preparation of Organic EL elements 11-1 (1) and 11-1(2) respectively, except that Comparative compound 8 was replaced with Example compound II-18. Thus, there were obtained:

Organic EL element 11-2(1) containing an electron transport layer having a thickness of 30 nm; and Organic EL element 11-2(2) containing an electron transport layer having a thickness of 55 nm.

Evaluation of Organic EL Elements 11-1(1), 11-1(2), 11-2(1) and 11-2(2)

In order to evaluate the obtained Organic EL elements 11-1(1), 11-1(2), 11-2(1) and 11-2(2), the same sealing processes was done as done to Organic EL elements 1-1 to 1-4 in Example 1, whereby the lighting device shown in FIGS. 5 and 6 was formed. The organic EL elements were evaluated using the lighting devices. The following evaluations were made.

(Voltage Increasing Ratio)

Driving voltage ratio of Organic EL elements 11-1(1), 11-1(2), 11-2(1) and 11-2(2) were measured in the same manner as in Example 10. The evaluation results are shown in Table 9

TABLE 9

| Pair of Organic EL elements | Electron transport compound | Driving voltage increasing ratio | Remarks |
|---|---|---|---|
| 11-1(2)/ 11-1(1) | Comparative compound 8 | 138 | Comparison |
| 11-2(2)/ 11-2(1) | II-18 | 108 | Invention |

As is clearly shown in Table 9, Organic EL elements of the present invention exhibited a small amount of driving voltage increase when the electron transport layer was increased compared with the comparative organic EL elements. As a result, it was possible to provide a thick organic EL element which can be driven with a small driving voltage.

Preparation of Organic EL Element 12-1(1)

Organic EL element 12-1(1) was prepared in the same manner as preparation of Organic EL element 10-1(1) until preparation of the light emitting layer, except that the following changes were made: Comparative compound 1 was replaced with Comparative compound 2; and D-26 was replaced with D-46.

Then, a solution of 50 mg of Electron transport compound 3 dissolved in 10 ml of hexafluoroisopropanol (HFIP) was applied on the aforesaid light emitting layer by using a spin coating method at 1,500 rpm for 30 seconds to form a film. The film was subjected to a vacuum drying at 60° C. for one hour to obtain an electron transport layer having a thickness of 25 nm.

Subsequently, the substrate was fixed to the substrate holder of the vacuum deposition apparatus, and the pressure of the vacuum tank was reduced to $4 \times 10^{-4}$ Pa. Then, 0.4 nm thick lithium fluoride was deposited to form a cathode buffer layer, then 110 nm thick aluminum was deposited to form a cathode, whereby Organic EL element 12-1(1) was prepared.

Preparation of Organic EL Element 12-1(2)

Organic EL element 12-1(2) was prepared in the same manner as preparation of Organic EL element 12-1 (1), except that the rotation rate of spin coating to form a light emitting layer was changed so as to form a light emitting layer having a thickness of 55 nm instead of 30 nm.

Preparation of Organic EL Elements 12-2(1) and 12-2(2)

Organic EL elements 12-2(1) and 12-2(2) were prepared in the same manner as preparation of Organic EL elements 12-1 (1) and 12-1(2) respectively, except that Comparative compound 2 was replaced with Example compound III-23. Thus, there were obtained:

Organic EL element 12-2(1) containing a light emitting layer having a thickness of 30 nm; and Organic EL element 12-2(2) containing a light emitting layer having a thickness of 55 nm.

Evaluation of Organic EL Elements 12-1(1), 12-1(2), 12-2(1) and 12-2(2)

In order to evaluate the obtained Organic EL elements 12-1(1), 12-1(2), 12-2(1) and 12-2(2), the same sealing processes was done as done to Organic EL elements 1-1 to 1-4 in Example 1, whereby the lighting device shown in FIGS. 5 and 6 was formed. The organic EL elements were evaluated using the lighting devices. The following evaluations were made.

(Voltage Increasing Ratio)

Driving voltage ratio of Organic EL elements 12-1(1), 12-1(2), 12-2(1) and 12-2(2) were measured in the same manner as in Example 10. The evaluation results are shown in Table 10.

TABLE 10

| Pair of Organic EL elements | Electron transport compound | Driving voltage increasing ratio | Remarks |
|---|---|---|---|
| 12-1(2)/ 12-1(1) | Comparative compound 2 | 140 | Comparison |
| 12-2(2)/ 12-2(1) | III-23 | 112 | Invention |

As is clearly shown in Table 10, Organic EL elements of the present invention exhibited a small amount of driving voltage increase when the electron transport layer was increased compared with the comparative organic EL elements. As a result, it was possible to provide a thick organic EL element which can be driven with a small driving voltage.

What is claimed is:

1. An organic electroluminescence element comprising an anode, a cathode and a plurality of organic compound layers between the anode and the cathode, provided that one of the organic compound layers is a light emitting layer containing a phosphorescence emitting compound, wherein at least one of the organic compound layers contains a compound represented by Formula (1),

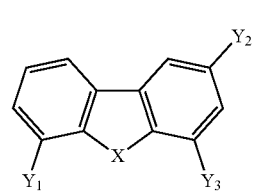

Formula (1)

wherein, X represents O or S; $Y_1$ to $Y_3$ each represents a hydrogen atom, a substituent or a group represented by Formula (A), provided that at least two of $Y_1$ to $Y_3$ are groups represented by Formula (A), not all of $Y_1$ to $Y_3$ are the same group, and at least one of the groups represented by Formula (A) has Ar of a carbazolyl group, or an azacarbazolyl group containing 2 to 5 nitrogen atoms,

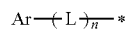  Formula (A)

wherein, L represents a divalent linking group derived from an aromatic hydrocarbon ring or an aromatic heterocycle; n represents an integer of 0 to 3, provided that when n is 2 or 3, a plurality of ns may be the same or different; "*" indicates a linking position with Formula (1); and Ar represents a group represented by Formula (A'),

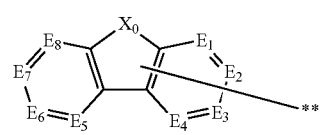  Formula (A')

wherein, $X_0$ represents N(R), O or S; $E_1$ to $E_8$ each represents $C(R_1)$, or N, provided that R and $R_1$ each represents a hydrogen atom, a substituent or a linking position with L; and "**" indicates a linking position with L.

2. The organic electroluminescence element of claim 1, wherein at least one of the groups represented by Formula (A) has Ar of a carbazolyl group.

3. The organic electroluminescence element of claim 1, wherein $Y_1$ in Formula (1) is represented by Formula (A); one of $Y_2$ and $Y_3$ is represented by Formula (A), and the other one of $Y_2$ and $Y_3$ is a hydrogen atom; and Ar in Formula (A) is a carbazolyl group which is bonded to L though a nitrogen position, provided that the carbazolyl group may have a substituent.

4. The organic electroluminescence element of claim 1, wherein $Y_1$ in Formula (1) is represented by Formula (A), and Ar in Formula (A) is an azacarbazolyl group containing 2 to 5 nitrogen atoms, provided that the azacarbazolyl group may have a substituent; and at least one of $Y_2$ and $Y_3$ is represented by Formula (A).

5. The organic electroluminescence element of claim 1, wherein n in Formula (A) represents an integer of 0 or 1.

6. The organic electroluminescence element of claim 1, wherein the compound represented by Formula (1) is contained in the light emitting layer.

7. The organic electroluminescence element of claim 1, wherein at least one of the organic compound layers is an electron transport layer and the compound represented by Formula (1) is contained in the electron transport layer.

8. The organic electroluminescence element of claim 1, wherein the organic compound layer containing the compound represented by Formula (1) is prepared with a wet coating process.

9. The organic electroluminescence element of claim 1, wherein the organic electroluminescence element emits a white light.

10. A lighting device comprising the organic electroluminescence element of claim 1.

11. A display device comprising the organic electroluminescence element of claim 1.

12. A compound represented by Formula (1),

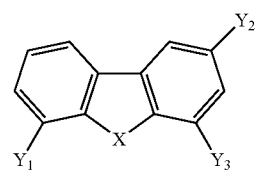  Formula (1)

wherein, X represents O or S; $Y_1$ to $Y_3$ each represents a hydrogen atom, a substituent or a group represented by Formula (A), provided that at least two of $Y_1$ to $Y_3$ are groups represented by Formula (A), not all of $Y_1$ to $Y_3$ are the same group, and at least one of the groups represented by Formula (A) has Ar of a carbazolyl group, or an azacarbazolyl group containing 2 to 5 nitrogen atoms,

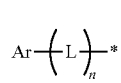  Formula (A)

wherein, L represents a divalent linking group derived from an aromatic hydrocarbon ring or an aromatic heterocycle; n represents an integer of 0 to 3, provided that when n is 2 or 3, a plurality of ns may be the same or different; "*" indicates a linking position with Formula (1); and Ar represents a group represented by Formula (A'),

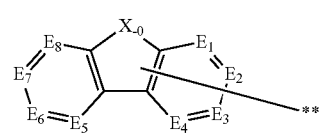  Formula (A')

wherein, $X_0$ represents N(R), O or S; $E_1$ to $E_8$ each represents $C(R_1)$, or N, provided that R and $R_1$ each represents a hydrogen atom, a substituent or a linking position with L; and "**" indicates a linking position with L.

* * * * *